(12) United States Patent
Oestergaard et al.

(10) Patent No.: US 10,479,981 B2
(45) Date of Patent: Nov. 19, 2019

(54) DNASE VARIANTS

(71) Applicant: Novozymes A/S, Bagsvaerd (DK)

(72) Inventors: Lars Henrik Oestergaard, Charlottelund (DK); Gernot J. Abel, Copenhagen (DK); Dorte Marie Koefoed Klitgaard, Bagsvaerd (DK); Annette Helle Johansen, Bronshoj (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/737,184

(22) PCT Filed: Oct. 14, 2016

(86) PCT No.: PCT/EP2016/074747
§ 371 (c)(1),
(2) Date: Dec. 15, 2017

(87) PCT Pub. No.: WO2017/064269
PCT Pub. Date: Apr. 20, 2017

(65) Prior Publication Data
US 2018/0163189 A1 Jun. 14, 2018

(30) Foreign Application Priority Data
Oct. 14, 2015 (DK) .................................. 2015 00632

(51) Int. Cl.
*C12N 9/22* (2006.01)
*C11D 3/386* (2006.01)

(52) U.S. Cl.
CPC ............ *C12N 9/22* (2013.01); *C11D 3/38636* (2013.01); *C12Y 301/21001* (2013.01)

(58) Field of Classification Search
None
See application file for complete search history.

(56) References Cited

U.S. PATENT DOCUMENTS

2004/0082053 A1    4/2004    Machida

FOREIGN PATENT DOCUMENTS

| WO | 2011/098579 A1 | 8/2011 |
| WO | 2014/087011 A1 | 6/2014 |
| WO | 2015/166075 A1 | 11/2015 |
| WO | 2015/181286 A1 | 12/2015 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Guo et al. (H. Guo et al., "Protein Tolerance to Random Amino Acid Change", PNAS 101(25): 9205-9210, Jun. 2004).*
Machida et al., Nature, vol. 438, No. 7071, pp. 1157-1161 (2005).
Machida et al., UniProt Accession No. Q2U877 (2006).
Moore et al., UniProt Accession No. A0A0L1J428 (2014).
Nierman et al., UniProt Accession No. B8NEA2 (2007).
Yu et al., UniProt Accession No. A0A0F0I7M9 (2015).
Zhao et al, Eukaryotic Cell, vol. 11, No. 9, p. 1178 (2012).
Zhao et al. GenBank Accession No. KDE80879 (2012).

* cited by examiner

*Primary Examiner* — Richard G Hutson
(74) *Attorney, Agent, or Firm* — Elias Lambiris

(57) ABSTRACT

The present invention relates to polypeptide variants and methods for obtaining variants. The present invention also relates to polynucleotides encoding the variants; nucleic acid constructs, vectors, and host cells comprising the polynucleotides; and methods of using the variants.

13 Claims, No Drawings

Specification includes a Sequence Listing.

SEQUENCE LISTING

<160> NUMBER OF SEQ ID NOS: 1

<210> SEQ ID NO 1
<211> LENGTH: 221
<212> TYPE: PRT
<213> ORGANISM: Aspergillus oryzae

<400> SEQUENCE: 1

Val Pro Val Asn Pro Glu Pro Asp Ala Thr Ser Val Glu Asn Val Ala
1               5                   10                  15

Leu Lys Thr Gly Ser Gly Asp Ser Gln Ser Asp Pro Ile Lys Ala Asp
            20                  25                  30

Leu Glu Val Lys Gly Gln Ser Ala Leu Pro Phe Asp Val Asp Cys Trp
        35                  40                  45

Ala Ile Leu Cys Lys Gly Ala Pro Asn Val Leu Gln Arg Val Asn Glu
    50                  55                  60

Lys Thr Lys Asn Ser Asn Arg Asp Arg Ser Gly Ala Asn Lys Gly Pro
65                  70                  75                  80

Phe Lys Asp Pro Gln Lys Trp Gly Ile Lys Ala Leu Pro Pro Lys Asn
                85                  90                  95

Pro Ser Trp Ser Ala Gln Asp Phe Lys Ser Pro Glu Glu Tyr Ala Phe
            100                 105                 110

Ala Ser Ser Leu Gln Gly Gly Thr Asn Ala Ile Leu Ala Pro Val Asn
        115                 120                 125

```
Leu Ala Ser Gln Asn Ser Gln Gly Gly Val Leu Asn Gly Phe Tyr Ser
    130             135             140
Ala Asn Lys Val Ala Gln Phe Asp Pro Ser Lys Pro Gln Gln Thr Lys
145             150             155             160
Gly Thr Trp Phe Gln Ile Thr Lys Phe Thr Gly Ala Ala Gly Pro Tyr
                165             170             175
Cys Lys Ala Leu Gly Ser Asn Asp Lys Ser Val Cys Asp Lys Asn Lys
            180             185             190
Asn Ile Ala Gly Asp Trp Gly Phe Asp Pro Ala Lys Trp Ala Tyr Gln
        195             200             205
Tyr Asp Glu Lys Asn Asn Lys Phe Asn Tyr Val Gly Lys
    210             215             220
```

DNASE VARIANTS

CROSS-REFERENCE TO RELATED APPLICATIONS

This application is a 35 U.S.C. 371 national application of PCT/EP2016/074747 filed Oct. 14, 2016, which claims priority or the benefit under 35 U.S.C. 119 of Danish application no. PA 2015 00632 filed Oct. 14, 2015. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to novel DNase variants exhibiting alterations relative to the parent DNase in one or more properties including: wash performance, detergent stability and/or storage stability. The variants of the invention are suitable for use in cleaning processes and detergent compositions, such as laundry compositions and dish wash compositions, including hand wash and automatic dish wash compositions. The present invention also relates to isolated DNA sequences encoding the variants, expression vectors, host cells, and methods for producing and using the DNase variants of the invention.

Description of the Related Art

Microorganisms generally live attached to surfaces in many natural, industrial, and medical environments, encapsulated by extracellular substances including biopolymers and macromolecules. The resulting layer of slime encapsulated microorganism is termed a biofilm. Biofilms are the predominant mode of growth of bacteria in the natural environment, and bacteria growing in biofilms exhibit distinct physiological properties. Compared to their planktonically grown counterparts, the bacteria in a biofilm are more resistant to antibiotics, UV irradiation, detergents and the host immune response.

A biofilm may include one or more microorganisms, including gram-positive and gram-negative bacteria, algae, protozoa, and/or yeast or filamentous fungi and viruses and/or bacteriophage. Examples of problematic biofilms are dental plaque, infections on medical implants, but also the initial fouling on ship hulls. Biofilms are attributed to the pathogenesis of many infections in humans and are a significant problem in industry in terms of biofouling of exposed surfaces, where biofilm colonisation can form the base component of a localised ecosystem which can disrupt and interfere with industrial processes and components.

When laundry items like T-shirts or sportswear are used, they are exposed to bacteria from the body of the user and from the rest of the environment in which they are used. Some of these bacteria are capable of adhering to the laundry item and form a biofilm on the item. The presence of bacteria implies that the laundry items become sticky and therefore soil adheres to the sticky areas. This soil has shown difficult to remove by commercially available detergent compositions. Further, when very dirty laundry items are washed together with less dirty laundry items the dirt present in the wash liquor tend to stick to the biofilm. As a result hereof the laundry item is more "soiled" after wash than before wash. Further, these bacteria are a source of bad odor, which develops after use of the laundry item. The bad odor is difficult to remove and may remain even after wash. The reason for this bad odor is adhesion of bacteria to the textile surface. Because of the adhesion to the textile, the bacteria may remain even after wash, and continue to be a source of bad odor.

International patent application WO2011/098579 (Newcastle UNIV.) and WO2014/087011 (Novozymes A/S) concern bacterial deoxyribonuclease compounds and methods for biofilm disruption and prevention.

SUMMARY OF THE INVENTION

The present invention relates to a DNase variant having at least one improved property compared to SEQ ID NO: 1, comprising a modification at one or more positions selected from the list consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 185, 186, 187, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 and 221, wherein the variant has an amino acid sequence which is at least 60%, at least 70%, at least 80%, at least 85%, at least 90% or at least 95% identical to SEQ ID NO: 1.

The invention further relates to variants of a DNase parent with at least 60% identity to SEQ ID NO: 1 wherein said variant comprises at least one of the following modifications compared to SEQ ID NO: 1: V1*, V1A, V1D, V1E, V1F, V1G, V1H, V1I, V1K, V1L, V1M, V1N, V1P, V1Q, V1R, V1S, V1T, V1W, V1Y, P2*, P2A, P2D, P2E, P2F, P2G, P2H, P2I, P2K, P2L, P2M, P2N, P2Q, P2R, P2S, P2T, P2V, P2W, P2Y, V3*, V3A, V3C, V3D, V3E, V3F, V3G, V3H, V3I, V3K, V3L, V3M, V3N, V3P, V3R, V3S, V3T, V3W, V3Y, N4*, N4A, N4D, N4E, N4F, N4G, N4H, N4I, N4K, N4L, N4M, N4P, N4Q, N4R, N4S, N4T, N4V, N4W, N4Y, P5*, P5A, P5D, P5E, P5F, P5G, P5H, P5I, P5K, P5L, P5M, P5N, P5Q, P5R, P5S, P5T, P5V, P5W, P5Y, E6*, E6A, E6D, E6F, E6G, E6H, E6I, E6K, E6L, E6M, E6N, E6P, E6Q, E6R, E6S, E6T, E6V, E6W, E6Y, P7*, P7A, P7D, P7E, P7F, P7G, P7H, P7I, P7K, P7L, P7M, P7N, P7Q, P7R, P7S, P7T, P7V, P7W, P7Y, D8*, D8A, D8E, D8F, D8G, D8H, D8I, D8K, D8L, D8M, D8N, D8P, D8Q, D8R, D8S, D8T, D8V, D8W, D8Y, A9*, A9D, A9E, A9F, A9G, A9H, A9I, A9K, A9L, A9M, A9N, A9P, A9Q, A9R, A9S, A9T, A9V, A9W, A9Y, T10*, T10A, T10D, T10E, T10F, T10G, T10H, T10I, T10K, T10L, T10M, T10N, T10P, T10Q, T10R, T10S, T10V, T10W, T10Y, S11*, S11A, S11D, S11E, S11F, S11G, S11H, S11I, S11K, S11L, S11M, S11N, S11P, S11Q, S11R, S11T, S11V, S11W, S11Y, V12*, V12A, V12D, V12E, V12F, V12G, V12H, V12I, V12K, V12L, V12M, V12N, V12P, V12Q, V12R, V12S, V12T, V12W, V12Y, E13*, E13A, E13D, E13F, E13G, E13H, E13I, E13K, E13L, E13M, E13N, E13P, E13Q, E13R, E13S, E13T, E13V, E13W, E13Y, N14*, N14A, N14D, N14E, N14F, N14G, N14H, N14I, N14K, N14L, N14M, N14P, N14Q, N14R, N14S, N14T, N14V, N14W, N14Y, V15*, V15A, V15D, V15E, V15F, V15G, V15H, V15I, V15K, V15L, V15M, V15N, V15P, V15Q, V15R, V15S, V15T, V15W, V15Y, A16*, A16D, A16E, A16F, A16G, A16H, A16I, A16K, A16L, A16M, A16N, A16P, A16Q, A16R, A16S, A16T, A16V, A16W, A16Y, L17*, L17A, L17D, L17E, L17F, L17G, L17H, L17I, L17K, L17M, L17N, L17P, L17Q, L17R, L17S, L17T, L17V, L17W, L17Y, K18*, K18A, K18D, K18E, K18F, K18G, K18H, K18I, K18L, K18M, K18N, K18P, K18Q, K18R, K18S, K18T, K18V, K18W, K18Y, T19*, T19A, T19D, T19E, T19F, T19G, T19H, T19I, T19K, T19L, T19M, T19N, T19P, T19Q, T19R, T19S, T19V, T19W, T19Y, G20*, G20A, G20D, G20E, G20F, G20H, G20I, G20K, G20L, G20M, G20N, G20P, G20Q, G20R, G20S, G20T, G20V, G20W, G20Y, S21*, S21A, S21D, S21E, S21F, S21G, S21H, S21I, S21K, S21L, S21M, S21N, S21P, S21Q, S21R, S21T, S21V, S21W, S21Y, G22*, G22A, G22D, G22E, G22F, G22H, G22I, G22K, G22L, G22M, G22N, G22P, G22Q, G22R, G22S, G22T, G22V, G22W, G22Y, Q23*, D23A, D23E, D23F, D23G, D23H, D23I, D23K, D23L, D23M, D23N, D23P, D23Q, D23R, D23S, D23T, D23V, D23W, D23Y, S24*, S24A, S24D, S24E, S24F, S24G, S24H, S24I, S24K, S24L, S24M, S24N, S24P, S24Q, S24R, S24T, S24V, S24W, S24Y, Q25*, Q25A, Q25D, Q25E, Q25F, Q25G, Q25H, Q25I, Q25K, Q25L, Q25M, Q25N, Q25P, Q25R, Q25S, Q25T, Q25V, Q25W, Q25Y, S26*, S26A, S26D, S26E, S26F, S26G, S26H, S26I, S26K, S26L, S26M, S26N, S26P, S26Q, S26R, S26T, S26V, S26W, S26Y, D27*, D27A, D27E, D27F, D27G, D27H, D27I, D27K, D27L, D27M, D27N, D27P, D27Q, D27R, D27S, D27T, D27V, D27W, D27Y, P28*, P28A, P28D, P28E, P28F, P28G, P28H, P28I, P28K, P28L, P28M, P28N, P28Q, P28R, P28S, P28T, P28V, P28W, P28Y, I29*, I29A, I29D, I29E, I29F, I29G, I29H, I29K, I29L, I29M, I29N, I29P, I29Q, I29R, I29S, I29T, I29V, I29W, I29Y, K30*, K30A, K30D, K30E, K30F, K30G, K30H, K30I, K30L, K30M, K30N, K30P, K30Q, K30R, K30S, K30T, K30V, K30W, K30Y, A31*, A31D, A31E, A31F, A31G, A31H, A31I, A31K, A31L, A31M, A31N, A31P, A31Q, A31R, A31S, A31T, A31V, A31W, A31Y, D32*, D32A, D32E, D32F, D32G, D32H, D32I, D32K, D32L, D32M, D32N, D32P, D32Q, D32R, D32S, D32T, D32V, D32W, D32Y, L33*, L33A, L33D, L33E, L33F, L33G, L33H, L33I, L33K, L33M, L33N, L33P, L33Q, L33R, L33S, L33T, L33V, L33W, L33Y, E34*, E34A, E34D, E34F, E34G, E34H, E34I, E34K, E34L, E34M, E34N, E34P, E34Q, E34R, E34S, E34T, E34V, E34W, E34Y, V35*, V35A, V35D, V35E, V35F, V35G, V35H, V35I, V35K, V35L, V35M, V35N, V35P, V35Q, V35R, V35S, V35T, V35W, V35Y, K36*, K36A, K36D, K36E, K36F, K36G, K36H, K36I, K36L, K36M, K36N, K36P, K36Q, K36R, K36S, K36T, K36V, K36W, K36Y, G37*, G37A, G37D, G37E, G37F, G37H, G37I, G37K, G37L, G37M, G37N, G37P, G37Q, G37R, G37S, G37T, G37V, G37W, G37Y, Q38*, Q38A, Q38D, Q38E, Q38F, Q38G, Q38H, Q38I, Q38K, Q38L, Q38M, Q38N, Q38P, Q38R, Q38S, Q38T, Q38V, Q38W, Q38Y, S39*, S39A, S39D, S39E, S39F, S39G, S39H, S39I, S39K, S39L, S39M, S39N, S39P, S39Q, S39R, S39T, S39V, S39W, S39Y, A40*, A40D, A40E, A40F, A40G, A40H, A40I, A40K, A40L, A40M, A40N, A40P, A40Q, A40R, A40S, A40T, A40V, A40W, A40Y, L41*, L41A, L41D, L41E, L41F, L41G, L41H, L41I, L41K, L41M, L41N, L41P, L41Q, L41R, L41S, L41T, L41V, L41W, L41Y, P42*, P42A, P42D, P42E, P42F, P42G, P42H, P42I, P42K, P42L, P42M, P42N, P42Q, P42R, P42S, P42T, P42V, P42W, P42Y, F43*, F43A, F43D, F43E, F43G, F43H, F43I, F43K, F43L, F43M, F43N, F43P, F43Q, F43R, F43S, F43T, F43V, F43W, F43Y, D44*, D44A, D44E, D44F, D44G, D44H, D44I, D44K, D44L, D44M, D44N, D44P, D44Q, D44R, D44S, D44T, D44V, D44W, D44Y, V45*, V45A, V45D, V45E, V45F, V45G, V45H, V45I, V45K, V45L, V45M, V45N, V45P, V45Q, V45R, V45S, V45T, V45W, V45Y, D46*, D46A, D46E, D46F, D46G, D46H, D46I, D46K, D46L, D46M, D46N, D46P, D46Q, D46R, D46S, D46T, D46V, D46W, D46Y, C47A, C47D, C47E, C47F, C47G, C47H, D47I, C47K, C47L, C47M, C47N, C47P, C47Q, C47R, C47S, C47T, 047V, C47W, C47Y, W48*, W48A, W48D, W48E, W48F, W48G, W48H, W48I, W48K, W48L, W48M, W48N, W48P, W48Q, W48R, W48S, W48T, W48V, W48Y, A49*, A49D, A49E, A49F, A49G, A49H, A49I, A49K, A49L, A49M, A49N, A49P, A49Q, A49R, A49S, A49T, A49V, A49W, A49Y, I50*, I50A, I50D, I50E, I50F, I50G, I50H, I50K, I50L, I50M, I50N, I50P, I50Q, I50R, I50S, I50T, I50V, I50W, I50Y, L51*, L51A, L51D, L51E, L51F, L51G, L51H, L51I, L51K, L51M, L51N, L51P, L51Q, L51R, L51S, L51T, L51V, L51W, L51Y, K53*, K53A, K53D, K53E, K53F, K53G, K53H, K53I, K53L, K53M, K53N, K53P, K53Q, K53S, K53T, K53V, K53W, K53Y, G54*, G54A, G54D, G54E, G54F, G54H, G54I, G54K, G54L, G54M, G54N, G54P, G54Q, G54R, G54S, G54T, G54V, G54W, G54Y, A55*, A55D, A55E, A55F, A55G, A55H, A55I, A55K, A55L, A55M, A55N, A55P, A55Q, A55R, A55S, A55T, A55V, A55W, A55Y, P56*, P56A, P56D, P56E, P56F, P56G, P56H, P56I, P56K, P56L, P56M, P56N, P56Q, P56R, P56S, P56T, P56V, P56W, P56Y, N57*, N57A, N57D, N57E, N57F, N57G, N57H, N57I, N57K, N57L, N57M, N57P, N57Q, N57R, N57S, N57T, N57V, N57W, N57Y, V58*, V58A, V58D, V58E, V58F, V58G, V58H, V58I, V58K, V58L, V58M, V58N, V58P, V58Q, V58R, V58S, V58T, V58W, V58YL59*, L59A, L59D, L59E, L59F, L59G, L59H, L59I, L59K, L59M, L59N, L59P, L59Q, L59R, L59S, L59T, L59V, L59W, L59Y, Q60*, Q60A, Q60D, Q60E, Q60F, Q60G, Q60H, Q60I, Q60K, Q60L, Q60M, Q60N, Q60P, Q60R, Q60S, Q60T, Q60V, Q60W, Q60Y, R61*, R61A, R61D, R61E, R61F, R61G, R61H, R61I, R61K, R61L, R61M, R61N, R61P, R61Q, R61S, R61T, R61V, R61W, R61Y, V62*, V62A, V62D, V62E, V62F, V62G, V62H, V62I, V62K, V62L, V62M, V62N, V62P, V62Q, V62R, V62S, V62T, V62W, V62Y, N63*, N63A, N63D, N63E, N63F, N63G, N63H, N63I, N63K, N63L, N63M, N63P, N63Q, N63R, N63S, N63T, N63V, N63W, N63Y, E64*, E64A, E64D, E64F, E64G, E64H, E64I, E64K, E64L, E64M, E64N, E64P, E64Q, E64R, E64S, E64T, E64V, E64W, E64Y, K65*, K65A, K65D, K65E, K65F, K65G, K65H, K65I, K65L, K65M, K65N, K65P, K65Q, K65R, K65S, K65T, K65V, K65W, K65Y, T66*, T66A, T66D, T66E, T66F, T66G, T66H, T66I, T66K, T66L, T66M, T66N, T66P, T66Q, T66R, T66S, T66V, T66W, T66Y, K67*, K67A, K67D, K67E, K67F, K67G, K67H, K67I, K67L, K67M, K67N, K67P, K67Q, K67R, K67S, K67T, K67V, K67W, K67Y, N68*, N68A, N68D, N68E, N68F, N68G, N68H, N68I, N68K, N68L, N68M, N68P, N68Q, N68R, N68S, N68T, N68V, N68W, N68Y, S69*, S69A, S69D, S69E, S69F, S69G, S69H, S69I, S69K, S69L, S69M, S69N, S69P, S69Q, S69R, S69T, S69V, S69W, S69Y, N70*, N70A, N70D, N70E, N70F, N70G, N70H, N70I, N70K, N70L, N70M, N70P, N70Q, N70R, N70S, N70T, N70V, N70W, N70Y, R71*, R71A, R71D, R71E, R71F, R71G, R71H, R71I, R71K, R71L, R71M, R71N, R71P, R71Q, R71S, R71T, R71V, R71W, R71Y, D72*, D72A, D72E, D72F, D72G, D72H, D72I, D72K, D72L, D72M, D72N, D72P, D72Q, D72R, D72S, D72T, D72V, D72W, D72Y, R73*, R73A, R73D, R73E, R73F, R73G, R73H, R73I, R73K, R73L, R73M, R73N, R73P, R73Q, R73S, R73T, R73V, R73W, R73Y, S74*, S74A, S74D, S74E, S74F, S74G, S74H, S74I, S74K, S74L, S74M, S74N, S74P, S74Q, S74R, S74T, S74V, S74W, S74Y, G75*, G75A, G75D, G75E, G75F, G75H, G75I, G75K, G75L, G75M, G75N, G75P, G75Q, G75R, G75S, G75T, G75V, G75W, G75Y, A76*, A76D, A76E, A76F, A76G, A76H, A76I, A76K, A76L, A76M, A76N, A76P, A76Q, A76R, A76S, A76T, A76V, A76W, A76Y, N77*, N77A, N77D, N77E, N77F, N77G, N77H, N77I, N77K, N77L, N77M, N77P, N77Q, N77R, N77S, N77T, N77V, N77W, N77Y, K78*, K78A, K78D, K78E, K78F, K78G, K78H, K78I, K78L, K78M, K78N, K78P, K78Q, K78R, K78S, K78T, K78V, K78W, K78Y, G79*, G79A, G79D, G79E, G79F, G79H, G79I, G79K, G79L, G79M, G79N, G79P, G79Q, G79R, G79S, G79T, G79V, G79W, G79Y, P80*, P80A, P80D, P80E, P80F, P80G, P80H, P80I, P80K, P80L, P80M, P80N, P80Q, P80R, P80S, P80T, P80V, P80W, P80Y, F81*, F81A, F81D, F81E, F81G, F81H, F81I, F81K, F81L, F81M, F81N, F81P, F81Q, F81R, F81S, F81T, F81V, F81W, F81Y, K82*, K82A, K82D, K82E, K82F, K82G, K82H, K82I, K82L, K82M, K82N, K82P, K82Q, K82R, K82S, K82T, K82V, K82W, K82Y, D83*, D83A, D83E, D83F, D83G, D83H, D83I, D83K, D83L, D83M, D83N, D83P, D83Q, D83R, D83S, D83T, D83V, D83W, D83Y, P84*, P84A, P84D, P84E, P84F, P84G, P84H, P84I, P84K, P84L, P84M, P84N, P84Q, P84R, P84S, P84T, P84V, P84W, P84Y, Q85*, Q85A, Q85D, Q85E, Q85F, Q85G, Q85H, Q85I, Q85K, Q85L, Q85M, Q85N, Q85P, Q85R, Q85S, Q85T, Q85V, Q85W, Q85Y, K86*, K86A, K86D, K86E, K86F, K86G, K86H, K86I, K86L, K86M, K86N, K86P, K86Q, K86R, K86S, K86T, K86V, K86W, K86Y, W87*, W87A, W87D, W87E, W87F, W87G, W87H, W87I, W87K, W87L, W87M, W87N, W87P, W87Q, W87R, W87S, W87T, W87V, W87Y, G88*, G88A, G88D, G88E, G88F, G88H, G88I, G88K, G88L, G88M, G88N, G88P, G88Q, G88R, G88S, G88T, G88V, G88W, G88Y, I89*, I89A, I89D, I89E, I89F, I89G, I89H, I89K, I89L, I89M, I89N, I89P, I89Q, I89R, I89S, I89T, I89V, I89W, I89Y, K90*, K90A, K90D, K90E, K90F, K90G, K90H, K90I, K90L, K90M, K90N, K90P, K90Q, K90R, K90S, K90T, K90V, K90W, K90Y, A91*, A91D, A91E, A91F, A91G, A91H, A91I, A91K, A91L, A91M, A91N, A91P, A91Q, A91R, A91S, A91T, A91V, A91W, A91Y, L92*, L92A, L92D, L92E, L92F, L92G, L92H, L92I, L92K, L92M, L92N, L92P, L92Q, L92R, L92S, L92T, L92V, L92W, L92Y, P93*, P93A, P93D, P93E, P93F, P93G, P93H, P93I, P93K, P93L, P93M, P93N, P93Q, P93R, P93S, P93T, P93V, P93W, P93Y, P94*, P94A, P94D, P94E, P94F, P94G, P94H, P94I, P94K, P94L, P94M, P94N, P94Q, P94R, P94S, P94T, P94V, P94W, P94Y, K95*, K95A, K95D, K95E, K95F, K95G, K95H, K95I, K95L, K95M, K95N, K95P, K95Q, K95R, K95S, K95T, K95V, K95W, K95Y, N96*, N96A, N96D, N96E, N96F, N96G, N96H, N96I, N96K, N96L, N96M, N96P, N96Q, N96R, N96S, N96T, N96V, N96W, N96Y, P97*, P97A, P97D, P97E, P97F, P97G, P97H, P97I, P97K, P97L, P97M, P97N, P97Q, P97R, P97S, P97T, P97V, P97W, P97Y, S98*, S98A, S98D, S98E, S98F, S98G, S98H, S98I, S98K, S98L, S98M, S98N, S98P, S98Q, S98R, S98T, S98V, S98W, S98Y, W99*, W99A, W99D, W99E, W99F, W99G, W99H, W99I, W99K, W99L, W99M, W99N, W99P, W99Q, W99R, W99S, W99T, W99V, W99Y, S100*, S100A, S100D, S100E, S100F, S100G, S100H, S100I, S100K, S100L, S100M, S100N, S100P, S100Q, S100R, S100T, S100V, S100W, S100Y, A101*, A101D, A101E, A101F, A101G, A101H, A101I, A101K, A101L, A101M, A101N, A101P, A101Q, A101R, A101S, A101T, A101V, A101W, A101Y, Q102*, Q102A, Q102D, Q102E, Q102F, Q102G, Q102H, Q102I, Q102K, Q102L, Q102M, Q102N, Q102P, Q102R, Q102S, Q102T, Q102V, Q102W, Q102Y, D103*, D103A, D103E, D103F, D103G, D103H, D103I, D103K, D103L, D103M, D103N, D103P, D103Q, D103R, D103S, D103T, D103V, D103W, D103Y, F104*, F104A, F104D, F104E, F104G, F104H, F104I, F104K, F104L, F104M, F104N, F104P, F104Q, F104R, F104S, F104T, F104V, F104W, F104Y, K105*, K105A, K105D, K105E, K105F, K105G, K105H, K105I, K105L, K105M, K105N, K105P, K105Q, K105R, K105S, K105T, K105V, K105W, K105Y, S106*, S106A, S106D, S106E, S106F, S106G, S106H, S106I, S106K, S106L, S106M, S106N, S106P, S106Q, S106R, S106T, S106V, S106W, S106Y, P107*, P107A, P107D, P107E, P107F, P107G, P107H, P107I, P107K, P107L, P107M, P107N, P107Q, P107R, P107S, P107T, P107V, P107W, P107Y, E108*, E108A, E108D, E108F, E108G, E108H, E108I, E108K, E108L, E108M, E108N, E108P, E108Q, E108R, E108S, E108T, E108V, E108W, E108Y, E109*, E109A, E109D, E109F, E109G, E109H, E109I, E109K, E109L, E109M, E109N, E109P, E109Q, E109R, E109S, E109T, E109V, E109W, E109Y, Y110*, Y110A, Y110D, Y110E, Y110F, Y110G, Y110H, Y110I, Y110K, Y110L, Y110M, Y110N, Y110P, Y110Q, Y110R, Y110S, Y110T, Y110V, Y110W, A111*, A111D, A111E, A111F, A111G, A111H, A111I, A111K, A111L, A111M, A111N, A111P, A111Q, A111R, A111S, A111T, A111V, A111W, A111Y, F112*, F112A, F112D, F112E, F112G, F112H, F112I, F112K, F112L, F112M, F112N, F112P, F112Q, F112R, F112S, F112T, F112V, F112W, F112Y, A113*, A113D, A113E, A113F, A113G, A113H, A113I, A113K, A113L, A113M, A113N, A113P, A113Q, A113R, A113S, A113T, A113V, A113W, A113Y, S114*, S114A, S114D, S114E, S114F, S114G, S114H, S114I, S114K, S114L, S114M, S114N, S114P, S114Q, S114R, S114T, S114V, S114W, S114Y, S115*, S115A, S115D, S115E, S115F, S115G, S115H, S115I, S115K, S115L, S115M, S115N, S115P, S115Q, S115R, S115T, S115V, S115W, S115Y, L116*, L116A, L116D, L116E, L116F, L116G, L116H, L116I, L116K, L116M, L116N, L116P, L116Q, L116R, L116S, L116T, L116V, L116W, L116Y, Q117*, Q117A, Q117D, Q117E, Q117F, Q117G, Q117H, Q117I, Q117K, Q117L, Q117M, Q117N, Q117P, Q117R, Q117S, Q117T, Q117V, Q117W, Q117Y, G118*, G118A, G118D, G118E, G118F, G118H, G118I, G118K, G118L, G118M, G118N, G118P, G118Q, G118R, G118S, G118T, G118V, G118W, G118Y, G119*, G119A, G119D, G119E, G119F, G119H, G119I, G119K, G119L, G119M, G119N, G119P, G119Q, G119R, G119S, G119T, G119V, G119W, G119Y, T120*, T120A, T120D, T120E, T120F, T120G, T120H, T120I, T120K, T120L, T120M, T120N, T120P, T120Q, T120R, T120S, T120V, T120W, T120Y, N121*, N121A, N121D, N121E, N121F, N121G, N121H, N121I, N121K, N121L, N121M, N121P, N121Q, N121R, N121S, N121T, N121V, N121W, N121Y, A122*, A122D, A122E, A122F, A122G, A122H, A122I, A122K, A122L, A122M, A122N, A122P, A122Q, A122R, A122S, A122T, A122V, A122W, A122Y, I123*, I123A, I123D, I123E, I123F, I123G, I123H, I123K, I123L, I123M, I123N, I123P, I123Q, I123R, I123S, I123T, I123V, I123W, I123Y, L124*, L124A, L124D, L124E, L124F, L124G, L124H, L124I, L124K, L124M, L124N, L124P, L124Q, L124R, L124S, L124T, L124V, L124W, L124Y, A125*, A125D, A125E, A125F, A125G, A125H, A125I, A125K, A125L, A125M, A125N, A125P, A125Q, A125R, A125S, A125T, A125V, A125W, A125Y, P126*, P126A, P126D, P126E, P126F, P126G, P126H, P126I, P126K, P126L, P126M, P126N, P126Q, P126R, P126S, P126T, P126V, P126W, P126Y, V127*, V127A, V127D, V127E, V127F, V127G, V127H, V127I, V127K, V127L, V127M, V127N, V127P, V127Q, V127R, V127S, V127T, V127W, V127Y, N128*, N128A, N128D, N128E, N128F, N128G, N128H, N128I, N128K, N128L, N128M, N128P, N128Q, N128R, N128S, N128T, N128V, N128W, N128Y, L129*, L129A, L129D, L129E, L129F, L129G, L129H, L129I, L129K, L129M, L129N, L129P, L129Q, L129R, L129S, L129T, L129V, L129W, L129Y, A130*, A130D, A130E, A130F, A130G, A130H, A130I, A130K, A130L, A130M, A130N, A130P, A130Q, A130R, A130S, A130T, A130V, A130W, A130Y, S131*, S131A, S131D, S131E, S131F, S131G, S131H, S131I, S131K, S131L, S131M, S131N, S131P, S131Q, S131R, S131T, S131V, S131W, S131Y, Q132*, Q132A, Q132D, Q132E, Q132F, Q132G, Q132H, Q132I, Q132K, Q132L, Q132M, Q132N, Q132P, Q132R, Q132S, Q132T, Q132V, Q132W, Q132Y, N133*, N133A, N133D, N133E, N133F, N133G, N133H, N133I, N133K, N133L, N133M, N133P, N133Q, N133R, N133S, N133T, N133V, N133W, N133Y, S134*, S134A, S134D, S134E, S134F, S134G, S134H, S134I, S134K, S134L, S134M, S134N, S134P, S134Q, S134R, S134T, S134V, S134W, S134Y, Q135*, Q135A, Q135D, Q135E, Q135F, Q135G, Q135H, Q135I, Q135K, Q135L, Q135M, Q135N, Q135P, Q135R, Q135S, Q135T, Q135V, Q135W, Q135Y, G136*, G136A, G136D, G136E, G136F, G136H, G136I, G136K, G136L, G136M, G136N, G136P, G136Q, G136R, G136S, G136T, G136V, G136W, G136Y, G137*, G137A, G137D, G137E, G137F, G137H, G137I, G137K, G137L, G137M, G137N, G137P, G137Q, G137R, G137S, G137T, G137V, G137W, G137Y, V138*, V138A, V138D, V138E, V138F, V138G, V138H, V138I, V138K, V138L, V138M, V138N, V138P, V138Q, V138R, V138S, V138T, V138W, V138Y, L139*, L139A, L139D, L139E, L139F, L139G, L139H, L139I, L139K, L139M, L139N, L139P, L139Q, L139R, L139S, L139T, L139V, L139W, L139Y, N140*, N140A, N140D, N140E, N140F, N140G, N140H, N140I, N140K, N140L, N140M, N140P, N140Q, N140R, N140S, N140T, N140V, N140W, N140Y, G141*, G141A, G141D, G141E, G141F, G141H, G141I, G141K, G141L, G141M, G141N, G141P, G141Q, G141R, G141S, G141T, G141V, G141W, G141Y, F142*, F142A, F142D, F142E, F142G, F142H, F142I, F142K, F142L, F142M, F142N, F142P, F142Q, F142R, F142S, F142T, F142V, F142W, F142Y, Y143*, Y143A, Y143D, Y143E, Y143F, Y143G, Y143H, Y143I, Y143K, Y143L, Y143M, Y143N, Y143P, Y143Q, Y143R, Y143S, Y143T, Y143V, Y143W, S144*, S144A, S144D, S144E, S144F, S144G, S144H, S144I, S144K, S144L, S144M, S144N, S144P, S144Q, S144R, S144T, S144V, S144W, S144Y, A145*, A145D, A145E, A145F, A145G, A145H, A145I, A145K, A145L, A145M, A145N, A145P, A145Q, A145R, A145S, A145T, A145V, A145W, A145Y, N146*, N146A, N146D, N146E, N146F, N146G, N146H, N146I, N146K, N146L, N146M, N146P, N146Q, N146R, N146S, N146T, N146V, N146W, N146Y, K147*, K147A, K147D, K147E, K147F, K147G, K147H, K147I, K147L, K147M, K147N, K147P, K147Q, K147R, K147S, K147T, K147V, K147W, K147Y, V148*, V148A, V148D, V148E, V148F, V148G, V148H, V148I, V148K, V148L, V148M, V148N, V148P, V148Q, V148R, V148S, V148T, V148W, V148Y, A149*, A149D, A149E, A149F, A149G, A149H, A149I, A149K, A149L, A149M, A149N, A149P, A149Q, A149R, A149S, A149T, A149V, A149W, A149Y, Q150*, Q150A, Q150D, Q150E, Q150F, Q150G, Q150H, Q150I, Q150K, Q150L, Q150M, Q150N, Q150P, Q150R, Q150S, Q150T, Q150V, Q150W, Q150Y, F151*, F151A, F151D, F151E, F151G, F151H, F151I, F151K, F151L, F151M, F151N, F151P, F151Q, F151R, F151S, F151T, F151V, F151W, F151Y, D152*, D152A, D152E, D152F, D152G, D152H, D152I, D152K, D152L, D152M, D152N, D152P, D152Q, D152R, D152S, D152T, D152V, D152W, D152Y, P153*, P153A, P153D, P153E, P153F, P153G, P153H, P153I, P153K, P153L, P153M, P153N, P153Q, P153R, P153S, P153T, P153V, P153W, P153Y, S154*, S154A, S154D, S154E, S154F, S154G, S154H, S154I, S154K, S154L, S154M, S154N, S154P, S154Q, S154R, S154T, S154V, S154W, S154Y, K155*, K155A, K155D, K155E, K155F, K155G, K155H, K155I, K155L, K155M, K155N, K155P, K155Q, K155R, K155S, K155T, K155V, K155W, K155Y, P156*, P156A, P156D, P156E, P156F, P156G, P156H, P156I, P156K, P156L, P156M, P156N, P156Q, P156R, P156S, P156T, P156V, P156W, P156Y, Q157*, Q157A, Q157D, Q157E, Q157F, Q157G, Q157H, Q157I, Q157K, Q157L, Q157M, Q157N, Q157P, Q157R, Q157S, Q157T, Q157V, Q157W, Q157Y, Q158*, Q158A, Q158D, Q158E, Q158F, Q158G, Q158H, Q158I, Q158K, Q158L, Q158M, Q158N, Q158P, Q158R, Q158S, Q158T, Q158V, Q158W, Q158Y, T159*, T159A, T159D, T159E, T159F, T159G, T159H, T159I, T159K, T159L, T159M, T159N, T159P, T159Q, T159R, T159S, T159V, T159W, T159Y, K160*, K160A, K160D, K160E, K160F, K160G, K160H, K160I, K160L, K160M, K160N, K160P, K160Q, K160R, K160S, K160T, K160V, K160W, K160Y, G161*, G161A, G161D, G161E, G161F, G161H, G161I, G161K, G161L, G161M, G161N, G161P, G161Q, G161R, G161S, G161T, G161V, G161W, G161Y, T162A, T162D, T162E, T162F, T162G, T162H, T162I, T162K, T162L, T162M, T162N, T162P, T162Q, T162R, T162S, T162T, T162V, T162W, T162Y, W163*, W163A, W163D, W163E, W163F, W163G, W163H, W163I, W163K, W163L, W163M, W163N, W163P, W163Q, W163R, W163S, W163T, W163V, W163Y, F164*, F164A, F164D, F164E, F164G, F164H, F164I, F164K, F164L, F164M, F164N, F164P, F164Q, F164R, F164S, F164T, F164V, F164W, F164Y, Q165*, Q165A, Q165D, Q165E, Q165F, Q165G, Q165H, Q165I, Q165K, Q165L, Q165M, Q165N, Q165P, Q165R, Q165S, Q165T, Q165V, Q165W, Q165Y, I166*, I166A, I166D, I166E, I166F, I166G, I166H, I166K, I166L, I166M, I166N, I166P, I166Q, I166R, I166S, I166T, I166V, I166W, I166Y, T167*, T167A, T167D, T167E, T167F, T167G, T167H, T167I, T167K, T167L, T167M, T167N, T167P, T167Q, T167R, T167S, T167V, T167W, T167Y, K168*, K168A, K168D, K168E, K168F, K168G, K168H, K168I, K168L, K168M, K168N, K168P, K168Q, K168R, K168S, K168T, K168V, K168W, K168Y, F169*, F169A, F169D, F169E, F169G, F169H, F169I, F169K, F169L, F169M, F169N, F169P, F169Q, F169R, F169S, F169T, F169V, F169W, F169Y, T170*, T170A, T170D, T170E, T170F, T170G, T170H, T170I, T170K, T170L, T170M, T170N, T170P, T170Q, T170R, T170S, T170V, T170W, T170Y, G171*, G171A, G171D, G171E, G171F, G171H, G171I, G171K, G171L, G171M, G171N, G171P, G171Q, G171R, G171S, G171T, G171V, G171W, G171Y, A172*, A172D, A172E, A172F, A172G, A172H, A172I, A172K, A172L, A172M, A172N, A172P, A172Q, A172R, A172S, A172T, A172V, A172W, A172Y, A173*, A173D, A173E, A173F, A173G, A173H, A173I, A173K, A173L, A173M, A173N, A173P, A173Q, A173R, A173S, A173T, A173V, A173W, A173Y, G174*, G174A, G174D, G174E, G174F, G174H, G174I, G174K, G174L, G174M, G174N, G174P, G174Q, G174R, G174S, G174T, G174V, G174W, G174Y, P175*, P175A, P175D, P175E, P175F, P175G, P175H, P175I, P175K, P175L, P175M, P175N, P175Q, P175R, P175S, P175T, P175V, P175W, P175Y, Y176*, Y176A, Y176D, Y176E, Y176F, Y176G, Y176H, Y176I, Y176K, Y176L, Y176M, Y176N, Y176P, Y176Q, Y176R, Y176S, Y176T, Y176V, Y176W, K178*, K178A, K178D, K178E, K178F, K178G, K178H, K178I, K178L, K178M, K178N, K178P, K178Q, K178R, K178S, K178T, K178V, K178W, K178Y, A179*, A179D, A179E, A179F, A179G, A179H, A179I, A179K, A179L, A179M, A179N, A179P, A179Q, A179R, A179S, A179T, A179V, A179W, A179Y, L180*, L180A, L180D, L180E, L180F, L180G, L180H, L180I, L180K, L180M, L180N, L180P, L180Q, L180R, L180S, L180T, L180V, L180W, L180Y, G181*, G181A, G181D, G181E, G181F, G181H, G181I, G181K, G181L, G181M, G181N, G181P, G181Q, G181R, G181S, G181T, G181V, G181W, G181Y, S182*, S182A, S182D, S182E, S182F, S182G, S182H, S182I, S182K, S182L, S182M, S182N, S182P, S182Q, S182R, S182T, S182V, S182W, S182Y, N183*, N183A, N183D, N183E, N183F, N183G, N183H, N183I, N183K, N183L, N183M, N183P, N183Q, N183R, N183S, N183T, N183V, N183W, N183Y, D184*, D184A, D184E, D184F, D184G, D184H, D184I, D184K, D184L, D184M, D184N, D184P, D184Q, D184R, D184S, D184T, D184V, D184W, D184Y, K185*, K185A, K185D, K185E, K185F, K185G, K185H, K185I, K185L, K185M, K185N, K185P, K185Q, K185R, K185S, K185T, K185V, K185W, K185Y, S186*, S186A, S186D, S186E, S186F, S186G, S186H, S186I, S186K, S186L, S186M, S186N, S186P, S186Q, S186R, S186T, S186V, S186W, S186Y, V187*, V187A, V187D, V187E, V187F, V187G, V187H, V187I, V187K, V187L, V187M, V187N, V187P, V187Q, V187R, V187S, V187T, V187W, V187Y, D189*, D189A, D189E, D189F, D189G, D189H, D189I, D189K, D189L, D189M, D189N, D189P, D189Q, D189R, D189S, D189T, D189V, D189W, D189Y, K190*, K190A, K190D, K190E, K190F, K190G, K190H, K190I, K190L, K190M, K190N, K190P, K190Q, K190R, K190S, K190T, K190V, K190W, K190Y, N191*, N191A, N191D, N191E, N191F, N191G, N191H, N191I, N191K, N191L, N191M, N191P, N191Q, N191R, N191S, N191T, N191V, N191W, N191Y, K192*, K192A, K192D, K192E, K192F, K192G, K192H, K192I, K192L, K192M, K192N, K192P, K192Q, K192R, K192S, K192T, K192V, K192W, K192Y, N193*, N193A, N193D, N193E, N193F, N193G, N193H, N193I, N193K, N193L, N193M, N193P, N193Q, N193R, N193S, N193T, N193V, N193W, N193Y, I194*, I194A, I194D, I194E, I194F, I194G, I194H, I194K, I194L, I194M, I194N, I194P, I194Q, I194R, I194S, I194T, I194V, I194W, I194Y, A195*, A195D, A195E, A195F, A195G, A195H, A195I, A195K, A195L, A195M, A195N, A195P, A195Q, A195R, A195S, A195T, A195V, A195W, A195Y, G196*, G196A, G196D, G196E, G196F, G196H, G196I, G196K, G196L, G196M, G196N, G196P, G196Q, G196R, G196S, G196T, G196V, G196W, G196Y, D197*, D197A, D197E, D197F, D197G, D197H, D197I, D197K, D197L, D197M, D197N, D197P, D197Q, D197R, D197S, D197T, D197V, D197W, D197Y, W198*, W198A, W198D, W198E, W198F, W198G, W198H, W198I, W198K, W198L, W198M, W198N, W198P, W198Q, W198R, W198S, W198T, W198V, W198Y, G199*, G199A, G199D, G199E, G199F, G199H, G199I, G199K, G199L, G199M, G199N, G199P, G199Q, G199R, G199S, G199T, G199V, G199W, G199Y, F200*, F200A, F200D, F200E, F200G, F200H, F200I, F200K, F200L, F200M, F200N, F200P, F200Q, F200R, F200S, F200T, F200V, F200W, F200Y, D201*, D201A, D201E, D201F, D201G, D201H, D201I, D201K, D201L, D201M, D201N, D201P, D201Q, D201R, D201S, D201T, D201V, D201W, D201Y, P202*, P202A, P202D, P202E, P202F, P202G, P202H, P202I, P202K, P202L, P202M, P202N, P202Q, P202R, P202S, P202T, P202V, P202W, P202Y, A203*, A203D, A203E, A203F, A203G, A203H, A203I, A203K, A203L, A203M, A203N, A203P, A203Q, A203R, A203S, A203T, A203V, A203W, A203Y, K204*, K204A, K204D, K204E, K204F, K204G, K204H, K204I, K204L, K204M, K204N, K204P, K204Q, K204R, K204S, K204T, K204V, K204W, K204Y, W205*, W205A, W205D, W205E, W205F, W205G, W205H, W205I, W205K, W205L, W205M, W205N, W205P, W205Q, W205R, W205S, W205T, W205V, W205Y, A206*, A206D, A206E, A206F, A206G, A206H, A206I, A206K, A206L, A206M, A206N, A206P, A206Q, A206R, A206S, A206T, A206V, A206W, A206Y, Y207*, Y207A, Y207D, Y207E, Y207F, Y207G, Y207H, Y207I, Y207K, Y207L, Y207M, Y207N, Y207P, Y207Q, Y207R, Y207S, Y207T, Y207V, Y207W, Q208*, Q208A, Q208D, Q208E, Q208F, Q208G, Q208H, Q208I, Q208K, Q208L, Q208M, Q208N, Q208P, Q208R, Q208S, Q208T, Q208V, Q208W, Q208Y, Y209*, Y209A, Y209D, Y209E, Y209F, Y209G, Y209H, Y209I, Y209K, Y209L, Y209M, Y209N, Y209P, Y209Q, Y209R, Y209S, Y209T, Y209V, Y209W, D210*, D210A, D210E, D210F, D210G, D210H, D210I, D210K, D210L, D210M, D210N, D210P, D210Q, D210R, D210S, D210T, D210V, D210W, D210Y, E211*, E211A, E211D, E211F, E211G, E211H, E211I, E211K, E211L, E211M, E211N, E211P, E211Q, E211R, E211S, E211T, E211V, E211W, E211Y, K212*, K212A, K212D, K212E, K212F, K212G, K212H, K212I, K212L, K212M, K212N, K212P, K212Q, K212R, K212S, K212T, K212V, K212W, K212Y, N213*, N213A, N213D, N213E, N213F, N213G, N213H, N213I, N213K, N213L, N213M, N213P, N213Q, N213R, N213S, N213T, N213V, N213W, N213Y, N214*, N214A, N214D, N214E, N214F, N214G, N214H, N214I, N214K, N214L, N214M, N214P, N214Q, N214R, N214S, N214T, N214V, N214W, N214Y, K215*, K215A, K215D, K215E, K215F, K215G, K215H, K215I, K215L, K215M, K215N, K215P, K215Q, K215R, K215S, K215T, K215V, K215W, K215Y, F216*, F216A, F216D, F216E, F216G, F216H, F216I, F216K, F216L, F216M, F216N, F216P, F216Q, F216R, F216S, F216T, F216V, F216W, F216Y, N217*, N217A, N217D, N217E, N217F, N217G, N217H, N217I, N217K, N217L, N217M, N217P, N217Q, N217R, N217S, N217T, N217V, N217W, N217Y, Y218*, Y218A, Y218D, Y218E, Y218F, Y218G, Y218H, Y218I, Y218K, Y218L, Y218M, Y218N, Y218P, Y218Q, Y218R, Y218S, Y218T, Y218V, Y218W, V219*, V219A, V219D, V219E, V219F, V219G, V219H, V219I, V219K, V219L, V219M, V219N, V219P, V219Q, V219R, V219S, V219T, V219W, V219Y, G220*, G220A, G220D, G220E, G220F, G220H, G220I, G220K, G220L, G220M, G220N, G220P, G220Q, G220R, G220S, G220T, G220V, G220W, G220Y, K221*, K221A, K221D, K221E, K221F, K221G, K221H, K221I, K221L, K221M, K221N, K221P, K221Q, K221R, K221S, K221T, K221V, K221W or K221Y, wherein the variant has an amino acid sequence which is at least 60%, at least 70%, at least 75%, at least 80%, at least 85%, at least 90% or at least 95% identical to SEQ ID NO: 1.

The present invention also relates to isolated polynucleotides encoding the variants; nucleic acid constructs, vectors, and host cells comprising the polynucleotides; and methods of producing the variants. The invention further relates to detergent compositions comprising such variants.

Definitions

DNase (deoxyribonuclease): The term "DNase" means a polypeptide with DNase activity that catalyzes the hydrolytic cleavage of phosphodiester linkages in DNA, thus degrading DNA. DNases belong to the esterases (EC-number 3.1), a subgroup of the hydrolases. The DNases are classified EC 3.1.21.1. For purposes of the present invention, DNase activity is determined according to the procedure described in the Assay I. In one aspect, the DNase variants of the present invention have improved DNase activity compared to the parent DNase. In one aspect, the DNase variants of the present invention have at least 100%, e.g., at least 110%, at least 120%, at least 130%, at least 140%, at least 150%, at least 160%, at least 170%, at least 180%, at least 190%, or at least 200% DNase activity compared to the polypeptide with SEQ ID NO: 1.

The term "parent": the term parent means any polypeptide with DNase activity to which an alteration is made to produce the DNase variants of the invention. Thus a DNase parent or precursor DNase means a DNase in which an alteration is made to produce the DNase variants of the present invention. The terms parent and precursor may be used interchangeably in the present application. Thus, the parent is a DNase having the identical amino acid sequence of the variant but not having the alterations at one or more of the specified positions. It will be understood, that in the present context the expression "having identical amino acid sequence" relates to 100% sequence identity. In a particular embodiment the DNase parent is a DNase with at least 60%, at least 61%, at least 62%, at least 63%, at least 64%, at least 65%, at least 66%, at least 67%, at least 68%, at least 69%, at least 70%, at least 72%, at least 73%, at least 74%, at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6 or 100% identity to a polypeptide with SEQ ID NO: 1.

The term "DNase variant" means a DNase having DNase activity and which comprises an alteration, i.e., a substitution, insertion, and/or deletion at one or more (or one or several) positions compared to its parent e.g. compared to SEQ ID NO: 1. A substitution means a replacement of an amino acid occupying a position with a different amino acid; a deletion means removal of an amino acid occupying a position; and an insertion means adding amino acids e.g. 1 to 10 amino acids, preferably 1-3 amino acids adjacent to an amino acid occupying a position. Preferably, the variant is modified by the hand of man. In one aspect, the variant is at least 1% pure, e.g., at least 5% pure, at least 10% pure, at least 20% pure, at least 40% pure, at least 60% pure, at least 80% pure, and at least 90% pure, as determined by SDS PAGE.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "isolated polynucleotide" means a polynucleotide that is modified by the hand of man. In one aspect, the isolated polynucleotide is at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

The term "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the variant is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The variants of the present invention are preferably in a substantially pure form. This can be accomplished, for example, by preparing the variant by well-known recombinant methods or by classical purification methods.

The term "wild-type DNase" means a DNase expressed by a naturally occurring organism, such as a fungal, bacterium, archaea, yeast, plant or animal found in nature.

The term "mature polypeptide" means a polypeptide in its final form following translation and any post-translational modifications, such as N-terminal processing, C-terminal truncation, glycosylation, phosphorylation, etc. In one aspect, the mature polypeptide corresponds to the amino acid sequence with SEQ ID NO: 1.

The term "mature polypeptide coding sequence" means a polynucleotide that encodes a mature polypeptide having DNase activity.

The term "cDNA" means a DNA molecule that can be prepared by reverse transcription from a mature, spliced, mRNA molecule obtained from a prokaryotic or eukaryotic cell. A cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

The term "operably linked" means a configuration in which a control sequence is placed at an appropriate position relative to the coding sequence of a polynucleotide such that the control sequence directs the expression of the coding sequence.

The term "control sequences" means all components necessary for the expression of a polynucleotide encoding a variant of the present invention. Each control sequence may be native or foreign to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

The term "expression" includes any step involved in the production of the variant including, but not limited to, transcription, post-transcriptional modification, translation, post-translational modification, and secretion.

The term "expression vector" means a linear or circular DNA molecule that comprises a polynucleotide encoding a variant and is operably linked to additional nucleotides that provide for its expression.

The term "transcription promoter" is used for a promoter which is a region of DNA that facilitates the transcription of a particular gene. Transcription promoters are typically located near the genes they regulate, on the same strand and upstream (towards the 5' region of the sense strand).

The term "transcription terminator" is used for a section of the genetic sequence that marks the end of gene or operon on genomic DNA for transcription.

The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "improved property" means a characteristic associated with a variant that is improved compared to the parent and/or compared to a DNase with SEQ ID NO: 1, or compared to a DNase having the identical amino acid sequence of said variant but not having the alterations at one or more of said specified positions. Such improved properties include, but are not limited to, stability, such as detergent stability, wash performance e.g. deep cleaning effect, the term "deep cleaning" is meant disruption or removal of a biofilm or components of a biofilm such as polysaccharides, proteins, DNA, soil or other components present in the biofilm.

A biofilm is any group of microorganisms in which cells stick to each other on a surface, such as a textile, dishware or hard surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from free-floating bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community. On laundry biofilm producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas* sp.

The term "improved DNase activity" is defined herein as an altered DNase activity e.g. by increased catalyse of hydrolytic cleavage of phosphodiester linkages in the DNA the DNase variant displaying an alteration of the activity relative (or compared) to the activity of the parent DNase, such as compared to a DNase with SEQ ID NO: 1.

The term "stability" includes storage stability and stability during use, e.g. during a wash process and reflects the stability of the DNase variant according to the invention as a function of time e.g. how much activity is retained when the DNase variant is kept in solution in particular in a detergent solution. The stability is influenced by many factors e.g. pH, temperature, detergent composition e.g. amount of builder, surfactants etc. The DNase stability may be measured as described in example 2. The term "improved stability" or "increased stability" is defined herein as a variant DNase displaying an increased stability in solutions, relative to the stability of the parent DNase and/or relative to SEQ ID NO: 1. "Improved stability" and "increased stability" includes detergent stability. The term "detergent stability" or "improved detergent stability may be improved stability of the DNase activity compared to the DNase parent. The DNase stability is measured as described in example 2.

The term "improved wash performance" may be defined as improved deep cleaning effect i.e. the disruption or removal of a biofilm or components of a DNase variant according to the invention compared to the DNase parent or the DNase with SEQ ID NO: 1. The DNase variants may also have improved malodor removal. By the term "malodor" is meant an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items for example curry or other exotic spices which smells strongly. One way of measuring the ability of an item to adhere malodor is by using Assay II disclosed herein.

Wash performance may be expressed as a Remission value of the stained swatches. After washing and rinsing the swatches are spread out flat and allowed to air dry at room temperature overnight. All washed swatches are evaluated the day after the wash. Light reflectance evaluations of the swatches are done using a Macbeth Color Eye 7000 reflectance spectrophotometer with very small aperture. The measurements are made without UV in the incident light and remission at 460 nm was extracted.

The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

The term "detergent composition", includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, soap bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types. The terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. The term "detergent composition" is not intended to be limited to compositions that contain surfactants. It is intended that in addition to the variants according to the invention, the term encompasses detergents that may contain, e.g., surfactants, builders, chelators or chelating agents, bleach system or bleach components, polymers, fabric conditioners, foam boosters, suds suppressors, dyes, perfume, tarnish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "fabric" encompasses any textile material. Thus, it is intended that the term encompass garments, as well as fabrics, yarns, fibers, non-woven materials, natural materials, synthetic materials, and any other textile material.

The term "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers. The term, "textile materials" is a general term for fibers, yarn intermediates, yarn, fabrics, and products made from fabrics (e.g., garments and other articles).

The term "non-fabric detergent compositions" include non-textile surface detergent compositions, including but not limited to compositions for hard surface cleaning, such as dishwashing detergent compositions including manual dish wash compositions, oral detergent compositions, denture detergent compositions, and personal cleansing compositions.

The term "effective amount of enzyme" refers to the quantity of enzyme necessary to achieve the enzymatic activity required in the specific application, e.g., in a defined detergent composition. Such effective amounts are readily ascertained by one of ordinary skill in the art and are based on many factors, such as the particular enzyme used, the cleaning application, the specific composition of the detergent composition, and whether a liquid or dry (e.g., granular, bar) composition is required, and the like. The term "effective amount" of a DNase variant refers to the quantity of DNase variant described hereinbefore that achieves a desired level of enzymatic activity, e.g., in a defined detergent composition.

The term "water hardness" or "degree of hardness" or "dH" or "° dH" as used herein refers to German degrees of hardness. One degree is defined as 10 milligrams of calcium oxide per liter of water.

The term "relevant washing conditions" is used herein to indicate the conditions, particularly washing temperature, time, washing mechanics, detergent concentration, type of detergent and water hardness, actually used in households in a detergent market segment.

The term "adjunct materials" means any liquid, solid or gaseous material selected for the particular type of detergent composition desired and the form of the product (e.g., liquid, granule, powder, bar, paste, spray, tablet, gel, or foam composition), which materials are also preferably compatible with the DNase variant enzyme used in the composition. In some embodiments, granular compositions are in "compact" form, while in other embodiments, the liquid compositions are in a "concentrated" form.

The term "low detergent concentration" system includes detergents where less than about 800 ppm of detergent components is present in the wash water. Asian, e.g., Japanese detergents are typically considered low detergent concentration systems.

The term "medium detergent concentration" system includes detergents wherein between about 800 ppm and about 2000 ppm of detergent components is present in the wash water. North American detergents are generally considered to be medium detergent concentration systems.

The term "high detergent concentration" system includes detergents wherein greater than about 2000 ppm of detergent components is present in the wash water. European detergents are generally considered to be high detergent concentration systems.

Conventions for Designation of Variants

For purposes of the present invention, the mature polypeptide disclosed in SEQ ID NO: 1 is used to determine the corresponding amino acid residue in another DNase. The amino acid sequence of another DNase is aligned with the polypeptide disclosed in SEQ ID NO: 1, and based on the alignment, the amino acid position number corresponding to any amino acid residue in the polypeptide disclosed in SEQ ID NO: 1 is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another DNase can be determined by an alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, Nucleic Acids Research 30: 3059-3066; Katoh et al., 2005, Nucleic Acids Research 33: 511-518; Katoh and Toh, 2007, Bioinformatics 23: 372-374; Katoh et al., 2009, Methods in Molecular Biology 537: 39-64; Katoh and Toh, 2010, Bioinformatics 26: 1899-1900), and EMBOSS EMMA employing ClustalW (1.83 or later; Thompson et al., 1994, Nucleic Acids Research 22: 4673-4680), using their respective default parameters.

When the other enzyme has diverged from the polypeptide of SEQ ID NO: 1 such that traditional sequence-based comparison fails to detect their relationship (Lindahl and Elofsson, 2000, J. Mol. Biol. 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, Nucleic Acids Res. 25: 3389-3402). Even greater sensitivity can be achieved if the family or superfamily for the polypeptide has one or more representatives in the protein structure databases. Programs such as GenTHREADER (Jones, 1999, J. Mol. Biol. 287: 797-815; McGuffin and Jones, 2003, Bioinformatics 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, J. Mol. Biol. 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example, the SCOP super families of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, Protein Engineering 11: 739-747), and implementation of these algorithms can additionally be utilized to query structure databases with a structure of interest in order to discover possible structural homologs (e.g., Holm and Park, 2000, Bioinformatics 16: 566-567).

In describing the variants of the present invention, the nomenclature described below is adapted for ease of reference. The accepted IUPAC single letter or three letters amino acid abbreviations are employed. Amino acid positions are indicated with $\#_1$, $\#_2$, etc.

Substitutions:

For an amino acid substitution, the following nomenclature is used: Original amino acid, position, substituted amino acid. Accordingly, the substitution of valine at position $\#_1$ with alanine is designated as "Val$\#_1$Ala" or "V$\#_1$A". Multiple mutations are separated by addition marks ("+") or by commas (,), e.g., "Val$\#_1$Ala+Pro$\#_2$Gly" or V$\#_1$A, P$\#_2$G, representing substitutions at positions $\#_1$ and $\#_2$ of valine (V) and proline with alanine (A) and glycine (G), respectively. If more than one amino acid may be substituted in a given position these are listed in brackets, such as [X] or {X} or alternatively separated by commas. Thus if both Trp and Lys according to the invention may be substituted instead of the amino acid occupying at position $\#_1$ this is indicated as X$\#_1${W, K}, X$\#_1$[W, K] or X$\#_1$ W, K; where the X indicate the amino acid residues of different DNases which according to the invention may be the parent DNase e.g. such as a DNase with SEQ ID NO: 1 or a DNase having at least 60% identity hereto. Thus in some cases the variants are represented as $\#_1${W,K} or X$\#_2$P indicating that the amino acids to be substituted vary depending on the parent. For convenience as SEQ ID NO: 1 is used for numbering the substitutions the amino acid in the corresponding position in SEQ ID NO: 1 is indicated e.g. VIA. However, it will be clear to the skilled artisan that a DNase variant comprising VIA is not limited to parent DNases having valine at a position corresponding to position 1 of SEQ ID NO: 1. In a parent DNase having e.g. asparagine in position 1, the skilled person would translate the mutation specification VIA to NIA. In the event the parent DNase has alanine in position 1, the skilled person would recognize that the parent DNase is not changed at this position.

Deletions:

For an amino acid deletion, the following nomenclature is used: Original amino acid, position, *. Accordingly, the deletion of serine at position $\#_1$ is designated as "Ser$\#_1$*" or "S$\#_1$*". Multiple deletions are separated by addition marks ("+") or commas, e.g., "Val$\#_1$*+Pro$\#_2$*" or "V$\#_1$*, P$\#_2$*".

Insertions:

The insertion of an additional amino acid residue such as e.g. a lysine after Val$\#_1$ may be indicated by: Val$\#_1$ValLys or V$\#_1$VK. Alternatively insertion of an additional amino acid residue such as lysine after V$\#_1$ may be indicated by: *$\#_1$aK. When more than one amino acid residue is inserted, such as e.g. a Lys, and Gly after $\#_1$ this may be indicated as: Ala$\#_1$AlaLysGly or A$\#_1$AKG. In such cases, the inserted amino acid residue(s) may also be numbered by the addition of lower case letters to the position number of the amino acid residue preceding the inserted amino acid residue(s), in this example: *$\#_1$aK*$\#_1$bG.

Multiple Alterations:

Variants comprising multiple alterations are separated by addition marks ("+") or by commas (,), e.g., "Val$\#_1$Trp+Pro$\#_2$Gly" or "V$\#_1$W, P$\#_2$G" representing a substitution of valine and proline at positions #$_1$ and #$_2$ with tryptophan and glycine, respectively as described above.

Different Alterations:

Where different alterations can be introduced at a position, the different alterations are separated by a comma, e.g., "Val#$_1$Trp, Lys" or V#$_1$W, K represents a substitution of valine at position #$_1$ with tryptophan or lysine. Thus, "Val#$_1$Trp, Lys+Pro#$_2$Asp" designates the following variants: "Val#$_1$Trp+Pro#$_2$Asp", "Val#$_1$Lys+Pro#$_2$Asp" or V#$_1$W, K+P#$_2$D.

DETAILED DESCRIPTION OF THE INVENTION

The present invention provides novel DNases obtained from *Aspergillus*, in particular, *Aspergillus oryzae*. The DNases of the invention comprise at least 60% sequence identity to a polypeptide with SEQ ID NO: 1 and comprise an alteration of at least one amino acid position compared to the DNase with SEQ ID NO: 1. In one embodiment, the DNase variants have an amino acid sequence comprising at least one substitution of an amino acid made at a position equivalent to a position in SEQ ID NO: 1. In one embodiment, the DNase variants have an amino acid sequence comprising at least one deletion of an amino acid made at a position equivalent to a position in SEQ ID NO: 1. In one embodiment, the DNase variants have an amino acid sequence comprising at least one insertion of an amino acid made at a position equivalent to a position in SEQ ID NO: 1. The present invention also relates to methods for of generating DNase variants. The invention further relates to a screening process comprising the steps of a) providing a mutant nucleic acid or variant polypeptide therefrom, b) determine a property of interest in the mutant nucleic acid or variant polypeptide and c) comparing the this property to the same property of parent nucleic acid or polypeptide (i.e. the nucleic acid or polypeptide not having the said specific alterations). It will be apparent to skilled artisan that the screening process is not limited to any specific property as it depends upon the property determined to be screened for. A particular preferred screenings method is the high-throughput screening, including multiple samples being screened simultaneously. Examples of properties which may be screened for includes wash performance, such as deep-cleaning performance, malodor reduction, high or low pH performance, improved low temperature performance, stability such as stability in detergent and/or storage stability. It is not intended that the present invention be limited to any particular method of variant generation or screening. Preferably the DNases of the present invention have at least one improved property compared to the parent DNase e.g. compared to SEQ ID NO: 1. Properties includes but are not limited to stability in detergent including storage, in wash and thermo stability, wash performance in particular deep-cleaning performance, increased expression level or malodor reduction.

Embodiments of the invention relates to DNase variants of SEQ ID NO: 1 or variants of a DNase having at least 60% identity hereto and to methods for generating a DNase variant of SEQ ID NO: 1 or a DNase having at least 60% identity hereto.

One embodiment relates to DNase variants having at least 60% identity to SEQ ID NO: 1, having DNase activity and comprise an alteration at one or more positions selected from the list consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 185, 186, 187, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 and 221, wherein each position corresponds to the position of the polypeptide of SEQ ID NO: 1. The alteration is independently a substitution, insertion or deletion. In an embodiment, the alteration is a substitution. In another embodiment, the alteration is a deletion.

One embodiment of the invention relates to a DNase variant comprising a substitution at one or more positions selected from the group consisting of 4, 17, 19, 19, 19, 36, 38, 39, 39, 40, 40, 41, 41, 45, 51, 53, 53, 54, 55, 57, 64, 64, 64, 64, 64, 64, 66, 67, 67, 68, 68, 68, 68, 68, 69, 69, 69, 69, 69, 69, 69, 69, 70, 70, 70, 71, 72, 74, 74, 75, 77, 82, 82, 83, 83, 83, 83, 83, 84, 85, 85, 85, 86, 86, 86, 88, 88, 91, 99, 101, 105, 105, 105, 105, 106, 115, 116, 135, 136, 138, 138, 138, 138, 139, 140, 140, 140, 141, 151, 152, 152, 152, 152, 153, 154, 162, 163, 164, 166, 166, 168, 169, 169, 173, 173, 173, 182, 183, 184, 185, 186, 189, 189, 212, 212 and 215, wherein each position corresponds to the position of the polypeptide of SEQ ID NO: 1.

In some embodiment, the DNase variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent DNase.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide shown in SEQ ID NO: 1.

The percent sequence identity is determined using the using the Needleman-Wunsch algorithm (Needleman and Wunsch, 1970, J. Mol. Biol. 48: 443-453) as described in "Conventions for Designation of Variants".

The invention further relates to variants of a DNase parent comprising SEQ ID NO: 1 wherein said variant comprises an alteration compared to SEQ ID NO: 1 in at least one position selected from the positions: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 185, 186, 187, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 and 221 corresponding to the positions of SEQ ID NO: 1, wherein the variant has an amino acid sequence which is at least 60%, at least 70%, at least 80%, at least 90% or at least 95% identical to SEQ ID NO: 1.

The invention further relates to variants of a DNase parent comprising SEQ ID NO: 1 wherein said variant comprises an alteration compared to SEQ ID NO: 1 in at least one position selected from the positions: 4, 17, 19, 19, 19, 36, 38, 39, 39, 40, 40, 41, 41, 45, 51, 53, 53, 54, 55, 57, 64, 64, 64, 64, 64, 64, 66, 67, 67, 68, 68, 68, 68, 69, 69, 69, 69, 69, 69, 69, 69, 70, 70, 70, 71, 72, 74, 74, 75, 77, 82, 82, 83, 83, 83, 83, 83, 84, 85, 85, 85, 86, 86, 86, 88, 88, 91, 99, 101, 105, 105, 105, 105, 106, 115, 116, 135, 136, 138, 138, 138, 138, 139, 140, 140, 140, 141, 151, 152, 152, 152, 153, 154, 162, 163, 164, 166, 166, 168, 169, 169, 173, 173, 173, 182, 183, 184, 185, 186, 189, 189, 212, 212 and 215, corresponding to the positions of SEQ ID NO: 1, wherein the variant has an amino acid sequence which is at least 60%, at least 70%, at least 80%, at least 90% or at least 95% identical to SEQ ID NO: 1.

The alteration is independently a substitution, insertion or deletion. In an embodiment, the alteration is a substitution. In another embodiment, the alteration is a deletion. In one aspect, the number of alterations in the variants of the present invention is 1-20, e.g., 1-10 and 1-5, such as 1, 2, 3, 4, 5, 6, 7, 8, 9 or 10 alterations.

In some preferred embodiments, the DNase variants have at least 60%, such as at least 70%, such as at least 80% such as at least 90% but less than 100% sequence identity to SEQ ID NO: 1, have DNase activity and comprises one or more alterations selected from the group consisting of: V1*, V1A, V1D, V1E, V1F, V1G, V1H, V1I, V1K, V1L, V1M, V1N, V1P, V1Q, V1R, V1S, V1T, V1W, V1Y, P2*, P2A, P2D, P2E, P2F, P2G, P2H, P2I, P2K, P2L, P2M, P2N, P2Q, P2R, P2S, P2T, P2V, P2W, P2Y, V3*, V3A, V3C, V3D, V3E, V3F, V3G, V3H, V3I, V3K, V3L, V3M, V3N, V3P, V3R, V3S, V3T, V3W, V3Y, N4*, N4A, N4D, N4E, N4F, N4G, N4H, N4I, N4K, N4L, N4M, N4P, N4Q, N4R, N4S, N4T, N4V, N4W, N4Y, P5*, P5A, P5D, P5E, P5F, P5G, P5H, P5I, P5K, P5L, P5M, P5N, P5Q, P5R, P5S, P5T, P5V, P5W, P5Y, E6*, E6A, E6D, E6F, E6G, E6H, E6I, E6K, E6L, E6M, E6N, E6P, E6Q, E6R, E6S, E6T, E6V, E6W, E6Y, P7*, P7A, P7D, P7E, P7F, P7G, P7H, P7I, P7K, P7L, P7M, P7N, P7Q, P7R, P7S, P7T, P7V, P7W, P7Y, D8*, D8A, D8E, D8F, D8G, D8H, D8I, D8K, D8L, D8M, D8N, D8P, D8Q, D8R, D8S, D8T, D8V, D8W, D8Y, A9*, A9D, A9E, A9F, A9G, A9H, A9I, A9K, A9L, A9M, A9N, A9P, A9Q, A9R, A9S, A9T, A9V, A9W, A9Y, T10*, T10A, T10D, T10E, T10F, T10G, T10H, T10I, T10K, T10L, T10M, T10N, T10P, T10Q, T10R, T10S, T10V, T10W, T10Y, S11*, S11A, S11D, S11E, S11F, S11G, S11H, S11I, S11K, S11L, S11M, S11N, S11P, S11Q, S11R, S11T, S11V, S11W, S11Y, V12*, V12A, V12D, V12E, V12F, V12G, V12H, V12I, V12K, V12L, V12M, V12N, V12P, V12Q, V12R, V12S, V12T, V12W, V12Y, E13*, E13A, E13D, E13F, E13G, E13H, E13I, E13K, E13L, E13M, E13N, E13P, E13Q, E13R, E13S, E13T, E13V, E13W, E13Y, N14*, N14A, N14D, N14E, N14F, N14G, N14H, N14I, N14K, N14L, N14M, N14P, N14Q, N14R, N14S, N14T, N14V, N14W, N14Y, V15*, V15A, V15D, V15E, V15F, V15G, V15H, V15I, V15K, V15L, V15M, V15N, V15P, V15Q, V15R, V15S, V15T, V15W, V15Y, A16*, A16D, A16E, A16F, A16G, A16H, A16I, A16K, A16L, A16M, A16N, A16P, A16Q, A16R, A16S, A16T, A16V, A16W, A16Y, L17*, L17A, L17D, L17E, L17F, L17G, L17H, L17I, L17K, L17M, L17N, L17P, L17Q, L17R, L17S, L17T, L17V, L17W, L17Y, K18*, K18A, K18D, K18E, K18F, K18G, K18H, K18I, K18L, K18M, K18N, K18P, K18Q, K18R, K18S, K18T, K18V, K18W, K18Y, T19*, T19A, T19D, T19E, T19F, T19G, T19H, T19I, T19K, T19L, T19M, T19N, T19P, T19Q, T19R, T19S, T19V, T19W, T19Y, G20*, G20A, G20D, G20E, G20F, G20H, G20I, G20K, G20L, G20M, G20N, G20P, G20Q, G20R, G20S, G20T, G20V, G20W, G20Y, S21*, S21A, S21D, S21E, S21F, S21G, S21H, S21I, S21K, S21L, S21M, S21N, S21P, S21Q, S21R, S21T, S21V, S21W, S21Y, G22*, G22A, G22D, G22E, G22F, G22H, G22I, G22K, G22L, G22M, G22N, G22P, G22Q, G22R, G22S, G22T, G22V, G22W, G22Y, D23*, D23A, D23E, D23F, D23G, D23H, D23I, D23K, D23L, D23M, D23N, D23P, D23Q, D23R, D23S, D23T, D23V, D23W, D23Y, S24*, S24A, S24D, S24E, S24F, S24G, S24H, S24I, S24K, S24L, S24M, S24N, S24P, S24Q, S24R, S24T, S24V, S24W, S24Y, Q25*, Q25A, Q25D, Q25E, Q25F, Q25G, Q25H, Q25I, Q25K, Q25L, Q25M, Q25N, Q25P, Q25R, Q25S, Q25T, Q25V, Q25W, Q25Y, S26*, S26A, S26D, S26E, S26F, S26G, S26H, S26I, S26K, S26L, S26M, S26N, S26P, S26Q, S26R, S26T, S26V, S26W, S26Y, D27*, D27A, D27E, D27F, D27G, D27H, D27I, D27K, D27L, D27M, D27N, D27P, D27Q, D27R, D27S, D27T, D27V, D27W, D27Y, P28*, P28A, P28D, P28E, P28F, P28G, P28H, P28I, P28K, P28L, P28M, P28N, P28Q, P28R, P28S, P28T, P28V, P28W, P28Y, I29*, I29A, I29D, I29E, I29F, I29G, I29H, I29K, I29L, I29M, I29N, I29P, I29Q, I29R, I29S, I29T, I29V, I29W, I29Y, K30*, K30A, K30D, K30E, K30F, K30G, K30H, K30I, K30L, K30M, K30N, K30P, K30Q, K30R, K30S, K30T, K30V, K30W, K30Y, A31*, A31D, A31E, A31F, A31G, A31H, A31I, A31K, A31L, A31M, A31N, A31P, A31Q, A31R, A31S, A31T, A31V, A31W, A31Y, D32*, D32A, D32E, D32F, D32G, D32H, D32I, D32K, D32L, D32M, D32N, D32P, D32Q, D32R, D32S, D32T, D32V, D32W, D32Y, L33*, L33A, L33D, L33E, L33F, L33G, L33H, L33I, L33K, L33M, L33N, L33P, L33Q, L33R, L33S, L33T, L33V, L33W, L33Y, E34*, E34A, E34D, E34F, E34G, E34H, E34I, E34K, E34L, E34M, E34N, E34P, E34Q, E34R, E34S, E34T, E34V, E34W, E34Y, V35*, V35A, V35D, V35E, V35F, V35G, V35H, V35I, V35K, V35L, V35M, V35N, V35P, V35Q, V35R, V35S, V35T, V35W, V35Y, K36*, K36A, K36D, K36E, K36F, K36G, K36H, K36I, K36L, K36M, K36N, K36P, K36Q, K36R, K36S, K36T, K36V, K36W, K36Y, G37*, G37A, G37D, G37E, G37F, G37H, G37I, G37K, G37L, G37M, G37N, G37P, G37Q, G37R, G37S, G37T, G37V, G37W, G37Y, Q38*, Q38A, Q38D, Q38E, Q38F, Q38G, Q38H, Q38I, Q38K, Q38L, Q38M, Q38N, Q38P, Q38R, Q38S, Q38T, Q38V, Q38W, Q38Y, S39*, S39A, S39D, S39E, S39F, S39G, S39H, S39I, S39K, S39L, S39M, S39N, S39P, S39Q, S39R, S39T, S39V, S39W, S39Y, A40*, A40D, A40E, A40F, A40G, A40H, A40I, A40K, A40L, A40M, A40N, A40P, A40Q, A40R, A40S, A40T, A40V, A40W, A40Y, L41*, L41A, L41D, L41E, L41F, L41G, L41H, L41I, L41K, L41M, L41N, L41P, L41Q, L41R, L41S, L41T, L41V, L41W, L41Y, P42*, P42A, P42D, P42E, P42F, P42G, P42H, P42I, P42K, P42L, P42M, P42N, P42Q, P42R, P42S, P42T, P42V, P42W, P42Y, F43*, F43A, F43D, F43E, F43G, F43H, F43I, F43K, F43L, F43M, F43N, F43P, F43Q, F43R, F43S, F43T, F43V, F43W, F43Y, D44*, D44A, D44E, D44F, D44G, D44H, D44I, D44K, D44L, D44M, D44N, D44P, D44Q, D44R, D44S, D44T, D44V, D44W, D44Y, V45*, V45A, V45D, V45E, V45F, V45G, V45H, V45I, V45K, V45L, V45M, V45N, V45P, V45Q, V45R, V45S, V45T, V45W, V45Y, D46*, D46A, D46E, D46F, D46G, D46H, D46I, D46K, D46L, D46M, D46N, D46P, D46Q, D46R, D46S, D46T, D46V, D46W, D46Y, C47A, C47D, C47E, C47F, C47G, C47H, D47I, C47K, C47L, C47M, C47N, C47P, C47Q, C47R, C47S, C47T, O47V, C47W, C47Y, W48*, W48A, W48D, W48E, W48F, W48G, W48H, W48I, W48K, W48L, W48M, W48N, W48P, W48Q, W48R, W48S, W48T, W48V, W48Y, A49*, A49D, A49E, A49F, A49G, A49H, A49I, A49K, A49L, A49M, A49N, A49P, A49Q, A49R, A49S, A49T, A49V, A49W, A49Y, I50*, I50A, I50D, I50E, I50F, I50G, I50H, I50K, I50L, I50M, I50N, I50P, I50Q, I50R, I50S, I50T, I50V, I50W, I50Y, L51*, L51A, L51D, L51E, L51F, L51G, L51H, L51I, L51K, L51M, L51N, L51P, L51Q, L51R, L51S, L51T, L51V, L51W, L51Y, K53*, K53A, K53D, K53E, K53F, K53G, K53H, K53I, K53L, K53M, K53N, K53P, K53Q, K53R, K53S, K53T, K53V, K53W, K53Y, G54*, G54A, G54D, G54E, G54F, G54H, G54I, G54K, G54L, G54M, G54N, G54P, G54Q, G54R, G54S, G54T, G54V, G54W, G54Y, A55*, A55D, A55E, A55F, A55G, A55H, A55I, A55K, A55L, A55M, A55N, A55P, A55Q, A55R, A55S, A55T, A55V, A55W, A55Y, P56*, P56A, P56D, P56E, P56F, P56G, P56H, P56I, P56K, P56L, P56M, P56N, P56Q, P56R, P56S, P56T, P56V, P56W, P56Y, N57*, N57A, N57D, N57E, N57F, N57G, N57H, N57I, N57K, N57L, N57M, N57P, N57Q, N57R, N57S, N57T, N57V, N57W, N57Y, V58*, V58A, V58D, V58E, V58F, V58G, V58H, V58I, V58K, V58L, V58M, V58N, V58P, V58Q, V58R, V58S, V58T, V58W, V58YL59*, L59A, L59D, L59E, L59F, L59G, L59H, L59I, L59K, L59M, L59N, L59P, L59Q, L59R, L59S, L59T, L59V, L59W, L59Y, Q60*, Q60A, Q60D, Q60E, Q60F, Q60G, Q60H, Q60I, Q60K, Q60L, Q60M, Q60N, Q60P, Q60R, Q60S, Q60T, Q60V, Q60W, Q60Y, R61*, R61A, R61D, R61E, R61F, R61G, R61H, R61I, R61K, R61L, R61M, R61N, R61P, R61Q, R61S, R61T, R61V, R61W, R61Y, V62*, V62A, V62D, V62E, V62F, V62G, V62H, V62I, V62K, V62L, V62M, V62N, V62P, V62Q, V62R, V62S, V62T, V62W, V62Y, N63*, N63A, N63D, N63E, N63F, N63G, N63H, N63I, N63K, N63L, N63M, N63P, N63Q, N63R, N63S, N63T, N63V, N63W, N63Y, E64*, E64A, E64D, E64F, E64G, E64H, E64I, E64K, E64L, E64M, E64N, E64P, E64Q, E64R, E64S, E64T, E64V, E64W, E64Y, K65*, K65A, K65D, K65E, K65F, K65G, K65H, K65I, K65L, K65M, K65N, K65P, K65Q, K65R, K65S, K65T, K65V, K65W, K65Y, T66*, T66A, T66D, T66E, T66F, T66G, T66H, T66I, T66K, T66L, T66M, T66N, T66P, T66Q, T66R, T66S, T66V, T66W, T66Y, K67*, K67A, K67D, K67E, K67F, K67G, K67H, K67I, K67L, K67M, K67N, K67P, K67Q, K67R, K67S, K67T, K67V, K67W, K67Y, N68*, N68A, N68D, N68E, N68F, N68G, N68H, N68I, N68K, N68L, N68M, N68P, N68Q, N68R, N68S, N68T, N68V, N68W, N68Y, S69*, S69A, S69D, S69E, S69F, S69G, S69H, S69I, S69K, S69L, S69M, S69N, S69P, S69Q, S69R, S69T, S69V, S69W, S69Y, N70*, N70A, N70D, N70E, N70F, N70G, N70H, N70I, N70K, N70L, N70M, N70P, N70Q, N70R, N70S, N70T, N70V, N70W, N70Y, R71*, R71A, R71D, R71E, R71F, R71G, R71H, R71I, R71K, R71L, R71M, R71N, R71P, R71Q, R71S, R71T, R71V, R71W, R71Y, D72*, D72A, D72E, D72F, D72G, D72H, D72I, D72K, D72L, D72M, D72N, D72P, D72Q, D72R, D72S, D72T, D72V, D72W, D72Y, R73*, R73A, R73D, R73E, R73F, R73G, R73H, R73I, R73K, R73L, R73M, R73N, R73P, R73Q, R73S, R73T, R73V, R73W, R73Y, S74*, S74A, S74D, S74E, S74F, S74G, S74H, S74I, S74K, S74L, S74M, S74N, S74P, S74Q, S74R, S74T, S74V, S74W, S74Y, G75*, G75A, G75D, G75E, G75F, G75H, G75I, G75K, G75L, G75M, G75N, G75P, G75Q, G75R, G75S, G75T, G75V, G75W, G75Y, A76*, A76D, A76E, A76F, A76G, A76H, A76I, A76K, A76L, A76M, A76N, A76P, A76Q, A76R, A76S, A76T, A76V, A76W, A76Y, N77*, N77A, N77D, N77E, N77F, N77G, N77H, N77I, N77K, N77L, N77M, N77P, N77Q, N77R, N77S, N77T, N77V, N77W, N77Y, K78*, K78A, K78D, K78E, K78F, K78G, K78H, K78I, K78L, K78M, K78N, K78P, K78Q, K78R, K78S, K78T, K78V, K78W, K78Y, G79*, G79A, G79D, G79E, G79F, G79H, G79I, G79K, G79L, G79M, G79N, G79P, G79Q, G79R, G79S, G79T, G79V, G79W, G79Y, P80*, P80A, P80D, P80E, P80F, P80G, P80H, P80I, P80K, P80L, P80M, P80N, P80Q, P80R, P80S, P80T, P80V, P80W, P80Y, F81*, F81A, F81D, F81E, F81G, F81H, F81I, F81K, F81L, F81M, F81N, F81P, F81Q, F81R, F81S, F81T, F81V, F81W, F81Y, K82*, K82A, K82D, K82E, K82F, K82G, K82H, K82I, K82L, K82M, K82N, K82P, K82Q, K82R, K82S, K82T, K82V, K82W, K82Y, D83*, D83A, D83E, D83F, D83G, D83H, D83I, D83K, D83L, D83M, D83N, D83P, D83Q, D83R, D83S, D83T, D83V, D83W, D83Y, P84*, P84A, P84D, P84E, P84F, P84G, P84H, P84I, P84K, P84L, P84M, P84N, P84Q, P84R, P84S, P84T, P84V, P84W, P84Y, Q85*, Q85A, Q85D, Q85E, Q85F, Q85G, Q85H, Q85I, Q85K, Q85L, Q85M, Q85N, Q85P, Q85R, Q85S, Q85T, Q85V, Q85W, Q85Y, K86*, K86A, K86D, K86E, K86F, K86G, K86H, K86I, K86L, K86M, K86N, K86P, K86Q, K86R, K86S, K86T, K86V, K86W, K86Y, W87*, W87A, W87D, W87E, W87F, W87G, W87H, W87I, W87K, W87L, W87M, W87N, W87P, W87Q, W87R, W87S, W87T, W87V, W87Y, G88*, G88A, G88D, G88E, G88F, G88H, G88I, G88K, G88L, G88M, G88N, G88P, G88Q, G88R, G88S, G88T, G88V, G88W, G88Y, I89*, I89A, I89D, I89E, I89F, I89G, I89H, I89K, I89L, I89M, I89N, I89P, I89Q, I89R, I89S, I89T, I89V, I89W, I89Y, K90*, K90A, K90D, K90E, K90F, K90G, K90H, K90I, K90L, K90M, K90N, K90P, K90Q, K90R, K90S, K90T, K90V, K90W, K90Y, A91*, A91D, A91E, A91F, A91G, A91H, A91I, A91K, A91L, A91M, A91N, A91P, A91Q, A91R, A91S, A91T, A91V, A91W, A91Y, L92*, L92A, L92D, L92E, L92F, L92G, L92H, L92I, L92K, L92M, L92N, L92P, L92Q, L92R, L92S, L92T, L92V, L92W, L92Y, P93*, P93A, P93D, P93E, P93F, P93G, P93H, P93I, P93K, P93L, P93M, P93N, P93Q, P93R, P93S, P93T, P93V, P93W, P93Y, P94*, P94A, P94D, P94E, P94F, P94G, P94H, P94I, P94K, P94L, P94M, P94N, P94Q, P94R, P94S, P94T, P94V, P94W, P94Y, K95*, K95A, K95D, K95E, K95F, K95G, K95H, K95I, K95L, K95M, K95N, K95P, K95Q, K95R, K95S, K95T, K95V, K95W, K95Y, N96*, N96A, N96D, N96E, N96F, N96G, N96H, N96I, N96K, N96L, N96M, N96P, N96Q, N96R, N96S, N96T, N96V, N96W, N96Y, P97*, P97A, P97D, P97E, P97F, P97G, P97H, P97I, P97K, P97L, P97M, P97N, P97Q, P97R, P97S, P97T, P97V, P97W, P97Y, S98*, S98A, S98D, S98E, S98F, S98G, S98H, S98I, S98K, S98L, S98M, S98N, S98P, S98Q, S98R, S98T, S98V, S98W, S98Y, W99*, W99A, W99D, W99E, W99F, W99G, W99H, W99I, W99K, W99L, W99M, W99N, W99P, W99Q, W99R, W99S, W99T, W99V, W99Y, S100*, S100A, S100D, S100E, S100F, S100G, S100H, S100I, S100K, S100L, S100M, S100N, S100P, S100Q, S100R, S100T, S100V, S100W, S100Y, A101*, A101D, A101E, A101F, A101G, A101H, A101I, A101K, A101L, A101M, A101N, A101P, A101Q, A101R, A101S, A101T, A101V, A101W, A101Y, Q102*, Q102A, Q102D, Q102E, Q102F, Q102G, Q102H, Q102I, Q102K, Q102L, Q102M, Q102N, Q102P, Q102R, Q102S, Q102T, Q102V, Q102W, Q102Y, D103*, D103A, D103E, D103F, D103G, D103H, D103I, D103K, D103L, D103M, D103N, D103P, D103Q, D103R, D103S, D103T, D103V, D103W, D103Y, F104*, F104A, F104D, F104E, F104G, F104H, F104I, F104K, F104L, F104M, F104N, F104P, F104Q, F104R, F104S, F104T, F104V, F104W, F104Y, K105*, K105A, K105D, K105E, K105F, K105G, K105H, K105I, K105L, K105M, K105N, K105P, K105Q, K105R, K105S, K105T, K105V, K105W, K105Y, S106*, S106A, S106D, S106E, S106F, S106G, S106H, S106I, S106K, S106L, S106M, S106N, S106P, S106Q, S106R, S106T, S106V, S106W, S106Y, P107*, P107A, P107D, P107E, P107F, P107G, P107H, P107I, P107K, P107L, P107M, P107N, P107Q, P107R, P107S, P107T, P107V, P107W, P107Y, E108*, E108A, E108D, E108F, E108G, E108H, E108I, E108K, E108L, E108M, E108N, E108P, E108Q, E108R, E108S, E108T, E108V, E108W, E108Y, E109*, E109A, E109D, E109F, E109G, E109H, E109I, E109K, E109L, E109M, E109N, E109P, E109Q, E109R, E109S, E109T, E109V, E109W, E109Y, Y110*, Y110A, Y110D, Y110E, Y110F, Y110G, Y110H, Y110I, Y110K, Y110L, Y110M, Y110N, Y110P, Y110Q, Y110R, Y110S, Y110T, Y110V, Y110W, A111*, A111D, A111E, A111F, A111G, A111H, A111I, A111K, A111L, A111M, A111N, A111P, A111Q, A111R, A111S, A111T, A111V, A111W, A111Y, F112*, F112A, F112D, F112E, F112G, F112H, F112I, F112K, F112L, F112M, F112N, F112P, F112Q, F112R, F112S, F112T, F112V, F112W, F112Y, A113*, A113D, A113E, A113F, A113G, A113H, A113I, A113K, A113L, A113M, A113N, A113P, A113Q, A113R, A113S, A113T, A113V, A113W, A113Y, S114*, S114A, S114D, S114E, S114F, S114G, S114H, S114I, S114K, S114L, S114M, S114N, S114P, S114Q, S114R, S114T, S114V, S114W, S114Y, S115*, S115A, S115D, S115E, S115F, S115G, S115H, S115I, S115K, S115L, S115M, S115N, S115P, S115Q, S115R, S115T, S115V, S115W, S115Y, L116*, L116A, L116D, L116E, L116F, L116G, L116H, L116I, L116K, L116M, L116N, L116P, L116Q, L116R, L116S, L116T, L116V, L116W, L116Y, Q117*, Q117A, Q117D, Q117E, Q117F, Q117G, Q117H, Q117I, Q117K, Q117L, Q117M, Q117N, Q117P, Q117R, Q117S, Q117T, Q117V, Q117W, Q117Y, G118*, G118A, G118D, G118E, G118F, G118H, G118I, G118K, G118L, G118M, G118N, G118P, G118Q, G118R, G118S, G118T, G118V, G118W, G118Y, G119*, G119A, G119D, G119E, G119F, G119H, G119I, G119K, G119L, G119M, G119N, G119P, G119Q, G119R, G119S, G119T, G119V, G119W, G119Y, T120*, T120A, T120D, T120E, T120F, T120G, T120H, T120I, T120K, T120L, T120M, T120N, T120P, T120Q, T120R, T120S, T120V, T120W, T120Y, N121*, N121A, N121D, N121E, N121F, N121G, N121H, N121I, N121K, N121L, N121M, N121P, N121Q, N121R, N121S, N121T, N121V, N121W, N121Y, A122*, A122D, A122E, A122F, A122G, A122H, A122I, A122K, A122L, A122M, A122N, A122P, A122Q, A122R, A122S, A122T, A122V, A122W, A122Y, I123*, I123A, I123D, I123E, I123F, I123G, I123H, I123K, I123L, I123M, I123N, I123P, I123Q, I123R, I123S, I123T, I123V, I123W, I123Y, L124*, L124A, L124D, L124E, L124F, L124G, L124H, L124I, L124K, L124M, L124N, L124P, L124Q, L124R, L124S, L124T, L124V, L124W, L124Y, A125*, A125D, A125E, A125F, A125G, A125H, A125I, A125K, A125L, A125M, A125N, A125P, A125Q, A125R, A125S, A125T, A125V, A125W, A125Y, P126*, P126A, P126D, P126E, P126F, P126G, P126H, P126I, P126K, P126L, P126M, P126N, P126Q, P126R, P126S, P126T, P126V, P126W, P126Y, V127*, V127A, V127D, V127E, V127F, V127G, V127H, V127I, V127K, V127L, V127M, V127N, V127P, V127Q, V127R, V127S, V127T, V127W, V127Y, N128*, N128A, N128D, N128E, N128F, N128G, N128H, N128I, N128K, N128L, N128M, N128P, N128Q, N128R, N128S, N128T, N128V, N128W, N128Y, L129*, L129A, L129D, L129E, L129F, L129G, L129H, L129I, L129K, L129M, L129N, L129P, L129Q, L129R, L129S, L129T, L129V, L129W, L129Y, A130*, A130D, A130E, A130F, A130G, A130H, A130I, A130K, A130L, A130M, A130N, A130P, A130Q, A130R, A130S, A130T, A130V, A130W, A130Y, S131*, S131A, S131D, S131E, S131F, S131G, S131H, S131I, S131K, S131L, S131M, S131N, S131P, S131Q, S131R, S131T, S131V, S131W, S131Y, Q132*, Q132A, Q132D, Q132E, Q132F, Q132G, Q132H, Q132I, Q132K, Q132L, Q132M, Q132N, Q132P, Q132R, Q132S, Q132T, Q132V, Q132W, Q132Y, N133*, N133A, N133D, N133E, N133F, N133G, N133H, N133I, N133K, N133L, N133M, N133P, N133Q, N133R, N133S, N133T, N133V, N133W, N133Y, S134*, S134A, S134D, S134E, S134F, S134G, S134H, S134I, S134K, S134L, S134M, S134N, S134P, S134Q, S134R, S134T, S134V, S134W, S134Y, Q135*, Q135A, Q135D, Q135E, Q135F, Q135G, Q135H, Q135I, Q135K, Q135L, Q135M, Q135N, Q135P, Q135R, Q135S, Q135T, Q135V, Q135W, Q135Y, G136*, G136A, G136D, G136E, G136F, G136H, G136I, G136K, G136L, G136M, G136N, G136P, G136Q, G136R, G136S, G136T, G136V, G136W, G136Y, G137*, G137A, G137D, G137E, G137F, G137H, G137I, G137K, G137L, G137M, G137N, G137P, G137Q, G137R, G137S, G137T, G137V, G137W, G137Y, V138*, V138A, V138D, V138E, V138F, V138G, V138H, V138I, V138K, V138L, V138M, V138N, V138P, V138Q, V138R, V138S, V138T, V138W, V138Y, L139*, L139A, L139D, L139E, L139F, L139G, L139H, L139I, L139K, L139M, L139N, L139P, L139Q, L139R, L139S, L139T, L139V, L139W, L139Y, N140*, N140A, N140D, N140E, N140F, N140G, N140H, N140I, N140K, N140L, N140M, N140P, N140Q, N140R, N140S, N140T, N140V, N140W, N140Y, G141*, G141A, G141D, G141E, G141F, G141H, G141I, G141K, G141L, G141M, G141N, G141P, G141Q, G141R, G141S, G141T, G141V, G141W, G141Y, F142*, F142A, F142D, F142E, F142G, F142H, F142I, F142K, F142L, F142M, F142N, F142P, F142Q, F142R, F142S, F142T, F142V, F142W, F142Y, Y143*, Y143A, Y143D, Y143E, Y143F, Y143G, Y143H, Y143I, Y143K, Y143L, Y143M, Y143N, Y143P, Y143Q, Y143R, Y143S, Y143T, Y143V, Y143W, S144*, S144A, S144D, S144E, S144F, S144G, S144H, S144I, S144K, S144L, S144M, S144N, S144P, S144Q, S144R, S144T, S144V, S144W, S144Y, A145*, A145D, A145E, A145F, A145G, A145H, A145I, A145K, A145L, A145M, A145N, A145P, A145Q, A145R, A145S, A145T, A145V, A145W, A145Y, N146*, N146A, N146D, N146E, N146F, N146G, N146H, N146I, N146K, N146L, N146M, N146P, N146Q, N146R, N146S, N146T, N146V, N146W, N146Y, K147*, K147A, K147D, K147E, K147F, K147G, K147H, K147I, K147L, K147M, K147N, K147P, K147Q, K147R, K147S, K147T, K147V, K147W, K147Y, V148*, V148A, V148D, V148E, V148F, V148G, V148H, V148I, V148K, V148L, V148M, V148N, V148P, V148Q, V148R, V148S, V148T, V148W, V148Y, A149*, A149D, A149E, A149F, A149G, A149H, A149I, A149K, A149L, A149M, A149N, A149P, A149Q, A149R, A149S, A149T, A149V, A149W, A149Y, Q150*, Q150A, Q150D, Q150E, Q150F, Q150G, Q150H, Q150I, Q150K, Q150L, Q150M, Q150N, Q150P, Q150R, Q150S, Q150T, Q150V, Q150W, Q150Y, F151*, F151A, F151D, F151E, F151G, F151H, F151I, F151K, F151L, F151M, F151N, F151P, F151Q, F151R, F151S, F151T, F151V, F151W, F151Y, D152*, D152A, D152E, D152F, D152G, D152H, D152I, D152K, D152L, D152M, D152N, D152P, D152Q, D152R, D152S, D152T, D152V, D152W, D152Y, P153*, P153A, P153D, P153E, P153F, P153G, P153H, P153I, P153K, P153L, P153M, P153N, P153Q, P153R, P153S, P153T, P153V, P153W, P153Y, S154*, S154A, S154D, S154E, S154F, S154G, S154H, S154I, S154K, S154L, S154M, S154N, S154P, S154Q, S154R, S154T, S154V, S154W, S154Y, K155*, K155A, K155D, K155E, K155F, K155G, K155H, K155I, K155L, K155M, K155N, K155P, K155Q, K155R, K155S, K155T, K155V, K155W, K155Y, P156*, P156A, P156D, P156E, P156F, P156G, P156H, P156I, P156K, P156L, P156M, P156N, P156Q, P156R, P156S, P156T, P156V, P156W, P156Y, Q157*, Q157A, Q157D, Q157E, Q157F, Q157G, Q157H, Q157I, Q157K, Q157L, Q157M, Q157N, Q157P, Q157R, Q157S, Q157T, Q157V, Q157W, Q157Y, Q158*, Q158A, Q158D, Q158E, Q158F, Q158G, Q158H, Q158I, Q158K, Q158L, Q158M, Q158N, Q158P, Q158R, Q158S, Q158T, Q158V, Q158W, Q158Y, T159*, T159A, T159D, T159E, T159F, T159G, T159H, T159I, T159K, T159L, T159M, T159N, T159P, T159Q, T159R, T159S, T159V, T159W, T159Y, K160*, K160A, K160D, K160E, K160F, K160G, K160H, K160I, K160L, K160M, K160N, K160P, K160Q, K160R, K160S, K160T, K160V, K160W, K160Y, G161*, G161A, G161D, G161E, G161F, G161H, G161I, G161K, G161L, G161M, G161N, G161P, G161Q, G161R, G161S, G161T, G161V, G161W, G161Y, T162A, T162D, T162E, T162F, T162G, T162H, T162I, T162K, T162L, T162M, T162N, T162P, T162Q, T162R, T162S, T162T, T162V, T162W, T162Y, W163*, W163A, W163D, W163E, W163F, W163G, W163H, W163I, W163K, W163L, W163M, W163N, W163P, W163Q, W163R, W163S, W163T, W163V, W163Y, F164*, F164A, F164D, F164E, F164G, F164H, F164I, F164K, F164L, F164M, F164N, F164P, F164Q, F164R, F164S, F164T, F164V, F164W, F164Y, Q165*, Q165A, Q165D, Q165E, Q165F, Q165G, Q165H, Q165I, Q165K, Q165L, Q165M, Q165N, Q165P, Q165R, Q165S, Q165T, Q165V, Q165W, Q165Y, I166*, I166A, I166D, I166E, I166F, I166G, I166H, I166K, I166L, I166M, I166N, I166P, I166Q, I166R, I166S, I166T, I166V, I166W, I166Y, T167*, T167A, T167D, T167E, T167F, T167G, T167H, T167I, T167K, T167L, T167M, T167N, T167P, T167Q, T167R, T167S, T167V, T167W, T167Y, K168*, K168A, K168D, K168E, K168F, K168G, K168H, K168I, K168L, K168M, K168N, K168P, K168Q, K168R, K168S, K168T, K168V, K168W, K168Y, F169*, F169A, F169D, F169E, F169G, F169H, F169I, F169K, F169L, F169M, F169N, F169P, F169Q, F169R, F169S, F169T, F169V, F169W, F169Y, T170*, T170A, T170D, T170E, T170F, T170G, T170H, T170I, T170K, T170L, T170M, T170N, T170P, T170Q, T170R, T170S, T170V, T170W, T170Y, G171*, G171A, G171D, G171E, G171F, G171H, G171I, G171K, G171L, G171M, G171N, G171P, G171Q, G171R, G171S, G171T, G171V, G171W, G171Y, A172*, A172D, A172E, A172F, A172G, A172H, A172I, A172K, A172L, A172M, A172N, A172P, A172Q, A172R, A172S, A172T, A172V, A172W, A172Y, A173*, A173D, A173E, A173F, A173G, A173H, A173I, A173K, A173L, A173M, A173N, A173P, A173Q, A173R, A173S, A173T, A173V, A173W, A173Y, G174*, G174A, G174D, G174E, G174F, G174H, G174I, G174K, G174L, G174M, G174N, G174P, G174Q, G174R, G174S, G174T, G174V, G174W, G174Y, P175*, P175A, P175D, P175E, P175F, P175G, P175H, P175I, P175K, P175L, P175M, P175N, P175Q, P175R, P175S, P175T, P175V, P175W, P175Y, Y176*, Y176A, Y176D, Y176E, Y176F, Y176G, Y176H, Y176I, Y176K, Y176L, Y176M, Y176N, Y176P, Y176Q, Y176R, Y176S, Y176T, Y176V, Y176W, K178*, K178A, K178D, K178E, K178F, K178G, K178H, K178I, K178L, K178M, K178N, K178P, K178Q, K178R, K178S, K178T, K178V, K178W, K178Y, A179*, A179D, A179E, A179F, A179G, A179H, A179I, A179K, A179L, A179M, A179N, A179P, A179Q, A179R, A179S, A179T, A179V, A179W, A179Y, L180*, L180A, L180D, L180E, L180F, L180G, L180H, L180I, L180K, L180M, L180N, L180P, L180Q, L180R, L180S, L180T, L180V, L180W, L180Y, G181*, G181A, G181D, G181E, G181F, G181H, G181I, G181K, G181L, G181M, G181N, G181P, G181Q, G181R, G181S, G181T, G181V, G181W, G181Y, S182*, S182A, S182D, S182E, S182F, S182G, S182H, S182I, S182K, S182L, S182M, S182N, S182P, S182Q, S182R, S182T, S182V, S182W, S182Y, N183*, N183A, N183D, N183E, N183F, N183G, N183H, N183I, N183K, N183L, N183M, N183P, N183Q, N183R, N183S, N183T, N183V, N183W, N183Y, D184*, D184A, D184E, D184F, D184G, D184H, D184I, D184K, D184L, D184M, D184N, D184P, D184Q, D184R, D184S, D184T, D184V, D184W, D184Y, K185*, K185A, K185D, K185E, K185F, K185G, K185H, K185I, K185L, K185M, K185N, K185P, K185Q, K185R, K185S, K185T, K185V, K185W, K185Y, S186*, S186A, S186D, S186E, S186F, S186G, S186H, S186I, S186K, S186L, S186M, S186N, S186P, S186Q, S186R, S186T, S186V, S186W, S186Y, V187*, V187A, V187D, V187E, V187F, V187G, V187H, V187I, V187K, V187L, V187M, V187N, V187P, V187Q, V187R, V187S, V187T, V187W, V187Y, D189*, D189A, D189E, D189F, D189G, D189H, D189I, D189K, D189L, D189M, D189N, D189P, D189Q, D189R, D189S, D189T, D189V, D189W, D189Y, K190*, K190A, K190D, K190E, K190F, K190G, K190H, K190I, K190L, K190M, K190N, K190P, K190Q, K190R, K190S, K190T, K190V, K190W, K190Y, N191*, N191A, N191D, N191E, N191F, N191G, N191H, N191I, N191K, N191L, N191M, N191P, N191Q, N191R, N191S, N191T, N191V, N191W, N191Y, K192*, K192A, K192D, K192E, K192F, K192G, K192H, K192I, K192L, K192M, K192N, K192P, K192Q, K192R, K192S, K192T, K192V, K192W, K192Y, N193*, N193A, N193D, N193E, N193F, N193G, N193H, N193I, N193K, N193L, N193M, N193P, N193Q, N193R, N193S, N193T, N193V, N193W, N193Y, I194*, I194A, I194D, I194E, I194F, I194G, I194H, I194K, I194L, I194M, I194N, I194P, I194Q, I194R, I194S, I194T, I194V, I194W, I194Y, A195*, A195D, A195E, A195F, A195G, A195H, A195I, A195K, A195L, A195M, A195N, A195P, A195Q, A195R, A195S, A195T, A195V, A195W, A195Y, G196*, G196A, G196D, G196E, G196F, G196H, G196I, G196K, G196L, G196M, G196N, G196P, G196Q, G196R, G196S, G196T, G196V, G196W, G196Y, G197*, G197A, G197D, G197E, G197F, G197G, G197H, G197I, G197K, G197L, G197M, G197N, G197P, G197Q, G197R, G197S, G197T, G197V, G197W, G197Y, W198*, W198A, W198D, W198E, W198F, W198G, W198H, W198I, W198K, W198L, W198M, W198N, W198P, W198Q, W198R, W198S, W198T, W198V, W198Y, G199*, G199A, G199D, G199E, G199F, G199H, G199I, G199K, G199L, G199M, G199N, G199P, G199Q, G199R, G199S, G199T, G199V, G199W, G199Y, F200*, F200A, F200D, F200E, F200G, F200H, F200I, F200K, F200L, F200M, F200N, F200P, F200Q, F200R, F200S, F200T, F200V, F200W, F200Y, D201*, D201A, D201E, D201F, D201G, D201H, D201I, D201K, D201L, D201M, D201N, D201P, D201Q, D201R, D201S, D201T, D201V, D201W, D201Y, P202*, P202A, P202D, P202E, P202F, P202G, P202H, P202I, P202K, P202L, P202M, P202N, P202Q, P202R, P202S, P202T, P202V, P202W, P202Y, A203*, A203D, A203E, A203F, A203G, A203H, A203I, A203K, A203L, A203M, A203N, A203P, A203Q, A203R, A203S, A203T, A203V, A203W, A203Y, K204*, K204A, K204D, K204E, K204F, K204G, K204H, K204I, K204L, K204M, K204N, K204P, K204Q, K204R, K204S, K204T, K204V, K204W, K204Y, W205*, W205A, W205D, W205E, W205F, W205G, W205H, W205I, W205K, W205L, W205M, W205N, W205P, W205Q, W205R, W205S, W205T, W205V, W205Y, A206*, A206D, A206E, A206F, A206G, A206H, A206I, A206K, A206L, A206M, A206N, A206P, A206Q, A206R, A206S, A206T, A206V, A206W, A206Y, Y207*, Y207A, Y207D, Y207E, Y207F, Y207G, Y207H, Y207I, Y207K, Y207L, Y207M, Y207N, Y207P, Y207Q, Y207R, Y207S, Y207T, Y207V, Y207W, Q208*, Q208A, Q208D, Q208E, Q208F, Q208G, Q208H, Q208I, Q208K, Q208L, Q208M, Q208N, Q208P, Q208R, Q208S, Q208T, Q208V, Q208W, Q208Y, Y209*, Y209A, Y209D, Y209E, Y209F, Y209G, Y209H, Y209I, Y209K, Y209L, Y209M, Y209N, Y209P, Y209Q, Y209R, Y209S, Y209T, Y209V, Y209W, D210*, D210A, D210E, D210F, D210G, D210H, D210I, D210K, D210L, D210M, D210N, D210P, D210Q, D210R, D210S, D210T, D210V, D210W, D210Y, E211*, E211A, E211D, E211F, E211G, E211H, E211I, E211K, E211L, E211M, E211N, E211P, E211Q, E211R, E211S, E211T, E211V, E211W, E211Y, K212*, K212A, K212D, K212E, K212F, K212G, K212H, K212I, K212L, K212M, K212N, K212P, K212Q, K212R, K212S, K212T, K212V, K212W, K212Y, N213*, N213A, N213D, N213E, N213F, N213G, N213H, N213I, N213K, N213L, N213M, N213P, N213Q, N213R, N213S, N213T, N213V, N213W, N213Y, N214*, N214A, N214D, N214E, N214F, N214G, N214H, N214I, N214L, N214M, N214P, N214Q, N214R, N214S, N214T, N214V, N214W, N214Y, K215*, K215A, K215D, K215E, K215F, K215G, K215H, K215I, K215L, K215M, K215N, K215P, K215Q, K215R, K215S, K215T, K215V, K215W, K215Y, F216*, F216A, F216D, F216E, F216G, F216H, F216I, F216K, F216L, F216M, F216N, F216P, F216Q, F216R, F216S, F216T, F216V, F216W, F216Y, N217*, N217A, N217D, N217E, N217F, N217G, N217H, N217I, N217K, N217L, N217M, N217P, N217Q, N217R, N217S, N217T, N217V, N217W, N217Y, Y218*, Y218A, Y218D, Y218E, Y218F, Y218G, Y218H, Y218I, Y218K, Y218L, Y218M, Y218N, Y218P, Y218Q, Y218R, Y218S, Y218T, Y218V, Y218W, V219*, V219A, V219D, V219E, V219F, V219G, V219H, V219I, V219K, V219L, V219M, V219N, V219P, V219Q, V219R, V219S, V219T, V219W, V219Y, G220*, G220A, G220D, G220E, G220F, G220H, G220I, G220K, G220L, G220M, G220N, G220P, G220Q, G220R, G220S, G220T, G220V, G220W, G220Y, K221*, K221A, K221D, K221E, K221F, K221G, K221H, K221I, K221L, K221M, K221N, K221P, K221Q, K221R, K221S, K221T, K221V, K221W and K221Y, wherein each position corresponds to the position of the polypeptide of SEQ ID NO: 1.

Some aspect of the invention relates to a variant of a DNase parent, wherein the has least 60%, such as at least 70%, such as at least 80% such as at least 90%, such as at least 95% but less than 100% sequence identity to SEQ ID NO: 1, wherein the variant has DNase activity and wherein the variant comprises one or more of the substitutions selected from the group consisting of: V1A, V1D, V1E, V1F, V1G, V1H, V1I, V1K, V1L, VIM, VIN, V1P, V1Q, V1R, V1S, V1T, V1W, V1Y, P2A, P2D, P2E, P2F, P2G, P2H, P2I, P2K, P2L, P2M, P2N, P2Q, P2R, P2S, P2T, P2V, P2W, P2Y, V3A, V3C, V3D, V3E, V3F, V3G, V3H, V3I, V3K, V3L, V3M, V3N, V3P, V3R, V3S, V3T, V3W, V3Y, N4A, N4D, N4E, N4F, N4G, N4H, N4I, N4K, N4L, N4M, N4P, N4Q, N4R, N4S, N4T, N4V, N4W, N4Y, P5A, P5D, P5E, P5F, P5G, P5H, P5I, P5K, P5L, P5M, P5N, P5Q, P5R, P5S, P5T, P5V, P5W, P5Y, E6A, E6D, E6F, E6G, E6H, E6I, E6K, E6L, E6M, E6N, E6P, E6Q, E6R, E6S, E6T, E6V, E6W, E6Y, P7A, P7D, P7E, P7F, P7G, P7H, P7I, P7K, P7L, P7M, P7N, P7Q, P7R, P7S, P7T, P7V, P7W, P7Y, D8A, D8E, D8F, D8G, D8H, D8I, D8K, D8L, D8M, D8N, D8P, D8Q, D8R, D8S, D8T, D8V, D8W, D8Y, A9D, A9E, A9F, A9G, A9H, A9I, A9K, A9L, A9M, A9N, A9P, A9Q, A9R, A9S, A9T, A9V, A9W, A9Y, T10A, T10D, T10E, T10F, T10G, T10H, T10I, T10K, T10L, T10M, T10N, T10P, T10Q, T10R, T10S, T10V, T10W, T10Y, S11A, S11D, S11E, S11F, S11G, S11H, S11I, S11K, S11L, S11M, S11N, S11P, S11Q, S11R, S11T, S11V, S11W, S11Y, V12A, V12D, V12E, V12F, V12G, V12H, V12I, V12K, V12L, V12M, V12N, V12P, V12Q, V12R, V12S, V12T, V12W, V12Y, E13A, E13D, E13F, E13G, E13H, E13I, E13K, E13L, E13M, E13N, E13P, E13Q, E13R, E13S, E13T, E13V, E13W, E13Y, N14A, N14D, N14E, N14F, N14G, N14H, N14I, N14K, N14L, N14M, N14P, N14Q, N14R, N14S, N14T, N14V, N14W, N14Y, V15A, V15D, V15E, V15F, V15G, V15H, V15I, V15K, V15L, V15M, V15N, V15P, V15Q, V15R, V15S, V15T, V15W, V15Y, A16D, A16E, A16F, A16G, A16H, A16I, A16K, A16L, A16M, A16N, A16P, A16Q, A16R, A16S, A16T, A16V, A16W, A16Y, L17A, L17D, L17E, L17F, L17G, L17H, L17I, L17K, L17M, L17N, L17P, L17Q, L17R, L17S, L17T, L17V, L17W, L17Y, K18A, K18D, K18E, K18F, K18G, K18H, K18I, K18L, K18M, K18N, K18P, K18Q, K18R, K18S, K18T, K18V, K18W, K18Y, T19A, T19D, T19E, T19F, T19G, T19H, T19I, T19K, T19L, T19M, T19N, T19P, T19Q, T19R, T19S, T19V, T19W, T19Y, G20A, G20D, G20E, G20F, G20H, G20I, G20K, G20L, G20M, G20N, G20P, G20Q, G20R, G20S, G20T, G20V, G20W, G20Y, S21A, S21D, S21E, S21F, S21G, S21H, S21I, S21K, S21L, S21M, S21N, S21P, S21Q, S21R, S21T, S21V, S21W, S21Y, G22A, G22D, G22E, G22F, G22H, G22I, G22K, G22L, G22M, G22N, G22P, G22Q, G22R, G22S, G22T, G22V, G22W, G22Y, D23A, D23E, D23F, D23G, D23H, D23I, D23K, D23L, D23M, D23N, D23P, D23Q, D23R, D23S, D23T, D23V, D23W, D23Y, S24A, S24D, S24E, S24F, S24G, S24H, S24I, S24K, S24L, S24M, S24N, S24P, S24Q, S24R, S24T, S24V, S24W, S24Y, Q25A, Q25D, Q25E, Q25F, Q25G, Q25H, Q25I, Q25K, Q25L, Q25M, Q25N, Q25P, Q25R, Q25S, Q25T, Q25V, Q25W, Q25Y, S26A, S26D, S26E, S26F, S26G, S26H, S26I, S26K, S26L, S26M, S26N, S26P, S26Q, S26R, S26T, S26V, S26W, S26Y, D27A, D27E, D27F, D27G, D27H, D27I, D27K, D27L, D27M, D27N, D27P, D27Q, D27R, D27S, D27T, D27V, D27W, D27Y, P28A, P28D, P28E, P28F, P28G, P28H, P28I, P28K, P28L, P28M, P28N, P28Q, P28R, P28S, P28T, P28V, P28W, P28Y, I29A, I29D, I29E, I29F, I29G, I29H, I29K, I29L, I29M, I29N, I29P, I29Q, I29R, I29S, I29T, I29V, I29W, I29Y, K30A, K30D, K30E, K30F, K30G, K30H, K30I, K30L, K30M, K30N, K30P, K30Q, K30R, K30S, K30T, K30V, K30W, K30Y, A31D, A31E, A31F, A31G, A31H, A31I, A31K, A31L, A31M, A31N, A31P, A31Q, A31R, A31S, A31T, A31V, A31W, A31Y, D32A, D32E, D32F, D32G, D32H, D32I, D32K, D32L, D32M, D32N, D32P, D32Q, D32R, D32S, D32T, D32V, D32W, D32Y, L33A, L33D, L33E, L33F, L33G, L33H, L33I, L33K, L33M, L33N, L33P, L33Q, L33R, L33S, L33T, L33V, L33W, L33Y, E34A, E34D, E34F, E34G, E34H, E34I, E34K, E34L, E34M, E34N, E34P, E34Q, E34R, E34S, E34T, E34V, E34W, E34Y, V35A, V35D, V35E, V35F, V35G, V35H, V35I, V35K, V35L, V35M, V35N, V35P, V35Q, V35R, V35S, V35T, V35W, V35Y, K36A, K36D, K36E, K36F, K36G, K36H, K36I, K36L, K36M, K36N, K36P, K36Q, K36R, K36S, K36T, K36V, K36W, K36Y, G37A, G37D, G37E, G37F, G37H, G37I, G37K, G37L, G37M, G37N, G37P, G37Q, G37R, G37S, G37T, G37V, G37W, G37Y, Q38A, Q38D, Q38E, Q38F, Q38G, Q38H, Q38I, Q38K, Q38L, Q38M, Q38N, Q38P, Q38R, Q38S, Q38T, Q38V, Q38W, Q38Y, S39A, S39D, S39E, S39F, S39G, S39H, S39I, S39K, S39L, S39M, S39N, S39P, S39Q, S39R, S39T, S39V, S39W, S39Y, A40D, A40E, A40F, A40G, A40H, A40I, A40K, A40L, A40M, A40N, A40P, A40Q, A40R, A40S, A40T, A40V, A40W, A40Y, L41A, L41D, L41E, L41F, L41G, L41H, L41I, L41K, L41M, L41N, L41P, L41Q, L41R, L41S, L41T, L41V, L41W, L41Y, P42A, P42D, P42E, P42F, P42G, P42H, P42I, P42K, P42L, P42M, P42N, P42Q, P42R, P42S, P42T, P42V, P42W, P42Y, F43A, F43D, F43E, F43G, F43H, F43I, F43K, F43L, F43M, F43N, F43P, F43Q, F43R, F43S, F43T, F43V, F43W, F43Y, D44A, D44E, D44F, D44G, D44H, D44I, D44K, D44L, D44M, D44N, D44P, D44Q, D44R, D44S, D44T, D44V, D44W, D44Y, V45A, V45D, V45E, V45F, V45G, V45H, V45I, V45K, V45L, V45M, V45N, V45P, V45Q, V45R, V45S, V45T, V45W, V45Y, D46A, D46E, D46F, D46G, D46H, D46I, D46K, D46L, D46M, D46N, D46P, D46Q, D46R, D46S, D46T, D46V, D46W, D46Y, C47A, C47D, C47E, C47F, C47G, C47H, D47I, C47K, C47L, C47M, C47N, C47P, C47Q, C47R, C47S, C47T, 047V, C47W, C47Y, W48A, W48D, W48E, W48F, W48G, W48H, W48I, W48K, W48L, W48M, W48N, W48P, W48Q, W48R, W48S, W48T, W48V, W48Y, A49D, A49E, A49F, A49G, A49H, A49I, A49K, A49L, A49M, A49N, A49P, A49Q, A49R, A49S, A49T, A49V, A49W, A49Y, I50A, I50D, I50E, I50F, I50G, I50H, I50K, I50L, I50M, I50N, I50P, I50Q, I50R, I50S, I50T, I50V, I50W, I50Y, L51A, L51D, L51E, L51F, L51G, L51H, L51I, L51K, L51M, L51N, L51P, L51Q, L51R, L51S, L51T, L51V, L51W, L51Y, K53A, K53D, K53E, K53F, K53G, K53H, K53I, K53L, K53M, K53N, K53P, K53Q, K53R, K53S, K53T, K53V, K53W, K53Y, G54A, G54D, G54E, G54F, G54H, G54I, G54K, G54L, G54M, G54N, G54P, G54Q, G54R, G54S, G54T, G54V, G54W, G54Y, A55D, A55E, A55F, A55G, A55H, A55I, A55K, A55L, A55M, A55N, A55P, A55Q, A55R, A55S, A55T, A55V, A55W, A55Y, P56A, P56D, P56E, P56F, P56G, P56H, P56I, P56K, P56L, P56M, P56N, P56Q, P56R, P56S, P56T, P56V, P56W, P56Y, N57A, N57D, N57E, N57F, N57G, N57H, N57I, N57K, N57L, N57M, N57P, N57Q, N57R, N57S, N57T, N57V, N57W, N57Y, V58A, V58D, V58E, V58F, V58G, V58H, V58I, V58K, V58L, V58M, V58N, V58P, V58Q, V58R, V58S, V58T, V58W, V58Y, L59A, L59D, L59E, L59F, L59G, L59H, L59I, L59K, L59M, L59N, L59P, L59Q, L59R, L59S, L59T, L59V, L59W, L59Y, Q60A, Q60D, Q60E, Q60F, Q60G, Q60H, Q60I, Q60K, Q60L, Q60M, Q60N, Q60P, Q60R, Q60S, Q60T, Q60V, Q60W, Q60Y, R61A, R61D, R61E, R61F, R61G, R61H, R61I, R61K, R61L, R61M, R61N, R61P, R61Q, R61S, R61T, R61V, R61W, R61Y, V62A, V62D, V62E, V62F, V62G, V62H, V62I, V62K, V62L, V62M, V62N, V62P, V62Q, V62R, V62S, V62T, V62W, V62Y, N63A, N63D, N63E, N63F, N63G, N63H, N63I, N63K, N63L, N63M, N63P, N63Q, N63R, N63S, N63T, N63V, N63W, N63Y, E64A, E64D, E64F, E64G, E64H, E64I, E64K, E64L, E64M, E64N, E64P, E64Q, E64R, E64S, E64T, E64V, E64W, E64Y, K65A, K65D, K65E, K65F, K65G, K65H, K65I, K65L, K65M, K65N, K65P, K65Q, K65R, K65S, K65T, K65V, K65W, K65Y, T66A, T66D, T66E, T66F, T66G, T66H, T66I, T66K, T66L, T66M, T66N, T66P, T66Q, T66R, T66S, T66V, T66W, T66Y, K67A, K67D, K67E, K67F, K67G, K67H, K67I, K67L, K67M, K67N, K67P, K67Q, K67R, K67S, K67T, K67V, K67W, K67Y, N68A, N68D, N68E, N68F, N68G, N68H, N68I, N68K, N68L, N68M, N68P, N68Q, N68R, N68S, N68T, N68V, N68W, N68Y, S69A, S69D, S69E, S69F, S69G, S69H, S69I, S69K, S69L, S69M, S69N, S69P, S69Q, S69R, S69T, S69V, S69W, S69Y, N70A, N70D, N70E, N70F, N70G, N70H, N70I, N70K, N70L, N70M, N70P, N70Q, N70R, N70S, N70T, N70V, N70W, N70Y, R71A, R71D, R71E, R71F, R71G, R71H, R71I, R71K, R71L, R71M, R71N, R71P, R71Q, R71S, R71T, R71V, R71W, R71Y, D72A, D72E, D72F, D72G, D72H, D72I, D72K, D72L, D72M, D72N, D72P, D72Q, D72R, D72S, D72T, D72V, D72W, D72Y, R73A, R73D, R73E, R73F, R73G, R73H, R73I, R73K, R73L, R73M, R73N, R73P, R73Q, R73S, R73T, R73V, R73W, R73Y, S74A, S74D, S74E, S74F, S74G, S74H, S74I, S74K, S74L, S74M, S74N, S74P, S74Q, S74R, S74T, S74V, S74W, S74Y, G75A, G75D, G75E, G75F, G75H, G75I, G75K, G75L, G75M, G75N, G75P, G75Q, G75R, G75S, G75T, G75V, G75W, G75Y, A76D, A76E, A76F, A76G, A76H, A76I, A76K, A76L, A76M, A76N, A76P, A76Q, A76R, A76S, A76T, A76V, A76W, A76Y, N77A, N77D, N77E, N77F, N77G, N77H, N77I, N77K, N77L, N77M, N77P, N77Q, N77R, N77S, N77T, N77V, N77W, N77Y, K78A, K78D, K78E, K78F, K78G, K78H, K78I, K78L, K78M, K78N, K78P, K78Q, K78R, K78S, K78T, K78V, K78W, K78Y, G79A, G79D, G79E, G79F, G79H, G79I, G79K, G79L, G79M, G79N, G79P, G79Q, G79R, G79S, G79T, G79V, G79W, G79Y, P80A, P80D, P80E, P80F, P80G, P80H, P80I, P80K, P80L, P80M, P80N, P80Q, P80R, P80S, P80T, P80V, P80W, P80Y, F81A, F81D, F81E, F81G, F81H, F81I, F81K, F81L, F81M, F81N, F81P, F81Q, F81R, F81S, F81T, F81V, F81W, F81Y, K82A, K82D, K82E, K82F, K82G, K82H, K82I, K82L, K82M, K82N, K82P, K82Q, K82R, K82S, K82T, K82V, K82W, K82Y, D83A, D83E, D83F, D83G, D83H, D83I, D83K, D83L, D83M, D83N, D83P, D83Q, D83R, D83S, D83T, D83V, D83W, D83Y, P84A, P84D, P84E, P84F, P84G, P84H, P84I, P84K, P84L, P84M, P84N, P84Q, P84R, P84S, P84T, P84V, P84W, P84Y, Q85A, Q85D, Q85E, Q85F, Q85G, Q85H, Q85I, Q85K, Q85L, Q85M, Q85N, Q85P, Q85R, Q85S, Q85T, Q85V, Q85W, Q85Y, K86A, K86D, K86E, K86F, K86G, K86H, K86I, K86L, K86M, K86N, K86P, K86Q, K86R, K86S, K86T, K86V, K86W, K86Y, W87A, W87D, W87E, W87F, W87G, W87H, W87I, W87K, W87L, W87M, W87N, W87P, W87Q, W87R, W87S, W87T, W87V, W87Y, G88A, G88D, G88E, G88F, G88H, G88I, G88K, G88L, G88M, G88N, G88P, G88Q, G88R, G88S, G88T, G88V, G88W, G88Y, I89A, I89D, I89E, I89F, I89G, I89H, I89K, I89L, I89M, I89N, I89P, I89Q, I89R, I89S, I89T, I89V, I89W, I89Y, K90A, K90D, K90E, K90F, K90G, K90H, K90I, K90L, K90M, K90N, K90P, K90Q, K90R, K90S, K90T, K90V, K90W, K90Y, A91D, A91E, A91F, A91G, A91H, A91I, A91K, A91L, A91M, A91N, A91P, A91Q, A91R, A91S, A91T, A91V, A91W, A91Y, L92A, L92D, L92E, L92F, L92G, L92H, L92I, L92K, L92M, L92N, L92P, L92Q, L92R, L92S, L92T, L92V, L92W, L92Y, P93A, P93D, P93E, P93F, P93G, P93H, P93I, P93K, P93L, P93M, P93N, P93Q, P93R, P93S, P93T, P93V, P93W, P93Y, P94A, P94D, P94E, P94F, P94G, P94H, P94I, P94K, P94L, P94M, P94N, P94Q, P94R, P94S, P94T, P94V, P94W, P94Y, K95A, K95D, K95E, K95F, K95G, K95H, K95I, K95L, K95M, K95N, K95P, K95Q, K95R, K95S, K95T, K95V, K95W, K95Y, N96A, N96D, N96E, N96F, N96G, N96H, N96I, N96K, N96L, N96M, N96P, N96Q, N96R, N96S, N96T, N96V, N96W, N96Y, P97A, P97D, P97E, P97F, P97G, P97H, P97I, P97K, P97L, P97M, P97N, P97Q, P97R, P97S, P97T, P97V, P97W, P97Y, S98A, S98D, S98E, S98F, S98G, S98H, S98I, S98K, S98L, S98M, S98N, S98P, S98Q, S98R, S98T, S98V, S98W, S98Y, W99A, W99D, W99E, W99F, W99G, W99H, W99I, W99K, W99L, W99M, W99N, W99P, W99Q, W99R, W99S, W99T, W99V, W99Y, S100A, S100D, S100E, S100F, S100G, S100H, S100I, S100K, S100L, S100M, S100N, S100P, S100Q, S100R, S100T, S100V, S100W, S100Y, A101D, A101E, A101F, A101G, A101H, A101I, A101K, A101L, A101M, A101N, A101P, A101Q, A101R, A101S, A101T, A101V, A101W, A101Y, Q102A, Q102D, Q102E, Q102F, Q102G, Q102H, Q102I, Q102K, Q102L, Q102M, Q102N, Q102P, Q102R, Q102S, Q102T, Q102V, Q102W, Q102Y, D103A, D103E, D103F, D103G, D103H, D103I, D103K, D103L, D103M, D103N, D103P, D103Q, D103R, D103S, D103T, D103V, D103W, D103Y, F104A, F104D, F104E, F104G, F104H, F104I, F104K, F104L, F104M, F104N, F104P, F104Q, F104R, F104S, F104T, F104V, F104W, F104Y, K105A, K105D, K105E, K105F, K105G, K105H, K105I, K105L, K105M, K105N, K105P, K105Q, K105R, K105S, K105T, K105V, K105W, K105Y, S106A, S106D, S106E, S106F, S106G, S106H, S106I, S106K, S106L, S106M, S106N, S106P, S106Q, S106R, S106T, S106V, S106W, S106Y, P107A, P107D, P107E, P107F, P107G, P107H, P107I, P107K, P107L, P107M, P107N, P107Q, P107R, P107S, P107T, P107V, P107W, P107Y, E108A, E108D, E108F, E108G, E108H, E108I, E108K, E108L, E108M, E108N, E108P, E108Q, E108R, E108S, E108T, E108V, E108W, E108Y, E109A, E109D, E109F, E109G, E109H, E109I, E109K, E109L, E109M, E109N, E109P, E109Q, E109R, E109S, E109T, E109V, E109W, E109Y, Y110A, Y110D, Y110E, Y110F, Y110G, Y110H, Y110I, Y110K, Y110L, Y110M, Y110N, Y110P, Y110Q, Y110R, Y110S, Y110T, Y110V, Y110W, A111D, A111E, A111F, A111G, A111H, A111I, A111K, A111L, A111M, A111N, A111P, A111Q, A111R, A111S, A111T, A111V, A111W, A111Y, F112A, F112D, F112E, F112G, F112H, F112I, F112K, F112L, F112M, F112N, F112P, F112Q, F112R, F112S, F112T, F112V, F112W, F112Y, A113D, A113E, A113F, A113G, A113H, A113I, A113K, A113L, A113M, A113N, A113P, A113Q, A113R, A113S, A113T, A113V, A113W, A113Y, S114A, S114D, S114E, S114F, S114G, S114H, S114I, S114K, S114L, S114M, S114N, S114P, S114Q, S114R, S114T, S114V, S114W, S114Y, S115A, S115D, S115E, S115F, S115G, S115H, S115I, S115K, S115L, S115M, S115N, S115P, S115Q, S115R, S115T, S115V, S115W, S115Y, L116A, L116D, L116E, L116F, L116G, L116H, L116I, L116K, L116M, L116N, L116P, L116Q, L116R, L116S, L116T, L116V, L116W, L116Y, Q117A, Q117D, Q117E, Q117F, Q117G, Q117H, Q117I, Q117K, Q117L, Q117M, Q117N, Q117P, Q117R, Q117S, Q117T, Q117V, Q117W, Q117Y, G118A, G118D, G118E, G118F, G118H, G118I, G118K, G118L, G118M, G118N, G118P, G118Q, G118R, G118S, G118T, G118V, G118W, G118Y, G119A, G119D, G119E, G119F, G119H, G119I, G119K, G119L, G119M, G119N, G119P, G119Q, G119R, G119S, G119T, G119V, G119W, G119Y, T120A, T120D, T120E, T120F, T120G, T120H, T120I, T120K, T120L, T120M, T120N, T120P, T120Q, T120R, T120S, T120V, T120W, T120Y, N121A, N121D, N121E, N121F, N121G, N121H, N121I, N121K, N121L, N121M, N121P, N121Q, N121R, N121S, N121T, N121V, N121W, N121Y, A122D, A122E, A122F, A122G, A122H, A122I, A122K, A122L, A122M, A122N, A122P, A122Q, A122R, A122S, A122T, A122V, A122W, A122Y, I123A, I123D, I123E, I123F, I123G, I123H, I123K, I123L, I123M, I123N, I123P, I123Q, I123R, I123S, I123T, I123V, I123W, I123Y, L124A, L124D, L124E, L124F, L124G, L124H, L124I, L124K, L124M, L124N, L124P, L124Q, L124R, L124S, L124T, L124V, L124W, L124Y, A125D, A125E, A125F, A125G, A125H, A125I, A125K, A125L, A125M, A125N, A125P, A125Q, A125R, A125S, A125T, A125V, A125W, A125Y, P126D, P126E, P126F, P126G, P126H, P126I, P126K, P126L, P126M, P126N, P126Q, P126R, P126S, P126T, P126V, P126W, P126Y, V127A, V127D, V127E, V127F, V127G, V127H, V127I, V127K, V127L, V127M, V127N, V127P, V127Q, V127R, V127S, V127T, V127W, V127Y, N128A, N128D, N128E, N128F, N128G, N128H, N128I, N128K, N128L, N128M, N128P, N128Q, N128R, N128S, N128T, N128V, N128W, N128Y, L129A, L129D, L129E, L129F, L129G, L129H, L129I, L129K, L129M, L129N, L129P, L129Q, L129R, L129S, L129T, L129V, L129W, L129Y, A130D, A130E, A130F, A130G, A130H, A130I, A130K, A130L, A130M, A130N, A130P, A130Q, A130R, A130S, A130T, A130V, A130W, A130Y, S131A, S131D, S131E, S131F, S131G, S131H, S131I, S131K, S131L, S131M, S131N, S131P, S131Q, S131R, S131T, S131V, S131W, S131Y, Q132A, Q132D, Q132E, Q132F, Q132G, Q132H, Q132I, Q132K, Q132L, Q132M, Q132N, Q132P, Q132R, Q132S, Q132T, Q132V, Q132W, Q132Y, N133A, N133D, N133E, N133F, N133G, N133H, N133I, N133K, N133L, N133M, N133P, N133Q, N133R, N133S, N133T, N133V, N133W, N133Y, S134A, S134D, S134E, S134F, S134G, S134H, S134I, S134K, S134L, S134M, S134N, S134P, S134Q, S134R, S134T, S134V, S134W, S134Y, Q135A, Q135D, Q135E, Q135F, Q135G, Q135H, Q135I, Q135K, Q135L, Q135M, Q135N, Q135P, Q135R, Q135S, Q135T, Q135V, Q135W, Q135Y, G136A, G136D, G136E, G136F, G136H, G136I, G136K, G136L, G136M, G136N, G136P, G136Q, G136R, G136S, G136T, G136V, G136W, G136Y, G137A, G137D, G137E, G137F, G137H, G137I, G137K, G137L, G137M, G137N, G137P, G137Q, G137R, G137S, G137T, G137V, G137W, G137Y, V138A, V138D, V138E, V138F, V138G, V138H, V138I, V138K, V138L, V138M, V138N, V138P, V138Q, V138R, V138S, V138T, V138W, V138Y, L139A, L139D, L139E, L139F, L139G, L139H, L139I, L139K, L139M, L139N, L139P, L139Q, L139R, L139S, L139T, L139V, L139W, L139Y, N140A, N140D, N140E, N140F, N140G, N140H, N140I, N140K, N140L, N140M, N140P, N140Q, N140R, N140S, N140T, N140V, N140W, N140Y, G141A, G141D, G141E, G141F, G141H, G141I, G141K, G141L, G141M, G141N, G141P, G141Q, G141R, G141S, G141T, G141V, G141W, G141Y, F142A, F142D, F142E, F142G, F142H, F142I, F142K, F142L, F142M, F142N, F142P, F142Q, F142R, F142S, F142T, F142V, F142W, F142Y, Y143A, Y143D, Y143E, Y143F, Y143G, Y143H, Y143I, Y143K, Y143L, Y143M, Y143N, Y143P, Y143Q, Y143R, Y143S, Y143T, Y143V, Y143W, S144A, S144D, S144E, S144F, S144G, S144H, S144I, S144K, S144L, S144M, S144N, S144P, S144Q, S144R, S144T, S144V, S144W, S144Y, A145D, A145E, A145F, A145G, A145H, A145I, A145K, A145L, A145M, A145N, A145P, A145Q, A145R, A145S, A145T, A145V, A145W, A145Y, N146A, N146D, N146E, N146F, N146G, N146H, N146I, N146K, N146L, N146M, N146P, N146Q, N146R, N146S, N146T, N146V, N146W, N146Y, K147A, K147D, K147E, K147F, K147G, K147H, K147I, K147L, K147M, K147N, K147P, K147Q, K147R, K147S, K147T, K147V, K147W, K147Y, V148A, V148D, V148E, V148F, V148G, V148H, V148I, V148K, V148L, V148M, V148N, V148P, V148Q, V148R, V148S, V148T, V148W, V148Y, A149D, A149E, A149F, A149G, A149H, A149I, A149K, A149L, A149M, A149N, A149P, A149Q, A149R, A149S, A149T, A149V, A149W, A149Y, Q150A, Q150D, Q150E, Q150F, Q150G, Q150H, Q150I, Q150K, Q150L, Q150M, Q150N, Q150P, Q150R, Q150S, Q150T, Q150V, Q150W, Q150Y, F151A, F151D, F151E, F151G, F151H, F151I, F151K, F151L, F151M, F151N, F151P, F151Q, F151R, F151S, F151T, F151V, F151W, F151Y, D152A, D152E, D152F, D152G, D152H, D152I, D152K, D152L, D152M, D152N, D152P, D152Q, D152R, D152S, D152T, D152V, D152W, D152Y, P153A, P153D, P153E, P153F, P153G, P153H, P153I, P153K, P153L, P153M, P153N, P153Q, P153R, P153S, P153T, P153V, P153W, P153Y, S154A, S154D, S154E, S154F, S154G, S154H, S154I, S154K, S154L, S154M, S154N, S154P, S154Q, S154R, S154T, S154V, S154W, S154Y, K155A, K155D, K155E, K155F, K155G, K155H, K155I, K155L, K155M, K155N, K155P, K155Q, K155R, K155S, K155T, K155V, K155W, K155Y, P156A, P156D, P156E, P156F, P156G, P156H, P156I, P156K, P156L, P156M, P156N, P156Q, P156R, P156S, P156T, P156V, P156W, P156Y, Q157A, Q157D, Q157E, Q157F, Q157G, Q157H, Q157I, Q157K, Q157L, Q157M, Q157N, Q157P, Q157R, Q157S, Q157T, Q157V, Q157W, Q157Y, Q158A, Q158D, Q158E, Q158F, Q158G, Q158H, Q158I, Q158K, Q158L, Q158M, Q158N, Q158P, Q158R, Q158S, Q158T, Q158V, Q158W, Q158Y, T159A, T159D, T159E, T159F, T159G, T159H, T159I, T159K, T159L, T159M, T159N, T159P, T159Q, T159R, T159S, T159V, T159W, T159Y, K160A, K160D, K160E, K160F, K160G, K160H, K160I, K160L, K160M, K160N, K160P, K160Q, K160R, K160S, K160T, K160V, K160W, K160Y, G161A, G161D, G161E, G161F, G161H, G161I, G161K, G161L, G161M, G161N, G161P, G161Q, G161R, G161S, G161T, G161V, G161W, G161Y, T162A, T162D, T162E, T162F, T162G, T162H, T162I, T162K, T162L, T162M, T162N, T162P, T162Q, T162R, T162S, T162T, T162V, T162W, T162Y, W163A, W163D, W163E, W163F, W163G, W163H, W163I, W163K, W163L, W163M, W163N, W163P, W163Q, W163R, W163S, W163T, W163V, W163Y, F164A, F164D, F164E, F164G, F164H, F164I, F164K, F164L, F164M, F164N, F164P, F164Q, F164R, F164S, F164T, F164V, F164W, F164Y, Q165A, Q165D, Q165E, Q165F, Q165G, Q165H, Q165I, Q165K, Q165L, Q165M, Q165N, Q165P, Q165R, Q165S, Q165T, Q165V, Q165W, Q165Y, I166A, I166D, I166E, I166F, I166G, I166H, I166K, I166L, I166M, I166N, I166P, I166Q, I166R, I166S, I166T, I166V, I166W, I166Y, T167A, T167D, T167E, T167F, T167G, T167H, T167I, T167K, T167L, T167M, T167N, T167P, T167Q, T167R, T167S, T167V, T167W, T167Y, K168A, K168D, K168E, K168F, K168G, K168H, K168I, K168L, K168M, K168N, K168P, K168Q, K168R, K168S, K168T, K168V, K168W, K168Y, F169A, F169D, F169E, F169G, F169H, F169I, F169K, F169L, F169M, F169N, F169P, F169Q, F169R, F169S, F169T, F169V, F169W, F169Y, T170A, T170D, T170E, T170F, T170G, T170H, T170I, T170K, T170L, T170M, T170N, T170P, T170Q, T170R, T170S, T170V, T170W, T170Y, G171A, G171D, G171E, G171F, G171H, G171I, G171K, G171L, G171M, G171N, G171P, G171Q, G171R, G171S, G171T, G171V, G171W, G171Y, A172D, A172E, A172F, A172G, A172H, A172I, A172K, A172L, A172M, A172N, A172P, A172Q, A172R, A172S, A172T, A172V, A172W, A172Y, A173D, A173E, A173F, A173G, A173H, A173I, A173K, A173L, A173M, A173N, A173P, A173Q, A173R, A173S, A173T, A173V, A173W, A173Y, G174A, G174D, G174E, G174F, G174H, G174I, G174K, G174L, G174M, G174N, G174P, G174Q, G174R, G174S, G174T, G174V, G174W, G174Y, P175A, P175D, P175E, P175F, P175G, P175H, P175I, P175K, P175L, P175M, P175N, P175Q, P175R, P175S, P175T, P175V, P175W, P175Y, Y176A, Y176D, Y176E, Y176F, Y176G, Y176H, Y176I, Y176K, Y176L, Y176M, Y176N, Y176P, Y176Q, Y176R, Y176S, Y176T, Y176V, Y176W, K178A, K178D, K178E, K178F, K178G, K178H, K178I, K178L, K178M, K178N, K178P, K178Q, K178R, K178S, K178T, K178V, K178W, K178Y, A179D, A179E, A179F, A179G, A179H, A179I, A179K, A179L, A179M, A179N, A179P, A179Q, A179R, A179S, A179T, A179V, A179W, A179Y, L180A, L180D, L180E, L180F, L180G, L180H, L180I, L180K, L180M, L180N, L180P, L180Q, L180R, L180S, L180T, L180V, L180W, L180Y, G181A, G181D, G181E, G181F, G181H, G181I, G181K, G181L, G181M, G181N, G181P, G181Q, G181R, G181S, G181T, G181V, G181W, G181Y, S182A, S182D, S182E, S182F, S182G, S182H, S182I, S182K, S182L, S182M, S182N, S182P, S182Q, S182R, S182T, S182V, S182W, S182Y, N183A, N183D, N183E, N183F, N183G, N183H, N183I, N183K, N183L, N183M, N183P, N183Q, N183R, N183S, N183T, N183V, N183W, N183Y, D184A, D184E, D184F, D184G, D184H, D184I, D184K, D184L, D184M, D184N, D184P, D184Q, D184R, D184S, D184T, D184V, D184W, D184Y, K185A, K185D, K185E, K185F, K185G, K185H, K185I, K185L, K185M, K185N, K185P, K185Q, K185R, K185S, K185T, K185V, K185W, K185Y, S186A, S186D, S186E, S186F, S186G, S186H, S186I, S186K, S186L, S186M, S186N, S186P, S186Q, S186R, S186T, S186V, S186W, S186Y, V187A, V187D, V187E, V187F, V187G, V187H, V187I, V187K, V187L, V187M, V187N, V187P, V187Q, V187R, V187S, V187T, V187W, V187Y, D189A, D189E, D189F, D189G, D189H, D189I, D189K, D189L, D189M, D189N, D189P, D189Q, D189R, D189S, D189T, D189V, D189W, D189Y, K190A, K190D, K190E, K190F, K190G, K190H, K190I, K190L, K190M, K190N, K190P, K190Q, K190R, K190S, K190T, K190V, K190W, K190Y, N191A, N191D, N191E, N191F, N191G, N191H, N191I, N191K, N191L, N191M, N191P, N191Q, N191R, N191S, N191T, N191V, N191W, N191Y, K192A, K192D, K192E, K192F, K192G, K192H, K192I, K192L, K192M, K192N, K192P, K192Q, K192R, K192S, K192T, K192V, K192W, K192Y, N193A, N193D, N193E, N193F, N193G, N193H, N193I, N193K, N193L, N193M, N193P, N193Q, N193R, N193S, N193T, N193V, N193W, N193Y, I194A, I194D, I194E, I194F, I194G, I194H, I194K, I194L, I194M, I194N, I194P, I194Q, I194R, I194S, I194T, I194V, I194W, I194Y, A195D, A195E, A195F, A195G, A195H, A195I, A195K, A195L, A195M, A195N, A195P, A195Q, A195R, A195S, A195T, A195V, A195W, A195Y, G196A, G196D, G196E, G196F, G196H, G196I, G196K, G196L, G196M, G196N, G196P, G196Q, G196R, G196S, G196T, G196V, G196W, G196Y, D197A, D197E, D197F, D197G, D197H, D197I, D197K, D197L, D197M, D197N, D197P, D197Q, D197R, D197S, D197T, D197V, D197W, D197Y, W198A, W198D, W198E, W198F, W198G, W198H, W198I, W198K, W198L, W198M, W198N, W198P, W198Q, W198R, W198S, W198T, W198V, W198Y, G199A, G199D, G199E, G199F, G199H, G199I, G199K, G199L, G199M, G199N, G199P, G199Q, G199R, G199S, G199T, G199V, G199W, G199Y, F200A, F200D, F200E, F200G, F200H, F200I, F200K, F200L, F200M, F200N, F200P, F200Q, F200R, F200S, F200T, F200V, F200W, F200Y, D201A, D201E, D201F, D201G, D201H, D201I, D201K, D201L, D201M, D201N, D201P, D201Q, D201R, D201S, D201T, D201V, D201W, D201Y, P202A, P202D, P202E, P202F, P202G, P202H, P202I, P202K, P202L, P202M, P202N, P202Q, P202R, P202S, P202T, P202V, P202W, P202Y, A203D, A203E, A203F, A203G, A203H, A203I, A203K, A203L, A203M, A203N, A203P, A203Q, A203R, A203S, A203T, A203V, A203W, A203Y, K204A, K204D, K204E, K204F, K204G, K204H, K204I, K204L, K204M, K204N, K204P, K204Q, K204R, K204S, K204T, K204V, K204W, K204Y, W205A, W205D, W205E, W205F, W205G, W205H, W205I, W205K, W205L, W205M, W205N, W205P, W205Q, W205R, W205S, W205T, W205V, W205Y, A206D, A206E, A206F, A206G, A206H, A206I, A206K, A206L, A206M, A206N, A206P, A206Q, A206R, A206S, A206T, A206V, A206W, A206Y, Y207A, Y207D, Y207E, Y207F, Y207G, Y207H, Y207I, Y207K,

Y207L, Y207M, Y207N, Y207P, Y207Q, Y207R, Y207S, Y207T, Y207V, Y207W, Q208A, Q208D, Q208E, Q208F, Q208G, Q208H, Q208I, Q208K, Q208L, Q208M, Q208N, Q208P, Q208R, Q208S, Q208T, Q208V, Q208W, Q208Y, Y209A, Y209D, Y209E, Y209F, Y209G, Y209H, Y209I, Y209K, Y209L, Y209M, Y209N, Y209P, Y209Q, Y209R, Y209S, Y209T, Y209V, Y209W, D210A, D210E, D210F, D210G, D210H, D210I, D210K, D210L, D210M, D210N, D210P, D210Q, D210R, D210S, D210T, D210V, D210W, D210Y, E211A, E211D, E211F, E211G, E211H, E211I, E211K, E211L, E211M, E211N, E211P, E211Q, E211R, E211S, E211T, E211V, E211W, E211Y, K212A, K212D, K212E, K212F, K212G, K212H, K212I, K212L, K212M, K212N, K212P, K212Q, K212R, K212S, K212T, K212V, K212W, K212Y, N213A, N213D, N213E, N213F, N213G, N213H, N213I, N213K, N213L, N213M, N213P, N213Q, N213R, N213S, N213T, N213V, N213W, N213Y, N214A, N214D, N214E, N214F, N214G, N214H, N214I, N214K, N214L, N214M, N214P, N214Q, N214R, N214S, N214T, N214V, N214W, N214Y, K215A, K215D, K215E, K215F, K215G, K215H, K215I, K215L, K215M, K215N, K215P, K215Q, K215R, K215S, K215T, K215V, K215W, K215Y, F216A, F216D, F216E, F216G, F216H, F216I, F216K, F216L, F216M, F216N, F216P, F216Q, F216R, F216S, F216T, F216V, F216W, F216Y, N217A, N217D, N217E, N217F, N217G, N217H, N217I, N217K, N217L, N217M, N217P, N217Q, N217R, N217S, N217T, N217V, N217W, N217Y, Y218A, Y218D, Y218E, Y218F, Y218G, Y218H, Y218I, Y218K, Y218L, Y218M, Y218N, Y218P, Y218Q, Y218R, Y218S, Y218T, Y218V, Y218W, V219A, V219D, V219E, V219F, V219G, V219H, V219I, V219K, V219L, V219M, V219N, V219P, V219Q, V219R, V219S, V219T, V219W, V219Y, G220A, G220D, G220E, G220F, G220H, G220I, G220K, G220L, G220M, G220N, G220P, G220Q, G220R, G220S, G220T, G220V, G220W, G220Y, K221A, K221D, K221E, K221F, K221G, K221H, K221I, K221L, K221M, K221N, K221P, K221Q, K221R, K221S, K221T, K221V, K221W and K221Y, wherein each position corresponds to the position of the polypeptide of SEQ ID NO: 1.

Some preferred aspect of the invention relates to a DNase variant having DNase activity, wherein the variant comprise one or more substitutions selected from the group consisting of: N4E, L17E, T19A, T19G, T19I, K36P, Q38P, S39V, S39R, A40P, A40H, L41T, L41H, V45H, L51G, K53T, K53P, G54P, A55P, N57H, E64A, E64Q, E64R, E64T, E64I, E64S, T66H, K67A, K67T, N68V, N68P, N68I, N68H, S69A, S69D, S69E, S69K, S69L, S69W, S69Y, S69Q, N70T, N70H, N70G, R71T, D72E, S74H, S74G, G75I, N77T, K82P, K82I, D83T, D83P, D83I, D83H, D83G, P84H, Q85T, Q85P, Q85H, K86T, K86P, K86H, G88P, G88H, A91P, W99T, A101W, K105E, K105N, K105T, K105D, S106T, S115T, L116I, Q135L, G136L, V138I, V138L, V138P, V138Q, L139A, N140R, N140L, N140A, G141L, F151R, D152Y, D152L, D152I, D152A, P153E, S154R, T162R, W163E, F164R, I166Y, I166R, K168N, F169R, F169E, A173I, A173R, A173T, S182R, N183E, D184I, K185Y, S186I, D189G, D189H, K212G, K212P and K215I, wherein each position corresponds to the position of the polypeptide of SEQ ID NO: 1 and wherein the variant has at least 80% sequence identity to the polypeptide shown in SEQ ID NO 1.

In one preferred aspect the invention relates to a DNase variant comprising one or more deletion compared to SEQ ID NO 1, wherein the amino acid in any of the position selected from positions 84, 88, 139, 179 and 180 is deleted.

In some aspect, the variant comprises or consists of an alteration at a position corresponding to position 1 of SEQ ID NO 1. In another aspect, the amino acid at a position corresponding to position 1 is substituted with Ala, Asp, Glu, Phe, Gly, His, Ile, Lys, Leu, Met, Asn, Pro, Gln, Arg, Ser, Thr, Trp or Tyr. In another aspect, the variant comprises or consists of any of the substitutions selected from V1A, V1D, V1E, V1F, V1G, V1H, V1I, V1K, V1L, V1M, V1N, V1P, V1Q, V1R, V1S, V1T, V1W and V1Y of the polypeptide shown in SEQ ID NO: 1 or a polypeptide having at least 80% sequence identity hereto.

In some aspect, the variant comprises or consists of an alteration at a position corresponding to position 2 of SEQ ID NO 1. In another aspect, the amino acid at a position corresponding to position 2 is substituted with Ala, Asp, Glu, Phe, Gly, His, Ile, Lys, Leu, Met, Asn, Gln, Arg, Ser, Val, Thr, Trp or Tyr. In another aspect, the variant comprises or consists of any of the substitutions selected from P2A, P2D, P2E, P2F, P2G, P2H, P2I, P2K, P2L, P2M, P2N, P2Q, P2R, P2S, P2T, P2V, P2W and P2Y of the polypeptide shown in SEQ ID NO: 1 or a polypeptide having at least 80% sequence identity hereto.

In some aspect, the variant comprises or consists of an alteration at a position corresponding to position 3 of SEQ ID NO 1. In another aspect, the amino acid at a position corresponding to position 3 is substituted with Ala, Cys, Asp, Glu, Phe, Gly, His, Ile, Lys, Leu, Met, Asn, Pro, Arg, Ser, Thr, Trp or Tyr. In another aspect, the variant comprises or consists of any of the substitutions selected from V3A, V3C, V3D, V3E, V3F, V3G, V3H, V3I, V3K, V3L, V3M, V3N, V3P, V3R, V3S, V3T, V3W and V3Y of the polypeptide shown in SEQ ID NO: 1 or a polypeptide having at least 80% sequence identity hereto.

In some aspect, the variant comprises or consists of an alteration at a position corresponding to position 4 of SEQ ID NO 1. In another aspect, the amino acid at a position corresponding to position 4 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N4A, N4D, N4E, N4F, N4G, N4H, N4I, N4K, N4L, N4M, N4P, N4Q, N4R, N4S, N4T, N4V, N4W and N4Y of the polypeptide shown in SEQ ID NO: 1 or a polypeptide having at least 80% sequence identity hereto. In a preferred aspect, the variant comprises or consists of the substitution N4E of the polypeptide shown in SEQ ID NO: 1 or a polypeptide having at least 80% sequence identity hereto.

In some aspect, the variant comprises or consists of an alteration at a position corresponding to position 5 of SEQ ID NO 1. In another aspect, the amino acid at a position corresponding to position 5 is substituted with Ala, Asp, Glu, Phe, Gly, His, Ile, Lys, Leu, Met, Asn, Gln, Arg, Ser, Thr, Val, Trp or Tyr. In another aspect, the variant comprises or consists of any of the substitutions selected from P5A, P5D, P5E, P5F, P5G, P5H, P5I, P5K, P5L, P5M, P5N, P5Q, P5R, P5S, P5T, P5V, P5W and P5Y of the polypeptide shown in SEQ ID NO: 1 or a polypeptide having at least 80% sequence identity hereto.

In some aspect, the variant comprises or consists of an alteration at a position corresponding to position 6 of SEQ ID NO 1. In another aspect, the amino acid at a position corresponding to position 6 is substituted with Ala, Asp, Phe, Gly, His, Ile, Lys, Leu, Met, Asn, Pro, Gln, Arg, Ser, Thr, Val, Trp or Tyr. In another aspect, the variant comprises or consists of any of the substitutions selected from E6A, E6D, E6F, E6G, E6H, E6I, E6K, E6L, E6M, E6N, E6P, E6Q, E6R, E6S, E6T, E6V, E6W, E6Y of the polypeptide shown in SEQ ID NO: 1 or a polypeptide having at least 80% sequence identity hereto.

In some aspect, the variant comprises or consists of an alteration at a position corresponding to position 7 of SEQ ID NO 1. In another aspect, the amino acid at a position corresponding to position 7 is substituted with Ala, Asp, Glu, Phe, Gly, His, Ile, Lys, Leu, Met, Asn, Gln, Arg, Ser, Thr, Val, Trp or Tyr. In another aspect, the variant comprises or consists of any of the substitutions selected from P7A, P7D, P7E, P7F, P7G, P7H, P7I, P7K, P7L, P7M, P7N, P7Q, P7R, P7S, P7T, P7V, P7W and P7Y of the polypeptide shown in SEQ ID NO: 1 or a polypeptide having at least 80% sequence identity hereto.

In some aspect, the variant comprises or consists of an alteration at a position corresponding to position 8 of SEQ ID NO 1. In another aspect, the amino acid at a position corresponding to position 8 is substituted with Ala, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from D8A, D8E, D8F, D8G, D8H, D8I, D8K, D8L, D8M, D8N, D8P, D8Q, D8R, D8S, D8T, D8V, D8W and D8Y of the polypeptide shown in SEQ ID NO: 1 or a polypeptide having at least 80% sequence identity hereto.

In some aspect, the variant comprises or consists of an alteration at a position corresponding to position 9 of SEQ ID NO 1. In another aspect, the amino acid at a position corresponding to position 9 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A9D, A9E, A9F, A9G, A9H, A9I, A9K, A9L, A9M, A9N, A9P, A9Q, A9R, A9S, A9T, A9V, A9W and A9Y of the polypeptide shown in SEQ ID NO: 1 or a polypeptide having at least 80% sequence identity hereto.

In some aspect, the variant comprises or consists of an alteration at a position corresponding to position 10 of SEQ ID NO 1. In another aspect, the amino acid at a position corresponding to position 10 is substituted with Ala, Asp, Glu, Phe, Gly, His, Ile, Lys, Leu, Met, Asn, Pro, Gln, Arg, Ser, Val, Trp or Tyr. In another aspect, the variant comprises or consists of any of the substitutions selected from T10A, T10D, T10E, T10F, T10G, T10H, T10I, T10K, T10L, T10M, T10N, T10P, T10Q, T10R, T10S, T10V, T10W and T10Y of the polypeptide shown in SEQ ID NO: 1 or a polypeptide having at least 80% sequence identity hereto.

In some aspect, the variant comprises or consists of an alteration at a position corresponding to position 11 of SEQ ID NO 1. In another aspect, the amino acid at a position corresponding to position 11 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S11A, S11D, S11E, S11F, S11G, S11H, S11I, S11K, S11L, S11M, S11N, S11P, S11Q, S11R, S11T, S11V, S11W and S11Y of the polypeptide shown in SEQ ID NO: 1 or a polypeptide having at least 80% sequence identity hereto.

In some aspect, the variant comprises or consists of an alteration at a position corresponding to position 12 of SEQ ID NO 1. In another aspect, the amino acid at a position corresponding to position 12 is substituted with Ala, Asp, Glu, Phe, Gly, His, Ile, Lys, Leu, Met, Asn, Pro, Gln, Arg, Ser, Thr, Trp or Tyr. In another aspect, the variant comprises or consists of any of the substitutions selected from V12A, V12D, V12E, V12F, V12G, V12H, V12I, V12K, V12L, V12M, V12N, V12P, V12Q, V12R, V12S, V12T, V12W and V12Y of the polypeptide shown in SEQ ID NO: 1 or a polypeptide having at least 80% sequence identity hereto.

In some aspect, the variant comprises or consists of an alteration at a position corresponding to position 13 of SEQ ID NO 1. In another aspect, the amino acid at a position corresponding to position 13 is substituted with Ala, Asp, Phe, Gly, His, Ile, Lys, Leu, Met, Asn, Pro, Gln, Arg, Ser, Thr, Val, Trp or Tyr. In another aspect, the variant comprises or consists of any of the substitutions selected from E13A, E13D, E13F, E13G, E13H, E13I, E13K, E13L, E13M, E13N, E13P, E13Q, E13R, E13S, E13T, E13V, E13W and E13Y of the polypeptide shown in SEQ ID NO: 1 or a polypeptide having at least 80% sequence identity hereto.

In some aspect, the variant comprises or consists of an alteration at a position corresponding to position 14 of SEQ ID NO 1. In another aspect, the amino acid at a position corresponding to position 14 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N14A, N14D, N14E, N14F, N14G, N14H, N14I, N14K, N14L, N14M, N14P, N14Q, N14R, N14S, N14T, N14V, N14W and N14Y of the polypeptide shown in SEQ ID NO: 1 or a polypeptide having at least 80% sequence identity hereto.

In some aspect, the variant comprises or consists of an alteration at a position corresponding to position 15 of SEQ ID NO 1. In another aspect, the amino acid at a position corresponding to position 15 is substituted with Ala, Asp, Glu, Phe, Gly, His, Ile, Lys, Leu, Met, Asn, Pro, Gln, Arg, Ser, Thr, Trp or Tyr. In another aspect, the variant comprises or consists of any of the substitutions selected from V15A, V15D, V15E, V15F, V15G, V15H, V15I, V15K, V15L, V15M, V15N, V15P, V15Q, V15R, V15S, V15T, V15W and V15Y of the polypeptide shown in SEQ ID NO: 1 or a polypeptide having at least 80% sequence identity hereto.

In some aspect, the variant comprises or consists of an alteration at a position corresponding to position 16 of SEQ ID NO 1. In another aspect, the amino acid at a position corresponding to position 16 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A16D, A16E, A16F, A16G, A16H, A16I, A16K, A16L, A16M, A16N, A16P, A16Q, A16R, A165, A16T, A16V, A16W and A16Y of the polypeptide shown in SEQ ID NO: 1 or a polypeptide having at least 80% sequence identity hereto.

In some aspect, the variant comprises or consists of an alteration at a position corresponding to position 17 of SEQ ID NO 1. In another aspect, the amino acid at a position corresponding to position 17 is substituted with Ala, Asp, Glu, Phe, Gly, His, Ile, Met, Asn, Pro, Gln, Arg, Ser, Thr, Val, Trp or Tyr. In another aspect, the variant comprises or consists of any of the substitutions selected from L17A, L17D, L17E, L17F, L17G, L17H, L17I, L17K, L17M, L17N, L17P, L17Q, L17R, L175, L17T, L17V, L17W and L17Y of the polypeptide shown in SEQ ID NO: 1 or a polypeptide having at least 80% sequence identity hereto. In a preferred aspect, the variant comprises or consists of the substitution L17E of the polypeptide shown in SEQ ID NO: 1 or a polypeptide having at least 80% sequence identity hereto.

In some aspect, the variant comprises or consists of an alteration at a position corresponding to position 18 of SEQ ID NO 1. In another aspect, the amino acid at a position corresponding to position 18 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K18A, K18D, K18E, K18F, K18G, K18H, K18I, K18L, K18M, K18N, K18P, K18Q, K18R, K18S, K18T, K18V, K18W and K18Y of the polypeptide shown in SEQ ID NO: 1 or a polypeptide having at least 80% sequence identity hereto.

In some aspect, the variant comprises or consists of an alteration at a position corresponding to position 19 of SEQ ID NO 1. In another aspect, the amino acid at a position corresponding to position 19 is substituted with Ala, Asp, Glu, Phe, Gly, His, Ile, Lys, Leu, Met, Asn, Pro, Gln, Arg, Ser, Val, Trp or Tyr. In another aspect, the variant comprises or consists of any of the substitutions selected from T19A, T19D, T19E, T19F, T19G, T19H, T19I, T19K, T19L, T19M, T19N, T19P, T19Q, T19R, T19S, T19V, T19W and T19Y of the polypeptide shown in SEQ ID NO: 1 or a polypeptide having at least 80% sequence identity hereto. In a preferred aspect, the variant comprises or consists of any of the substitutions T19A, T19G or T19I of the polypeptide shown in SEQ ID NO: 1 or a polypeptide having at least 80% sequence identity hereto.

In some aspect, the variant comprises or consists of an alteration at a position corresponding to position 20 of SEQ ID NO 1. In another aspect, the amino acid at a position corresponding to position 20 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G20A, G20D, G20E, G20F, G20H, G20I, G20K, G20L, G20M, G20N, G20P, G20Q, G20R, G20S, G20T, G20V, G20W and G20Y of the polypeptide shown in SEQ ID NO: 1 or a polypeptide having at least 80% sequence identity hereto.

In some aspect, the variant comprises or consists of an alteration at a position corresponding to position 21 of SEQ ID NO 1. In another aspect, the amino acid at a position corresponding to position 21 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S21A, S21D, S21E, S21F, S21G, S21H, S21I, S21K, S21L, S21M, S21N, S21P, S21Q, S21R, S21T, S21V, S21W and S21Y of the polypeptide shown in SEQ ID NO: 1 or a polypeptide having at least 80% sequence identity hereto.

In some aspect, the variant comprises or consists of an alteration at a position corresponding to position 22 of SEQ ID NO 1. In another aspect, the amino acid at a position corresponding to position 22 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G22A, G22D, G22E, G22F, G22H, G22I, G22K, G22L, G22M, G22N, G22P, G22Q, G22R, G22S, G22T, G22V, G22W and G22Y of the polypeptide shown in SEQ ID NO: 1 or a polypeptide having at least 80% sequence identity hereto.

In some aspect, the variant comprises or consists of an alteration at a position corresponding to position 23 of SEQ ID NO 1. In another aspect, the amino acid at a position corresponding to position 23 is substituted with Ala, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from D23A, D23E, D23F, D23G, D23H, D23I, D23K, D23L, D23M, D23N, D23P, D23Q, D23R, D23S, D23T, D23V, D23W and D23Y of the polypeptide shown in SEQ ID NO: 1 or a polypeptide having at least 80% sequence identity hereto.

In some aspect, the variant comprises or consists of an alteration at a position corresponding to position 24 of SEQ ID NO 1. In another aspect, the amino acid at a position corresponding to position 24 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S24A, S24D, S24E, S24F, S24G, S24H, 5241, S24K, S24L, S24M, S24N, S24P, S24Q, S24R, S24T, S24V, S24W and S24Y of the polypeptide shown in SEQ ID NO: 1 or a polypeptide having at least 80% sequence identity hereto.

In some aspect, the variant comprises or consists of an alteration at a position corresponding to position 25 of SEQ ID NO 1. In another aspect, the amino acid at a position corresponding to position 25 is substituted with Ala, Asp, Glu, Phe, Gly, His, Ile, Lys, Leu, Met, Asn, Pro, Arg, Ser, Thr, Val, Trp or Tyr. In another aspect, the variant comprises or consists of any of the substitutions selected from Q25A, Q25D, Q25E, Q25F, Q25G, Q25H, Q25I, Q25K, Q25L, Q25M, Q25N, Q25P, Q25R, Q25S, Q25T, Q25V, Q25W and Q25Y of the polypeptide shown in SEQ ID NO: 1 or a polypeptide having at least 80% sequence identity hereto.

In some aspect, the variant comprises or consists of an alteration at a position corresponding to position 26 of SEQ ID NO 1. In another aspect, the amino acid at a position corresponding to position 26 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S26A, S26D, S26E, S26F, S26G, S26H, 5261, S26K, S26L, S26M, S26N, S26P, S26Q, S26R, S26T, S26V, S26W and S26Y of the polypeptide shown in SEQ ID NO: 1 or a polypeptide having at least 80% sequence identity hereto.

In some aspect, the variant comprises or consists of an alteration at a position corresponding to position 27 of SEQ ID NO 1. In another aspect, the amino acid at a position corresponding to position 27 is substituted with Ala, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from D27A, D27E, D27F, D27G, D27H, D27I, D27K, D27L, D27M, D27N, D27P, D27Q, D27R, D27S, D27T, D27V, D27W and D27Y of the polypeptide shown in SEQ ID NO: 1 or a polypeptide having at least 80% sequence identity hereto.

In some aspect, the variant comprises or consists of an alteration at a position corresponding to position 28 of SEQ ID NO 1. In another aspect, the amino acid at a position corresponding to position 28 is substituted with Ala, Asp, Glu, Phe, Gly, His, Ile, Lys, Leu, Met, Asn, Gln, Arg, Ser, Thr, Val, Trp or Tyr. In another aspect, the variant comprises or consists of any of the substitutions selected from P28A, P28D, P28E, P28F, P28G, P28H, P28I, P28K, P28L, P28M, P28N, P28Q, P28R, P28S, P28T, P28V, P28W and P28Y of the polypeptide shown in SEQ ID NO: 1 or a polypeptide having at least 80% sequence identity hereto.

In some aspect, the variant comprises or consists of an alteration at a position corresponding to position 29 of SEQ ID NO 1. In another aspect, the amino acid at a position corresponding to position 29 is substituted with Ala, Asp, Glu, Phe, Gly, His, Lys, Leu, Met, Asn, Pro, Gln, Arg, Ser, Thr, Val, Trp or Tyr. In another aspect, the variant comprises or consists of any of the substitutions selected from I29A, I29D, I29E, I29F, I29G, I29H, I29K, I29L, I29M, I29N, I29P, I29Q, I29R, I129S, I29T, I29V, I29W and I29Y of the polypeptide shown in SEQ ID NO: 1 or a polypeptide having at least 80% sequence identity hereto.

In some aspect, the variant comprises or consists of an alteration at a position corresponding to position 30 of SEQ ID NO 1. In another aspect, the amino acid at a position corresponding to position 30 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K30A, K30D, K30E, K30F, K30G, K30H, K30I, K30L, K30M, K30N, K30P, K30Q, K30R, K30S, K30T, K30V, K30W and K30Y of the polypeptide shown in SEQ ID NO: 1 or a polypeptide having at least 80% sequence identity hereto.

In some aspect, the variant comprises or consists of an alteration at a position corresponding to position 31 of SEQ ID NO 1. In another aspect, the amino acid at a position corresponding to position 31 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A31D, A31E, A31F, A31G, A31H, A31I, A31K, A31L, A31M, A31N, A31P, A31Q, A31R, A31S, A31T, A31V, A31W and A31Y of the polypeptide shown in SEQ ID NO: 1 or a polypeptide having at least 80% sequence identity hereto.

In some aspect, the variant comprises or consists of an alteration at a position corresponding to position 32 of SEQ ID NO 1. In another aspect, the amino acid at a position corresponding to position 32 is substituted with Ala, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from D32A, D32E, D32F, D32G, D32H, D32I, D32K, D32L, D32M, D32N, D32P, D32Q, D32R, D32S, D32T, D32V, D32W and D32Y of the polypeptide shown in SEQ ID NO: 1 or a polypeptide having at least 80% sequence identity hereto.

In some aspect, the variant comprises or consists of an alteration at a position corresponding to position 33 of SEQ ID NO 1. In another aspect, the amino acid at a position corresponding to position 33 is substituted with Ala, Asp, Glu, Phe, Gly, His, Ile, Lys, Met, Asn, Pro, Gln, Arg, Ser, Thr, Val, Trp or Tyr. In another aspect, the variant comprises or consists of any of the substitutions selected from L33A, L33D, L33E, L33F, L33G, L33H, L33I, L33K, L33M, L33N, L33P, L33Q, L33R, L33S, L33T, L33V, L33W and L33Y of the polypeptide shown in SEQ ID NO: 1 or a polypeptide having at least 80% sequence identity hereto.

In some aspect, the variant comprises or consists of an alteration at a position corresponding to position 34 of SEQ ID NO 1. In another aspect, the amino acid at a position corresponding to position 34 is substituted with Ala, Asp, Phe, Gly, His, Ile, Lys, Leu, Met, Asn, Pro, Gln, Arg, Ser, Thr, Val, Trp or Tyr. In another aspect, the variant comprises or consists of any of the substitutions selected from E34A, E34D, E34F, E34G, E34H, E34I, E34K, E34L, E34M, E34N, E34P, E34Q, E34R, E34S, E34T, E34V, E34W and E34Y of the polypeptide shown in SEQ ID NO: 1 or a polypeptide having at least 80% sequence identity hereto.

In some aspect, the variant comprises or consists of an alteration at a position corresponding to position 35 of SEQ ID NO 1. In another aspect, the amino acid at a position corresponding to position 35 is substituted with Ala, Asp, Glu, Phe, Gly, His, Ile, Lys, Leu, Met, Asn, Pro, Gln, Arg, Ser, Thr, Trp or Tyr. In another aspect, the variant comprises or consists of any of the substitutions selected from V35A, V35D, V35E, V35F, V35G, V35H, V35I, V35K, V35L, V35M, V35N, V35P, V35Q, V35R, V35S, V35T, V35W and V35Y of the polypeptide shown in SEQ ID NO: 1 or a polypeptide having at least 80% sequence identity hereto.

In some aspect, the variant comprises or consists of an alteration at a position corresponding to position 36 of SEQ ID NO 1. In another aspect, the amino acid at a position corresponding to position 36 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K36A, K36D, K36E, K36F, K36G, K36H, K36I, K36L, K36M, K36N, K36P, K36Q, K36R, K36S, K36T, K36V, K36W and K36Y of the polypeptide shown in SEQ ID NO: 1 or a polypeptide having at least 80% sequence identity hereto. In a preferred aspect, the variant comprises or consists of the substitution K36P of the polypeptide shown in SEQ ID NO: 1 or a polypeptide having at least 80% sequence identity hereto.

In some aspect, the variant comprises or consists of an alteration at a position corresponding to position 37 of SEQ ID NO 1. In another aspect, the amino acid at a position corresponding to position 37 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G37A, G37D, G37E, G37F, G37H, G37I, G37K, G37L, G37M, G37N, G37P, G37Q, G37R, G37S, G37T, G37V, G37W and G37Y of the polypeptide shown in SEQ ID NO: 1 or a polypeptide having at least 80% sequence identity hereto.

In some aspect, the variant comprises or consists of an alteration at a position corresponding to position 38 of SEQ ID NO 1. In another aspect, the amino acid at a position corresponding to position 38 is substituted with Ala, Asp, Glu, Phe, Gly, His, Ile, Lys, Leu, Met, Asn, Pro, Arg, Ser, Thr, Val, Trp or Tyr. In another aspect, the variant comprises or consists of any of the substitutions selected from Q38A, Q38D, Q38E, Q38F, Q38G, Q38H, Q38I, Q38K, Q38L, Q38M, Q38N, Q38P, Q38R, Q38S, Q38T, Q38V, Q38W and Q38Y of the polypeptide shown in SEQ ID NO: 1 or a polypeptide having at least 80% sequence identity hereto. In a preferred aspect, the variant comprises or consists of the substitution Q38P of the polypeptide shown in SEQ ID NO: 1 or a polypeptide having at least 80% sequence identity hereto.

In some aspect, the variant comprises or consists of an alteration at a position corresponding to position 39 of SEQ ID NO 1. In another aspect, the amino acid at a position corresponding to position 39 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S39A, S39D, S39E, S39F, S39G, S39H, S39I, S39K, S39L, S39M, S39N, S39P, S39Q, S39R, S39T, S39V, S39W and S39Y of the polypeptide shown in SEQ ID NO: 1 or a polypeptide having at least 80% sequence identity hereto. In a preferred aspect, the variant comprises or consists of any of the substitutions S39V or S39R of the polypeptide shown in SEQ ID NO: 1 or a polypeptide having at least 80% sequence identity hereto.

In some aspect, the variant comprises or consists of an alteration at a position corresponding to position 40 of SEQ ID NO 1. In another aspect, the amino acid at a position corresponding to position 40 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A40D, A40E, A40F, A40G, A40H, A40I, A40K, A40L, A40M, A40N, A40P, A40Q, A40R, A40S, A40T, A40V, A40W, A40Y of the polypeptide shown in SEQ ID NO: 1 or a polypeptide having at least 80% sequence identity hereto. In a preferred aspect, the variant comprises or consists of any of the substitutions A40P or A40H of the polypeptide shown in SEQ ID NO: 1 or a polypeptide having at least 80% sequence identity hereto.

In some aspect, the variant comprises or consists of an alteration at a position corresponding to position 41 of SEQ ID NO 1. In another aspect, the amino acid at a position corresponding to position 41 is substituted with Ala, Asp, Glu, Phe, Gly, His, Ile, Lys, Met, Asn, Pro, Gln, Arg, Ser, Thr, Val, Trp or Tyr. In another aspect, the variant comprises or consists of any of the substitutions selected from L41A, L41D, L41E, L41F, L41G, L41H, L41I, L41K, L41M, L41N, L41P, L41Q, L41R, L41S, L41T, L41V, L41W and L41Y of the polypeptide shown in SEQ ID NO: 1 or a polypeptide having at least 80% sequence identity hereto. In a preferred aspect, the variant comprises or consists of any of the substitutions L41T or L41H of the polypeptide shown in SEQ ID NO: 1 or a polypeptide having at least 80% sequence identity hereto.

In some aspect, the variant comprises or consists of an alteration at a position corresponding to position 42 of SEQ ID NO 1. In another aspect, the amino acid at a position corresponding to position 42 is substituted with Ala, Asp, Glu, Phe, Gly, His, Ile, Lys, Leu, Met, Asn, Gln, Arg, Ser, Thr, Val, Trp or Tyr. In another aspect, the variant comprises or consists of any of the substitutions selected from P42A, P42D, P42E, P42F, P42G, P42H, P42I, P42K, P42L, P42M, P42N, P42Q, P42R, P42S, P42T, P42V, P42W and P42Y of the polypeptide shown in SEQ ID NO: 1 or a polypeptide having at least 80% sequence identity hereto.

In some aspect, the variant comprises or consists of an alteration at a position corresponding to position 43 of SEQ ID NO 1. In another aspect, the amino acid at a position corresponding to position 43 is substituted with Ala, Asp, Glu, Gly, His, Ile, Lys, Leu, Met, Asn, Pro, Gln, Arg, Ser, Thr, Val, Trp or Tyr. In another aspect, the variant comprises or consists of any of the substitutions selected from F43A, F43D, F43E, F43G, F43H, F43I, F43K, F43L, F43M, F43N, F43P, F43Q, F43R, F43S, F43T, F43V, F43W and F43Y of the polypeptide shown in SEQ ID NO: 1 or a polypeptide having at least 80% sequence identity hereto.

In some aspect, the variant comprises or consists of an alteration at a position corresponding to position 44 of SEQ ID NO 1. In another aspect, the amino acid at a position corresponding to position 44 is substituted with Ala, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from D44A, D44E, D44F, D44G, D44H, D44I, D44K, D44L, D44M, D44N, D44P, D44Q, D44R, D44S, D44T, D44V, D44W and D44Y of the polypeptide shown in SEQ ID NO: 1 or a polypeptide having at least 80% sequence identity hereto.

In some aspect, the variant comprises or consists of an alteration at a position corresponding to position 45 of SEQ ID NO 1. In another aspect, the amino acid at a position corresponding to position 45 is substituted with Ala, Asp, Glu, Phe, Gly, His, Ile, Lys, Leu, Met, Asn, Pro, Gln, Arg, Ser, Thr, Trp or Tyr. In another aspect, the variant comprises or consists of any of the substitutions selected from V45A, V45D, V45E, V45F, V45G, V45H, V45I, V45K, V45L, V45M, V45N, V45P, V45Q, V45R, V45S, V45T, V45W and V45Y of the polypeptide shown in SEQ ID NO: 1 or a polypeptide having at least 80% sequence identity hereto. In a preferred aspect, the variant comprises or consists of the substitution V45H of the polypeptide shown in SEQ ID NO: 1 or a polypeptide having at least 80% sequence identity hereto.

In some aspect, the variant comprises or consists of an alteration at a position corresponding to position 46 of SEQ ID NO 1. In another aspect, the amino acid at a position corresponding to position 46 is substituted with Ala, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from D46A, D46E, D46F, D46G, D46H, D46I, D46K, D46L, D46M, D46N, D46P, D46Q, D46R, D46S, D46T, D46V, D46W and D46Y of the polypeptide shown in SEQ ID NO: 1 or a polypeptide having at least 80% sequence identity hereto.

In some aspect, the variant comprises or consists of an alteration at a position corresponding to position 47 of SEQ ID NO 1. In another aspect, the amino acid at a position corresponding to position 47 is substituted with Ala, Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from C47A, C47D, C47E, C47F, C47G, C47H, C47I, C47K, C47L, C47M, C47N, C47P, C47Q, C47R, C47S, C47T, C47V, C47W and C47Y of the polypeptide shown in SEQ ID NO: 1 or a polypeptide having at least 80% sequence identity hereto.

In some aspect, the variant comprises or consists of an alteration at a position corresponding to position 48 of SEQ ID NO 1. In another aspect, the amino acid at a position corresponding to position 48 is substituted with Ala, Asp, Glu, Phe, Gly, His, Ile, Lys, Leu, Met, Asn, Pro, Gln, Arg, Ser, Thr, Val or Tyr. In another aspect, the variant comprises or consists of any of the substitutions selected from W48A, W48D, W48E, W48F, W48G, W48H, W48I, W48K, W48L, W48M, W48N, W48P, W48Q, W48R, W48S, W48T, W48V and W48Y of the polypeptide shown in SEQ ID NO: 1 or a polypeptide having at least 80% sequence identity hereto.

In some aspect, the variant comprises or consists of an alteration at a position corresponding to position 49 of SEQ ID NO 1. In another aspect, the amino acid at a position corresponding to position 49 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A49D, A49E, A49F, A49G, A49H, A49I, A49K, A49L, A49M, A49N, A49P, A49Q, A49R, A49S, A49T, A49V, A49W and A49Y of the polypeptide shown in SEQ ID NO: 1 or a polypeptide having at least 80% sequence identity hereto.

In some aspect, the variant comprises or consists of an alteration at a position corresponding to position 50 of SEQ ID NO 1. In another aspect, the amino acid at a position corresponding to position 50 is substituted with Ala, Asp, Glu, Phe, Gly, His, Lys, Leu, Met, Asn, Pro, Gln, Arg, Ser, Thr, Val, Trp or Tyr. In another aspect, the variant comprises or consists of any of the substitutions selected from I50A, I50D, I50E, I50F, I50G, I50H, I50K, I50L, I50M, I50N, I50P, I50Q, I50R, I50S, I50T, I50V, I50W and I50Y of the polypeptide shown in SEQ ID NO: 1 or a polypeptide having at least 80% sequence identity hereto.

In some aspect, the variant comprises or consists of an alteration at a position corresponding to position 51 of SEQ ID NO 1. In another aspect, the amino acid at a position corresponding to position 51 is substituted with Ala, Asp, Glu, Phe, Gly, His, Ile, Lys, Met, Asn, Pro, Gln, Arg, Ser, Thr, Val, Trp or Tyr. In another aspect, the variant comprises or consists of any of the substitutions selected from L51A, L51D, L51E, L51F, L51G, L51H, L51I, L51K, L51M, L51N, L51P, L51Q, L51R, L51S, L51T, L51V, L51W and L51Y of the polypeptide shown in SEQ ID NO: 1 or a polypeptide having at least 80% sequence identity hereto. In a preferred aspect, the variant comprises or consists of the substitution L51G of the polypeptide shown in SEQ ID NO: 1 or a polypeptide having at least 80% sequence identity hereto.

In some aspect, the variant comprises or consists of an alteration at a position corresponding to position 53 of SEQ ID NO 1. In another aspect, the amino acid at a position corresponding to position 53 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K53A, K53D, K53E, K53F, K53G, K53H, K53I, K53L, K53M, K53N, K53P, K53Q, K53R, K53S, K53T, K53V, K53W and K53Y of the polypeptide shown in SEQ ID NO: 1 or a polypeptide having at least 80% sequence identity hereto. In a preferred aspect, the variant comprises or consists of any of the substitutions K53T or K53P of the polypeptide shown in SEQ ID NO: 1 or a polypeptide having at least 80% sequence identity hereto.

In some aspect, the variant comprises or consists of an alteration at a position corresponding to position 54 of SEQ ID NO 1. In another aspect, the amino acid at a position corresponding to position 54 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G54A, G54D, G54E, G54F, G54H, G54I, G54K, G54L, G54M, G54N, G54P, G54Q, G54R, G54S, G54T, G54V, G54W and G54Y of the polypeptide shown in SEQ ID NO: 1 or a polypeptide having at least 80% sequence identity hereto. In a preferred aspect, the variant comprises or consists of the substitution G54P of the polypeptide shown in SEQ ID NO: 1 or a polypeptide having at least 80% sequence identity hereto.

In some aspect, the variant comprises or consists of an alteration at a position corresponding to position 55 of SEQ ID NO 1. In another aspect, the amino acid at a position corresponding to position 55 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A55D, A55E, A55F, A55G, A55H, A55I, A55K, A55L, A55M, A55N, A55P, A55Q, A55R, A55S, A55T, A55V, A55W and A55Y of the polypeptide shown in SEQ ID NO: 1 or a polypeptide having at least 80% sequence identity hereto. In a preferred aspect, the variant comprises or consists of the substitution A55P of the polypeptide shown in SEQ ID NO: 1 or a polypeptide having at least 80% sequence identity hereto.

In some aspect, the variant comprises or consists of an alteration at a position corresponding to position 56 of SEQ ID NO 1. In another aspect, the amino acid at a position corresponding to position 56 is substituted with Ala, Asp, Glu, Phe, Gly, His, Ile, Lys, Leu, Met, Asn, Gln, Arg, Ser, Thr, Val, Trp or Tyr. In another aspect, the variant comprises or consists of any of the substitutions selected from P56A, P56D, P56E, P56F, P56G, P56H, P56I, P56K, P56L, P56M, P56N, P56Q, P56R, P56S, P56T, P56V, P56W and P56Y of the polypeptide shown in SEQ ID NO: 1 or a polypeptide having at least 80% sequence identity hereto.

In some aspect, the variant comprises or consists of an alteration at a position corresponding to position 57 of SEQ ID NO 1. In another aspect, the amino acid at a position corresponding to position 57 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N57A, N57D, N57E, N57F, N57G, N57H, N57I, N57K, N57L, N57M, N57P, N57Q, N57R, N57S, N57T, N57V, N57W and N57Y of the polypeptide shown in SEQ ID NO: 1 or a polypeptide having at least 80% sequence identity hereto. In a preferred aspect, the variant comprises or consists of the substitution N57H of the polypeptide shown in SEQ ID NO: 1 or a polypeptide having at least 80% sequence identity hereto.

In some aspect, the variant comprises or consists of an alteration at a position corresponding to position 58 of SEQ ID NO 1. In another aspect, the amino acid at a position corresponding to position 58 is substituted with Ala, Asp, Glu, Phe, Gly, His, Ile, Lys, Leu, Met, Asn, Pro, Gln, Arg, Ser, Thr, Trp or Tyr. In another aspect, the variant comprises or consists of any of the substitutions selected from V58A, V58D, V58E, V58F, V58G, V58H, V58I, V58K, V58L, V58M, V58N, V58P, V58Q, V58R, V58S, V58T, V58W and V58Y of the polypeptide shown in SEQ ID NO: 1 or a polypeptide having at least 80% sequence identity hereto.

In some aspect, the variant comprises or consists of an alteration at a position corresponding to position 59 of SEQ ID NO 1. In another aspect, the amino acid at a position corresponding to position 59 is substituted with Ala, Asp, Glu, Phe, Gly, His, Ile, Lys, Met, Asn, Pro, Gln, Arg, Ser, Thr, Val, Trp or Tyr. In another aspect, the variant comprises or consists of any of the substitutions selected from L59A, L59D, L59E, L59F, L59G, L59H, L59I, L59K, L59M, L59N, L59P, L59Q, L59R, L59S, L59T, L59V, L59W and L59Y of the polypeptide shown in SEQ ID NO: 1 or a polypeptide having at least 80% sequence identity hereto.

In some aspect, the variant comprises or consists of an alteration at a position corresponding to position 60 of SEQ ID NO 1. In another aspect, the amino acid at a position corresponding to position 60 is substituted with Ala, Asp, Glu, Phe, Gly, His, Ile, Lys, Leu, Met, Asn, Pro, Arg, Ser, Thr, Val, Trp or Tyr. In another aspect, the variant comprises or consists of any of the substitutions selected from Q60A, Q60D, Q60E, Q60F, Q60G, Q60H, Q60I, Q60K, Q60L, Q60M, Q60N, Q60P, Q60R, Q60S, Q60T, Q60V, Q60W and Q60Y of the polypeptide shown in SEQ ID NO: 1 or a polypeptide having at least 80% sequence identity hereto.

In some aspect, the variant comprises or consists of an alteration at a position corresponding to position 61 of SEQ ID NO 1. In another aspect, the amino acid at a position corresponding to position 61 is substituted with Ala, Asp, Glu, Phe, Gly, His, Ile, Lys, Leu, Met, Asn, Pro, Gln, Ser, Thr, Val, Trp or Tyr. In another aspect, the variant comprises or consists of any of the substitutions selected from R61A, R61D, R61E, R61F, R61G, R61H, R61I, R61K, R61L, R61M, R61N, R61P, R61Q, R61S, R61T, R61V, R61W and R61Y of the polypeptide shown in SEQ ID NO: 1 or a polypeptide having at least 80% sequence identity hereto.

In some aspect, the variant comprises or consists of an alteration at a position corresponding to position 62 of SEQ ID NO 1. In another aspect, the amino acid at a position corresponding to position 62 is substituted with Ala, Asp, Glu, Phe, Gly, His, Ile, Lys, Leu, Met, Asn, Pro, Gln, Arg, Ser, Thr, Trp or Tyr. In another aspect, the variant comprises or consists of any of the substitutions selected from V62A, V62D, V62E, V62F, V62G, V62H, V62I, V62K, V62L, V62M, V62N, V62P, V62Q, V62R, V62S, V62T, V62W and V62Y of the polypeptide shown in SEQ ID NO: 1 or a polypeptide having at least 80% sequence identity hereto.

In some aspect, the variant comprises or consists of an alteration at a position corresponding to position 63 of SEQ ID NO 1. In another aspect, the amino acid at a position corresponding to position 63 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N63A, N63D, N63E, N63F, N63G, N63H, N63I, N63K, N63L, N63M, N63P, N63Q, N63R, N63S, N63T, N63V, N63W and N63Y of the polypeptide shown in SEQ ID NO: 1 or a polypeptide having at least 80% sequence identity hereto.

In some aspect, the variant comprises or consists of an alteration at a position corresponding to position 64 of SEQ ID NO 1. In another aspect, the amino acid at a position corresponding to position 64 is substituted with Ala, Asp, Phe, Gly, His, Ile, Lys, Leu, Met, Asn, Pro, Gln, Arg, Ser, Thr, Val, Trp or Tyr. In another aspect, the variant comprises or consists of any of the substitutions selected from E64A, E64D, E64F, E64G, E64H, E64I, E64K, E64L, E64M, E64N, E64P, E64Q, E64R, E64S, E64T, E64V, E64W and E64Y of the polypeptide shown in SEQ ID NO: 1 or a polypeptide having at least 80% sequence identity hereto. In a preferred aspect, the variant comprises or consists of any of the substitutions E64A, E64Q, E64R, E64T, E64I or E64S of the polypeptide shown in SEQ ID NO: 1 or a polypeptide having at least 80% sequence identity hereto.

In some aspect, the variant comprises or consists of an alteration at a position corresponding to position 65 of SEQ ID NO 1. In another aspect, the amino acid at a position corresponding to position 65 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K65A, K65D, K65E, K65F, K65G, K65H, K65I, K65L, K65M, K65N, K65P, K65Q, K65R, K65S, K65T, K65V, K65W and K65Y of the polypeptide shown in SEQ ID NO: 1 or a polypeptide having at least 80% sequence identity hereto.

In some aspect, the variant comprises or consists of an alteration at a position corresponding to position 66 of SEQ ID NO 1. In another aspect, the amino acid at a position corresponding to position 66 is substituted with Ala, Asp, Glu, Phe, Gly, His, Ile, Lys, Leu, Met, Asn, Pro, Gln, Arg, Ser, Val, Trp or Tyr. In another aspect, the variant comprises or consists of any of the substitutions selected from T66A, T66D, T66E, T66F, T66G, T66H, T66I, T66K, T66L, T66M, T66N, T66P, T66Q, T66R, T66S, T66V, T66W and T66Y of the polypeptide shown in SEQ ID NO: 1 or a polypeptide having at least 80% sequence identity hereto. In a preferred aspect, the variant comprises or consists of the substitutions T66H of the polypeptide shown in SEQ ID NO: 1 or a polypeptide having at least 80% sequence identity hereto.

In some aspect, the variant comprises or consists of an alteration at a position corresponding to position 67 of SEQ ID NO 1. In another aspect, the amino acid at a position corresponding to position 67 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K67A, K67D, K67E, K67F, K67G, K67H, K67I, K67L, K67M, K67N, K67P, K67Q, K67R, K67S, K67T, K67V, K67W and K67Y of the polypeptide shown in SEQ ID NO: 1 or a polypeptide having at least 80% sequence identity hereto. In a preferred aspect, the variant comprises or consists of any of the substitutions K67A or K67T of the polypeptide shown in SEQ ID NO: 1 or a polypeptide having at least 80% sequence identity hereto.

In some aspect, the variant comprises or consists of an alteration at a position corresponding to position 68 of SEQ ID NO 1. In another aspect, the amino acid at a position corresponding to position 68 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N68A, N68D, N68E, N68F, N68G, N68H, N68I, N68K, N68L, N68M, N68P, N68Q, N68R, N68S, N68T, N68V, N68W and N68Y of the polypeptide shown in SEQ ID NO: 1 or a polypeptide having at least 80% sequence identity hereto. In a preferred aspect, the variant comprises or consists of any of the substitutions N68V, N68P, N68I or N68H of the polypeptide shown in SEQ ID NO: 1 or a polypeptide having at least 80% sequence identity hereto.

In some aspect, the variant comprises or consists of an alteration at a position corresponding to position 69 of SEQ ID NO 1. In another aspect, the amino acid at a position corresponding to position 69 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S69A, S69D, S69E, S69F, S69G, S69H, S69I, S69K, S69L, S69M, S69N, S69P, S69Q, S69R, S69T, S69V, S69W and S69Y of the polypeptide shown in SEQ ID NO: 1 or a polypeptide having at least 80% sequence identity hereto. In a preferred aspect, the variant comprises or consists of any of the substitutions S69A, S69D, S69E, S69K, S69L, S69W, S69Y or S69Q of the polypeptide shown in SEQ ID NO: 1 or a polypeptide having at least 80% sequence identity hereto.

In some aspect, the variant comprises or consists of an alteration at a position corresponding to position 70 of SEQ ID NO 1. In another aspect, the amino acid at a position corresponding to position 70 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N70A, N70D, N70E, N70F, N70G, N70H, N70I, N70K, N70L, N70M, N70P, N70Q, N70R, N70S, N70T, N70V, N70W and N70Y of the polypeptide shown in SEQ ID NO: 1 or a polypeptide having at least 80% sequence identity hereto. In a preferred aspect, the variant comprises or consists of any of the substitutions N70T, N70H or N70G of the polypeptide shown in SEQ ID NO: 1 or a polypeptide having at least 80% sequence identity hereto.

In some aspect, the variant comprises or consists of an alteration at a position corresponding to position 71 of SEQ ID NO 1. In another aspect, the amino acid at a position corresponding to position 71 is substituted with Ala, Asp, Glu, Phe, Gly, His, Ile, Lys, Leu, Met, Asn, Pro, Gln, Ser, Thr, Val, Trp or Tyr. In another aspect, the variant comprises or consists of any of the substitutions selected from R71A, R71D, R71E, R71F, R71G, R71H, R71I, R71K, R71L, R71M, R71N, R71P, R71Q, R71S, R71T, R71V, R71W and R71Y of the polypeptide shown in SEQ ID NO: 1 or a polypeptide having at least 80% sequence identity hereto. In a preferred aspect, the variant comprises or consists of the substitution R71T of the polypeptide shown in SEQ ID NO: 1 or a polypeptide having at least 80% sequence identity hereto.

In some aspect, the variant comprises or consists of an alteration at a position corresponding to position 72 of SEQ ID NO 1. In another aspect, the amino acid at a position corresponding to position 72 is substituted with Ala, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from D72A, D72E, D72F, D72G, D72H, D72I, D72K, D72L, D72M, D72N, D72P, D72Q, D72R, D72S, D72T, D72V, D72W and D72Y of the polypeptide shown in SEQ ID NO: 1 or a polypeptide having at least 80% sequence identity hereto. In a preferred aspect, the variant comprises or consists of the substitution D72E of the polypeptide shown in SEQ ID NO: 1 or a polypeptide having at least 80% sequence identity hereto.

In some aspect, the variant comprises or consists of an alteration at a position corresponding to position 73 of SEQ ID NO 1. In another aspect, the amino acid at a position corresponding to position 73 is substituted with Ala, Asp, Glu, Phe, Gly, His, Ile, Lys, Leu, Met, Asn, Pro, Gln, Ser, Thr, Val, Trp or Tyr. In another aspect, the variant comprises or consists of any of the substitutions selected from R73A, R73D, R73E, R73F, R73G, R73H, R73I, R73K, R73L, R73M, R73N, R73P, R73Q, R73S, R73T, R73V, R73W and R73Y of the polypeptide shown in SEQ ID NO: 1 or a polypeptide having at least 80% sequence identity hereto.

In some aspect, the variant comprises or consists of an alteration at a position corresponding to position 74 of SEQ ID NO 1. In another aspect, the amino acid at a position corresponding to position 74 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S74A, S74D, S74E, S74F, S74G, S74H, S74I, S74K, S74L, S74M, S74N, S74P, S74Q, S74R, S74T, S74V, S74W and S74Y of the polypeptide shown in SEQ ID NO: 1 or a polypeptide having at least 80% sequence identity hereto. In a preferred aspect, the variant comprises or consists of any of the substitutions S74H or S74G of the polypeptide shown in SEQ ID NO: 1 or a polypeptide having at least 80% sequence identity hereto.

In some aspect, the variant comprises or consists of an alteration at a position corresponding to position 75 of SEQ ID NO 1. In another aspect, the amino acid at a position corresponding to position 75 is substituted with Ala, Asp, Glu, Phe, His, Ile, Lys, Leu, Met, Asn, Pro, Gln, Ser, Arg, Thr, Val, Trp or Tyr. In another aspect, the variant comprises or consists of any of the substitutions selected from G75A, G75D, G75E, G75F, G75H, G75I, G75K, G75L, G75M, G75N, G75P, G75Q, G75R, G75S, G75T, G75V, G75W and G75Y of the polypeptide shown in SEQ ID NO: 1 or a polypeptide having at least 80% sequence identity hereto. In a preferred aspect, the variant comprises or consists of the substitution G75I of the polypeptide shown in SEQ ID NO: 1 or a polypeptide having at least 80% sequence identity hereto.

In some aspect, the variant comprises or consists of an alteration at a position corresponding to position 76 of SEQ ID NO 1. In another aspect, the amino acid at a position corresponding to position 76 is substituted with Asp, Glu, Phe, Gly, His, Ile, Lys, Leu, Met, Asn, Pro, Gln, Ser, Arg, Thr, Val, Trp or Tyr. In another aspect, the variant comprises or consists of any of the substitutions selected from A76D, A76E, A76F, A76G, A76H, A76I, A76K, A76L, A76M, A76N, A76P, A76Q, A76R, A76S, A76T, A76V, A76W and A76Y of the polypeptide shown in SEQ ID NO: 1 or a polypeptide having at least 80% sequence identity hereto.

In some aspect, the variant comprises or consists of an alteration at a position corresponding to position 77 of SEQ ID NO 1. In another aspect, the amino acid at a position corresponding to position 77 is substituted with Ala, Asp, Glu, Phe, Gly, His, Ile, Lys, Leu, Met, Pro, Gln, Ser, Arg, Thr, Val, Trp or Tyr. In another aspect, the variant comprises or consists of any of the substitutions selected from N77A, N77D, N77E, N77F, N77G, N77H, N77I, N77K, N77L, N77M, N77P, N77Q, N77R, N77S, N77T, N77V, N77W and N77Y, of the polypeptide shown in SEQ ID NO: 1 or a polypeptide having at least 80% sequence identity hereto. In a preferred aspect, the variant comprises or consists of the substitutions N77T of the polypeptide shown in SEQ ID NO: 1 or a polypeptide having at least 80% sequence identity hereto.

In some aspect, the variant comprises or consists of an alteration at a position corresponding to position 78 of SEQ ID NO 1. In another aspect, the amino acid at a position corresponding to position 78 is substituted with Ala, Asp, Glu, Phe, Gly, His, Ile, Leu, Met, Asn, Pro, Gln, Ser, Arg, Thr, Val, Trp or Tyr. In another aspect, the variant comprises or consists of any of the substitutions selected from K78A, K78D, K78E, K78F, K78G, K78H, K78I, K78L, K78M, K78N, K78P, K78Q, K78R, K78S, K78T, K78V, K78W and K78Y of the polypeptide shown in SEQ ID NO: 1 or a polypeptide having at least 80% sequence identity hereto.

In some aspect, the variant comprises or consists of an alteration at a position corresponding to position 79 of SEQ ID NO 1. In another aspect, the amino acid at a position corresponding to position 79 is substituted with Ala, Asp, Glu, Phe, His, Ile, Lys, Leu, Met, Asn, Pro, Gln, Ser, Arg, Thr, Val, Trp or Tyr. In another aspect, the variant comprises or consists of any of the substitutions selected from G79A, G79D, G79E, G79F, G79H, G79I, G79K, G79L, G79M, G79N, G79P, G79Q, G79R, G79S, G79T, G79V, G79W and G79Y of the polypeptide shown in SEQ ID NO: 1 or a polypeptide having at least 80% sequence identity hereto.

In some aspect, the variant comprises or consists of an alteration at a position corresponding to position 80 of SEQ ID NO 1. In another aspect, the amino acid at a position corresponding to position 80 is substituted with Ala, Asp, Glu, Phe, Gly, His, Ile, Lys, Leu, Met, Asn, Gln, Ser, Arg, Thr, Val, Trp or Tyr. In another aspect, the variant comprises or consists of any of the substitutions selected from P80A, P80D, P80E, P80F, P80G, P80H, P80I, P80K, P80L, P80M, P80N, P80Q, P80R, P80S, P80T, P80V, P80W and P80Y of the polypeptide shown in SEQ ID NO: 1 or a polypeptide having at least 80% sequence identity hereto.

In some aspect, the variant comprises or consists of an alteration at a position corresponding to position 81 of SEQ ID NO 1. In another aspect, the amino acid at a position corresponding to position 81 is substituted with Ala, Asp, Glu, Gly, His, Ile, Lys, Leu, Met, Asn, Pro, Gln, Ser, Arg, Thr, Val, Trp or Tyr. In another aspect, the variant comprises or consists of any of the substitutions selected from F81A, F81D, F81E, F81G, F81H, F81I, F81K, F81L, F81M, F81N, F81P, F81Q, F81R, F81S, F81T, F81V, F81W and F81Y of the polypeptide shown in SEQ ID NO: 1 or a polypeptide having at least 80% sequence identity hereto.

In some aspect, the variant comprises or consists of an alteration at a position corresponding to position 82 of SEQ ID NO 1. In another aspect, the amino acid at a position corresponding to position 82 is substituted with Ala, Asp, Glu, Phe, Gly, His, Ile, Leu, Met, Asn, Pro, Gln, Ser, Arg, Thr, Val, Trp or Tyr. In another aspect, the variant comprises or consists of any of the substitutions selected from K82A, K82D, K82E, K82F, K82G, K82H, K82I, K82L, K82M, K82N, K82P, K82Q, K82R, K82S, K82T, K82V, K82W and K82Y of the polypeptide shown in SEQ ID NO: 1 or a polypeptide having at least 80% sequence identity hereto. In a preferred aspect, the variant comprises or consists of any of the substitutions K82P or K82I of the polypeptide shown in SEQ ID NO: 1 or a polypeptide having at least 80% sequence identity hereto.

In some aspect, the variant comprises or consists of an alteration at a position corresponding to position 83 of SEQ ID NO 1. In another aspect, the amino acid at a position corresponding to position 83 is substituted with Ala, Glu, Phe, Gly, His, Ile, Lys, Leu, Met, Asn, Pro, Gln, Ser, Arg, Thr, Val, Trp or Tyr. In another aspect, the variant comprises or consists of any of the substitutions selected from D83A, D83E, D83F, D83G, D83H, D83I, D83K, D83L, D83M, D83N, D83P, D83Q, D83R, D83S, D83T, D83V, D83W and D83Y of the polypeptide shown in SEQ ID NO: 1 or a polypeptide having at least 80% sequence identity hereto. In a preferred aspect, the variant comprises or consists of any of the substitutions D83T, D83P, D83I, D83H or D83G of the polypeptide shown in SEQ ID NO: 1 or a polypeptide having at least 80% sequence identity hereto.

In some aspect, the variant comprises or consists of an alteration at a position corresponding to position 84 of SEQ ID NO 1. In another aspect, the amino acid at a position corresponding to position 84 is substituted with Ala, Asp, Glu, Phe, Gly, His, Ile, Lys, Leu, Met, Asn, Gln, Ser, Arg, Thr, Val, Trp or Tyr. In another aspect, the variant comprises or consists of any of the substitutions selected from P84A, P84D, P84E, P84F, P84G, P84H, P84I, P84K, P84L, P84M, P84N, P84Q, P84R, P84S, P84T, P84V, P84W and P84Y of the polypeptide shown in SEQ ID NO: 1 or a polypeptide having at least 80% sequence identity hereto. In a preferred aspect, the variant comprises or consists of the substitution P84H of the polypeptide shown in SEQ ID NO: 1 or a polypeptide having at least 80% sequence identity hereto.

In some aspect, the variant comprises or consists of an alteration at a position corresponding to position 85 of SEQ ID NO 1. In another aspect, the amino acid at a position corresponding to position 85 is substituted with Ala, Asp, Glu, Phe, Gly, His, Ile, Lys, Leu, Met, Asn, Pro, Ser, Arg, Thr, Val, Trp or Tyr. In another aspect, the variant comprises or consists of any of the substitutions selected from Q85A, Q85D, Q85E, Q85F, Q85G, Q85H, Q85I, Q85K, Q85L, Q85M, Q85N, Q85P, Q85R, Q85S, Q85T, Q85V, Q85W and Q85Y of the polypeptide shown in SEQ ID NO: 1 or a polypeptide having at least 80% sequence identity hereto. In a preferred aspect, the variant comprises or consists of any of the substitutions Q85T, Q85P or Q85H of the polypeptide shown in SEQ ID NO: 1 or a polypeptide having at least 80% sequence identity hereto.

In some aspect, the variant comprises or consists of an alteration at a position corresponding to position 86 of SEQ ID NO 1. In another aspect, the amino acid at a position corresponding to position 86 is substituted with Ala, Asp, Glu, Phe, Gly, His, Ile, Leu, Met, Asn, Pro, Gln, Ser, Arg, Thr, Val, Trp or Tyr. In another aspect, the variant comprises or consists of any of the substitutions selected from K86A, K86D, K86E, K86F, K86G, K86H, K86I, K86L, K86M, K86N, K86P, K86Q, K86R, K86S, K86T, K86V, K86W and K86Y of the polypeptide shown in SEQ ID NO: 1 or a polypeptide having at least 80% sequence identity hereto. In a preferred aspect, the variant comprises or consists of any of the substitutions K86T, K86P or K86H of the polypeptide shown in SEQ ID NO: 1 or a polypeptide having at least 80% sequence identity hereto.

In some aspect, the variant comprises or consists of an alteration at a position corresponding to position 87 of SEQ ID NO 1. In another aspect, the amino acid at a position corresponding to position 87 is substituted with Ala, Asp, Glu, Phe, Gly, His, Ile, Lys, Leu, Met, Asn, Pro, Gln, Ser, Arg, Thr, Val or Tyr. In another aspect, the variant comprises or consists of any of the substitutions selected from W87A, W87D, W87E, W87F, W87G, W87H, W87I, W87K, W87L, W87M, W87N, W87P, W87Q, W87R, W87S, W87T, W87V and W87Y of the polypeptide shown in SEQ ID NO: 1 or a polypeptide having at least 80% sequence identity hereto.

In some aspect, the variant comprises or consists of an alteration at a position corresponding to position 88 of SEQ ID NO 1. In another aspect, the amino acid at a position corresponding to position 88 is substituted with Ala, Asp, Glu, Phe, His, Ile, Lys, Leu, Met, Asn, Pro, Gln, Ser, Arg, Thr, Val, Trp or Tyr. In another aspect, the variant comprises or consists of any of the substitutions selected from G88A, G88D, G88E, G88F, G88H, G88I, G88K, G88L, G88M, G88N, G88P, G88Q, G88R, G88S, G88T, G88V, G88W and G88Y of the polypeptide shown in SEQ ID NO: 1 or a polypeptide having at least 80% sequence identity hereto. In a preferred aspect, the variant comprises or consists of any of the substitutions G88P or G88H of the polypeptide shown in SEQ ID NO: 1 or a polypeptide having at least 80% sequence identity hereto.

In some aspect, the variant comprises or consists of an alteration at a position corresponding to position 89 of SEQ ID NO 1. In another aspect, the amino acid at a position corresponding to position 89 is substituted with Ala, Asp, Glu, Phe, Gly, His, Lys, Leu, Met, Asn, Pro, Gln, Ser, Arg, Thr, Val, Trp or Tyr. In another aspect, the variant comprises or consists of any of the substitutions selected from I89A, I89D, I89E, I89F, I89G, I89H, I89K, I89L, I89M, I89N, I89P, I89Q, I89R, I89S, I89T, I89V, I89W and I89Y of the polypeptide shown in SEQ ID NO: 1 or a polypeptide having at least 80% sequence identity hereto.

In some aspect, the variant comprises or consists of an alteration at a position corresponding to position 90 of SEQ ID NO 1. In another aspect, the amino acid at a position corresponding to position 90 is substituted with Ala, Asp, Glu, Phe, Gly, His, Ile, Leu, Met, Asn, Pro, Gln, Ser, Arg, Thr, Val, Trp or Tyr. In another aspect, the variant comprises or consists of any of the substitutions selected from K90A, K90D, K90E, K90F, K90G, K90H, K90I, K90L, K90M, K90N, K90P, K90Q, K90R, K90S, K90T, K90V, K90W and K90Y of the polypeptide shown in SEQ ID NO: 1 or a polypeptide having at least 80% sequence identity hereto.

In some aspect, the variant comprises or consists of an alteration at a position corresponding to position 91 of SEQ ID NO 1. In another aspect, the amino acid at a position corresponding to position 91 is substituted with Asp, Glu, Phe, Gly, His, Ile, Lys, Leu, Met, Asn, Pro, Gln, Ser, Arg, Thr, Val, Trp or Tyr. In another aspect, the variant comprises or consists of any of the substitutions selected from A91D, A91E, A91F, A91G, A91H, A91I, A91K, A91L, A91M, A91N, A91P, A91Q, A91R, A91S, A91T, A91V, A91W and A91Y of the polypeptide shown in SEQ ID NO: 1 or a polypeptide having at least 80% sequence identity hereto. In a preferred aspect, the variant comprises or consists of the substitution A91P of the polypeptide shown in SEQ ID NO: 1 or a polypeptide having at least 80% sequence identity hereto.

In some aspect, the variant comprises or consists of an alteration at a position corresponding to position 92 of SEQ ID NO 1. In another aspect, the amino acid at a position corresponding to position 92 is substituted with Ala, Asp, Glu, Phe, Gly, His, Ile, Lys, Met, Asn, Pro, Gln, Ser, Arg, Thr, Val, Trp or Tyr. In another aspect, the variant comprises or consists of any of the substitutions selected from L92A, L92D, L92E, L92F, L92G, L92H, L92I, L92K, L92M, L92N, L92P, L92Q, L92R, L92S, L92T, L92V, L92W and L92Y of the polypeptide shown in SEQ ID NO: 1 or a polypeptide having at least 80% sequence identity hereto.

In some aspect, the variant comprises or consists of an alteration at a position corresponding to position 93 of SEQ ID NO 1. In another aspect, the amino acid at a position corresponding to position 93 is substituted with Ala, Asp, Glu, Phe, Gly, His, Ile, Lys, Leu, Met, Asn, Gln, Ser, Arg, Thr, Val, Trp or Tyr. In another aspect, the variant comprises or consists of any of the substitutions selected from P93A, P93D, P93E, P93F, P93G, P93H, P93I, P93K, P93L, P93M, P93N, P93Q, P93R, P93S, P93T, P93V, P93W and P93Y of the polypeptide shown in SEQ ID NO: 1 or a polypeptide having at least 80% sequence identity hereto.

In some aspect, the variant comprises or consists of an alteration at a position corresponding to position 94 of SEQ ID NO 1. In another aspect, the amino acid at a position corresponding to position 94 is substituted with Ala, Asp, Glu, Phe, Gly, His, Ile, Lys, Leu, Met, Asn, Gln, Ser, Arg, Thr, Val, Trp or Tyr. In another aspect, the variant comprises or consists of any of the substitutions selected from P94A, P94D, P94E, P94F, P94G, P94H, P94I, P94K, P94L, P94M, P94N, P94Q, P94R, P94S, P94T, P94V, P94W and P94Y of the polypeptide shown in SEQ ID NO: 1 or a polypeptide having at least 80% sequence identity hereto.

In some aspect, the variant comprises or consists of an alteration at a position corresponding to position 95 of SEQ ID NO 1. In another aspect, the amino acid at a position corresponding to position 95 is substituted with Ala, Asp, Glu, Phe, Gly, His, Ile, Leu, Met, Asn, Pro, Gln, Ser, Arg, Thr, Val, Trp or Tyr. In another aspect, the variant comprises or consists of any of the substitutions selected from K95A, K95D, K95E, K95F, K95G, K95H, K95I, K95L, K95M, K95N, K95P, K95Q, K95R, K95S, K95T, K95V, K95W and K95Y of the polypeptide shown in SEQ ID NO: 1 or a polypeptide having at least 80% sequence identity hereto.

In some aspect, the variant comprises or consists of an alteration at a position corresponding to position 96 of SEQ ID NO 1. In another aspect, the amino acid at a position corresponding to position 96 is substituted with Ala, Asp, Glu, Phe, Gly, His, Ile, Lys, Leu, Met, Pro, Gln, Ser, Arg, Thr, Val, Trp or Tyr. In another aspect, the variant comprises or consists of any of the substitutions selected from N96A, N96D, N96E, N96F, N96G, N96H, N96I, N96K, N96L, N96M, N96P, N96Q, N96R, N96S, N96T, N96V, N96W and N96Y of the polypeptide shown in SEQ ID NO: 1 or a polypeptide having at least 80% sequence identity hereto.

In some aspect, the variant comprises or consists of an alteration at a position corresponding to position 97 of SEQ ID NO 1. In another aspect, the amino acid at a position corresponding to position 97 is substituted with Ala, Asp, Glu, Phe, Gly, His, Ile, Lys, Leu, Met, Asn, Gln, Ser, Arg, Thr, Val, Trp or Tyr. In another aspect, the variant comprises or consists of any of the substitutions selected from P97A, P97D, P97E, P97F, P97G, P97H, P97I, P97K, P97L, P97M, P97N, P97Q, P97R, P97S, P97T, P97V, P97W and P97Y of the polypeptide shown in SEQ ID NO: 1 or a polypeptide having at least 80% sequence identity hereto.

In some aspect, the variant comprises or consists of an alteration at a position corresponding to position 98 of SEQ ID NO 1. In another aspect, the amino acid at a position corresponding to position 98 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S98A, S98D, S98E, S98F, S98G, S98H, S98I, S98K, S98L, S98M, S98N, S98P, S98Q, S98R, S98T, S98V, S98W and S98Y of the polypeptide shown in SEQ ID NO: 1 or a polypeptide having at least 80% sequence identity hereto.

In some aspect, the variant comprises or consists of an alteration at a position corresponding to position 99 of SEQ ID NO 1. In another aspect, the amino acid at a position corresponding to position 99 is substituted with Ala, Asp, Glu, Phe, Gly, His, Ile, Lys, Leu, Met, Asn, Pro, Gln, Arg, Ser, Thr, Val or Tyr. In another aspect, the variant comprises or consists of any of the substitutions selected from W99A, W99D, W99E, W99F, W99G, W99H, W99I, W99K, W99L, W99M, W99N, W99P, W99Q, W99R, W99S, W99T, W99V and W99Y of the polypeptide shown in SEQ ID NO: 1 or a polypeptide having at least 80% sequence identity hereto. In a preferred aspect, the variant comprises or consists of the substitutions W99T of the polypeptide shown in SEQ ID NO: 1 or a polypeptide having at least 80% sequence identity hereto.

In some aspect, the variant comprises or consists of an alteration at a position corresponding to position 100 of SEQ ID NO 1. In another aspect, the amino acid at a position corresponding to position 100 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S100A, S100D, S100E, S100F, S100G, S100H, S100I, S100K, S100L, S100M, S100N, S100P, S100Q, S100R, S100T, S100V, S100W and S100Y of the polypeptide shown in SEQ ID NO: 1 or a polypeptide having at least 80% sequence identity hereto.

In some aspect, the variant comprises or consists of an alteration at a position corresponding to position 101 of SEQ ID NO 1. In another aspect, the amino acid at a position corresponding to position 101 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A101D, A101E, A101F, A101G, A101H, A101I, A101K, A101L, A101M, A101N, A101P, A101Q, A101R, A101S, A101T, A101V, A101W and A101Y of the polypeptide shown in SEQ ID NO: 1 or a polypeptide having at least 80% sequence identity hereto. In a preferred aspect, the variant comprises or consists of the substitution A101W of the polypeptide shown in SEQ ID NO: 1 or a polypeptide having at least 80% sequence identity hereto.

In some aspect, the variant comprises or consists of an alteration at a position corresponding to position 102 of SEQ ID NO 1. In another aspect, the amino acid at a position corresponding to position 102 is substituted with Ala, Asp, Glu, Phe, Gly, His, Ile, Lys, Leu, Met, Asn, Pro, Arg, Ser, Thr, Val, Trp or Tyr. In another aspect, the variant comprises or consists of any of the substitutions selected from Q102A, Q102D, Q102E, Q102F, Q102G, Q102H, Q102I, Q102K, Q102L, Q102M, Q102N, Q102P, Q102R, Q102S, Q102T, Q102V, Q102W and Q102Y of the polypeptide shown in SEQ ID NO: 1 or a polypeptide having at least 80% sequence identity hereto.

In some aspect, the variant comprises or consists of an alteration at a position corresponding to position 103 of SEQ ID NO 1. In another aspect, the amino acid at a position corresponding to position 103 is substituted with Ala, Glu, Phe, Gly, His, Ile, Lys, Leu, Met, Asn, Gln, Pro, Arg, Ser, Thr, Val, Trp or Tyr. In another aspect, the variant comprises or consists of any of the substitutions selected from D103A, D103E, D103F, D103G, D103H, D103I, D103K, D103L, D103M, D103N, D103P, D103Q, D103R, D103S, D103T, D103V, D103W and D103Y of the polypeptide shown in SEQ ID NO: 1 or a polypeptide having at least 80% sequence identity hereto.

In some aspect, the variant comprises or consists of an alteration at a position corresponding to position 104 of SEQ ID NO 1. In another aspect, the amino acid at a position corresponding to position 104 is substituted with Ala, Asp, Glu, Gly, His, Ile, Lys, Leu, Met, Asn, Gln, Pro, Arg, Ser, Thr, Val, Trp or Tyr. In another aspect, the variant comprises or consists of any of the substitutions selected from F104A, F104D, F104E, F104G, F104H, F104I, F104K, F104L, F104M, F104N, F104P, F104Q, F104R, F104S, F104T, F104V, F104W and F104Y of the polypeptide shown in SEQ ID NO: 1 or a polypeptide having at least 80% sequence identity hereto.

In some aspect, the variant comprises or consists of an alteration at a position corresponding to position 105 of SEQ ID NO 1. In another aspect, the amino acid at a position corresponding to position 105 is substituted with Ala, Asp, Glu, Phe, Gly, His, Ile, Leu, Met, Asn, Gln, Pro, Arg, Ser, Thr, Val, Trp or Tyr. In another aspect, the variant comprises or consists of any of the substitutions selected from K105A, K105D, K105E, K105F, K105G, K105H, K105I, K105L, K105M, K105N, K105P, K105Q, K105R, K105S, K105T, K105V, K105W and K105Y of the polypeptide shown in SEQ ID NO: 1 or a polypeptide having at least 80% sequence identity hereto. In a preferred aspect, the variant comprises or consists of any of the substitutions K105E, K105N, K105T or K105D of the polypeptide shown in SEQ ID NO: 1 or a polypeptide having at least 80% sequence identity hereto.

In some aspect, the variant comprises or consists of an alteration at a position corresponding to position 106 of SEQ ID NO 1. In another aspect, the amino acid at a position corresponding to position 106 is substituted with Ala, Asp, Glu, Phe, Gly, His, Ile, Lys, Leu, Met, Asn, Gln, Pro, Arg, Thr, Val, Trp or Tyr. In another aspect, the variant comprises or consists of any of the substitutions selected from S106A, S106D, S106E, S106F, S106G, S106H, 51061, S106K, S106L, S106M, S106N, S106P, S106Q, S106R, S106T, S106V, S106W and S106Y of the polypeptide shown in SEQ ID NO: 1 or a polypeptide having at least 80% sequence identity hereto. In a preferred aspect, the variant comprises or consists of the substitution S106T of the polypeptide shown in SEQ ID NO: 1 or a polypeptide having at least 80% sequence identity hereto.

In some aspect, the variant comprises or consists of an alteration at a position corresponding to position 107 of SEQ ID NO 1. In another aspect, the amino acid at a position corresponding to position 107 is substituted with Ala, Asp, Glu, Phe, Gly, His, Ile, Lys, Leu, Met, Asn, Gln, Arg, Ser, Thr, Val, Trp or Tyr. In another aspect, the variant comprises or consists of any of the substitutions selected from P107A, P107D, P107E, P107F, P107G, P107H, P107I, P107K, P107L, P107M, P107N, P107Q, P107R, P107S, P107T, P107V, P107W and P107Y of the polypeptide shown in SEQ ID NO: 1 or a polypeptide having at least 80% sequence identity hereto.

In some aspect, the variant comprises or consists of an alteration at a position corresponding to position 108 of SEQ ID NO 1. In another aspect, the amino acid at a position corresponding to position 108 is substituted with Ala, Asp, Phe, Gly, His, Ile, Lys, Leu, Met, Asn, Pro, Gln, Arg, Ser, Thr, Val, Trp or Tyr. In another aspect, the variant comprises or consists of any of the substitutions selected from E108A, E108D, E108F, E108G, E108H, E108I, E108K, E108L, E108M, E108N, E108P, E108Q, E108R, E108S, E108T, E108V, E108W and E108Y of the polypeptide shown in SEQ ID NO: 1 or a polypeptide having at least 80% sequence identity hereto.

In some aspect, the variant comprises or consists of an alteration at a position corresponding to position 109 of SEQ ID NO 1. In another aspect, the amino acid at a position corresponding to position 109 is substituted with Ala, Asp, Phe, Gly, His, Ile, Lys, Leu, Met, Asn, Pro, Gln, Arg, Ser, Thr, Val, Trp or Tyr. In another aspect, the variant comprises or consists of any of the substitutions selected from E109A, E109D, E109F, E109G, E109H, E109I, E109K, E109L, E109M, E109N, E109P, E109Q, E109R, E109S, E109T, E109V, E109W and E109Y of the polypeptide shown in SEQ ID NO: 1 or a polypeptide having at least 80% sequence identity hereto.

In some aspect, the variant comprises or consists of an alteration at a position corresponding to position 110 of SEQ ID NO 1. In another aspect, the amino acid at a position corresponding to position 110 is substituted with Ala, Asp, Glu, Phe, Gly, His, Ile, Lys, Leu, Met, Asn, Pro, Gln, Arg, Ser, Thr, Val or Trp. In another aspect, the variant comprises or consists of any of the substitutions selected from Y110A, Y110D, Y110E, Y110F, Y110G, Y110H, Y110I, Y110K, Y110L, Y110M, Y110N, Y110P, Y110Q, Y110R, Y110S, Y110T, Y110V and Y110W of the polypeptide shown in SEQ ID NO: 1 or a polypeptide having at least 80% sequence identity hereto.

In some aspect, the variant comprises or consists of an alteration at a position corresponding to position 111 of SEQ ID NO 1. In another aspect, the amino acid at a position corresponding to position 111 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A111D, A111E, A111F, A111G, A111H, A111I, A111K, A111L, A111M, A111N, A111P, A111Q, A111R, A111S, A111T, A111V, A111W and A111Y of the polypeptide shown in SEQ ID NO: 1 or a polypeptide having at least 80% sequence identity hereto.

In some aspect, the variant comprises or consists of an alteration at a position corresponding to position 112 of SEQ ID NO 1. In another aspect, the amino acid at a position corresponding to position 112 is substituted with Ala, Asp, Glu, Gly, His, Ile, Lys, Leu, Met, Asn, Pro, Gln, Arg, Ser, Thr, Val, Trp or Tyr. In another aspect, the variant comprises or consists of any of the substitutions selected from F112A, F112D, F112E, F112G, F112H, F112I, F112K, F112L, F112M, F112N, F112P, F112Q, F112R, F112S, F112T, F112V, F112W and F112Y of the polypeptide shown in SEQ ID NO: 1 or a polypeptide having at least 80% sequence identity hereto.

In some aspect, the variant comprises or consists of an alteration at a position corresponding to position 113 of SEQ ID NO 1. In another aspect, the amino acid at a position corresponding to position 113 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A113D, A113E, A113F, A113G, A113H, A113I, A113K, A113L, A113M, A113N, A113P, A113Q, A113R, A113S, A113T, A113V, A113W and A113Y of the polypeptide shown in SEQ ID NO: 1 or a polypeptide having at least 80% sequence identity hereto.

In some aspect, the variant comprises or consists of an alteration at a position corresponding to position 114 of SEQ ID NO 1. In another aspect, the amino acid at a position corresponding to position 114 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S114A, S114D, S114E, S114F, S114G, S114H, S114I, S114K, S114L, S114M, S114N, S114P, S114Q, S114R, S114T, S114V, S114W and S114Y of the polypeptide shown in SEQ ID NO: 1 or a polypeptide having at least 80% sequence identity hereto.

In some aspect, the variant comprises or consists of an alteration at a position corresponding to position 115 of SEQ ID NO 1. In another aspect, the amino acid at a position corresponding to position 115 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S115A, S115D, S115E, S115F, S115G, S115H, S115I, S115K, S115L, S115M, S115N, S115P, S115Q, S115R, S115T, S115V, S115W and S115Y of the polypeptide shown in SEQ ID NO: 1 or a polypeptide having at least 80% sequence identity hereto. In a preferred aspect, the variant comprises or consists of the substitution S115T of the polypeptide shown in SEQ ID NO: 1 or a polypeptide having at least 80% sequence identity hereto.

In some aspect, the variant comprises or consists of an alteration at a position corresponding to position 116 of SEQ ID NO 1. In another aspect, the amino acid at a position corresponding to position 116 is substituted with Ala, Asp, Glu, Phe, Gly, His, Ile, Lys, Met, Asn, Pro, Gln, Arg, Ser, Thr, Val, Trp or Tyr. In another aspect, the variant comprises or consists of any of the substitutions selected from L116A, L116D, L116E, L116F, L116G, L116H, L116I, L116K, L116M, L116N, L116P, L116Q, L116R, L116S, L116T, L116V, L116W and L116Y of the polypeptide shown in SEQ ID NO: 1 or a polypeptide having at least 80% sequence identity hereto. In a preferred aspect, the variant comprises or consists of the substitution L116I of the polypeptide shown in SEQ ID NO: 1 or a polypeptide having at least 80% sequence identity hereto.

In some aspect, the variant comprises or consists of an alteration at a position corresponding to position 117 of SEQ ID NO 1. In another aspect, the amino acid at a position corresponding to position 117 is substituted with Ala, Asp, Glu, Phe, Gly, His, Ile, Lys, Leu, Met, Asn, Pro, Arg, Ser, Thr, Val, Trp or Tyr. In another aspect, the variant comprises or consists of any of the substitutions selected from Q117A, Q117D, Q117E, Q117F, Q117G, Q117H, Q117I, Q117K, Q117L, Q117M, Q117N, Q117P, Q117R, Q117S, Q117T, Q117V, Q117W and Q117Y of the polypeptide shown in SEQ ID NO: 1 or a polypeptide having at least 80% sequence identity hereto.

In some aspect, the variant comprises or consists of an alteration at a position corresponding to position 118 of SEQ ID NO 1. In another aspect, the amino acid at a position corresponding to position 118 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G118A, G118D, G118E, G118F, G118H, G118I, G118K, G118L, G118M, G118N, G118P, G118Q, G118R, G118S, G118T, G118V, G118W and G118Y of the polypeptide shown in SEQ ID NO: 1 or a polypeptide having at least 80% sequence identity hereto.

In some aspect, the variant comprises or consists of an alteration at a position corresponding to position 119 of SEQ ID NO 1. In another aspect, the amino acid at a position corresponding to position 119 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G119A, G119D, G119E, G119F, G119H, G119I, G119K, G119L, G119M, G119N, G119P, G119Q, G119R, G119S, G119T, G119V, G119W and G119Y of the polypeptide shown in SEQ ID NO: 1 or a polypeptide having at least 80% sequence identity hereto.

In some aspect, the variant comprises or consists of an alteration at a position corresponding to position 120 of SEQ ID NO 1. In another aspect, the amino acid at a position corresponding to position 120 is substituted with Ala, Asp, Glu, Phe, Gly, His, Ile, Lys, Leu, Met, Asn, Pro, Gln, Arg, Ser, Val, Trp or Tyr. In another aspect, the variant comprises or consists of any of the substitutions selected from T120A, T120D, T120E, T120F, T120G, T120H, T120I, T120K, T120L, T120M, T120N, T120P, T120Q, T120R, T120S, T120V, T120W and T120Y of the polypeptide shown in SEQ ID NO: 1 or a polypeptide having at least 80% sequence identity hereto.

In some aspect, the variant comprises or consists of an alteration at a position corresponding to position 121 of SEQ ID NO 1. In another aspect, the amino acid at a position corresponding to position 121 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N121A, N121D, N121E, N121F, N121G, N121H, N121I, N121I, N121K, N121L, N121M, N121P, N121Q, N121R, N121S, N121T, N121V, N121W and N121Y of the polypeptide shown in SEQ ID NO: 1 or a polypeptide having at least 80% sequence identity hereto.

In some aspect, the variant comprises or consists of an alteration at a position corresponding to position 122 of SEQ ID NO 1. In another aspect, the amino acid at a position corresponding to position 122 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A122D, A122E, A122F, A122G, A122H, A122I, A122K, A122L, A122M, A122N, A122P, A122Q, A122R, A122S, A122T, A122V, A122W and A122Y of the polypeptide shown in SEQ ID NO: 1 or a polypeptide having at least 80% sequence identity hereto.

In some aspect, the variant comprises or consists of an alteration at a position corresponding to position 123 of SEQ ID NO 1. In another aspect, the amino acid at a position corresponding to position 123 is substituted with Ala, Asp, Glu, Phe, Gly, His, Lys, Leu, Met, Asn, Pro, Gln, Arg, Ser, Thr, Val, Trp or Tyr. In another aspect, the variant comprises or consists of any of the substitutions selected from I123A, I123D, I123E, I123F, I123G, I123H, I123K, I123L, I123M, I123N, I123P, I123Q, I123R, I123S, I123T, I123V, I123W and I123Y of the polypeptide shown in SEQ ID NO: 1 or a polypeptide having at least 80% sequence identity hereto.

In some aspect, the variant comprises or consists of an alteration at a position corresponding to position 124 of SEQ ID NO 1. In another aspect, the amino acid at a position corresponding to position 124 is substituted with Ala, Asp, Glu, Phe, Gly, His, Ile, Lys, Met, Asn, Pro, Gln, Arg, Ser, Thr, Val, Trp or Tyr. In another aspect, the variant comprises or consists of any of the substitutions selected from L124A, L124D, L124E, L124F, L124G, L124H, L124I, L124K, L124M, L124N, L124P, L124Q, L124R, L124S, L124T, L124V, L124W and L124Y of the polypeptide shown in SEQ ID NO: 1 or a polypeptide having at least 80% sequence identity hereto.

In some aspect, the variant comprises or consists of an alteration at a position corresponding to position 125 of SEQ ID NO 1. In another aspect, the amino acid at a position corresponding to position 125 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A125D, A125E, A125F, A125G, A125H, A125I, A125K, A125L, A125M, A125N, A125P, A125Q, A125R, A125S, A125T, A125V, A125W and A125Y of the polypeptide shown in SEQ ID NO: 1 or a polypeptide having at least 80% sequence identity hereto.

In some aspect, the variant comprises or consists of an alteration at a position corresponding to position 126 of SEQ ID NO 1. In another aspect, the amino acid at a position corresponding to position 126 is substituted with Ala, Asp, Glu, Phe, Gly, His, Ile, Lys, Leu, Met, Asn, Gln, Arg, Ser, Thr, Val, Trp or Tyr. In another aspect, the variant comprises or consists of any of the substitutions selected from P126A, P126D, P126E, P126F, P126G, P126H, P126I, P126K, P126L, P126M, P126N, P126Q, P126R, P126S, P126T, P126V, P126W and P126Y of the polypeptide shown in SEQ ID NO: 1 or a polypeptide having at least 80% sequence identity hereto.

In some aspect, the variant comprises or consists of an alteration at a position corresponding to position 127 of SEQ ID NO 1. In another aspect, the amino acid at a position corresponding to position 127 is substituted with Ala, Asp, Glu, Phe, Gly, His, Ile, Lys, Leu, Met, Asn, Pro, Gln, Arg, Ser, Thr, Trp or Tyr. In another aspect, the variant comprises or consists of any of the substitutions selected from V127A, V127D, V127E, V127F, V127G, V127H, V127I, V127K, V127L, V127M, V127N, V127P, V127Q, V127R, V127S, V127T, V127W and V127Y of the polypeptide shown in SEQ ID NO: 1 or a polypeptide having at least 80% sequence identity hereto.

In some aspect, the variant comprises or consists of an alteration at a position corresponding to position 128 of SEQ ID NO 1. In another aspect, the amino acid at a position corresponding to position 128 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N128A, N128D, N128E, N128F, N128G, N128H, N128I, N128K, N128L, N128M, N128P, N128Q, N128R, N128S, N128T, N128V, N128W and N128Y of the polypeptide shown in SEQ ID NO: 1 or a polypeptide having at least 80% sequence identity hereto.

In some aspect, the variant comprises or consists of an alteration at a position corresponding to position 129 of SEQ ID NO 1. In another aspect, the amino acid at a position corresponding to position 129 is substituted with Ala, Asp, Glu, Phe, Gly, His, Ile, Lys, Met, Asn, Pro, Gln, Arg, Ser, Thr, Val, Trp or Tyr. In another aspect, the variant comprises or consists of any of the substitutions selected from L129A, L129D, L129E, L129F, L129G, L129H, L129I, L129K, L129M, L129N, L129P, L129Q, L129R, L129S, L129T, L129V, L129W and L129Y of the polypeptide shown in SEQ ID NO: 1 or a polypeptide having at least 80% sequence identity hereto.

In some aspect, the variant comprises or consists of an alteration at a position corresponding to position 130 of SEQ ID NO 1. In another aspect, the amino acid at a position corresponding to position 130 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A130D, A130E, A130F, A130G, A130H, A130I, A130K, A130L, A130M, A130N, A130P, A130Q, A130R, A130S, A130T, A130V, A130W and A130Y of the polypeptide shown in SEQ ID NO: 1 or a polypeptide having at least 80% sequence identity hereto.

In some aspect, the variant comprises or consists of an alteration at a position corresponding to position 131 of SEQ ID NO 1. In another aspect, the amino acid at a position corresponding to position 131 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S131A, S131D, S131E, S131F, S131G, S131H, S131I, S131K, S131L, S131M, S131N, S131P, S131Q, S131R, S131T, S131V, S131W and S131Y of the polypeptide shown in SEQ ID NO: 1 or a polypeptide having at least 80% sequence identity hereto.

In some aspect, the variant comprises or consists of an alteration at a position corresponding to position 132 of SEQ ID NO 1. In another aspect, the amino acid at a position corresponding to position 132 is substituted with Ala, Asp, Glu, Phe, Gly, His, Ile, Lys, Leu, Met, Asn, Pro, Arg, Ser, Thr, Val, Trp or Tyr. In another aspect, the variant comprises or consists of any of the substitutions selected from Q132A, Q132D, Q132E, Q132F, Q132G, Q132H, Q132I, Q132K, Q132L, Q132M, Q132N, Q132P, Q132R, Q132S, Q132T, Q132V, Q132W and Q132Y of the polypeptide shown in SEQ ID NO: 1 or a polypeptide having at least 80% sequence identity hereto.

In some aspect, the variant comprises or consists of an alteration at a position corresponding to position 133 of SEQ ID NO 1. In another aspect, the amino acid at a position corresponding to position 133 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N133A, N133D, N133E, N133F, N133G, N133H, N133I, N133K, N133L, N133M, N133P, N133Q, N133R, N133S, N133T, N133V, N133W or N133Y of the polypeptide shown in SEQ ID NO: 1 or a polypeptide having at least 80% sequence identity hereto.

In some aspect, the variant comprises or consists of an alteration at a position corresponding to position 134 of SEQ ID NO 1. In another aspect, the amino acid at a position corresponding to position 134 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S134A, S134D, S134E, S134F, S134G, S134H, S134I, S134K, S134L, S134M, S134N, S134P, S134Q, S134R, S134T, S134V, S134W and S134Y of the polypeptide shown in SEQ ID NO: 1 or a polypeptide having at least 80% sequence identity hereto.

In some aspect, the variant comprises or consists of an alteration at a position corresponding to position 135 of SEQ ID NO 1. In another aspect, the amino acid at a position corresponding to position 135 is substituted with Ala, Asp, Glu, Phe, Gly, His, Ile, Lys, Leu, Met, Asn, Pro, Arg, Ser, Thr, Val, Trp or Tyr. In another aspect, the variant comprises or consists of any of the substitutions selected from Q135A, Q135D, Q135E, Q135F, Q135G, Q135H, Q135I, Q135K, Q135L, Q135M, Q135N, Q135P, Q135R, Q135S, Q135T, Q135V, Q135W and Q135Y of the polypeptide shown in SEQ ID NO: 1 or a polypeptide having at least 80% sequence identity hereto. In a preferred aspect, the variant comprises or consists of the substitution Q135L of the polypeptide shown in SEQ ID NO: 1 or a polypeptide having at least 80% sequence identity hereto.

In some aspect, the variant comprises or consists of an alteration at a position corresponding to position 136 of SEQ ID NO 1. In another aspect, the amino acid at a position corresponding to position 136 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G136A, G136D, G136E, G136F, G136H, G136I, G136K, G136L, G136M, G136N, G136P, G136Q, G136R, G136S, G136T, G136V, G136W and G136Y of the polypeptide shown in SEQ ID NO: 1 or a polypeptide having at least 80% sequence identity hereto. In a preferred aspect, the variant comprises or consists of the substitution G136L of the polypeptide shown in SEQ ID NO: 1 or a polypeptide having at least 80% sequence identity hereto.

In some aspect, the variant comprises or consists of an alteration at a position corresponding to position 137 of SEQ ID NO 1. In another aspect, the amino acid at a position corresponding to position 137 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G137A, G137D, G137E, G137F, G137H, G137I, G137K, G137L, G137M, G137N, G137P, G137Q, G137R, G137S, G137T, G137V, G137W and G137Y of the polypeptide shown in SEQ ID NO: 1 or a polypeptide having at least 80% sequence identity hereto.

In some aspect, the variant comprises or consists of an alteration at a position corresponding to position 138 of SEQ ID NO 1. In another aspect, the amino acid at a position corresponding to position 138 is substituted with Ala, Asp, Glu, Phe, Gly, His, Ile, Lys, Leu, Met, Asn, Pro, Gln, Arg, Ser, Thr, Trp or Tyr. In another aspect, the variant comprises or consists of any of the substitutions selected from V138A, V138D, V138E, V138F, V138G, V138H, V138I, V138K, V138L, V138M, V138N, V138P, V138Q, V138R, V138S, V138T, V138W and V138Y of the polypeptide shown in SEQ ID NO: 1 or a polypeptide having at least 80% sequence identity hereto. In a preferred aspect, the variant comprises or consists of any of the substitutions V138I, V138L, V138P or V138Q of the polypeptide shown in SEQ ID NO: 1 or a polypeptide having at least 80% sequence identity hereto.

In some aspect, the variant comprises or consists of an alteration at a position corresponding to position 139 of SEQ ID NO 1. In another aspect, the amino acid at a position corresponding to position 139 is substituted with Ala, Asp, Glu, Phe, Gly, His, Ile, Lys, Met, Asn, Pro, Gln, Arg, Ser, Thr, Val, Trp or Tyr. In another aspect, the variant comprises or consists of any of the substitutions selected from L139A, L139D, L139E, L139F, L139G, L139H, L139I, L139K, L139M, L139N, L139P, L139Q, L139R, L139S, L139T, L139V, L139W and L139Y of the polypeptide shown in SEQ ID NO: 1 or a polypeptide having at least 80% sequence identity hereto. In a preferred aspect, the variant comprises or consists of the substitution L139A of the polypeptide shown in SEQ ID NO: 1 or a polypeptide having at least 80% sequence identity hereto.

In some aspect, the variant comprises or consists of an alteration at a position corresponding to position 140 of SEQ ID NO 1. In another aspect, the amino acid at a position corresponding to position 140 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N140A, N140D, N140E, N140F, N140G, N140H, N140I, N140K, N140L, N140M, N140P, N140Q, N140R, N140S, N140T, N140V, N140W and N140Y of the polypeptide shown in SEQ ID NO: 1 or a polypeptide having at least 80% sequence identity hereto. In a preferred aspect, the variant comprises or consists of any of the substitutions N140R, N140L or N140A of the polypeptide shown in SEQ ID NO: 1 or a polypeptide having at least 80% sequence identity hereto.

In some aspect, the variant comprises or consists of an alteration at a position corresponding to position 141 of SEQ ID NO 1. In another aspect, the amino acid at a position corresponding to position 141 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G141A, G141D, G141E, G141F, G141H, G141I, G141K, G141L, G141M, G141N, G141P, G141Q, G141R, G141S, G141T, G141V, G141W and G141Y of the polypeptide shown in SEQ ID NO: 1 or a polypeptide having at least 80% sequence identity hereto. In a preferred aspect, the variant comprises or consists of the substitution G141L of the polypeptide shown in SEQ ID NO: 1 or a polypeptide having at least 80% sequence identity hereto.

In some aspect, the variant comprises or consists of an alteration at a position corresponding to position 142 of SEQ ID NO 1. In another aspect, the amino acid at a position corresponding to position 142 is substituted with Ala, Asp, Glu, Gly, His, Ile, Lys, Leu, Met, Asn, Pro, Gln, Arg, Ser, Thr, Val, Trp or Tyr. In another aspect, the variant comprises or consists of any of the substitutions selected from F142A, F142D, F142E, F142G, F142H, F142I, F142K, F142L, F142M, F142N, F142P, F142Q, F142R, F142S, F142T, F142V, F142W and F142Y of the polypeptide shown in SEQ ID NO: 1 or a polypeptide having at least 80% sequence identity hereto.

In some aspect, the variant comprises or consists of an alteration at a position corresponding to position 143 of SEQ ID NO 1. In another aspect, the amino acid at a position corresponding to position 143 is substituted with Ala, Asp, Glu, Phe, Gly, His, Ile, Lys, Leu, Met, Asn, Pro, Gln, Arg, Ser, Thr, Val or Trp. In another aspect, the variant comprises or consists of any of the substitutions selected from Y143A, Y143D, Y143E, Y143F, Y143G, Y143H, Y143I, Y143K, Y143L, Y143M, Y143N, Y143P, Y143Q, Y143R, Y143S, Y143T, Y143V and Y143W of the polypeptide shown in SEQ ID NO: 1 or a polypeptide having at least 80% sequence identity hereto.

In some aspect, the variant comprises or consists of an alteration at a position corresponding to position 144 of SEQ ID NO 1. In another aspect, the amino acid at a position corresponding to position 144 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S144A, S144D, S144E, S144F, S144G, S144H, S144I, S144K, S144L, S144M, S144N, S144P, S144Q, S144R, S144T, S144V, S144W and S144Y of the polypeptide shown in SEQ ID NO: 1 or a polypeptide having at least 80% sequence identity hereto.

In some aspect, the variant comprises or consists of an alteration at a position corresponding to position 145 of SEQ ID NO 1. In another aspect, the amino acid at a position corresponding to position 145 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A145D, A145E, A145F, A145G, A145H, A145I, A145K, A145L, A145M, A145N, A145P, A145Q, A145R, A145S, A145T, A145V, A145W and A145Y of the polypeptide shown in SEQ ID NO: 1 or a polypeptide having at least 80% sequence identity hereto.

In some aspect, the variant comprises or consists of an alteration at a position corresponding to position 146 of SEQ ID NO 1. In another aspect, the amino acid at a position corresponding to position 146 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N146A, N146D, N146E, N146F, N146G, N146H, N146I, N146K, N146L, N146M, N146P, N146Q, N146R, N146S, N146T, N146V, N146W and N146Y of the polypeptide shown in SEQ ID NO: 1 or a polypeptide having at least 80% sequence identity hereto.

In some aspect, the variant comprises or consists of an alteration at a position corresponding to position 147 of SEQ ID NO 1. In another aspect, the amino acid at a position corresponding to position 147 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K147A, K147D, K147E, K147F, K147G, K147H, K147I, K147L, K147M, K147N, K147P, K147Q, K147R, K147S, K147T, K147V, K147W and K147Y of the polypeptide shown in SEQ ID NO: 1 or a polypeptide having at least 80% sequence identity hereto.

In some aspect, the variant comprises or consists of an alteration at a position corresponding to position 148 of SEQ ID NO 1. In another aspect, the amino acid at a position corresponding to position 148 is substituted with Ala, Asp, Glu, Phe, Gly, His, Ile, Lys, Leu, Met, Asn, Pro, Gln, Arg, Ser, Thr, Trp or Tyr. In another aspect, the variant comprises or consists of any of the substitutions selected from V148A, V148D, V148E, V148F, V148G, V148H, V148I, V148K, V148L, V148M, V148N, V148P, V148Q, V148R, V148S, V148T, V148W and V148Y of the polypeptide shown in SEQ ID NO: 1 or a polypeptide having at least 80% sequence identity hereto.

In some aspect, the variant comprises or consists of an alteration at a position corresponding to position 149 of SEQ ID NO 1. In another aspect, the amino acid at a position corresponding to position 149 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A149D, A149E, A149F, A149G, A149H, A149I, A149K, A149L, A149M, A149N, A149P, A149Q, A149R, A149S, A149T, A149V, A149W and A149Y of the polypeptide shown in SEQ ID NO: 1 or a polypeptide having at least 80% sequence identity hereto.

In some aspect, the variant comprises or consists of an alteration at a position corresponding to position 150 of SEQ ID NO 1. In another aspect, the amino acid at a position corresponding to position 150 is substituted with Ala, Asp, Glu, Phe, Gly, His, Ile, Lys, Leu, Met, Asn, Pro, Arg, Ser, Thr, Val, Trp or Tyr. In another aspect, the variant comprises or consists of any of the substitutions selected from Q150A, Q150D, Q150E, Q150F, Q150G, Q150H, Q150I, Q150K, Q150L, Q150M, Q150N, Q150P, Q150R, Q150S, Q150T, Q150V, Q150W and Q150Y of the polypeptide shown in SEQ ID NO: 1 or a polypeptide having at least 80% sequence identity hereto.

In some aspect, the variant comprises or consists of an alteration at a position corresponding to position 151 of SEQ ID NO 1. In another aspect, the amino acid at a position corresponding to position 151 is substituted with Ala, Asp, Glu, Gly, His, Ile, Lys, Leu, Met, Asn, Pro, Gln, Arg, Ser, Thr, Val, Trp or Tyr. In another aspect, the variant comprises or consists of any of the substitutions selected from F151A, F151D, F151E, F151G, F151H, F151I, F151K, F151L, F151M, F151N, F151P, F151Q, F151R, F151S, F151T, F151V, F151W and F151Y of the polypeptide shown in SEQ ID NO: 1 or a polypeptide having at least 80% sequence identity hereto. In a preferred aspect, the variant comprises or consists of the substitution F151R of the polypeptide shown in SEQ ID NO: 1 or a polypeptide having at least 80% sequence identity hereto.

In some aspect, the variant comprises or consists of an alteration at a position corresponding to position 152 of SEQ ID NO 1. In another aspect, the amino acid at a position corresponding to position 152 is substituted with Ala, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from D152A, D152E, D152F, D152G, D152H, D152I, D152K, D152L, D152M, D152N, D152P, D152Q, D152R, D152S, D152T, D152V, D152W and D152Y of the polypeptide shown in SEQ ID NO: 1 or a polypeptide having at least 80% sequence identity hereto In a preferred aspect, the variant comprises or consists of any of the substitutions D152Y, D152L, D152I or D152A of the polypeptide shown in SEQ ID NO: 1 or a polypeptide having at least 80% sequence identity hereto.

In some aspect, the variant comprises or consists of an alteration at a position corresponding to position 153 of SEQ ID NO 1. In another aspect, the amino acid at a position corresponding to position 153 is substituted with Ala, Asp, Glu, Phe, Gly, His, Ile, Lys, Leu, Met, Asn, Gln, Arg, Ser, Thr, Val, Trp or Tyr. In another aspect, the variant comprises or consists of any of the substitutions selected from P153A, P153D, P153E, P153F, P153G, P153H, P153I, P153K, P153L, P153M, P153N, P153Q, P153R, P153S, P153T, P153V, P153W and P153Y of the polypeptide shown in SEQ ID NO: 1 or a polypeptide having at least 80% sequence identity hereto. In a preferred aspect, the variant comprises or consists of the substitution P153E of the polypeptide shown in SEQ ID NO: 1 or a polypeptide having at least 80% sequence identity hereto.

In some aspect, the variant comprises or consists of an alteration at a position corresponding to position 154 of SEQ ID NO 1. In another aspect, the amino acid at a position corresponding to position 154 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S154A, S154D, S154E, S154F, S154G, S154H, S154I, S154K, S154L, S154M, S154N, S154P, S154Q, S154R, S154T, S154V, S154W and S154Y of the polypeptide shown in SEQ ID NO: 1 or a polypeptide having at least 80% sequence identity hereto. In a preferred aspect, the variant comprises or consists of the substitution S154R of the polypeptide shown in SEQ ID NO: 1 or a polypeptide having at least 80% sequence identity hereto.

In some aspect, the variant comprises or consists of an alteration at a position corresponding to position 155 of SEQ ID NO 1. In another aspect, the amino acid at a position corresponding to position 155 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K155A, K155D, K155E, K155F, K155G, K155H, K155I, K155L, K155M, K155N, K155P, K155Q, K155R, K155S, K155T, K155V, K155W and K155Y of the polypeptide shown in SEQ ID NO: 1 or a polypeptide having at least 80% sequence identity hereto.

In some aspect, the variant comprises or consists of an alteration at a position corresponding to position 156 of SEQ ID NO 1. In another aspect, the amino acid at a position corresponding to position 156 is substituted with Ala, Asp, Glu, Phe, Gly, His, Ile, Lys, Leu, Met, Asn, Gln, Arg, Ser, Thr, Val, Trp or Tyr. In another aspect, the variant comprises or consists of any of the substitutions selected from P156A, P156D, P156E, P156F, P156G, P156H, P156I, P156K, P156L, P156M, P156N, P156Q, P156R, P156S, P156T, P156V, P156W and P156Y of the polypeptide shown in SEQ ID NO: 1 or a polypeptide having at least 80% sequence identity hereto.

In some aspect, the variant comprises or consists of an alteration at a position corresponding to position 157 of SEQ ID NO 1. In another aspect, the amino acid at a position corresponding to position 157 is substituted with Ala, Asp, Glu, Phe, Gly, His, Ile, Lys, Leu, Met, Asn, Pro, Arg, Ser, Thr, Val, Trp or Tyr. In another aspect, the variant comprises or consists of any of the substitutions selected from Q157A, Q157D, Q157E, Q157F, Q157G, Q157H, Q157I, Q157K, Q157L, Q157M, Q157N, Q157P, Q157R, Q157S, Q157T, Q157V, Q157W and Q157Y of the polypeptide shown in SEQ ID NO: 1 or a polypeptide having at least 80% sequence identity hereto.

In some aspect, the variant comprises or consists of an alteration at a position corresponding to position 158 of SEQ ID NO 1. In another aspect, the amino acid at a position corresponding to position 158 is substituted with Ala, Asp, Glu, Phe, Gly, His, Ile, Lys, Leu, Met, Asn, Pro, Arg, Ser, Thr, Val, Trp or Tyr. In another aspect, the variant comprises or consists of any of the substitutions selected from Q158A, Q158D, Q158E, Q158F, Q158G, Q158H, Q158I, Q158K, Q158L, Q158M, Q158N, Q158P, Q158R, Q158S, Q158T, Q158V, Q158W and Q158Y of the polypeptide shown in SEQ ID NO: 1 or a polypeptide having at least 80% sequence identity hereto.

In some aspect, the variant comprises or consists of an alteration at a position corresponding to position 159 of SEQ ID NO 1. In another aspect, the amino acid at a position corresponding to position 159 is substituted with Ala, Asp, Glu, Phe, Gly, His, Ile, Lys, Leu, Met, Asn, Pro, Gln, Arg, Ser, Val, Trp or Tyr. In another aspect, the variant comprises or consists of any of the substitutions selected from T159A, T159D, T159E, T159F, T159G, T159H, T159I, T159K, T159L, T159M, T159N, T159P, T159Q, T159R, T159S, T159V, T159W and T159Y of the polypeptide shown in SEQ ID NO: 1 or a polypeptide having at least 80% sequence identity hereto.

In some aspect, the variant comprises or consists of an alteration at a position corresponding to position 160 of SEQ ID NO 1. In another aspect, the amino acid at a position corresponding to position 160 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K160A, K160D, K160E, K160F, K160G, K160H, K160I, K160L, K160M, K160N, K160P, K160Q, K160R, K160S, K160T, K160V, K160W and K160Y of the polypeptide shown in SEQ ID NO: 1 or a polypeptide having at least 80% sequence identity hereto.

In some aspect, the variant comprises or consists of an alteration at a position corresponding to position 161 of SEQ ID NO 1. In another aspect, the amino acid at a position corresponding to position 161 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G161A, G161D, G161E, G161F, G161H, G161I, G161K, G161L, G161M, G161N, G161P, G161Q, G161R, G161S, G161T, G161V, G161W and G161Y of the polypeptide shown in SEQ ID NO: 1 or a polypeptide having at least 80% sequence identity hereto.

In some aspect, the variant comprises or consists of an alteration at a position corresponding to position 162 of SEQ ID NO 1. In another aspect, the amino acid at a position corresponding to position 162 is substituted with Ala, Asp, Glu, Phe, Gly, His, Ile, Lys, Leu, Met, Asn, Pro, Gln, Arg, Ser, Val, Trp or Tyr. In another aspect, the variant comprises or consists of any of the substitutions selected from T162A, T162D, T162E, T162F, T162G, T162H, T162I, T162K, T162L, T162M, T162N, T162P, T162Q, T162R, T162S, T162T, T162V, T162W and T162Y of the polypeptide shown in SEQ ID NO: 1 or a polypeptide having at least 80% sequence identity hereto. In a preferred aspect, the variant comprises or consists of the substitution T162R of the polypeptide shown in SEQ ID NO: 1 or a polypeptide having at least 80% sequence identity hereto.

In some aspect, the variant comprises or consists of an alteration at a position corresponding to position 163 of SEQ ID NO 1. In another aspect, the amino acid at a position corresponding to position 163 is substituted with Ala, Asp, Glu, Phe, Gly, His, Ile, Lys, Leu, Met, Asn, Pro, Gln, Arg, Ser, Thr, Val or Tyr. In another aspect, the variant comprises or consists of any of the substitutions selected from W163A, W163D, W163E, W163F, W163G, W163H, W163I, W163K, W163L, W163M, W163N, W163P, W163Q, W163R, W163S, W163T, W163V and W163Y of the polypeptide shown in SEQ ID NO: 1 or a polypeptide having at least 80% sequence identity hereto. In a preferred aspect, the variant comprises or consists of the substitution W163E of the polypeptide shown in SEQ ID NO: 1 or a polypeptide having at least 80% sequence identity hereto.

In some aspect, the variant comprises or consists of an alteration at a position corresponding to position 164 of SEQ ID NO 1. In another aspect, the amino acid at a position corresponding to position 164 is substituted with Ala, Asp, Glu, Gly, His, Ile, Lys, Leu, Met, Asn, Pro, Gln, Arg, Ser, Thr, Val, Trp or Tyr. In another aspect, the variant comprises or consists of any of the substitutions selected from F164A, F164D, F164E, F164G, F164H, F164I, F164K, F164L, F164M, F164N, F164P, F164Q, F164R, F164S, F164T, F164V, F164W and F164Y of the polypeptide shown in SEQ ID NO: 1 or a polypeptide having at least 80% sequence identity hereto. In a preferred aspect, the variant comprises or consists of the substitution F164R of the polypeptide shown in SEQ ID NO: 1 or a polypeptide having at least 80% sequence identity hereto.

In some aspect, the variant comprises or consists of an alteration at a position corresponding to position 165 of SEQ ID NO 1. In another aspect, the amino acid at a position corresponding to position 165 is substituted with Ala, Asp, Glu, Phe, Gly, His, Ile, Lys, Leu, Met, Asn, Pro, Arg, Ser, Thr, Val, Trp or Tyr. In another aspect, the variant comprises or consists of any of the substitutions selected from Q165A, Q165D, Q165E, Q165F, Q165G, Q165H, Q165I, Q165K, Q165L, Q165M, Q165N, Q165P, Q165R, Q165S, Q165T, Q165V, Q165W and Q165Y of the polypeptide shown in SEQ ID NO: 1 or a polypeptide having at least 80% sequence identity hereto.

In some aspect, the variant comprises or consists of an alteration at a position corresponding to position 166 of SEQ ID NO 1. In another aspect, the amino acid at a position corresponding to position 166 is substituted with Ala, Asp, Glu, Phe, Gly, His, Lys, Leu, Met, Asn, Pro, Gln, Arg, Ser, Thr, Val, Trp or Tyr. In another aspect, the variant comprises or consists of any of the substitutions selected from I166A, I166D, I166E, I166F, I166G, I166H, I166K, I166L, I166M, I166N, I166P, I166Q, I166R, I166S, I166T, I166V, I166W and I166Y of the polypeptide shown in SEQ ID NO: 1 or a polypeptide having at least 80% sequence identity hereto. In a preferred aspect, the variant comprises or consists of any of the substitutions I166Y or I166R of the polypeptide shown in SEQ ID NO: 1 or a polypeptide having at least 80% sequence identity hereto.

In some aspect, the variant comprises or consists of an alteration at a position corresponding to position 167 of SEQ ID NO 1. In another aspect, the amino acid at a position corresponding to position 167 is substituted with Ala, Asp, Glu, Phe, Gly, His, Ile, Lys, Leu, Met, Asn, Pro, Gln, Arg, Ser, Val, Trp or Tyr. In another aspect, the variant comprises or consists of any of the substitutions selected from T167A, T167D, T167E, T167F, T167G, T167H, T167I, T167K, T167L, T167M, T167N, T167P, T167Q, T167R, T167S, T167V, T167W and T167Y of the polypeptide shown in SEQ ID NO: 1 or a polypeptide having at least 80% sequence identity hereto.

In some aspect, the variant comprises or consists of an alteration at a position corresponding to position 168 of SEQ ID NO 1. In another aspect, the amino acid at a position corresponding to position 168 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K168A, K168D, K168E, K168F, K168G, K168H, K168I, K168L, K168M, K168N, K168P, K168Q, K168R, K168S, K168T, K168V, K168W and K168Y of the polypeptide shown in SEQ ID NO: 1 or a polypeptide having at least 80% sequence identity hereto. In a preferred aspect, the variant comprises or consists of the substitution K168N of the polypeptide shown in SEQ ID NO: 1 or a polypeptide having at least 80% sequence identity hereto.

In some aspect, the variant comprises or consists of an alteration at a position corresponding to position 169 of SEQ ID NO 1. In another aspect, the amino acid at a position corresponding to position 169 is substituted with Ala, Asp, Glu, Gly, His, Ile, Lys, Leu, Met, Asn, Pro, Gln, Arg, Ser, Thr, Val, Trp or Tyr. In another aspect, the variant comprises or consists of any of the substitutions selected from F169A, F169D, F169E, F169G, F169H, F169I, F169K, F169L, F169M, F169N, F169P, F169Q, F169R, F169S, F169T, F169V, F169W and F169Y of the polypeptide shown in SEQ ID NO: 1 or a polypeptide having at least 80% sequence identity hereto. In a preferred aspect, the variant comprises or consists of any of the substitutions F169R or F169E of the polypeptide shown in SEQ ID NO: 1 or a polypeptide having at least 80% sequence identity hereto.

In some aspect, the variant comprises or consists of an alteration at a position corresponding to position 170 of SEQ ID NO 1. In another aspect, the amino acid at a position corresponding to position 170 is substituted with Ala, Asp, Glu, Phe, Gly, His, Ile, Lys, Leu, Met, Asn, Pro, Gln, Arg, Ser, Val, Trp or Tyr. In another aspect, the variant comprises or consists of any of the substitutions selected from T170A, T170D, T170E, T170F, T170G, T170H, T170I, T170K, T170L, T170M, T170N, T170P, T170Q, T170R, T170S, T170V, T170W and T170Y of the polypeptide shown in SEQ ID NO: 1 or a polypeptide having at least 80% sequence identity hereto.

In some aspect, the variant comprises or consists of an alteration at a position corresponding to position 171 of SEQ ID NO 1. In another aspect, the amino acid at a position corresponding to position 171 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G171A, G171D, G171E, G171F, G171H, G171I, G171K, G171L, G171M, G171N, G171P, G171Q, G171R, G171S, G171T, G171V, G171W and G171Y of the polypeptide shown in SEQ ID NO: 1 or a polypeptide having at least 80% sequence identity hereto.

In some aspect, the variant comprises or consists of an alteration at a position corresponding to position 172 of SEQ ID NO 1. In another aspect, the amino acid at a position corresponding to position 172 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A172D, A172E, A172F, A172G, A172H, A172I, A172K, A172L, A172M, A172N, A172P, A172Q, A172R, A172S, A172T, A172V, A172W and A172Y of the polypeptide shown in SEQ ID NO: 1 or a polypeptide having at least 80% sequence identity hereto.

In some aspect, the variant comprises or consists of an alteration at a position corresponding to position 173 of SEQ ID NO 1. In another aspect, the amino acid at a position corresponding to position 173 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A173D, A173E, A173F, A173G, A173H, A173I, A173K, A173L, A173M, A173N, A173P, A173Q, A173R, A173S, A173T, A173V, A173W and A173Y of the polypeptide shown in SEQ ID NO: 1 or a polypeptide having at least 80% sequence identity hereto. In a preferred aspect, the variant comprises or consists of any of the substitutions A173I, A173R or A173T of the polypeptide shown in SEQ ID NO: 1 or a polypeptide having at least 80% sequence identity hereto.

In some aspect, the variant comprises or consists of an alteration at a position corresponding to position 174 of SEQ ID NO 1. In another aspect, the amino acid at a position corresponding to position 174 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G174A, G174D, G174E, G174F, G174H, G174I, G174K, G174L, G174M, G174N, G174P, G174Q, G174R, G174S, G174T, G174V, G174W and G174Y of the polypeptide shown in SEQ ID NO: 1 or a polypeptide having at least 80% sequence identity hereto.

In some aspect, the variant comprises or consists of an alteration at a position corresponding to position 175 of SEQ ID NO 1. In another aspect, the amino acid at a position corresponding to position 175 is substituted with Ala, Asp, Glu, Phe, Gly, His, Ile, Lys, Leu, Met, Asn, Gln, Arg, Ser, Thr, Val, Trp or Tyr. In another aspect, the variant comprises or consists of any of the substitutions selected from P175A, P175D, P175E, P175F, P175G, P175H, P175I, P175K, P175L, P175M, P175N, P175Q, P175R, P175S, P175T, P175V, P175W and P175Y of the polypeptide shown in SEQ ID NO: 1 or a polypeptide having at least 80% sequence identity hereto.

In some aspect, the variant comprises or consists of an alteration at a position corresponding to position 176 of SEQ ID NO 1. In another aspect, the amino acid at a position corresponding to position 176 is substituted with Ala, Asp, Glu, Phe, Gly, His, Ile, Lys, Leu, Met, Asn, Pro, Gln, Arg, Ser, Thr, Val or Trp. In another aspect, the variant comprises or consists of any of the substitutions selected from Y176A, Y176D, Y176E, Y176F, Y176G, Y176H, Y176I, Y176K, Y176L, Y176M, Y176N, Y176P, Y176Q, Y176R, Y176S, Y176T, Y176V and Y176W of the polypeptide shown in SEQ ID NO: 1 or a polypeptide having at least 80% sequence identity hereto.

In some aspect, the variant comprises or consists of an alteration at a position corresponding to position 178 of SEQ ID NO 1. In another aspect, the amino acid at a position corresponding to position 178 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K178A, K178D, K178E, K178F, K178G, K178H, K178I, K178L, K178M, K178N, K178P, K178Q, K178R, K178S, K178T, K178V, K178W and K178Y of the polypeptide shown in SEQ ID NO: 1 or a polypeptide having at least 80% sequence identity hereto.

In some aspect, the variant comprises or consists of an alteration at a position corresponding to position 179 of SEQ ID NO 1. In another aspect, the amino acid at a position corresponding to position 179 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A179D, A179E, A179F, A179G, A179H, A179I, A179K, A179L, A179M, A179N, A179P, A179Q, A179R, A179S, A179T, A179V, A179W and A179Y of the polypeptide shown in SEQ ID NO: 1 or a polypeptide having at least 80% sequence identity hereto.

In some aspect, the variant comprises or consists of an alteration at a position corresponding to position 180 of SEQ ID NO 1. In another aspect, the amino acid at a position corresponding to position 180 is substituted with Ala, Asp, Glu, Phe, Gly, His, Ile, Lys, Met, Asn, Pro, Gln, Arg, Ser, Thr, Val, Trp or Tyr. In another aspect, the variant comprises or consists of any of the substitutions selected from L180A, L180D, L180E, L180F, L180G, L180H, L180I, L180K, L180M, L180N, L180P, L180Q, L180R, L180S, L180T, L180V, L180W and L180Y of the polypeptide shown in SEQ ID NO: 1 or a polypeptide having at least 80% sequence identity hereto.

In some aspect, the variant comprises or consists of an alteration at a position corresponding to position 181 of SEQ ID NO 1. In another aspect, the amino acid at a position corresponding to position 181 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G181A, G181D, G181E, G181F, G181H, G181I, G181K, G181L, G181M, G181N, G181P, G181Q, G181R, G181S, G181T, G181V, G181W and G181Y of the polypeptide shown in SEQ ID NO: 1 or a polypeptide having at least 80% sequence identity hereto.

In some aspect, the variant comprises or consists of an alteration at a position corresponding to position 182 of SEQ ID NO 1. In another aspect, the amino acid at a position corresponding to position 182 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S182A, S182D, S182E, S182F, S182G, S182H, S182I, S182K, S182L, S182M, S182N, S182P, S182Q, S182R, S182T, S182V, S182W and S182Y of the polypeptide shown in SEQ ID NO: 1 or a polypeptide having at least 80% sequence identity hereto. In a preferred aspect, the variant comprises or consists of any of the substitutions S182Y of the polypeptide shown in SEQ ID NO: 1 or a polypeptide having at least 80% sequence identity hereto.

In some aspect, the variant comprises or consists of an alteration at a position corresponding to position 183 of SEQ ID NO 1. In another aspect, the amino acid at a position corresponding to position 183 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N183A, N183D, N183E, N183F, N183G, N183H, N183I, N183K, N183L, N183M, N183P, N183Q, N183R, N183S, N183T, N183V, N183W and N183Y of the polypeptide shown in SEQ ID NO: 1 or a polypeptide having at least 80% sequence identity hereto. In a preferred aspect, the variant comprises or consists of the substitution N183E of the polypeptide shown in SEQ ID NO: 1 or a polypeptide having at least 80% sequence identity hereto.

In some aspect, the variant comprises or consists of an alteration at a position corresponding to position 184 of SEQ ID NO 1. In another aspect, the amino acid at a position corresponding to position 184 is substituted with Ala, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from D184A, D184E, D184F, D184G, D184H, D184I, D184K, D184L, D184M, D184N, D184P, D184Q, D184R, D184S, D184T, D184V, D184W and D184Y of the polypeptide shown in SEQ ID NO: 1 or a polypeptide having at least 80% sequence identity hereto. In a preferred aspect, the variant comprises or consists of the substitution D184I of the polypeptide shown in SEQ ID NO: 1 or a polypeptide having at least 80% sequence identity hereto.

In some aspect, the variant comprises or consists of an alteration at a position corresponding to position 185 of SEQ ID NO 1. In another aspect, the amino acid at a position corresponding to position 185 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K185A, K185D, K185E, K185F, K185G, K185H, K185I, K185L, K185M, K185N, K185P, K185Q, K185R, K185S, K185T, K185V, K185W and K185Y of the polypeptide shown in SEQ ID NO: 1 or a polypeptide having at least 80% sequence identity hereto. In a preferred aspect, the variant comprises or consists of the substitution K185Y of the polypeptide shown in SEQ ID NO: 1 or a polypeptide having at least 80% sequence identity hereto.

In some aspect, the variant comprises or consists of an alteration at a position corresponding to position 186 of SEQ ID NO 1. In another aspect, the amino acid at a position corresponding to position 186 is substituted with Ala, Asp, Glu, Phe, Gly, His, Ile, Lys, Leu, Met, Asn, Pro, Gln, Arg, Thr, Val, Trp or Tyr. In another aspect, the variant comprises or consists of any of the substitutions selected from S186A, S186D, S186E, S186F, S186G, S186H, S186I, S186K, S186L, S186M, S186N, S186P, S186Q, S186R, S186T, S186V, S186W and S186Y of the polypeptide shown in SEQ ID NO: 1 or a polypeptide having at least 80% sequence identity hereto. In a preferred aspect, the variant comprises or consists of the substitution S186I of the polypeptide shown in SEQ ID NO: 1 or a polypeptide having at least 80% sequence identity hereto.

In some aspect, the variant comprises or consists of an alteration at a position corresponding to position 187 of SEQ ID NO 1. In another aspect, the amino acid at a position corresponding to position 187 is substituted with Ala, Asp, Glu, Phe, Gly, His, Ile, Lys, Leu, Met, Asn, Pro, Gln, Arg, Ser, Thr, Trp or Tyr. In another aspect, the variant comprises or consists of any of the substitutions selected from V187A, V187D, V187E, V187F, V187G, V187H, V187I, V187K, V187L, V187M, V187N, V187P, V187Q, V187R, V187S, V187T, V187W and V187Y of the polypeptide shown in SEQ ID NO: 1 or a polypeptide having at least 80% sequence identity hereto.

In some aspect, the variant comprises or consists of an alteration at a position corresponding to position 189 of SEQ ID NO 1. In another aspect, the amino acid at a position corresponding to position 189 is substituted with Ala, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from D189A, D189E, D189F, D189G, D189H, D189I, D189K, D189L, D189M, D189N, D189P, D189Q, D189R, D189S, D189T, D189V, D189W and D189Y of the polypeptide shown in SEQ ID NO: 1 or a polypeptide having at least 80% sequence identity hereto. In a preferred aspect, the variant comprises or consists of any of the substitutions D189G or D189H of the polypeptide shown in SEQ ID NO: 1 or a polypeptide having at least 80% sequence identity hereto.

In some aspect, the variant comprises or consists of an alteration at a position corresponding to position 190 of SEQ ID NO 1. In another aspect, the amino acid at a position corresponding to position 190 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K190A, K190D, K190E, K190F, K190G, K190H, K190I, K190L, K190M, K190N, K190P, K190Q, K190R, K190S, K190T, K190V, K190W and K190Y of the polypeptide shown in SEQ ID NO: 1 or a polypeptide having at least 80% sequence identity hereto.

In some aspect, the variant comprises or consists of an alteration at a position corresponding to position 191 of SEQ ID NO 1. In another aspect, the amino acid at a position corresponding to position 191 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N191A, N191D, N191E, N191F, N191G, N191H, N191I, N191K, N191L, N191M, N191P, N191Q, N191R, N191S, N191T, N191V, N191W and N191Y of the polypeptide shown in SEQ ID NO: 1 or a polypeptide having at least 80% sequence identity hereto.

In some aspect, the variant comprises or consists of an alteration at a position corresponding to position 192 of SEQ ID NO 1. In another aspect, the amino acid at a position corresponding to position 192 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K192A, K192D, K192E, K192F, K192G, K192H, K192I, K192L, K192M, K192N, K192P, K192Q, K192R, K192S, K192T, K192V, K192W and K192Y of the polypeptide shown in SEQ ID NO: 1 or a polypeptide having at least 80% sequence identity hereto.

In some aspect, the variant comprises or consists of an alteration at a position corresponding to position 193 of SEQ ID NO 1. In another aspect, the amino acid at a position corresponding to position 193 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N193A, N193D, N193E, N193F, N193G, N193H, N193I, N193K, N193L, N193M, N193P, N193Q, N193R, N193S, N193T, N193V, N193W and N193Y of the polypeptide shown in SEQ ID NO: 1 or a polypeptide having at least 80% sequence identity hereto.

In some aspect, the variant comprises or consists of an alteration at a position corresponding to position 194 of SEQ ID NO 1. In another aspect, the amino acid at a position corresponding to position 194 is substituted with Ala, Asp, Glu, Phe, Gly, His, Lys, Leu, Met, Asn, Pro, Gln, Arg, Ser, Thr, Val, Trp or Tyr. In another aspect, the variant comprises or consists of any of the substitutions selected from I194A, I194D, I194E, I194F, I194G, I194H, I194K, I194L, I194M, I194N, I194P, I194Q, I194R, I194S, I194T, I194V, I194W and I194Y of the polypeptide shown in SEQ ID NO: 1 or a polypeptide having at least 80% sequence identity hereto.

In some aspect, the variant comprises or consists of an alteration at a position corresponding to position 195 of SEQ ID NO 1. In another aspect, the amino acid at a position corresponding to position 195 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A195D, A195E, A195F, A195G, A195H, A195I, A195K, A195L, A195M, A195N, A195P, A195Q, A195R, A195S, A195T, A195V, A195W and A195Y of the polypeptide shown in SEQ ID NO: 1 or a polypeptide having at least 80% sequence identity hereto.

In some aspect, the variant comprises or consists of an alteration at a position corresponding to position 196 of SEQ ID NO 1. In another aspect, the amino acid at a position corresponding to position 196 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G196A, G196D, G196E, G196F, G196H, G196I, G196K, G196L, G196M, G196N, G196P, G196Q, G196R, G196S, G196T, G196V, G196W and G196Y of the polypeptide shown in SEQ ID NO: 1 or a polypeptide having at least 80% sequence identity hereto.

In some aspect, the variant comprises or consists of an alteration at a position corresponding to position 197 of SEQ ID NO 1. In another aspect, the amino acid at a position corresponding to position 197 is substituted with Ala, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from D197A, D197E, D197F, D197G, D197H, D197I, D197K, D197L, D197M, D197N, D197P, D197Q, D197R, D197S, D197T, D197V, D197W and D197Y of the polypeptide shown in SEQ ID NO: 1 or a polypeptide having at least 80% sequence identity hereto.

In some aspect, the variant comprises or consists of an alteration at a position corresponding to position 198 of SEQ ID NO 1. In another aspect, the amino acid at a position corresponding to position 198 is substituted with Ala, Asp, Glu, Phe, Gly, His, Ile, Lys, Leu, Met, Asn, Pro, Gln, Arg, Ser, Thr, Val, or Tyr. In another aspect, the variant comprises or consists of any of the substitutions selected from W198A, W198D, W198E, W198F, W198G, W198H, W198I, W198K, W198L, W198M, W198N, W198P, W198Q, W198R, W198S, W198T, W198V and W198Y of the polypeptide shown in SEQ ID NO: 1 or a polypeptide having at least 80% sequence identity hereto.

In some aspect, the variant comprises or consists of an alteration at a position corresponding to position 199 of SEQ ID NO 1. In another aspect, the amino acid at a position corresponding to position 199 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G199A, G199D, G199E, G199F, G199H, G199I, G199K, G199L, G199M, G199N, G199P, G199Q, G199R, G199S, G199T, G199V, G199W and G199Y of the polypeptide shown in SEQ ID NO: 1 or a polypeptide having at least 80% sequence identity hereto.

In some aspect, the variant comprises or consists of an alteration at a position corresponding to position 200 of SEQ ID NO 1. In another aspect, the amino acid at a position corresponding to position 200 is substituted with Ala, Asp, Glu, Gly, His, Ile, Lys, Leu, Met, Asn, Pro, Gln, Arg, Ser, Thr, Val, Trp or Tyr. In another aspect, the variant comprises or consists of any of the substitutions selected from F200A, F200D, F200E, F200G, F200H, F200I, F200K, F200L, F200M, F200N, F200P, F200Q, F200R, F200S, F200T, F200V, F200W and F200Y of the polypeptide shown in SEQ ID NO: 1 or a polypeptide having at least 80% sequence identity hereto.

In some aspect, the variant comprises or consists of an alteration at a position corresponding to position 201 of SEQ ID NO 1. In another aspect, the amino acid at a position corresponding to position 201 is substituted with Ala, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from D201A, D201E, D201F, D201G, D201H, D201I, D201K, D201L, D201M, D201N, D201P, D201Q, D201R, D201S, D201T, D201V, D201W and D201Y of the polypeptide shown in SEQ ID NO: 1 or a polypeptide having at least 80% sequence identity hereto.

In some aspect, the variant comprises or consists of an alteration at a position corresponding to position 202 of SEQ ID NO 1. In another aspect, the amino acid at a position corresponding to position 202 is substituted with Ala, Asp, Glu, Phe, Gly, His, Ile, Lys, Leu, Met, Asn, Gln, Arg, Ser, Thr, Val, Trp or Tyr. In another aspect, the variant comprises or consists of any of the substitutions selected from P202A, P202D, P202E, P202F, P202G, P202H, P202I, P202K, P202L, P202M, P202N, P202Q, P202R, P202S, P202T, P202V, P202W and P202Y of the polypeptide shown in SEQ ID NO: 1 or a polypeptide having at least 80% sequence identity hereto.

In some aspect, the variant comprises or consists of an alteration at a position corresponding to position 203 of SEQ ID NO 1. In another aspect, the amino acid at a position corresponding to position 203 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A203D, A203E, A203F, A203G, A203H, A203I, A203K, A203L, A203M, A203N, A203P, A203Q, A203R, A203S, A203T, A203V, A203W and A203Y of the polypeptide shown in SEQ ID NO: 1 or a polypeptide having at least 80% sequence identity hereto.

In some aspect, the variant comprises or consists of an alteration at a position corresponding to position 204 of SEQ ID NO 1. In another aspect, the amino acid at a position corresponding to position 204 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K204A, K204D, K204E, K204F, K204G, K204H, K204I, K204L, K204M, K204N, K204P, K204Q, K204R, K204S, K204T, K204V, K204W and K204Y of the polypeptide shown in SEQ ID NO: 1 or a polypeptide having at least 80% sequence identity hereto.

In some aspect, the variant comprises or consists of an alteration at a position corresponding to position 205 of SEQ ID NO 1. In another aspect, the amino acid at a position corresponding to position 205 is substituted with Ala, Asp, Glu, Phe, Gly, His, Ile, Lys, Leu, Met, Asn, Pro, Gln, Arg, Ser, Thr, Val or Tyr. In another aspect, the variant comprises or consists of any of the substitutions selected from W205A, W205D, W205E, W205F, W205G, W205H, W205I, W205K, W205L, W205M, W205N, W205P, W205Q, W205R, W205S, W205T, W205V and W205Y of the polypeptide shown in SEQ ID NO: 1 or a polypeptide having at least 80% sequence identity hereto.

In some aspect, the variant comprises or consists of an alteration at a position corresponding to position 206 of SEQ ID NO 1. In another aspect, the amino acid at a position corresponding to position 206 is substituted with Asp, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from A206D, A206E, A206F, A206G, A206H, A206I, A206K, A206L, A206M, A206N, A206P, A206Q, A206R, A206S, A206T, A206V, A206W and A206Y of the polypeptide shown in SEQ ID NO: 1 or a polypeptide having at least 80% sequence identity hereto.

In some aspect, the variant comprises or consists of an alteration at a position corresponding to position 207 of SEQ ID NO 1. In another aspect, the amino acid at a position corresponding to position 207 is substituted with Ala, Asp, Glu, Phe, Gly, His, Ile, Lys, Leu, Met, Asn, Pro, Gln, Arg, Ser, Thr, Val or Trp. In another aspect, the variant comprises or consists of any of the substitutions selected from Y207A, Y207D, Y207E, Y207F, Y207G, Y207H, Y207I, Y207K, Y207L, Y207M, Y207N, Y207P, Y207Q, Y207R, Y207S, Y207T, Y207V and Y207W of the polypeptide shown in SEQ ID NO: 1 or a polypeptide having at least 80% sequence identity hereto.

In some aspect, the variant comprises or consists of an alteration at a position corresponding to position 208 of SEQ ID NO 1. In another aspect, the amino acid at a position corresponding to position 208 is substituted with Ala, Asp, Glu, Phe, Gly, His, Ile, Lys, Leu, Met, Asn, Pro, Arg, Ser, Thr, Val, Trp or Tyr. In another aspect, the variant comprises or consists of any of the substitutions selected from Q208A, Q208D, Q208E, Q208F, Q208G, Q208H, Q208I, Q208K, Q208L, Q208M, Q208N, Q208P, Q208R, Q208S, Q208T, Q208V, Q208W and Q208Y of the polypeptide shown in SEQ ID NO: 1 or a polypeptide having at least 80% sequence identity hereto.

In some aspect, the variant comprises or consists of an alteration at a position corresponding to position 209 of SEQ ID NO 1. In another aspect, the amino acid at a position corresponding to position 209 is substituted with Ala, Asp, Glu, Phe, Gly, His, Ile, Lys, Leu, Met, Asn, Pro, Gln, Arg, Ser, Thr, Val or Trp. In another aspect, the variant comprises or consists of any of the substitutions selected from Y209A, Y209D, Y209E, Y209F, Y209G, Y209H, Y209I, Y209K, Y209L, Y209M, Y209N, Y209P, Y209Q, Y209R, Y209S, Y209T, Y209V and Y209W of the polypeptide shown in SEQ ID NO: 1 or a polypeptide having at least 80% sequence identity hereto.

In some aspect, the variant comprises or consists of an alteration at a position corresponding to position 210 of SEQ ID NO 1. In another aspect, the amino acid at a position corresponding to position 210 is substituted with Ala, Glu, Phe, Gly, His, Ile, Lys, Leu, Met, Asn, Pro, Gln, Arg, Ser, Thr, Val, Trp or Tyr. In another aspect, the variant comprises or consists of any of the substitutions selected from D210A, D210E, D210F, D210G, D210H, D210I, D210K, D210L, D210M, D210N, D210P, D210Q, D210R, D210S, D210T, D210V, D210W and D210Y of the polypeptide shown in SEQ ID NO: 1 or a polypeptide having at least 80% sequence identity hereto.

In some aspect, the variant comprises or consists of an alteration at a position corresponding to position 211 of SEQ ID NO 1. In another aspect, the amino acid at a position corresponding to position 211 is substituted with Ala, Asp, Phe, Gly, His, Ile, Lys, Leu, Met, Asn, Pro, Gln, Arg, Ser, Thr, Val, Trp or Tyr. In another aspect, the variant comprises or consists of any of the substitutions selected from E211A, E211D, E211F, E211G, E211H, E211I, E211K, E211L, E211M, E211N, E211P, E211Q, E211R, E211S, E211T, E211V, E211W and E211Y of the polypeptide shown in SEQ ID NO: 1 or a polypeptide having at least 80% sequence identity hereto.

In some aspect, the variant comprises or consists of an alteration at a position corresponding to position 212 of SEQ ID NO 1. In another aspect, the amino acid at a position corresponding to position 212 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K212A, K212D, K212E, K212F, K212G, K212H, K212I, K212L, K212M, K212N, K212P, K212Q, K212R, K212S, K212T, K212V, K212W and K212Y of the polypeptide shown in SEQ ID NO: 1 or a polypeptide having at least 80% sequence identity hereto. In a preferred aspect, the variant comprises or consists of any of the substitutions K212G or K212P of the polypeptide shown in SEQ ID NO: 1 or a polypeptide having at least 80% sequence identity hereto.

In some aspect, the variant comprises or consists of an alteration at a position corresponding to position 213 of SEQ ID NO 1. In another aspect, the amino acid at a position corresponding to position 213 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N213A, N213D, N213E, N213F, N213G, N213H, N213I, N213K, N213L, N213M, N213P, N213Q, N213R, N213S, N213T, N213V, N213W and N213Y of the polypeptide shown in SEQ ID NO: 1 or a polypeptide having at least 80% sequence identity hereto.

In some aspect, the variant comprises or consists of an alteration at a position corresponding to position 214 of SEQ ID NO 1. In another aspect, the amino acid at a position corresponding to position 214 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N214A, N214D, N214E, N214F, N214G, N214H, N214I, N214K, N214L, N214M, N214P, N214Q, N214R, N214S, N214T, N214V, N214W and N214Y of the polypeptide shown in SEQ ID NO: 1 or a polypeptide having at least 80% sequence identity hereto.

In some aspect, the variant comprises or consists of an alteration at a position corresponding to position 215 of SEQ ID NO 1. In another aspect, the amino acid at a position corresponding to position 215 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K215A, K215D, K215E, K215F, K215G, K215H, K215I, K215L, K215M, K215N, K215P, K215Q, K215R, K215S, K215T, K215V, K215W and K215Y of the polypeptide shown in SEQ ID NO: 1 or a polypeptide having at least 80% sequence identity hereto. In a preferred aspect, the variant comprises or consists of the substitution K215I of the polypeptide shown in SEQ ID NO: 1 or a polypeptide having at least 80% sequence identity hereto.

In some aspect, the variant comprises or consists of an alteration at a position corresponding to position 216 of SEQ ID NO 1. In another aspect, the amino acid at a position corresponding to position 216 is substituted with Ala, Asp, Glu, Gly, His, Ile, Lys, Leu, Met, Asn, Pro, Gln, Arg, Ser, Thr, Val, Trp or Tyr. In another aspect, the variant comprises or consists of any of the substitutions selected from F216A, F216D, F216E, F216G, F216H, F216I, F216K, F216L, F216M, F216N, F216P, F216Q, F216R, F216S, F216T, F216V, F216W and F216Y of the polypeptide shown in SEQ ID NO: 1 or a polypeptide having at least 80% sequence identity hereto.

In some aspect, the variant comprises or consists of an alteration at a position corresponding to position 217 of SEQ ID NO 1. In another aspect, the amino acid at a position corresponding to position 217 is substituted with Ala, Asp, Glu, Phe, Gly, His, Ile, Lys, Leu, Met, Pro, Gln, Arg, Ser, Thr, Val, Trp or Tyr. In another aspect, the variant comprises or consists of any of the substitutions selected from N217A, N217D, N217E, N217F, N217G, N217H, N217I, N217K, N217L, N217M, N217P, N217Q, N217R, N217S, N217T, N217V, N217W and N217Y of the polypeptide shown in SEQ ID NO: 1 or a polypeptide having at least 80% sequence identity hereto.

In some aspect, the variant comprises or consists of an alteration at a position corresponding to position 218 of SEQ ID NO 1. In another aspect, the amino acid at a position corresponding to position 218 is substituted with Ala, Asp, Glu, Phe, Gly, His, Ile, Lys, Leu, Met, Asn, Pro, Gln, Arg, Ser, Thr, Val or Trp. In another aspect, the variant comprises or consists of any of the substitutions selected from Y218A, Y218D, Y218E, Y218F, Y218G, Y218H, Y218I, Y218K, Y218L, Y218M, Y218N, Y218P, Y218Q, Y218R, Y218S, Y218T, Y218V and Y218W of the polypeptide shown in SEQ ID NO: 1 or a polypeptide having at least 80% sequence identity hereto.

In some aspect, the variant comprises or consists of an alteration at a position corresponding to position 219 of SEQ ID NO 1. In another aspect, the amino acid at a position corresponding to position 219 is substituted with Ala, Asp, Glu, Phe, Gly, His, Ile, Lys, Leu, Met, Asn, Pro, Gln, Arg, Ser, Thr, Trp or Tyr. In another aspect, the variant comprises or consists of any of the substitutions selected from V219A, V219D, V219E, V219F, V219G, V219H, V219I, V219K, V219L, V219M, V219N, V219P, V219Q, V219R, V219S, V219T, V219W and V219Y of the polypeptide shown in SEQ ID NO: 1 or a polypeptide having at least 80% sequence identity hereto.

In some aspect, the variant comprises or consists of an alteration at a position corresponding to position 220 of SEQ ID NO 1. In another aspect, the amino acid at a position corresponding to position 220 is substituted with Ala, Asp, Glu, Phe, His, Ile, Lys, Leu, Met, Asn, Pro, Gln, Arg, Ser, Thr, Val, Trp or Tyr. In another aspect, the variant comprises or consists of any of the substitutions selected from G220A, G220D, G220E, G220F, G220H, G220I, G220K, G220L, G220M, G220N, G220P, G220Q, G220R, G220S, G220T, G220V, G220W and G220Y of the polypeptide shown in SEQ ID NO: 1 or a polypeptide having at least 80% sequence identity hereto.

In some aspect, the variant comprises or consists of an alteration at a position corresponding to position 221 of SEQ ID NO 1. In another aspect, the amino acid at a position corresponding to position 221 is substituted with Ala, Asp, Glu, Phe, Gly, His, Ile, Leu, Met, Asn, Pro, Gln, Arg, Ser, Thr, Val, Trp or Tyr. In another aspect, the variant comprises or consists of any of the substitutions selected from K221A, K221D, K221E, K221F, K221G, K221H, K221I, K221L, K221M, K221N, K221P, K221Q, K221R, K221S, K221T, K221V, K221W and K221Y of the polypeptide shown in SEQ ID NO: 1 or a polypeptide having at least 80% sequence identity hereto.

By the term "of the polypeptide" shown in SEQ ID NO: 1 is meant that the substitutions is made in SEQ ID NO 1 and the positions correspond to the positions of SEQ ID NO 1. Thus the above variants are variants of a DNase having SEQ ID NO 1 or a DNase having at least 80% sequence identity hereto. The above mentioned variants have at least at least 60%, at least 61%, at least 62%, at least 63%, at least 64%, at least 65%, at least 66%, at least 67%, at least 68%, at least 69%, at least 70%, at least 72%, at least 73%, at least 74%, at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5 but less than 100% identity to a polypeptide shown in SEQ ID NO: 1.

Some aspect of the invention relates to a DNase variant wherein the variant has DNase activity, wherein the DNase variant has at least 80% sequence identity to the polypeptide shown in SEQ ID NO 1 and wherein the variant when compared to the polypeptide shown in SEQ ID NO 1 comprises a deletion of the amino acid in any of the positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 48, 49, 50, 51, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 163, 164, 165, 166, 167, 168, 169, 170, 171, 172, 173, 174, 175, 176, 178, 179, 180, 181, 182, 183, 185, 186, 187, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 or 221 of the polypeptide shown in SEQ ID NO: 1, with the proviso that maximum number of deletions are 10 amino acids compared to the mature polypeptide shown in SEQ ID NO 1. Some preferred aspect of the invention relates to a DNase variant wherein the variant has DNase activity, wherein the DNase variant has at least 80% sequence identity to the polypeptide shown in SEQ ID NO 1 and wherein the variant when compared to the polypeptide shown in SEQ ID NO 1 comprises a deletion of the amino acid in any of the positions 84, 88, 139, 179 or 180 of the polypeptide shown in SEQ ID NO: 1.

When the DNase variant of the invention comprises one or more deletion the DNase variant preferably comprises 1, 2, 3, 4, 5, 6, 7, 8, 9 or 10 deletion(s) compared to the polypeptide shown in SEQ ID NO 1, preferably, 1, preferably 2, preferably 3 or preferably 4 deletion(s) compared to the polypeptide shown in SEQ ID NO 1, wherein the DNase variant has DNase activity and wherein the DNase variant has at least 60%, at least 61%, at least 62%, at least 63%, at least 64%, at least 65%, at least 66%, at least 67%, at least 68%, at least 69%, at least 70%, at least 72%, at least 73%, at least 74%, at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99% but less than 100% identity to a polypeptide shown in SEQ ID NO: 1.

In one embodiment, the DNase variants of the invention have improved DNase activity compared to a reference DNase e.g. SEQ ID NO: 1, wherein the activity is tested in Assay I described in Assays and detergent compositions below.

In one embodiment, the DNase variants of the invention have improved stability in detergent compared to a reference DNase e.g. SEQ ID NO: 1, wherein stability is tested as described in example 2.

In one embodiment, the DNase variants generated in the library as described above have improved deep cleaning performance compared to a reference DNase, e.g. SEQ ID NO: 1.

In one embodiment, the DNase variants of the invention have improved deep cleaning performance compared to a reference DNase, e.g. SEQ ID NO: 1.

When items like T-shirts or sportswear are used, they are exposed to bacteria from the body of the user and from the rest of the environment in which they are used. This may cause malodor on the item even after the item is washed. The present invention therefore also relates to removal or reduction of malodor on textile. The malodor may be caused by bacteria producing compounds with an unpleasant smell. One example of such unpleasant smelling compounds is E-2-nonenal. The malodor can be present on newly washed textile which is still wet. Or the malodor can be present on newly washed textile, which has subsequently been dried. The malodor may also be present on textile, which has been stored for some time after wash. The present invention may relates to the reduction or removal of malodor such as E-2-nonenal from wet or dry textile using a DNase variant according to the invention.

In one embodiment, the DNase variants according to the invention have improved malodor removal properties compared to a reference DNase e.g. SEQ ID NO: 1, wherein the malodor is measured as described in Assay II.

Further, the invention relates to the use of a DNase variant according to the invention for preventing, reducing or removing the adherence of soil to an item. In one embodiment, the item is textile. When the soil does not adhere to the item, the item appears cleaner. Thus, the invention further concerns the use of a DNase variant according to the invention for maintaining or improving the whiteness of the item.

The present invention further concerns detergent compositions comprising a DNase variant according to the invention preferably with a detergent adjunct ingredient. The detergent composition comprising a DNase variants according to the invention may be used for preventing, reducing or removing biofilm from an item, for preventing, reducing or removing the stickiness of an item, for pretreating stains on the item, for preventing, reducing or removing redeposition of soil during a wash cycle, for reducing or removing adherence of soil to an item, for maintaining or improving the whiteness of an item and for preventing, reducing or removing malodor from an item, such as E-2-nonenal (as described in Assay II).

In one embodiment, the detergent composition is a liquid or powder laundry detergent, suitable for e.g. washing at high temperature and/or pH, such as at or above 40° C. and/or at or above pH 8. In one embodiment the detergent composition is a liquid or powder laundry detergent, suitable for e.g. washing at low temperature and/or pH, such as at or below 20° C. and/or pH 6. The detergent may also be formulated as a unit dose detergent and/or compact detergent optionally with minimum or no water. The detergent may also be a dish wash detergent. The laundry and dish wash detergents are preferably phosphate-free. The detergent composition may further comprise at least one additional enzyme, such as carbohydrate-active enzymes like carbohydrase, pectinase, mannanase, amylase, cellulase, arabinase, galactanase, xylanase, protease such as metalloproteases, lipase, a, cutinase, oxidase, e.g., a laccase, and/or peroxidase.

In some further embodiments, the present invention relates to DNase variants having at least 60% to SEQ ID NO: 1 identity hereto wherein when the variant having at least one improved property compared to SEQ ID NO: 1 when tested in a relevant assay. One embodiment of the invention relates to DNase variants having an improvement factor above 1 when the DNase variants are tested for a property of interest in a relevant assay, wherein the property of the reference DNase is given a value of 1. In one embodiment, the property is stability, such as storage stability in detergent in another embodiment the property is wash performance, such as deep cleaning performance.

In one embodiment, the variants according to the invention have one or more improved property relative to the parent measured as an Improvement Factor (IF) that is greater than 1.0, wherein the improved property is stability such as stability in detergent.

In one embodiment, the variants according to the invention have an Improvement Factor (IF) which is greater than 1.0 in at least one of two different set of conditions A or B as described in example 2.

In one embodiment, the variants according to the invention have an Improvement Factor (IF) which is greater than 1.0 in one or both of conditions A and B.

In some aspects, the variants according to the invention have an Improvement Factor (IF) which is at least 1.1; 1.2; 1.3; 1.4; 1.5; 1.6; 1.7; 1.8; 1.9; 2.0; 2.1; 2.3; 2.4; 2.5, 2.6, 2.7, 2.8, 2.9 or 3.0.

In some aspects, the variants according to the invention have an Improvement Factor (IF) which is at least 1.1; 1.5; 2.0; 3.0, 3.5, 4.0, 5.0, 5.5, 6.0, 6.5, 7.0, 7.5, 8.0, 8.5, 9.0, 9.5 or 10.

Amino acid positions within a protein that are useful for making variants are those positions wherein at least one alterations leads to a variant exhibiting an improved characteristic as compared to the unchanged protein i.e. parent i.e. IF>1.0. The improved characteristic may be determined using the assay I or II or as described in example 2.

One embodiment of the invention relates to DNase variants having at least 60% identity to SEQ ID NO: 1, having DNase activity and comprising one or more alterations selected from the group consisting of V1*, V1A, V1D, V1E, V1F, V1G, V1H, V1I, V1K, V1L, V1M, V1N, V1P, V1Q, V1R, V1S, V1T, V1W, V1Y, P2*, P2A, P2D, P2E, P2F, P2G, P2H, P2I, P2K, P2L, P2M, P2N, P2Q, P2R, P2S, P2T, P2V, P2W, P2Y, V3*, V3A, V3C, V3D, V3E, V3F, V3G, V3H, V3I, V3K, V3L, V3M, V3N, V3P, V3R, V3S, V3T, V3W, V3Y, N4*, N4A, N4D, N4E, N4F, N4G, N4H, N4I, N4K, N4L, N4M, N4P, N4Q, N4R, N4S, N4T, N4V, N4W, N4Y, P5*, P5A, P5D, P5E, P5F, P5G, P5H, P5I, P5K, P5L, P5M, P5N, P5Q, P5R, P5S, P5T, P5V, P5W, P5Y, E6*, E6A, E6D, E6F, E6G, E6H, E6I, E6K, E6L, E6M, E6N, E6P, E6Q, E6R, E6S, E6T, E6V, E6W, E6Y, P7*, P7A, P7D, P7E, P7F, P7G, P7H, P7I, P7K, P7L, P7M, P7N, P7Q, P7R, P7S, P7T, P7V, P7W, P7Y, D8*, D8A, D8E, D8F, D8G, D8H, D8I, D8K, D8L, D8M, D8N, D8P, D8Q, D8R, D8S, D8T, D8V, D8W, D8Y, A9*, A9D, A9E, A9F, A9G, A9H, A9I, A9K, A9L, A9M, A9N, A9P, A9Q, A9R, A9S, A9T, A9V, A9W, A9Y, T10*, T10A, T10D, T10E, T10F, T10G, T10H, T10I, T10K, T10L, T10M, T10N, T10P, T10Q, T10R, T10S, T10V, T10W, T10Y, S11*, S11A, S11D, S11E, S11F, S11G, S11H, S11I, S11K, S11L, S11M, S11N, S11P, S11Q, S11R, S11T, S11V, S11W, S11Y, V12*, V12A, V12D, V12E, V12F, V12G, V12H, V12I, V12K, V12L, V12M, V12N, V12P, V12Q, V12R, V12S, V12T, V12W, V12Y, E13*, E13A, E13D, E13F, E13G, E13H, E13I, E13K, E13L, E13M, E13N, E13P, E13Q, E13R, E13S, E13T, E13V, E13W, E13Y, N14*, N14A, N14D, N14E, N14F, N14G, N14H, N14I, N14K, N14L, N14M, N14P, N14Q, N14R, N14S, N14T, N14V, N14W, N14Y, V15*, V15A, V15D, V15E, V15F, V15G, V15H, V15I, V15K, V15L, V15M, V15N, V15P, V15Q, V15R, V15S, V15T, V15W, V15Y, A16*, A16D, A16E, A16F, A16G, A16H, A16I, A16K, A16L, A16M, A16N, A16P, A16Q, A16R, A16S, A16T, A16V, A16W, A16Y, L17*, L17A, L17D, L17E, L17F, L17G, L17H, L17I, L17K, L17M, L17N, L17P, L17Q, L17R, L17S, L17T, L17V, L17W, L17Y, K18*, K18A, K18D, K18E, K18F, K18G, K18H, K18I, K18L, K18M, K18N, K18P, K18Q, K18R, K18S, K18T, K18V, K18W, K18Y, T19*, T19A, T19D, T19E, T19F, T19G, T19H, T19I, T19K, T19L, T19M, T19N, T19P, T19Q, T19R, T19S, T19V, T19W, T19Y, G20*, G20A, G20D, G20E, G20F, G20H, G20I, G20K, G20L, G20M, G20N, G20P, G20Q, G20R, G20S, G20T, G20V, G20W, G20Y, S21*, S21A, S21D, S21E, S21F, S21G, S21H, S21I, S21K, S21L, S21M, S21N, S21P, S21Q, S21R, S21T, S21V, S21W, S21Y, G22*, G22A, G22D, G22E, G22F, G22H, G22I, G22K, G22L, G22M, G22N, G22P, G22Q, G22R, G22S, G22T, G22V, G22W, G22Y, D23*, D23A, D23E, D23F, D23G, D23H, D23I, D23K, D23L, D23M, D23N, D23P, D23Q, D23R, D23S, D23T, D23V, D23W, D23Y, S24*, S24A, S24D, S24E, S24F, S24G, S24H, S24I, S24K, S24L, S24M, S24N, S24P, S24Q, S24R, S24T, S24V, S24W, S24Y, Q25*, Q25A, Q25D, Q25E, Q25F, Q25G, Q25H, Q25I, Q25K, Q25L, Q25M, Q25N, Q25P, Q25R, Q25S, Q25T, Q25V, Q25W, Q25Y, S26*, S26A, S26D, S26E, S26F, S26G, S26H, S26I, S26K, S26L, S26M, S26N, S26P, S26Q, S26R, S26T, S26V, S26W, S26Y, D27*, D27A, D27E, D27F, D27G, D27H, D27I, D27K, D27L, D27M, D27N, D27P, D27Q, D27R, D27S, D27T, D27V, D27W, D27Y, P28*, P28A, P28D, P28E, P28F, P28G, P28H, P28I, P28K, P28L, P28M, P28N, P28Q, P28R, P28S, P28T, P28V, P28W, P28Y, I29*, I29A, I29D, I29E, I29F, I29G, I29H, I29K, I29L, I29M, I29N, I29P, I29Q, I29R, I29S, I29T, I29V, I29W, I29Y, K30*, K30A, K30D, K30E, K30F, K30G, K30H, K30I, K30L, K30M, K30N, K30P, K30Q, K30R, K30S, K30T, K30V, K30W, K30Y, A31*, A31D, A31E, A31F, A31G, A31H, A31I, A31K, A31L, A31M, A31N, A31P, A31Q, A31R, A31S, A31T, A31V, A31W, A31Y, D32*, D32A, D32E, D32F, D32G, D32H, D32I, D32K, D32L, D32M, D32N, D32P, D32Q, D32R, D32S, D32T, D32V, D32W, D32Y, L33*, L33A, L33D, L33E, L33F, L33G, L33H, L33I, L33K, L33M, L33N, L33P, L33Q, L33R, L33S, L33T, L33V, L33W, L33Y, E34*, E34A, E34D, E34F, E34G, E34H, E34I, E34K, E34L, E34M, E34N, E34P, E34Q, E34R, E34S, E34T, E34V, E34W, E34Y, V35*, V35A, V35D, V35E, V35F, V35G, V35H, V35I, V35K, V35L, V35M, V35N, V35P, V35Q, V35R, V35S, V35T, V35W, V35Y, K36*, K36A, K36D, K36E, K36F, K36G, K36H, K36I, K36L, K36M, K36N, K36P, K36Q, K36R, K36S, K36T, K36V, K36W, K36Y, G37*, G37A, G37D, G37E, G37F, G37H, G37I, G37K, G37L, G37M, G37N, G37P, G37Q, G37R, G37S, G37T, G37V, G37W, G37Y, Q38*, Q38A, Q38D, Q38E, Q38F, Q38G, Q38H, Q38I, Q38K, Q38L, Q38M, Q38N, Q38P, Q38R, Q38S, Q38T, Q38V, Q38W, Q38Y, S39*, S39A, S39D, S39E, S39F, S39G, S39H, S39I, S39K, S39L, S39M, S39N, S39P, S39Q, S39R, S39T, S39V, S39W, S39Y, A40*, A40D, A40E, A40F, A40G, A40H, A40I, A40K, A40L, A40M, A40N, A40P, A40Q, A40R, A40S, A40T, A40V, A40W, A40Y, L41*, L41A, L41D, L41E, L41F, L41G, L41H, L41I, L41K, L41M, L41N, L41P, L41Q, L41R, L41S, L41T, L41V, L41W, L41Y, P42*, P42A, P42D, P42E, P42F, P42G, P42H, P42I, P42K, P42L, P42M, P42N, P42Q, P42R, P42S, P42T, P42V, P42W, P42Y, F43*, F43A, F43D, F43E, F43G, F43H, F43I, F43K, F43L, F43M, F43N, F43P, F43Q, F43R, F43S, F43T, F43V, F43W, F43Y, D44*, D44A, D44E, D44F, D44G, D44H, D44I, D44K, D44L, D44M, D44N, D44P, D44Q, D44R, D44S, D44T, D44V, D44W, D44Y, V45*, V45A, V45D, V45E, V45F, V45G, V45H, V45I, V45K, V45L, V45M, V45N, V45P, V45Q, V45R, V45S, V45T, V45W, V45Y, D46*, D46A, D46E, D46F, D46G, D46H, D46I, D46K, D46L, D46M, D46N, D46P, D46Q, D46R, D46S, D46T, D46V, D46W, D46Y, C47A, C47D, C47E, C47F, C47G, C47H, D47I, C47K, C47L, C47M, C47N, C47P, C47Q, C47R, C47S, C47T, 047V, C47W, C47Y, W48*, W48A, W48D, W48E, W48F, W48G, W48H, W48I, W48K, W48L, W48M, W48N, W48P, W48Q, W48R, W48S, W48T, W48V, W48Y, A49*, A49D, A49E, A49F, A49G, A49H, A49I, A49K, A49L, A49M, A49N, A49P, A49Q, A49R, A49S, A49T, A49V, A49W, A49Y, I50*, I50A, I50D, I50E, I50F, I50G, I50H, I50K, I50L, I50M, I50N, I50P, I50Q, I50R, I50S, I50T, I50V, I50W, I50Y, L51*, L51A, L51D, L51E, L51F, L51G, L51H, L51I, L51K, L51M, L51N, L51P, L51Q, L51R, L51S, L51T, L51V, L51W, L51Y, K53*, K53A, K53D, K53E, K53F, K53G, K53H, K53I, K53L, K53M, K53N, K53P, K53Q, K53R, K53S, K53T, K53V, K53W, K53Y, G54*, G54A, G54D, G54E, G54F, G54H, G54I, G54K, G54L, G54M, G54N, G54P, G54Q, G54R, G54S, G54T, G54V, G54W, G54Y, A55*, A55D, A55E, A55F, A55G, A55H, A55I, A55K, A55L, A55M, A55N, A55P, A55Q, A55R, A55S, A55T, A55V, A55W, A55Y, P56*, P56A, P56D, P56E, P56F, P56G, P56H, P56I, P56K, P56L, P56M, P56N, P56Q, P56R, P56S, P56T, P56V, P56W, P56Y, N57*, N57A, N57D, N57E, N57F, N57G, N57H, N57I, N57K, N57L, N57M, N57P, N57Q, N57R, N57S, N57T, N57V, N57W, N57Y, V58*, V58A, V58D, V58E, V58F, V58G, V58H, V58I, V58K, V58L, V58M, V58N, V58P, V58Q, V58R, V58S, V58T, V58W, V58Y L59*, L59A, L59D, L59E, L59F, L59G, L59H, L59I, L59K, L59M, L59N, L59P, L59Q, L59R, L59S, L59T, L59V, L59W, L59Y, Q60*, Q60A, Q60D, Q60E, Q60F, Q60G, Q60H, Q60I, Q60K, Q60L, Q60M, Q60N, Q60P, Q60R, Q60S, Q60T, Q60V, Q60W, Q60Y, R61*, R61A, R61D, R61E, R61F, R61G, R61H, R61I, R61K, R61L, R61M, R61N, R61P, R61Q, R61S, R61T, R61V, R61W, R61Y, V62*, V62A, V62D, V62E, V62F, V62G, V62H, V62I, V62K, V62L, V62M, V62N, V62P, V62Q, V62R, V62S, V62T, V62W, V62Y, N63*, N63A, N63D, N63E, N63F, N63G, N63H, N63I, N63K, N63L, N63M, N63P, N63Q, N63R, N63S, N63T, N63V, N63W, N63Y, E64*, E64A, E64D, E64F, E64G, E64H, E64I, E64K, E64L, E64M, E64N, E64P, E64Q, E64R, E64S, E64T, E64V, E64W, E64Y, K65*, K65A, K65D, K65E, K65F, K65G, K65H, K65I, K65L, K65M, K65N, K65P, K65Q, K65R, K65S, K65T, K65V, K65W, K65Y, T66*, T66A, T66D, T66E, T66F, T66G, T66H, T66I, T66K, T66L, T66M, T66N, T66P, T66Q, T66R, T66S, T66V, T66W, T66Y, K67*, K67A, K67D, K67E, K67F, K67G, K67H, K67I, K67L, K67M, K67N, K67P, K67Q, K67R, K67S, K67T, K67V, K67W, K67Y, N68*, N68A, N68D, N68E, N68F, N68G, N68H, N68I, N68K, N68L, N68M, N68P, N68Q, N68R, N68S, N68T, N68V, N68W, N68Y, S69*, S69A, S69D, S69E, S69F, S69G, S69H, S69I, S69K, S69L, S69M, S69N, S69P, S69Q, S69R, S69T, S69V, S69W, S69Y, N70*, N70A, N70D, N70E, N70F, N70G, N70H, N70I, N70K, N70L, N70M, N70P, N70Q, N70R, N70S, N70T, N70V, N70W, N70Y, R71*, R71A, R71D, R71E, R71F, R71G, R71H, R71I, R71K, R71L, R71M, R71N, R71P, R71Q, R71S, R71T, R71V, R71W, R71Y, D72*, D72A, D72E, D72F, D72G, D72H, D72I, D72K, D72L, D72M, D72N, D72P, D72Q, D72R, D72S, D72T, D72V, D72W, D72Y, R73*, R73A, R73D, R73E, R73F, R73G, R73H, R73I, R73K, R73L, R73M, R73N, R73P, R73Q, R73S, R73T, R73V, R73W, R73Y, S74*, S74A, S74D, S74E, S74F, S74G, S74H, S74I, S74K, S74L, S74M, S74N, S74P, S74Q, S74R, S74T, S74V, S74W, S74Y, G75*, G75A, G75D, G75E, G75F, G75H, G75I, G75K, G75L, G75M, G75N, G75P, G75Q, G75R, G75S, G75T, G75V, G75W, G75Y, A76*, A76D, A76E, A76F, A76G, A76H, A76I, A76K, A76L, A76M, A76N, A76P, A76Q, A76R, A76S, A76T, A76V, A76W, A76Y, N77*, N77A, N77D, N77E, N77F, N77G, N77H, N77I, N77K, N77L, N77M, N77P, N77Q, N77R, N77S, N77T, N77V, N77W, N77Y, K78*, K78A, K78D, K78E, K78F, K78G, K78H, K78I, K78L, K78M, K78N, K78P, K78Q, K78R, K78S, K78T, K78V, K78W, K78Y, G79*, G79A, G79D, G79E, G79F, G79H, G79I, G79K, G79L, G79M, G79N, G79P, G79Q, G79R, G79S, G79T, G79V, G79W, G79Y, P80*, P80A, P80D, P80E, P80F, P80G, P80H, P80I, P80K, P80L, P80M, P80N, P80Q, P80R, P80S, P80T, P80V, P80W, P80Y, F81*, F81A, F81D, F81E, F81G, F81H, F81I, F81K, F81L, F81M, F81N, F81P, F81Q, F81R, F81S, F81T, F81V, F81W, F81Y, K82*, K82A, K82D, K82E, K82F, K82G, K82H, K82I, K82L, K82M, K82N, K82P, K82Q, K82R, K82S, K82T, K82V, K82W, K82Y, D83*, D83A, D83E, D83F, D83G, D83H, D83I, D83K, D83L, D83M, D83N, D83P, D83Q, D83R, D83S, D83T, D83V, D83W, D83Y, P84*, P84A, P84D, P84E, P84F, P84G, P84H, P84I, P84K, P84L, P84M, P84N, P84Q, P84R, P84S, P84T, P84V, P84W, P84Y, Q85*, Q85A, Q85D, Q85E, Q85F, Q85G, Q85H, Q85I, Q85K, Q85L, Q85M, Q85N, Q85P, Q85R, Q85S, Q85T, Q85V, Q85W, Q85Y, K86*, K86A, K86D, K86E, K86F, K86G, K86H, K86I, K86L, K86M, K86N, K86P, K86Q, K86R, K86S, K86T, K86V, K86W, K86Y, W87*, W87A, W87D, W87E, W87F, W87G, W87H, W87I, W87K, W87L, W87M, W87N, W87P, W87Q, W87R, W87S, W87T, W87V, W87Y, G88*, G88A, G88D, G88E, G88F, G88H, G88I, G88K, G88L, G88M, G88N, G88P, G88Q, G88R, G88S, G88T, G88V, G88W, G88Y, I89*, I89A, I89D, I89E, I89F, I89G, I89H, I89K, I89L, I89M, I89N, I89P, I89Q, I89R, I89S, I89T, I89V, I89W, I89Y, K90*, K90A, K90D, K90E, K90F, K90G, K90H, K90I, K90L, K90M, K90N, K90P, K90Q, K90R, K90S, K90T, K90V, K90W, K90Y, A91*, A91D, A91E, A91F, A91G, A91H, A91I, A91K, A91L, A91M, A91N, A91P, A91Q, A91R, A91S, A91T, A91V, A91W, A91Y, L92*, L92A, L92D, L92E, L92F, L92G, L92H, L92I, L92K, L92M, L92N, L92P, L92Q, L92R, L92S, L92T, L92V, L92W, L92Y, P93*, P93A, P93D, P93E, P93F, P93G, P93H, P93I, P93K, P93L, P93M, P93N, P93Q, P93R, P93S, P93T, P93V, P93W, P93Y, P94*, P94A, P94D, P94E, P94F, P94G, P94H, P94I, P94K, P94L, P94M, P94N, P94Q, P94R, P94S, P94T, P94V, P94W, P94Y, K95*, K95A, K95D, K95E, K95F, K95G, K95I, K95L, K95M, K95N, K95P, K95Q, K95R, K95S, K95T, K95V, K95W, K95Y, N96*, N96A, N96D, N96E, N96F, N96G, N96H, N96I, N96K, N96L, N96M, N96P, N96Q, N96R, N96S, N96T, N96V, N96W, N96Y, P97*, P97A, P97D, P97E, P97F, P97G, P97H, P97I, P97K, P97L, P97M, P97N, P97Q, P97R, P97S, P97T, P97V, P97W, P97Y, S98*, S98A, S98D, S98E, S98F, S98G, S98H, S98I, S98K, S98L, S98M, S98N, S98P, S98Q, S98R, S98T, S98V, S98W, S98Y, W99*, W99A, W99D, W99E, W99F, W99G, W99H, W99I, W99K, W99L, W99M, W99N, W99P, W99Q, W99R, W99S, W99T, W99V, W99Y, S100*, S100A, S100D, S100E, S100F, S100G, S100H, S100I, S100K, S100L, S100M, S100N, S100P, S100Q, S100R, S100T, S100V, S100W, S100Y, A101*, A101D, A101E, A101F, A101G, A101H, A101I, A101K, A101L, A101M, A101N, A101P, A101Q, A101R, A101S, A101T, A101V, A101W, A101Y, Q102*, Q102A, Q102D, Q102E, Q102F, Q102G, Q102H, Q102I, Q102K, Q102L, Q102M, Q102N, Q102P, Q102R, Q102S, Q102T, Q102V, Q102W, Q102Y, D103*, D103A, D103E, D103F, D103G, D103H, D103I, D103K, D103L, D103M, D103N, D103P, D103Q, D103R, D103S, D103T, D103V, D103W, D103Y, F104*, F104A, F104D, F104E, F104G, F104H, F104I, F104K, F104L, F104M, F104N, F104P, F104Q, F104R, F104S, F104T, F104V, F104W, F104Y, K105*, K105A, K105D, K105E, K105F, K105G, K105H, K105I, K105L, K105M, K105N, K105P, K105Q, K105R, K105S, K105T, K105V, K105W, K105Y, S106*, S106A, S106D, S106E, S106F, S106G, S106H, S106I, S106K, S106L, S106M, S106N, S106P, S106Q, S106R, S106T, S106V, S106W, S106Y, P107*, P107A, P107D, P107E, P107F, P107G, P107H, P107I, P107K, P107L, P107M, P107N, P107Q, P107R, P107S, P107T, P107V, P107W, P107Y, E108*, E108A, E108D, E108F, E108G, E108H, E108I, E108K, E108L, E108M, E108N, E108P, E108Q, E108R, E108S, E108T, E108V, E108W, E108Y, E109*, E109A, E109D, E109F, E109G, E109H, E109I, E109K, E109L, E109M, E109N, E109P, E109Q, E109R, E109S, E109T, E109V, E109W, E109Y, Y110*, Y110A, Y110D, Y110E, Y110F, Y110G, Y110H, Y110I, Y110K, Y110L, Y110M, Y110N, Y110P, Y110Q, Y110R, Y110S, Y110T, Y110V, Y110W, A111*, A111D, A111E, A111F, A111G, A111H, A111I, A111K, A111L, A111M, A111N, A111P, A111Q, A111R, A111S, A111T, A111V, A111W, A111Y, F112*, F112A, F112D, F112E, F112G, F112H, F112I, F112K, F112L, F112M, F112N, F112P, F112Q, F112R, F112S, F112T, F112V, F112W, F112Y, A113*, A113D, A113E, A113F, A113G, A113H, A113I, A113K, A113L, A113M, A113N, A113P, A113Q, A113R, A113S, A113T, A113V, A113W, A113Y, S114*, S114A, S114D, S114E, S114F, S114G, S114H, S114I, S114K, S114L, S114M, S114N, S114P, S114Q, S114R, S114T, S114V, S114W, S114Y, S115*, S115A, S115D, S115E, S115F, S115G, S115H, S115I, S115K, S115L, S115M, S115N, S115P, S115Q, S115R, S115T, S115V, S115W, S115Y, L116*, L116A, L116D, L116E, L116F, L116G, L116H, L116I, L116K, L116M, L116N, L116P, L116Q, L116R, L116S, L116T, L116V, L116W, L116Y, Q117*, Q117A, Q117D, Q117E, Q117F, Q117G, Q117H, Q117I, Q117K, Q117L, Q117M, Q117N, Q117P, Q117R, Q117S, Q117T, Q117V, Q117W, Q117Y, G118*, G118A, G118D, G118E, G118F, G118H, G118I, G118K, G118L, G118M, G118N, G118P, G118Q, G118R, G118S, G118T, G118V, G118W, G118Y, G119*, G119A, G119D, G119E, G119F, G119H, G119I, G119K, G119L, G119M, G119N, G119P, G119Q, G119R, G119S, G119T, G119V, G119W, G119Y, T120*, T120A, T120D, T120E, T120F, T120G, T120H, T120I, T120K, T120L, T120M, T120N, T120P, T120Q, T120R, T120S, T120V, T120W, T120Y, N121*, N121A, N121D, N121E, N121F, N121G, N121H, N121I, N121K, N121L, N121M, N121P, N121Q, N121R, N121S, N121T, N121V, N121W, N121Y, A122*, A122D, A122E, A122F, A122G, A122H, A122I, A122K, A122L, A122M, A122N, A122P, A122Q, A122R, A122S, A122T, A122V, A122W, A122Y, I123*, I123A, I123D, I123E, I123F, I123G, I123H, I123K, I123L, I123M, I123N, I123P, I123Q, I123R, I123S, I123T, I123V, I123W, I123Y, L124*, L124A, L124D, L124E, L124F, L124G, L124H, L124I, L124K, L124M, L124N, L124P, L124Q, L124R, L124S, L124T, L124V, L124W, L124Y, A125*, A125D, A125E, A125F, A125G, A125H, A125I, A125K, A125L, A125M, A125N, A125P, A125Q, A125R, A125S, A125T, A125V, A125W, A125Y, P126*, P126A, P126D, P126E, P126F, P126G, P126H, P126I, P126K, P126L, P126M, P126N, P126Q, P126R, P126S, P126T, P126V, P126W, P126Y, V127*, V127A, V127D, V127E, V127F, V127G, V127H, V127I, V127K, V127L, V127M, V127N, V127P, V127Q, V127R, V127S, V127T, V127W, V127Y, N128*, N128A, N128D, N128E, N128F, N128G, N128H, N128I, N128K, N128L, N128M, N128P, N128Q, N128R, N128S, N128T, N128V, N128W, N128Y, L129*, L129A, L129D, L129E, L129F, L129G, L129H, L129I, L129K, L129M, L129N, L129P, L129Q, L129R, L129S, L129T, L129V, L129W, L129Y, A130*, A130D, A130E, A130F, A130G, A130H, A130I, A130K, A130L, A130M, A130N, A130P, A130Q, A130R, A130S, A130T, A130V, A130W, A130Y, S131*, S131A, S131D, S131E, S131F, S131G, S131H, S131I, S131K, S131L, S131M, S131N, S131P, S131Q, S131R, S131T, S131V, S131W, S131Y, Q132*, Q132A, Q132D, Q132E, Q132F, Q132G, Q132H, Q132I, Q132K, Q132L, Q132M, Q132N, Q132P, Q132R, Q132S, Q132T, Q132V, Q132W, Q132Y, N133*, N133A, N133D, N133E, N133F, N133G, N133H, N133I, N133K, N133L, N133M, N133P, N133Q, N133R, N133S, N133T, N133V, N133W, N133Y, S134*, S134A, S134D, S134E, S134F, S134G, S134H, S134I, S134K, S134L, S134M, S134N, S134P, S134Q, S134R, S134T, S134V, S134W, S134Y, Q135*, Q135A, Q135D, Q135E, Q135F, Q135G, Q135H, Q135I, Q135K, Q135L, Q135M, Q135N, Q135P, Q135R, Q135S, Q135T, Q135V, Q135W, Q135Y, G136*, G136A, G136D, G136E, G136F, G136H, G136I, G136K, G136L, G136M, G136N, G136P, G136Q, G136R, G136S, G136T, G136V, G136W, G136Y, G137*, G137A, G137D, G137E, G137F, G137H, G137I, G137K, G137L, G137M, G137N, G137P, G137Q, G137R, G137S, G137T, G137V, G137W, G137Y, V138*, V138A, V138D, V138E, V138F, V138G, V138H, V138I, V138K, V138L, V138M, V138N, V138P, V138Q, V138R, V138S, V138T, V138W, V138Y, L139*, L139A, L139D, L139E, L139F, L139G, L139H, L139I, L139K, L139M, L139N, L139P, L139Q, L139R, L139S, L139T, L139V, L139W, L139Y, N140*, N140A, N140D, N140E, N140F, N140G, N140H, N140I, N140K, N140L, N140M, N140P, N140Q, N140R, N140S, N140T, N140V, N140W, N140Y, G141*, G141A, G141D, G141E, G141F, G141H, G141I, G141K, G141L, G141M, G141N, G141P, G141Q, G141R, G141S, G141T, G141V, G141W, G141Y, F142*, F142A, F142D, F142E, F142G, F142H, F142I, F142K, F142L, F142M, F142N, F142P, F142Q, F142R, F142S, F142T, F142V, F142W, F142Y, Y143*, Y143A, Y143D, Y143E, Y143F, Y143G, Y143H, Y143I, Y143K, Y143L, Y143M, Y143N, Y143P, Y143Q, Y143R, Y143S, Y143T, Y143V, Y143W, S144*, S144A, S144D, S144E, S144F, S144G, S144H, S144I, S144K, S144L, S144M, S144N, S144P, S144Q, S144R, S144T, S144V, S144W, S144Y, A145*, A145D, A145E, A145F, A145G, A145H, A145I, A145K, A145L, A145M, A145N, A145P, A145Q, A145R, A145S, A145T, A145V, A145W, A145Y, N146*, N146A, N146D, N146E, N146F, N146G, N146H, N146I, N146K, N146L, N146M, N146P, N146Q, N146R, N146S, N146T, N146V, N146W, N146Y, K147*, K147A, K147D, K147E, K147F, K147G, K147H, K147I, K147L, K147M, K147N, K147P, K147Q, K147R, K147S, K147T, K147V, K147W, K147Y, V148*, V148A, V148D, V148E, V148F, V148G, V148H, V148I, V148K, V148L, V148M, V148N, V148P, V148Q, V148R, V148S, V148T, V148W, V148Y, A149*, A149D, A149E, A149F, A149G, A149H, A149I, A149K, A149L, A149M, A149N, A149P, A149Q, A149R, A149S, A149T, A149V, A149W, A149Y, Q150*, Q150A, Q150D, Q150E, Q150F, Q150G, Q150H, Q150I, Q150K, Q150L, Q150M, Q150N, Q150P, Q150R, Q150S, Q150T, Q150V, Q150W, Q150Y, F151*, F151A, F151D, F151E, F151G, F151H, F151I, F151K, F151L, F151M, F151N, F151P, F151Q, F151R, F151S, F151T, F151V, F151W, F151Y, D152*, D152A, D152E, D152F, D152G, D152H, D152I, D152K, D152L, D152M, D152N, D152P, D152Q, D152R, D152S, D152T, D152V, D152W, D152Y, P153*, P153A, P153D, P153E, P153F, P153G, P153H, P153I, P153K, P153L, P153M, P153N, P153Q, P153R, P153S, P153T, P153V, P153W, P153Y, S154*, S154A, S154D, S154E, S154F, S154G, S154H, S154I, S154K, S154L, S154M, S154N, S154P, S154Q, S154R, S154T, S154V, S154W, S154Y, K155*, K155A, K155D, K155E, K155F, K155G, K155H, K155I, K155L, K155M, K155N, K155P, K155Q, K155R, K155S, K155T, K155V, K155W, K155Y, P156*, P156A, P156D, P156E, P156F, P156G, P156H, P156I, P156K, P156L, P156M, P156N, P156Q, P156R, P156S, P156T, P156V, P156W, P156Y, Q157*, Q157A, Q157D, Q157E, Q157F, Q157G, Q157H, Q157I, Q157K, Q157L, Q157M, Q157N, Q157P, Q157R, Q157S, Q157T, Q157V, Q157W, Q157Y, Q158*, Q158A, Q158D, Q158E, Q158F, Q158G, Q158H, Q158I, Q158K, Q158L, Q158M, Q158N, Q158P, Q158R, Q158S, Q158T, Q158V, Q158W, Q158Y, T159*, T159A, T159D, T159E, T159F, T159G, T159H, T159I, T159K, T159L, T159M, T159N, T159P, T159Q, T159R, T159S, T159V, T159W, T159Y, K160*, K160A, K160D, K160E, K160F, K160G, K160H, K160I, K160L, K160M, K160N, K160P, K160Q, K160R, K160S, K160T, K160V, K160W, K160Y, G161*, G161A, G161D, G161E, G161F, G161H, G161I, G161K, G161L, G161M, G161N, G161P, G161Q, G161R, G161S, G161T, G161V, G161W, G161Y, T162A, T162D, T162E, T162F, T162G, T162H, T162I, T162K, T162L, T162M, T162N, T162P, T162Q, T162R, T162S, T162T, T162V, T162W, T162Y, W163*, W163A, W163D, W163E, W163F, W163G, W163H, W163I, W163K, W163L, W163M, W163N, W163P, W163Q, W163R, W163S, W163T, W163V, W163Y, F164*, F164A, F164D, F164E, F164G, F164H, F164I, F164K, F164L, F164M, F164N, F164P, F164Q, F164R, F164S, F164T, F164V, F164W, F164Y, Q165*, Q165A, Q165D, Q165E, Q165F, Q165G, Q165H, Q165I, Q165K, Q165L, Q165M, Q165N, Q165P, Q165R, Q165S, Q165T, Q165V, Q165W, Q165Y, I166*, I166A, I166D, I166E, I166F, I166G, I166H, I166K, I166L, I166M, I166N, I166P, I166Q, I166R, I166S, I166T, I166V, I166W, I166Y, T167*, T167A, T167D, T167E, T167F, T167G, T167H, T167I, T167K, T167L, T167M, T167N, T167P, T167Q, T167R, T167S, T167V, T167W, T167Y, K168*, K168A, K168D, K168E, K168F, K168G, K168H, K168I, K168L, K168M, K168N, K168P, K168Q, K168R, K168S, K168T, K168V, K168W, K168Y, F169*, F169A, F169D, F169E, F169G, F169H, F169I, F169K, F169L, F169M, F169N, F169P, F169Q, F169R, F169S, F169T, F169V, F169W, F169Y, T170*, T170A, T170D, T170E, T170F, T170G, T170H, T170I, T170K, T170L, T170M, T170N, T170P, T170Q, T170R, T170S, T170V, T170W, T170Y, G171*, G171A, G171D, G171E, G171F, G171H, G171I, G171K, G171L, G171M, G171N, G171P, G171Q, G171R, G171S, G171T, G171V, G171W, G171Y, A172*, A172D, A172E, A172F, A172G, A172H, A172I, A172K, A172L, A172M, A172N, A172P, A172Q, A172R, A172S, A172T, A172V, A172W, A172Y, A173*, A173D, A173E, A173F, A173G, A173H, A173I, A173K, A173L, A173M, A173N, A173P, A173Q, A173R, A173S, A173T, A173V, A173W, A173Y, G174*, G174A, G174D, G174E, G174F, G174H, G174I, G174K, G174L, G174M, G174N, G174P, G174Q, G174R, G174S, G174T, G174V, G174W, G174Y, P175*, P175A, P175D, P175E, P175F, P175G, P175H, P175I, P175K, P175L, P175M, P175N, P175Q, P175R, P175S, P175T, P175V, P175W, P175Y, Y176*, Y176A, Y176D, Y176E, Y176F, Y176G, Y176H, Y176I, Y176K, Y176L, Y176M, Y176N, Y176P, Y176Q, Y176R, Y176S, Y176T, Y176V, Y176W, K178*, K178A, K178D, K178E, K178F, K178G, K178H, K178I, K178L, K178M, K178N, K178P, K178Q, K178R, K178S, K178T, K178V, K178W, K178Y, A179*, A179D, A179E, A179F, A179G, A179H, A179I, A179K, A179L, A179M, A179N, A179P, A179Q, A179R, A179S, A179T, A179V, A179W, A179Y, L180*, L180A, L180D, L180E, L180F, L180G, L180H, L180I, L180K, L180M, L180N, L180P, L180Q, L180R, L180S, L180T, L180V, L180W, L180Y, G181*, G181A, G181D, G181E, G181F, G181H, G181I, G181K, G181L, G181M, G181N, G181P, G181Q, G181R, G181S, G181T, G181V, G181W, G181Y, S182*, S182A, S182D, S182E, S182F, S182G, S182H, S182I, S182K, S182L, S182M, S182N, S182P, S182Q, S182R, S182T, S182V, S182W, S182Y, N183*, N183A, N183D, N183E, N183F, N183G, N183H, N183I, N183K, N183L, N183M, N183P, N183Q, N183R, N183S, N183T, N183V, N183W, N183Y, D184*, D184A, D184E, D184F, D184G, D184H, D184I, D184K, D184L, D184M, D184N, D184P, D184Q, D184R, D184S, D184T, D184V, D184W, D184Y, K185*, K185A, K185D, K185E, K185F, K185G, K185H, K185I, K185L, K185M, K185N, K185P, K185Q, K185R, K185S, K185T, K185V, K185W, K185Y, S186*, S186A, S186D, S186E, S186F, S186G, S186H, S186I, S186K, S186L, S186M, S186N, S186P, S186Q, S186R, S186T, S186V, S186W, S186Y, V187*, V187A, V187D, V187E, V187F, V187G, V187H, V187I, V187K, V187L, V187M, V187N, V187P, V187Q, V187R, V187S, V187T, V187W, V187Y, D189*, D189A, D189E, D189F, D189G, D189H, D189I, D189K, D189L, D189M, D189N, D189P, D189Q, D189R, D189S, D189T, D189V, D189W, D189Y, K190*, K190A, K190D, K190E, K190F, K190G, K190H, K190I, K190L, K190M, K190N, K190P, K190Q, K190R, K190S, K190T, K190V, K190W, K190Y, N191*, N191A, N191D, N191E, N191F, N191G, N191H, N191I, N191K, N191L, N191M, N191P, N191Q, N191R, N191S, N191T, N191V, N191W, N191Y, K192*, K192A, K192D, K192E, K192F, K192G, K192H, K192I, K192L, K192M, K192N, K192P, K192Q, K192R, K192S, K192T, K192V, K192W, K192Y, N193*, N193A, N193D, N193E, N193F, N193G, N193H, N193I, N193K, N193L, N193M, N193P, N193Q, N193R, N193S, N193T, N193V, N193W, N193Y, I194*, I194A, I194D, I194E, I194F, I194G, I194H, I194K, I194L, I194M, I194N, I194P, I194Q, I194R, I194S, I194T, I194V, I194W, I194Y, A195*, A195D, A195E, A195F, A195G, A195H, A195I, A195K, A195L, A195M, A195N, A195P, A195Q, A195R, A195S, A195T, A195V, A195W, A195Y, G196*, G196A, G196D, G196E, G196F, G196H, G196I, G196K, G196L, G196M, G196N, G196P, G196Q, G196R, G196S, G196T, G196V, G196W, G196Y, D197*, D197A, D197E, D197F, D197G, D197H, D197I, D197K, D197L, D197M, D197N, D197P, D197Q, D197R, D197S, D197T, D197V, D197W, D197Y, W198*, W198A, W198D, W198E, W198F, W198G, W198H, W198I, W198K, W198L, W198M, W198N, W198P, W198Q, W198R, W198S, W198T, W198V, W198Y, G199*, G199A, G199D, G199E, G199F, G199H, G199I, G199K, G199L, G199M, G199N, G199P, G199Q, G199R, G199S, G199T, G199V, G199W, G199Y, F200*, F200A, F200D, F200E, F200G, F200H, F200I, F200K, F200L, F200M, F200N, F200P, F200Q, F200R, F200S, F200T, F200V, F200W, F200Y, D201*, D201A, D201E, D201F, D201G, D201H, D201I, D201K, D201L, D201M, D201N, D201P, D201Q, D201R, D201S, D201T, D201V, D201W, D201Y, P202*, P202A, P202D, P202E, P202F, P202G, P202H, P202I, P202K, P202L, P202M, P202N, P202Q, P202R, P202S, P202T, P202V, P202W, P202Y, A203*, A203D, A203E, A203F, A203G, A203H, A203I, A203K, A203L, A203M, A203N, A203P, A203Q, A203R, A203S, A203T, A203V, A203W, A203Y, K204*, K204A, K204D, K204E, K204F, K204G, K204H, K204I, K204L, K204M, K204N, K204P, K204Q, K204R, K204S, K204T, K204V, K204W, K204Y, W205*, W205A, W205D, W205E, W205F, W205G, W205H, W205I, W205K, W205L, W205M, W205N, W205P, W205Q, W205R, W205S, W205T, W205V, W205Y, A206*, A206D, A206E, A206F, A206G, A206H, A206I, A206K, A206L, A206M, A206N, A206P, A206Q, A206R, A206S, A206T, A206V, A206W, A206Y, Y207*, Y207A, Y207D, Y207E, Y207F, Y207G, Y207H, Y207I, Y207K, Y207L, Y207M, Y207N, Y207P, Y207Q, Y207R, Y207S, Y207T, Y207V, Y207W, Q208*, Q208A, Q208D, Q208E, Q208F, Q208G, Q208H, Q208I, Q208K, Q208L, Q208M, Q208N, Q208P, Q208R, Q208S, Q208T, Q208V, Q208W, Q208Y, Y209*, Y209A, Y209D, Y209E, Y209F, Y209G, Y209H, Y209I, Y209K, Y209L, Y209M, Y209N, Y209P, Y209Q, Y209R, Y209S, Y209T, Y209V, Y209W, D210*, D210A, D210E, D210F, D210G, D210H, D210I, D210K, D210L, D210M, D210N, D210P, D210Q, D210R, D210S, D210T, D210V, D210W, D210Y, E211*, E211A, E211D, E211F, E211G, E211H, E211I, E211K, E211L, E211M, E211N, E211P, E211Q, E211R, E211S, E211T, E211V, E211W, E211Y, K212*, K212A, K212D, K212E, K212F, K212G, K212H, K212I, K212L, K212M, K212N, K212P, K212Q, K212R, K212S, K212T, K212V, K212W, K212Y, N213*, N213A, N213D, N213E, N213F, N213G, N213H, N213I, N213K, N213L, N213M, N213P, N213Q, N213R, N213S, N213T, N213V, N213W, N213Y, N214*, N214A, N214D, N214E, N214F, N214G, N214H, N214I, N214K, N214L, N214M, N214P, N214Q, N214R, N214S, N214T, N214V, N214W, N214Y, K215*, K215A, K215D, K215E, K215F, K215G, K215H, K215I, K215L, K215M, K215N, K215P, K215Q, K215R, K215S, K215T, K215V, K215W, K215Y, F216*, F216A, F216D, F216E, F216G, F216H, F216I, F216K, F216L, F216M, F216N, F216P, F216Q, F216R, F216S, F216T, F216V, F216W, F216Y, N217*, N217A, N217D, N217E, N217F, N217G, N217H, N217I, N217K, N217L, N217M, N217P, N217Q, N217R, N217S, N217T, N217V, N217W, N217Y, Y218*, Y218A, Y218D, Y218E, Y218F, Y218G, Y218H, Y218I, Y218K, Y218L, Y218M, Y218N, Y218P, Y218Q, Y218R, Y218S, Y218T, Y218V, Y218W, V219*, V219A, V219D, V219E, V219F, V219G, V219H, V219I, V219K, V219L, V219M, V219N, V219P, V219Q, V219R, V219S, V219T, V219W, V219Y, G220*, G220A, G220D, G220E, G220F, G220H, G220I, G220K, G220L, G220M, G220N, G220P, G220Q, G220R, G220S, G220T, G220V, G220W, G220Y, K221*, K221A, K221D, K221E, K221F, K221G, K221H, K221I, K221L, K221M, K221N, K221P, K221Q, K221R, K221S, K221T, K221V, K221W and K221Y, wherein each position corresponds to the position of the polypeptide of SEQ ID NO 1, and wherein the variant have improved activity as compared to the reference DNase e.g. SEQ ID NO 1, when measured in the activity Assay I as described in Assays and Detergents below.

One embodiment of the invention relates to DNase variants having at least 60% identity to SEQ ID NO: 1, having DNase activity and comprising one or more substitutions selected from the group consisting of V1A, V1D, V1E, V1F, V1G, V1H, V1I, V1K, V1L, V1M, V1N, V1P, V1Q, V1R, V1S, V1T, V1W, V1Y, P2A, P2D, P2E, P2F, P2G, P2H, P2I, P2K, P2L, P2M, P2N, P2Q, P2R, P2S, P2T, P2V, P2W, P2Y, V3A, V3C, V3D, V3E, V3F, V3G, V3H, V3I, V3K, V3L, V3M, V3N, V3P, V3R, V3S, V3T, V3W, V3Y, N4A, N4D, N4E, N4F, N4G, N4H, N4I, N4K, N4L, N4M, N4P, N4Q, N4R, N4S, N4T, N4V, N4W, N4Y, P5A, P5D, P5E, P5F, P5G, P5H, P5I, P5K, P5L, P5M, P5N, P5Q, P5R, P5S, P5T, P5V, P5W, P5Y, E6A, E6D, E6F, E6G, E6H, E6I, E6K, E6L, E6M, E6N, E6P, E6Q, E6R, E6S, E6T, E6V, E6W, E6Y, P7A, P7D, P7E, P7F, P7G, P7H, P7I, P7K, P7L, P7M, P7N, P7Q, P7R, P7S, P7T, P7V, P7W, P7Y, D8A, D8E, D8F, D8G, D8H, D8I, D8K, D8L, D8M, D8N, D8P, D8Q, D8R, D8S, D8T, D8V, D8W, D8Y, A9D, A9E, A9F, A9G, A9H, A9I, A9K, A9L, A9M, A9N, A9P, A9Q, A9R, A9S, A9T, A9V, A9W, A9Y, T10A, T10D, T10E, T10F, T10G, T10H, T10I, T10K, T10L, T10M, T10N, T10P, T10Q, T10R, T10S, T10V, T10W, T10Y, S11A, S11D, S11E, S11F, S11G, S11H, S11I, S11K, S11L, S11M, S11N, S11P, S11Q, S11R, S11T, S11V, S11W, S11Y, V12A, V12D, V12E, V12F, V12G, V12H, V12I, V12K, V12L, V12M, V12N, V12P, V12Q, V12R, V12S, V12T, V12W, V12Y, E13A, E13D, E13F, E13G, E13H, E13I, E13K, E13L, E13M, E13N, E13P, E13Q, E13R, E13S, E13T, E13V, E13W, E13Y, N14A, N14D, N14E, N14F, N14G, N14H, N14I, N14K, N14L, N14M, N14P, N14Q, N14R, N14S, N14T, N14V, N14W, N14Y, V15A, V15D, V15E, V15F, V15G, V15H, V15I, V15K, V15L, V15M, V15N, V15P, V15Q, V15R, V15S, V15T, V15W, V15Y, A16D, A16E, A16F, A16G, A16H, A16I, A16K, A16L, A16M, A16N, A16P, A16Q, A16R, A16S, A16T, A16V, A16W, A16Y, L17A, L17D, L17E, L17F, L17G, L17H, L17I, L17K, L17M, L17N, L17P, L17Q, L17R, L17S, L17T, L17V, L17W, L17Y, K18A, K18D, K18E, K18F, K18G, K18H, K18I, K18L, K18M, K18N, K18P, K18Q, K18R, K18S, K18T, K18V, K18W, K18Y, T19A, T19D, T19E, T19F, T19G, T19H, T19I, T19K, T19L, T19M, T19N, T19P, T19Q, T19R, T19S, T19V, T19W, T19Y, G20A, G20D, G20E, G20F, G20H, G20I, G20K, G20L, G20M, G20N, G20P, G20Q, G20R, G20S, G20T, G20V, G20W, G20Y, S21A, S21D, S21E, S21F, S21G, S21H, S21I, S21K, S21L, S21M, S21N, S21P, S21Q, S21R, S21T, S21V, S21W, S21Y, G22A, G22D, G22E, G22F, G22H, G22I, G22K, G22L, G22M, G22N, G22P, G22Q, G22R, G22S, G22T, G22V, G22W, G22Y, D23A, D23E, D23F, D23G, D23H, D23I, D23K, D23L, D23M, D23N, D23P, D23Q, D23R, D23S, D23T, D23V, D23W, D23Y, S24A, S24D, S24E, S24F, S24G, S24H, S24I, S24K, S24L, S24M, S24N, S24P, S24Q, S24R, S24T, S24V, S24W, S24Y, Q25A, Q25D, Q25E, Q25F, Q25G, Q25H, Q25I, Q25K, Q25L, Q25M, Q25N, Q25P, Q25R, Q25S, Q25T, Q25V, Q25W, Q25Y, S26A, S26D, S26E, S26F, S26G, S26H, S26I, S26K, S26L, S26M, S26N, S26P, S26Q, S26R, S26T, S26V, S26W, S26Y, D27A, D27E, D27F, D27G, D27H, D27I, D27K, D27L, D27M, D27N, D27P, D27Q, D27R, D27S, D27T, D27V, D27W, D27Y, P28A, P28D, P28E, P28F, P28G, P28H, P28I, P28K, P28L, P28M, P28N, P28Q, P28R, P28S, P28T, P28V, P28W, P28Y, I29A, I29D, I29E, I29F, I29G, I29H, I29K, I29L, I29M, I29N, I29P, I29Q, I29R, I29S, I29T, I29V, I29W, I29Y, K30A, K30D, K30E, K30F, K30G, K30H, K30I, K30L, K30M, K30N, K30P, K30Q, K30R, K30S, K30T, K30V, K30W, K30Y, A31D, A31E, A31F, A31G, A31H, A31I, A31K, A31L, A31M, A31N, A31P, A31Q, A31R, A31S, A31T, A31V, A31W, A31Y, D32A, D32E, D32F, D32G, D32H, D32I, D32K, D32L, D32M, D32N, D32P, D32Q, D32R, D32S, D32T, D32V, D32W, D32Y, L33A, L33D, L33E, L33F, L33G, L33H, L33I, L33K, L33M, L33N, L33P, L33Q, L33R, L33S, L33T, L33V, L33W, L33Y, E34A, E34D, E34F, E34G, E34H, E34I, E34K, E34L, E34M, E34N, E34P, E34Q, E34R, E34S, E34T, E34V, E34W, E34Y, V35A, V35D, V35E, V35F, V35G, V35H, V35I, V35K, V35L, V35M, V35N, V35P, V35Q, V35R, V35S, V35T, V35W, V35Y, K36A, K36D, K36E, K36F, K36G, K36H, K36I, K36L, K36M, K36N, K36P, K36Q, K36R, K36S, K36T, K36V, K36W, K36Y, G37A, G37D, G37E, G37F, G37H, G37I, G37K, G37L, G37M, G37N, G37P, G37Q, G37R, G37S, G37T, G37V, G37W, G37Y, Q38A, Q38D, Q38E, Q38F, Q38G, Q38H, Q38I, Q38K, Q38L, Q38M, Q38N, Q38P, Q38R, Q38S, Q38T, Q38V, Q38W, Q38Y, S39A, S39D, S39E, S39F, S39G, S39H, S39I, S39K, S39L, S39M, S39N, S39P, S39Q, S39R, S39T, S39V, S39W, S39Y, A40D, A40E, A40F, A40G, A40H, A40I, A40K, A40L, A40M, A40N, A40P, A40Q, A40R, A40S, A40T, A40V, A40W, A40Y, L41A, L41D, L41E, L41F, L41G, L41H, L41I, L41K, L41M, L41N, L41P, L41Q, L41R, L41S, L41T, L41V, L41W, L41Y, P42A, P42D, P42E, P42F, P42G, P42H, P42I, P42K, P42L, P42M, P42N, P42Q, P42R, P42S, P42T, P42V, P42W, P42Y, F43A, F43D, F43E, F43G, F43H, F43I, F43K, F43L, F43M, F43N, F43P, F43Q, F43R, F43S, F43T, F43V, F43W, F43Y, D44A, D44E, D44F, D44G, D44H, D44I, D44K, D44L, D44M, D44N, D44P, D44Q, D44R, D44S, D44T, D44V, D44W, D44Y, V45A, V45D, V45E, V45F, V45G, V45H, V45I, V45K, V45L, V45M, V45N, V45P, V45Q, V45R, V45S, V45T, V45W, V45Y, D46A, D46E, D46F, D46G, D46H, D46I, D46K, D46L, D46M, D46N, D46P, D46Q, D46R, D46S, D46T, D46V, D46W, D46Y, 047A, C47D, C47E, C47F, C47G, C47H, D47I, C47K, C47L, C47M, C47N, C47P, C47Q, C47R, C47S, C47T, C47V, C47W, C47Y, W48A, W48D, W48E, W48F, W48G, W48H, W48I, W48K, W48L, W48M, W48N, W48P, W48Q, W48R, W48S, W48T, W48V, W48Y, A49D, A49E, A49F, A49G, A49H, A49I, A49K, A49L, A49M, A49N, A49P, A49Q, A49S, A49T, A49V, A49W, A49Y, I50A, I50D, I50E, I50F, I50G, I50H, I50K, I50L, I50M, I50N, I50P, I50Q, I50R, I50S, I50T, I50V, I50W, I50Y, L51A, L51D, L51E, L51F, L51G, L51H, L51I, L51K, L51M, L51N, L51P, L51Q, L51R, L51S, L51T, L51V, L51W, L51Y, K53A, K53D, K53E, K53F, K53G, K53H, K53I, K53L, K53M, K53N, K53P, K53Q, K53R, K53S, K53T, K53V, K53W, K53Y, G54A, G54D, G54E, G54F, G54H, G54I, G54K, G54L, G54M, G54N, G54P, G54Q, G54R, G54S, G54T, G54V, G54W, G54Y, A55D, A55E, A55F, A55G, A55H, A55I, A55K, A55L, A55M, A55N, A55P, A55Q, A55R, A55S, A55T, A55V, A55W, A55Y, P56A, P56D, P56E, P56F, P56G, P56H, P56I, P56K, P56L, P56M, P56N, P56Q, P56R, P56S, P56T, P56V, P56W, P56Y, N57A, N57D, N57E, N57F, N57G, N57H, N57I, N57K, N57L, N57M, N57P, N57Q, N57R, N57S, N57T, N57V, N57W, N57Y, V58A, V58D, V58E, V58F, V58G, V58H, V58I, V58K, V58L, V58M, V58N, V58P, V58Q, V58R, V58S, V58T, V58W, V58Y, L59A, L59D, L59E, L59F, L59G, L59H, L59I, L59K, L59M, L59N, L59P, L59Q, L59R, L59S, L59T, L59V, L59W, L59Y, Q60A, Q60D, Q60E, Q60F, Q60G, Q60H, Q60I, Q60K, Q60L, Q60M, Q60N, Q60P, Q60R, Q60S, Q60T, Q60V, Q60W, Q60Y, R61A, R61D, R61E, R61F, R61G, R61H, R61I, R61K, R61L, R61M, R61N, R61P, R61Q, R61S, R61T, R61V, R61W, R61Y, V62A, V62D, V62E, V62F, V62G, V62H, V62I, V62K, V62L, V62M, V62N, V62P, V62Q, V62R, V62S, V62T, V62W, V62Y, N63A, N63D, N63E, N63F, N63G, N63H, N63I, N63K, N63L, N63M, N63P, N63Q, N63R, N63S, N63T, N63V, N63W, N63Y, E64A, E64D, E64F, E64G, E64H, E64I, E64K, E64L, E64M, E64N, E64P, E64Q, E64R, E64S, E64T, E64V, E64W, E64Y, K65A, K65D, K65E, K65F, K65G, K65H, K65I, K65L, K65M, K65N, K65P, K65Q, K65R, K65S, K65T, K65V, K65W, K65Y, T66A, T66D, T66E, T66F, T66G, T66H, T66I, T66K, T66L, T66M, T66N, T66P, T66Q, T66R, T66S, T66V, T66W, T66Y, K67A, K67D, K67E, K67F, K67G, K67H, K67I, K67L, K67M, K67N, K67P, K67Q, K67R, K67S, K67T, K67V, K67W, K67Y, N68A, N68D, N68E, N68F, N68G, N68H, N68I, N68K, N68L, N68M, N68P, N68Q, N68R, N68S, N68T, N68V, N68W, N68Y, S69A, S69D, S69E, S69F, S69G, S69H, S69I, S69K, S69L, S69M, S69N, S69P, S69Q, S69R, S69T, S69V, S69W, S69Y, N70A, N70D, N70E, N70F, N70G, N70H, N70I, N70K, N70L, N70M, N70P, N70Q, N70R, N70S, N70T, N70V, N70W, N70Y, R71A, R71D, R71E, R71F, R71G, R71H, R71I, R71K, R71L, R71M, R71N, R71P, R71Q, R71S, R71T, R71V, R71W, R71Y, D72A, D72E, D72F, D72G, D72H, D72I, D72K, D72L, D72M, D72N, D72P, D72Q, D72R, D72S, D72T, D72V, D72W, D72Y, R73A, R73D, R73E, R73F, R73G, R73H, R73I, R73K, R73L, R73M, R73N, R73P, R73Q, R73S, R73T, R73V, R73W, R73Y, S74A, S74D, S74E, S74F, S74G, S74H, S74I, S74K, S74L, S74M, S74N, S74P, S74Q, S74R, S74T, S74V, S74W, S74Y, G75A, G75D, G75E, G75F, G75H, G75I, G75K, G75L, G75M, G75N, G75P, G75Q, G75R, G75S, G75T, G75V, G75W, G75Y, A76D, A76E, A76F, A76G, A76H, A76I, A76K, A76L, A76M, A76N, A76P, A76Q, A76R, A76S, A76T, A76V, A76W, A76Y, N77A, N77D, N77E, N77F, N77G, N77H, N77I, N77K, N77L, N77M, N77P, N77Q, N77R, N77S, N77T, N77V, N77W, N77Y, K78A, K78D, K78E, K78F, K78G, K78H, K78I, K78L, K78M, K78N, K78P, K78Q, K78R, K78S, K78T, K78V, K78W, K78Y, G79A, G79D, G79E, G79F, G79H, G79I, G79K, G79L, G79M, G79N, G79P, G79Q, G79R, G79S, G79T, G79V, G79W, G79Y, P80A, P80D, P80E, P80F, P80G, P80H, P80I, P80K, P80L, P80M, P80N, P80Q, P80R, P80S, P80T, P80V, P80W, P80Y, F81A, F81D, F81E, F81G, F81H, F81I, F81K, F81L, F81M, F81N, F81P, F81Q, F81R, F81S, F81T, F81V, F81W, F81Y, K82A, K82D, K82E, K82F, K82G, K82H, K82I, K82L, K82M, K82N, K82P, K82Q, K82R, K82S, K82T, K82V, K82W, K82Y, D83A, D83E, D83F, D83G, D83H, D83I, D83K, D83L, D83M, D83N, D83P, D83Q, D83R, D83S, D83T, D83V, D83W, D83Y, P84A, P84D, P84E, P84F, P84G, P84H, P84I, P84K, P84L, P84M, P84N, P84Q, P84R, P84S, P84T, P84V, P84W, P84Y, Q85A, Q85D, Q85E, Q85F, Q85G, Q85H, Q85I, Q85K, Q85L, Q85M, Q85N, Q85P, Q85R, Q85S, Q85T, Q85V, Q85W, Q85Y, K86A, K86D, K86E, K86F, K86G, K86H, K86I, K86L, K86M, K86N, K86P, K86Q, K86R, K86S, K86T, K86V, K86W, K86Y, W87A, W87D, W87E, W87F, W87G, W87H, W87I, W87K, W87L, W87M, W87N, W87P, W87Q, W87R, W87S, W87T, W87V, W87Y, G88A, G88D, G88E, G88F, G88H, G88I, G88K, G88L, G88M, G88N, G88P, G88Q, G88R, G88S, G88T, G88V, G88W, G88Y, I89A, I89D, I89E, I89F, I89G, I89H, I89K, I89L, I89M, I89N, I89P, I89Q, I89R, I89S, I89T, I89V, I89W, I89Y, K90A, K90D, K90E, K90F, K90G, K90H, K90I, K90L, K90M, K90N, K90P, K90Q, K90R, K90S, K90T, K90V, K90W, K90Y, A91D, A91E, A91F, A91G, A91H, A91I, A91K, A91L, A91M, A91N, A91P, A91Q, A91R, A91S, A91T, A91V, A91W, A91Y, L92A, L92D, L92E, L92F, L92G, L92H, L92I, L92K, L92M, L92N, L92P, L92Q, L92R, L92S, L92T, L92V, L92W, L92Y, P93A, P93D, P93E, P93F, P93G, P93H, P93I, P93K, P93L, P93M, P93N, P93Q, P93R, P93S, P93T, P93V, P93W, P93Y, P94A, P94D, P94E, P94F, P94G, P94H, P94I, P94K, P94L, P94M, P94N, P94Q, P94R, P94S, P94T, P94V, P94W, P94Y, K95A, K95D, K95E, K95F, K95G, K95H, K95I, K95L, K95M, K95N, K95P, K95Q, K95R, K95S, K95T, K95V, K95W, K95Y, N96A, N96D, N96E, N96F, N96G, N96H, N96I, N96K, N96L, N96M, N96P, N96Q, N96R, N96S, N96T, N96V, N96W, N96Y, P97A, P97D, P97E, P97F, P97G, P97H, P97I, P97K, P97L, P97M, P97N, P97Q, P97R, P97S, P97T, P97V, P97W, P97Y, S98A, S98D, S98E, S98F, S98G, S98H, S98I, S98K, S98L, S98M, S98N, S98P, S98Q, S98R, S98T, S98V, S98W, S98Y, W99A, W99D, W99E, W99F, W99G, W99H, W99I, W99K, W99L, W99M, W99N, W99P, W99Q, W99R, W99S, W99T, W99V, W99Y, S100A, S100D, S100E, S100F, S100G, S100H, S100I, S100K, S100L, S100M, S100N, S100P, S100Q, S100R, S100T, S100V, S100W, S100Y, A101D, A101E, A101F, A101G, A101H, A101I, A101K, A101L, A101M, A101N, A101P, A101Q, A101R, A101S, A101T, A101V, A101W, A101Y, Q102A, Q102D, Q102E, Q102F, Q102G, Q102H, Q102I, Q102K, Q102L, Q102M, Q102N, Q102P, Q102R, Q102S, Q102T, Q102V, Q102W, Q102Y, D103A, D103E, D103F, D103G, D103H, D103I, D103K, D103L, D103M, D103N, D103P, D103Q, D103R, D103S, D103T, D103V, D103W, D103Y, F104A, F104D, F104E, F104G, F104H, F104I, F104K, F104L, F104M, F104N, F104P, F104Q, F104R, F104S, F104T, F104V, F104W, F104Y, K105A, K105D, K105E, K105F, K105G, K105H, K105I, K105L, K105M, K105N, K105P, K105Q, K105R, K105S, K105T, K105V, K105W, K105Y, S106A, S106D, S106E, S106F, S106G, S106H, S106I, S106K, S106L, S106M, S106N, S106P, S106Q, S106R, S106T, S106V, S106W, S106Y, P107A, P107D, P107E, P107F, P107G, P107H, P107I, P107K, P107L, P107M, P107N, P107Q, P107R, P107S, P107T, P107V, P107W, P107Y, E108A, E108D, E108F, E108G, E108H, E108I, E108K, E108L, E108M, E108N, E108P, E108Q, E108R, E108S, E108T, E108V, E108W, E108Y, E109A, E109D, E109F, E109G, E109H, E109I, E109K, E109L, E109M, E109N, E109P, E109Q, E109R, E109S, E109T, E109V, E109W, E109Y, Y110A, Y110D, Y110E, Y110F, Y110G, Y110H, Y110I, Y110L, Y110M, Y110N, Y110P, Y110Q, Y110R, Y110S, Y110T, Y110V, Y110W, A111D, A111E, A111F, A111G, A111H, A111I, A111K, A111L, A111M, A111N, A111P, A111Q, A111R, A111S, A111T, A111V, A111W, A111Y, F112A, F112D, F112E, F112G, F112H, F112I, F112K, F112L, F112M, F112N, F112P, F112Q, F112R, F112S, F112T, F112V, F112W, F112Y, A113D, A113E, A113F, A113G, A113H, A113I, A113K, A113L, A113M, A113N, A113P, A113Q, A113R, A113S, A113T, A113V, A113W, A113Y, S114A, S114D, S114E, S114F, S114G, S114H, S114I, S114K, S114L, S114M, S114N, S114P, S114Q, S114R, S114T, S114V, S114W, S114Y, S115A, S115D, S115E, S115F, S115G, S115H, S115I, S115K, S115L, S115M, S115N, S115P, S115Q, S115R, S115T, S115V, S115W, S115Y, L116A, L116D, L116E, L116F, L116G, L116H, L116I, L116K, L116M, L116N, L116P, L116Q, L116R, L116S, L116T, L116V, L116W, L116Y, Q117A, Q117D, Q117E, Q117F, Q117G, Q117H, Q117I, Q117K, Q117L, Q117M, Q117N, Q117P, Q117R, Q117S, Q117T, Q117V, Q117W, Q117Y, G118D, G118E, G118F, G118H, G118I, G118K, G118L, G118M, G118N, G118P, G118Q, G118R, G118S, G118T, G118V, G118W, G118Y, G119A, G119D, G119E, G119F, G119H, G119I, G119K, G119L, G119M, G119N, G119P, G119Q, G119R, G119S, G119T, G119V, G119W, G119Y, T120A, T120D, T120E, T120F, T120G, T120H, T120I, T120K, T120L, T120M, T120N, T120P, T120Q, T120R, T120S, T120V, T120W, T120Y, N121A, N121D, N121E, N121F, N121G, N121H, N121I, N121K, N121L, N121M, N121P, N121Q, N121R, N121S, N121T, N121V, N121W, N121Y, A122D, A122E, A122F, A122G, A122H, A122I, A122K, A122L, A122M, A122N, A122P, A122Q, A122R, A122S, A122T, A122V, A122W, A122Y, I123A, I123D, I123E, I123F, I123G, I123H, I123K, I123L, I123M, I123N, I123P, I123Q, I123R, I123S, I123T, I123V, I123W, I123Y, L124A, L124D, L124E, L124F, L124G, L124H, L124I, L124K, L124M, L124N, L124P, L124Q, L124R, L124S, L124T, L124V, L124W, L124Y, A125D, A125E, A125F, A125G, A125H, A125I, A125K, A125L, A125M, A125N, A125P, A125Q, A125R, A125S, A125T, A125V, A125W, A125Y, P126A, P126D, P126E, P126F, P126G, P126H, P126I, P126K, P126L, P126M, P126N, P126Q, P126R, P126S, P126T, P126V, P126W, P126Y, V127A, V127D, V127E, V127F, V127G, V127H, V127I, V127K, V127L, V127M, V127N, V127P, V127Q, V127R, V127S, V127T, V127W, V127Y, N128A, N128D, N128E, N128F, N128G, N128H, N128I, N128K, N128L, N128M, N128P, N128Q, N128R, N128S, N128T, N128V, N128W, N128Y, L129A, L129D, L129E, L129F, L129G, L129H, L129I, L129K, L129M, L129N, L129P, L129Q, L129R, L129S, L129T, L129V, L129W, L129Y, A130D, A130E, A130F, A130G, A130H, A130I, A130K, A130L, A130M, A130N, A130P, A130Q, A130R, A130S, A130T, A130V, A130W, A130Y, S131A, S131D, S131E, S131F, S131G, S131H, S131I, S131K, S131L, S131M, S131N, S131P, S131Q, S131R, S131T, S131V, S131W, S131Y, Q132A, Q132D, Q132E, Q132F, Q132G, Q132H, Q132I, Q132K, Q132L, Q132M, Q132N, Q132P, Q132R, Q132S, Q132T, Q132V, Q132W, Q132Y, N133A, N133D, N133E, N133F, N133G, N133H, N133I, N133K, N133L, N133M, N133P, N133Q, N133R, N133S, N133T, N133V, N133W, N133Y, S134A, S134D, S134E, S134F, S134G, S134H, S134I, S134K, S134L, S134M, S134N, S134P, S134Q, S134R, S134T, S134V, S134W, S134Y, Q135A, Q135D, Q135E, Q135F, Q135G, Q135H, Q135I, Q135K, Q135L, Q135M, Q135N, Q135P, Q135R, Q135S, Q135T, Q135V, Q135W, Q135Y, G136A, G136D, G136E, G136F, G136H, G136I, G136K, G136L, G136M, G136N, G136P, G136Q, G136R, G136S, G136T, G136V, G136W, G136Y, G137A, G137D, G137E, G137F, G137H, G137I, G137K, G137L, G137M, G137N, G137P, G137Q, G137R, G137S, G137T, G137V, G137W, G137Y, V138A, V138D, V138E, V138F, V138G, V138H, V138I, V138K, V138L, V138M, V138N, V138P, V138Q, V138R, V138S, V138T, V138W, V138Y, L139A, L139D, L139E, L139F, L139G, L139H, L139I, L139K, L139M, L139N, L139P, L139Q, L139R, L139S, L139T, L139V, L139W, L139Y, N140A, N140D, N140E, N140F, N140G, N140H, N140I, N140K, N140L, N140M, N140P, N140Q, N140R, N140S, N140T, N140V, N140W, N140Y, G141A, G141D, G141E, G141F, G141H, G141I, G141K, G141L, G141M, G141N, G141P, G141Q, G141R, G141S, G141T, G141V, G141W, G141Y, F142A, F142D, F142E, F142G, F142H, F142I, F142K, F142L, F142M, F142N, F142P, F142Q, F142R, F142S, F142T, F142V, F142W, F142Y, Y143A, Y143D, Y143E, Y143F, Y143G, Y143H, Y143I, Y143K, Y143L, Y143M, Y143N, Y143P, Y143Q, Y143R, Y143S, Y143T, Y143V, Y143W, S144A, S144D, S144E, S144F, S144G, S144H, S144I, S144L, S144M, S144N, S144P, S144Q, S144R, S144T, S144V, S144W, S144Y, A145D, A145E, A145F, A145G, A145H, A145I, A145K, A145L, A145M, A145N, A145P, A145Q, A145R, A145S, A145T, A145V, A145W, A145Y, N146A, N146D, N146E, N146F, N146G, N146H, N146I, N146K, N146L, N146M, N146P, N146Q, N146R, N146S, N146T, N146V, N146W, N146Y, K147A, K147D, K147E, K147F, K147G, K147H, K147I, K147L, K147M, K147N, K147P, K147Q, K147R, K147S, K147T, K147V, K147W, K147Y, V148A, V148D, V148E, V148F, V148G, V148H, V148I, V148K, V148L, V148M, V148N, V148P, V148Q, V148R, V148S, V148T, V148W, V148Y, A149D, A149E, A149F, A149G, A149H, A149I, A149K, A149L, A149M, A149N, A149P, A149Q, A149R, A149S, A149T, A149V, A149W, A149Y, Q150A, Q150D, Q150E, Q150F, Q150G, Q150H, Q150I, Q150K, Q150L, Q150M, Q150N, Q150P, Q150R, Q150S, Q150T, Q150V, Q150W, Q150Y, F151A, F151D, F151E, F151G, F151H, F151I, F151K, F151L, F151M, F151N, F151P, F151Q, F151R, F151S, F151T, F151V, F151W, F151Y, D152A, D152E, D152F, D152G, D152H, D152I, D152K, D152L, D152M, D152N, D152P, D152Q, D152R, D152S, D152T, D152V, D152W, D152Y, P153A, P153D, P153E, P153F, P153G, P153H, P153I, P153K, P153L, P153M, P153N, P153Q, P153R, P153S, P153T, P153V, P153W, P153Y, S154A, S154D, S154E, S154F, S154G, S154H, S154I, S154K, S154L, S154M, S154N, S154P, S154Q, S154R, S154T, S154V, S154W, S154Y, K155A, K155D, K155E, K155F, K155G, K155H, K155I, K155L, K155M, K155N, K155P, K155Q, K155R, K155S, K155T, K155V, K155W, K155Y, P156A, P156D, P156E, P156F, P156G, P156H, P156I, P156K, P156L, P156M, P156N, P156Q, P156R, P156S, P156T, P156V, P156W, P156Y, Q157A, Q157D, Q157E, Q157F, Q157G, Q157H, Q157I, Q157K, Q157L, Q157M, Q157N, Q157P, Q157R, Q157S, Q157T, Q157V, Q157W, Q157Y, Q158A, Q158D, Q158E, Q158F, Q158G, Q158H, Q158I, Q158K, Q158L, Q158M, Q158N, Q158P, Q158R, Q158S, Q158T, Q158V, Q158W, Q158Y, T159A, T159D, T159E, T159F, T159G, T159H, T159I, T159K, T159L, T159M, T159N, T159P, T159Q, T159R, T159S, T159V, T159W, T159Y, K160A, K160D, K160E, K160F, K160G, K160H, K160I, K160L, K160M, K160N, K160P, K160Q, K160R, K160S, K160T, K160V, K160W, K160Y, G161A, G161D, G161E, G161F, G161H, G161I, G161K, G161L, G161M, G161N, G161P, G161Q, G161R, G161S, G161T, G161V, G161W, G161Y, T162A, T162D, T162E, T162F, T162G, T162H, T162I, T162K, T162L, T162M, T162N, T162P, T162Q, T162R, T162S, T162T, T162V, T162W, T162Y, W163A, W163D, W163E, W163F, W163G, W163H, W163I, W163K, W163L, W163M, W163N, W163P, W163Q, W163R, W163S, W163T, W163V, W163Y, F164A, F164D, F164E, F164G, F164H, F164I, F164K, F164L, F164M, F164N, F164P, F164Q, F164R, F164S, F164T, F164V, F164W, F164Y, Q165A, Q165D, Q165E, Q165F, Q165G, Q165H, Q165I, Q165K, Q165L, Q165M, Q165N, Q165P, Q165R, Q165S, Q165T, Q165V, Q165W, Q165Y, I166A, I166D, I166E, I166F, I166G, I166H, I166K, I166L, I166M, I166N, I166P, I166Q, I166R, I166S, I166T, I166V, I166W, I166Y, T167A, T167D, T167E, T167F, T167G, T167H, T167I, T167K, T167L, T167M, T167N, T167P, T167Q, T167R, T167S, T167V, T167W, T167Y, K168A, K168D, K168E, K168F, K168G, K168H, K168I, K168L, K168M, K168N, K168P, K168Q, K168R, K168S, K168T, K168V, K168W, K168Y, F169A, F169D, F169E, F169G, F169H, F169I, F169K, F169L, F169M, F169N, F169P, F169Q, F169R, F169S, F169T, F169Y, F169V, F169W, F169Y, T170D, T170E, T170F, T170G, T170H, T170I, T170K, T170L, T170M, T170N, T170P, T170Q, T170R, T170S, T170V, T170W, T170Y, G171A, G171D, G171E, G171F, G171H, G171I, G171K, G171L, G171M, G171N, G171P, G171Q, G171R, G171S, G171T, G171V, G171W, G171Y, A172D, A172E, A172F, A172G, A172H, A172I, A172K, A172L, A172M, A172N, A172P, A172Q, A172R, A172S, A172T, A172V, A172W, A172Y, A173D, A173E, A173F, A173G, A173H, A173I, A173K, A173L, A173M, A173N, A173P, A173Q, A173R, A173S, A173T, A173V, A173W, A173Y, G174A, G174D, G174E, G174F, G174H, G174I, G174K, G174L, G174M, G174N, G174P, G174Q, G174R, G174S, G174T, G174V, G174W, G174Y, P175A, P175D, P175E, P175F, P175G, P175H, P175I, P175K, P175L, P175M, P175N, P175Q, P175R, P175S, P175T, P175V, P175W, P175Y, Y176A, Y176D, Y176E, Y176F, Y176G, Y176H, Y176I, Y176K, Y176L, Y176M, Y176N, Y176P, Y176Q, Y176R, Y176S, Y176T, Y176V, Y176W, K178A, K178D, K178E, K178F, K178G, K178H, K178I, K178L, K178M, K178N, K178P, K178Q, K178R, K178S, K178T, K178V, K178W, K178Y, A179D, A179E, A179F, A179G, A179H, A179I, A179K, A179L, A179M, A179N, A179P, A179Q, A179R, A179S, A179T, A179V, A179W, A179Y, L180A, L180D, L180E, L180F, L180G, L180H, L180I, L180K, L180M, L180N, L180P, L180Q, L180R, L180S, L180T, L180V, L180W, L180Y, G181A, G181D, G181E, G181F, G181H, G181I, G181K, G181L, G181M, G181N, G181P, G181Q, G181R, G181S, G181T, G181V, G181W, G181Y, S182A, S182D, S182E, S182F, S182G, S182H, S182I, S182K, S182L, S182M, S182N, S182P, S182Q, S182R, S182T, S182V, S182W, S182Y, N183A, N183D, N183E, N183F, N183G, N183H, N183I, N183K, N183L, N183M, N183P, N183Q, N183R, N183S, N183T, N183V, N183W, N183Y, D184A, D184E, D184F, D184G, D184H, D184I, D184K, D184L, D184M, D184N, D184P, D184Q, D184R, D184S, D184T, D184V, D184W, D184Y, K185A, K185D, K185E, K185F, K185G, K185H, K185I, K185L, K185M, K185N, K185P, K185Q, K185R, K185S, K185T, K185V, K185W, K185Y, S186A, S186D, S186E, S186F, S186G, S186H, S186I, S186K, S186L, S186M, S186N, S186P, S186Q, S186R, S186T, S186V, S186W, S186Y, V187A, V187D, V187E, V187F, V187G, V187H, V187I, V187K, V187L, V187M, V187N, V187P, V187Q, V187R, V187S, V187T, V187W, V187Y, D189A, D189E, D189F, D189G, D189H, D189I, D189K, D189L, D189M, D189N, D189P, D189Q, D189R, D189S, D189T, D189V, D189W, D189Y, K190A, K190D, K190E, K190F, K190G, K190H, K190I, K190L, K190M, K190N, K190P, K190Q, K190R, K190S, K190T, K190V, K190W, K190Y, N191A, N191D, N191E, N191F, N191G, N191H, N191I, N191K, N191L, N191M, N191P, N191Q, N191R, N191S, N191T, N191V, N191W, N191Y, K192A, K192D, K192E, K192F, K192G, K192H, K192I, K192L, K192M, K192N, K192P, K192Q, K192R, K192S, K192T, K192V, K192W, K192Y, N193A, N193D, N193E, N193F, N193G, N193H, N193I, N193K, N193L, N193M, N193P, N193Q, N193R, N193S, N193T, N193V, N193W, N193Y, I194A, I194D, I194E, I194F, I194G, I194H, I194K, I194L, I194M, I194N, I194P, I194Q, I194R, I194S, I194T, I194V, I194W, I194Y, A195D, A195E, A195F, A195G, A195H, A195I, A195K, A195L, A195M, A195N, A195P, A195Q, A195R, A195S, A195T, A195V, A195W, A195Y, G196A, G196D, G196E, G196F, G196H, G196I, G196K, G196L, G196M, G196N, G196P, G196Q, G196R, G196S, G196T, G196V, G196W, G196Y, D197A, D197E, D197F, D197G, D197H, D197I, D197K, D197L, D197N, D197P, D197Q, D197R, D197S, D197T, D197V, D197W, D197Y, W198A, W198D, W198E, W198F, W198G, W198H, W198I, W198K, W198L, W198M, W198N, W198P, W198Q, W198R, W198S, W198T, W198V, W198Y, G199A, G199D, G199E, G199F, G199H,

G199I, G199K, G199L, G199M, G199N, G199P, G199Q, G199R, G199S, G199T, G199V, G199W, G199Y, F200A, F200D, F200E, F200G, F200H, F200I, F200K, F200L, F200M, F200N, F200P, F200Q, F200R, F200S, F200T, F200V, F200W, F200Y, D201A, D201E, D201F, D201G, D201H, D201I, D201K, D201L, D201M, D201N, D201P, D201Q, D201R, D201S, D201T, D201V, D201W, D201Y, P202A, P202D, P202E, P202F, P202G, P202H, P202I, P202K, P202L, P202M, P202N, P202Q, P202R, P202S, P202T, P202V, P202W, P202Y, A203D, A203E, A203F, A203G, A203H, A203I, A203K, A203L, A203M, A203N, A203P, A203Q, A203R, A203S, A203T, A203V, A203W, A203Y, K204A, K204D, K204E, K204F, K204G, K204H, K204I, K204L, K204M, K204N, K204P, K204Q, K204R, K204S, K204T, K204V, K204W, K204Y, W205A, W205D, W205E, W205F, W205G, W205H, W205I, W205K, W205L, W205M, W205N, W205P, W205Q, W205R, W205S, W205T, W205V, W205Y, A206D, A206E, A206F, A206G, A206H, A206I, A206K, A206L, A206M, A206N, A206P, A206Q, A206R, A206S, A206T, A206V, A206W, A206Y, Y207A, Y207D, Y207E, Y207F, Y207G, Y207H, Y207I, Y207K, Y207L, Y207M, Y207N, Y207P, Y207Q, Y207R, Y207S, Y207T, Y207V, Y207W, Q208A, Q208D, Q208E, Q208F, Q208G, Q208H, Q208I, Q208K, Q208L, Q208M, Q208N, Q208P, Q208R, Q208S, Q208T, Q208V, Q208W, Q208Y, Y209A, Y209D, Y209E, Y209F, Y209G, Y209H, Y209I, Y209K, Y209L, Y209M, Y209N, Y209P, Y209Q, Y209R, Y209S, Y209T, Y209V, Y209W, D210A, D210E, D210F, D210G, D210H, D210I, D210K, D210L, D210M, D210N, D210P, D210Q, D210R, D210S, D210T, D210V, D210W, D210Y, E211A, E211D, E211F, E211G, E211H, E211I, E211K, E211L, E211M, E211N, E211P, E211Q, E211R, E211S, E211T, E211V, E211W, E211Y, K212A, K212D, K212E, K212F, K212G, K212H, K212I, K212L, K212M, K212N, K212P, K212Q, K212R, K212S, K212T, K212V, K212W, K212Y, N213A, N213D, N213E, N213F, N213G, N213H, N213I, N213K, N213L, N213M, N213P, N213Q, N213R, N213S, N213T, N213V, N213W, N213Y, N214A, N214D, N214E, N214F, N214G, N214H, N214I, N214K, N214L, N214M, N214P, N214Q, N214R, N214S, N214T, N214V, N214W, N214Y, K215A, K215D, K215E, K215F, K215G, K215H, K215I, K215L, K215M, K215N, K215P, K215Q, K215R, K215S, K215T, K215V, K215W, K215Y, F216A, F216D, F216E, F216G, F216H, F216I, F216K, F216L, F216M, F216N, F216P, F216Q, F216R, F216S, F216T, F216V, F216W, F216Y, N217A, N217D, N217E, N217F, N217G, N217H, N217I, N217K, N217L, N217M, N217P, N217Q, N217R, N217S, N217T, N217V, N217W, N217Y, Y218A, Y218D, Y218E, Y218F, Y218G, Y218H, Y218I, Y218K, Y218L, Y218M, Y218N, Y218P, Y218Q, Y218R, Y218S, Y218T, Y218V, Y218W, V219A, V219D, V219E, V219F, V219G, V219H, V219I, V219K, V219L, V219M, V219N, V219P, V219Q, V219R, V219S, V219T, V219W, V219Y, G220A, G220D, G220E, G220F, G220H, G220I, G220K, G220L, G220M, G220N, G220P, G220Q, G220R, G220S, G220T, G220V, G220W, G220Y, K221A, K221D, K221E, K221F, K221G, K221H, K221I, K221L, K221M, K221N, K221P, K221Q, K221R, K221S, K221T, K221V, K221W and K221Y, wherein each position corresponds to the position of the polypeptide of SEQ ID NO 1, and wherein the variant having improved stability as compared to the reference DNase e.g. SEQ ID NO 1 i.e. IF>1.0 when measured in the stability assay as described in Example 2.

One embodiment of the invention relates to DNase variants having at least 80% sequence identity to the polypeptide shown in SEQ ID NO: 1, having DNase activity and comprising one or more substitutions selected from the group consisting of N4E, L17E, T19A, T19G, T19I, K36P, Q38P, S39V, S39R, A40P, A40H, L41T, L41H, V45H, L51G, K53T, K53P, G54P, A55P, N57H, E64A, E64Q, E64R, E64T, E64I, E64S, T66H, K67A, K67T, N68V, N68P, N68I, N68H, S69A, S69D, S69E, S69K, S69L, S69W, S69Y, S69Q, N70T, N70H, N70G, R71T, D72E, S74H, S74G, G75I, N77T, K82P, K82I, D83T, D83P, D83I, D83H, D83G, P84H, Q85T, Q85P, Q85H, K86T, K86P, K86H, G88P, G88H, A91P, W99T, A101W, K105E, K105N, K105T, K105D, S106T, S115T, L116I, Q135L, G136L, V138I, V138L, V138P, V138Q, L139A, N140R, N140L, N140A, G141L, F151R, D152Y, D152L, D152I, D152A, P153E, S154R, T162R, W163E, F164R, I166Y, I166R, K168N, F169R, F169E, A173I, A173R, A173T, S182R, N183E, D184I, K185Y, S186I, D189G, D189H, K212G, K212P and K215I, wherein each position corresponds to the position of the polypeptide of SEQ ID NO 1, and wherein the variant having improved stability as compared to the reference DNase e.g. SEQ ID NO 1 i.e. IF>1.0 when measured in the stability assay as described in Example 2.

The variants according to the invention may have improved stability and/or also have improved deep cleaning performance. Thus, in a preferred embodiment the variants according to the invention have improved detergent stability and/or improved deep cleaning performance compared to a DNase with SEQ ID NO: 1. In a preferred embodiment, the DNase variant comprises a substitution at one or more positions selected from: N4E, L17E, T19A, T19G, T19I, K36P, Q38P, S39V, S39R, A40P, A40H, L41T, L41H, V45H, L51G, K53T, K53P, G54P, A55P, N57H, E64A, E64Q, E64R, E64T, E64I, E64S, T66H, K67A, K67T, N68V, N68P, N68I, N68H, S69A, S69D, S69E, S69K, S69L, S69W, S69Y, S69Q, N70T, N70H, N70G, R71T, D72E, S74H, S74G, G75I, N77T, K82P, K82I, D83T, D83P, D83I, D83H, D83G, P84H, Q85T, Q85P, Q85H, K86T, K86P, K86H, G88P, G88H, A91P, W99T, A101W, K105E, K105N, K105T, K105D, S106T, S115T, L116I, Q135L, G136L, V138I, V138L, V138P, V138Q, L139A, N140R, N140L, N140A, G141L, F151R, D152Y, D152L, D152I, D152A, P153E, S154R, T162R, W163E, F164R, I166Y, I166R, K168N, F169R, F169E, A173I, A173R, A173T, S182R, N183E, D184I, K185Y, S186I, D189G, D189H, K212G, K212P and K215I, wherein each position corresponds to the position of the polypeptide of SEQ ID NO 1 and wherein the variant has at least 60%, such as at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99%, sequence identity to SEQ ID NO: 1.

The variants according to the invention may further comprise one or more additional alterations at one or more (e.g., several) other positions. The amino acid changes may be of a minor nature, that is conservative amino acid substitutions or insertions that do not significantly affect the folding and/or activity of the protein; small deletions, typically of 1-5 amino acids; small amino- or carboxyl-terminal extensions, such as an amino-terminal methionine residue; a small linker peptide of up to 20-25 residues, located at the amino- or carboxyl terminal; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Asn/Gln, Thr/Ser, Ala/Gly, Ala/Thr, Ser/Asn, Ala/Val, Ser/Gly, Tyr/Phe, Ala/Pro, Lys/Arg, Asp/Asn, Glu/Gln, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for DNase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Substantially DNases variants may have one or more (several) amino acid substitutions, deletions and/or insertions as described above. In the present context the term "one or more" is used interchangeably with the term "several". The DNase variants of the invention may further comprise changes which preferably are of a minor nature, e.g. conservative amino acid substitutions and other substitutions that do not significantly affect the three-dimensional folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, or protein A (Nilsson et al., 1985, *EMBO J.* 4: 1075; Nilsson et al., 1991, *Methods Enzymol.* 198: 3. See, also, in general, Ford et al., 1991, *Protein Expression and Purification* 2: 95-107.

Although the changes described above preferably are of a minor nature, such changes may also be of a substantive nature such as fusion of larger polypeptides of up to 300 amino acids or more both as amino- or carboxyl-terminal extensions.

The parent DNase may comprise or consist of the amino acid sequence of SEQ ID NO: 1 or an allelic variant thereof; or a fragment thereof having DNase activity. In one aspect, the parent DNase comprises or consists of the amino acid sequence of SEQ ID NO: 1.

In a preferred aspect of the invention the parent DNase comprise a polypeptide having at least 60%, such as at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 1

The parent DNase may be (a) a polypeptide having at least 60% sequence identity to the polypeptide of SEQ ID NO: 1; (b) a polypeptide encoded by a polynucleotide that hybridizes under medium or high stringency conditions with (i) the mature polypeptide coding sequence of SEQ ID NO: 1, (ii) the cDNA sequence thereof, or (iii) the full-length complement of (i) or (ii); or (c)

In another aspect, the parent DNase is encoded by a polynucleotide that hybridizes under very low stringency conditions, low stringency conditions, medium stringency conditions, or high stringency conditions, or very high stringency conditions with (i) the mature polypeptide coding sequence, (ii) the cDNA sequence thereof, or (iii) the full-length complement of (i) or (ii) (Sambrook et al., 1989, Molecular Cloning, A Laboratory Manual, 2d edition, Cold Spring Harbor, N.Y.).

The polynucleotide or a subsequence thereof, as well as the polypeptide of SEQ ID NO: 1 or a fragment thereof may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides or at least 600 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having DNase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with a polynucleotide encoding SEQ ID NO: 1 or a subsequence thereof, the carrier material is used in a Southern blot.

For purposes of the present invention, hybridization indicates that the polynucleotide hybridizes to a labeled nucleic acid probe corresponding to (i) the mature polypeptide coding sequence; (ii) the cDNA sequence thereof; (iii) the full-length complement thereof; or (iv) a subsequence thereof; under very low, low stringency conditions, low-medium stringency conditions, medium stringency conditions, medium-high stringency conditions, high stringency conditions to very high stringency conditions. Molecules to which the nucleic acid probe hybridizes under these conditions can be detected using, for example, X ray film or any other detection means known in the art.

The parent DNase may be obtained from organisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a fungal DNase. For example, the parent may be an *Aspergillus* DNase. In one aspect, the parent is an *Aspergillus oryzae* DNase, e.g., a DNase with SEQ ID NO: 1.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to a method for obtaining a DNase variant having at least one improved property compared to SEQ ID NO: 1, comprising a) introducing into a parent DNase with at least 60% identity to of SEQ ID NO: 1 an alteration at one or more positions selected from: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 185, 186, 187, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 and 221, wherein the variant has an amino acid sequence which is at least 60%, at least 70%, at least 80%, at least 85%, at least 90% or at least 95% identical to SEQ ID NO: 1; and b) recovering the variant.

The present invention relates to a method for obtaining a DNase variant having at least one improved property compared to SEQ ID NO: 1, comprising introducing into a parent DNase with at least 60% identity to SEQ ID NO: 1 an alteration at one or more positions: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 185, 186, 187, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 or 221, wherein the variant has an amino acid sequence which is at least 60%, at least 70%, at least 80%, at least 90% or at least 95% identical to SEQ ID NO: 1; and recovering the variant.

The present invention also relates to a method for obtaining a DNase variant having at least one improved property compared to SEQ ID NO: 1, comprising a) introducing into a parent DNase with at least 80% identity to of SEQ ID NO: 1 an alteration at one or more positions selected from: N4E, L17E, T19A, T19G, T19I, K36P, Q38P, S39V, S39R, A40P, A40H, L41T, L41H, V45H, L51G, K53T, K53P, G54P, A55P, N57H, E64A, E64Q, E64R, E64T, E64I, E64S, T66H, K67A, K67T, N68V, N68P, N68I, N68H, S69A, S69D, S69E, S69K, S69L, S69W, S69Y, S69Q, N70T, N70H, N70G, R71T, D72E, S74H, S74G, G75I, N77T, K82P, K82I, D83T, D83P, D83I, D83H, D83G, P84H, Q85T, Q85P, Q85H, K86T, K86P, K86H, G88P, G88H, A91P, W99T, A101W, K105E, K105N, K105T, K105D, S106T, S115T, L116I, Q135L, G136L, V138I, V138L, V138P, V138Q, L139A, N140R, N140L, N140A, G141L, F151R, D152Y, D152L, D152I, D152A, P153E, S154R, T162R, W163E, F164R, I166Y, I166R, K168N, F169R, F169E, A173I, A173R, A173T, S182R, N183E, D184I, K185Y, S186I, D189G, D189H, K212G, K212P and K215I, wherein the variant has an amino acid sequence which is at least 60%, at least 70%, at least 80%, at least 85%, at least 90% or at least 95% identical to SEQ ID NO: 1; and b) recovering the variant.

The variants of the invention may also be prepared by procedures such as those mentioned below.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2 tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO 1), *Saccharomyces cerevisiae* galactokinase (GAL1), *Saccharomyces cerevisiae* alcohol dehydrogenase/glyceraldehyde-3 phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3 phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3' terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3 phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene. Examples of suitable mRNA stabilizer regions are obtained from a *Bacillus thuringiensis* cryIIIA gene (WO 94/25612) and a *Bacillus subtilis* SP82 gene (Hue et al., 1995, Journal of Bacteriology 177: 3465-3471).

The control sequence may also be a leader, a nontranslated region of an mRNA that is important for translation by the host cell. The leader is operably linked to the 5' terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO 1), *Saccharomyces cerevisiae* 3 phosphoglycerate kinase, *Saccharomyces cerevisiae* alpha-factor, and *Saccharomyces cerevisiae* alcohol dehydrogenase/glyceraldehyde-3 phosphate dehydrogenase (ADH2/GAP).

The control sequence may also be a polyadenylation sequence; a sequence operably linked to the 3' terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N terminus of a polypeptide and directs the polypeptide into the cell's secretory pathway. The 5' end of the coding sequence of the polynucleotide may inherently contain a signal peptide coding sequence naturally linked in translation reading frame with the segment of the coding sequence that encodes the polypeptide. Alternatively, the 5' end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N terminus of a polypeptide and the signal peptide sequence is positioned next to the N terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression. In a further embodiment, polynucleotide sequence codons have been modified by nucleotide substitutions to correspond to the codon usage of the host organism intended for production of the polypeptide of the present invention. The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are Bacillus licheniformis or Bacillus subtilis dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5' phosphate decarboxylase), sC (sulfate adenyltransferase), and trpC (anthranilate synthase), as well as equivalents thereof. Preferred for use in an Aspergillus cell are Aspergillus nidulans or Aspergillus oryzae amdS and pyrG genes and a Streptomyces hygroscopicus bar gene. Preferred for use in a Trichoderma cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome. For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in E. coli, and pUB110, pE194, pTA1060, and pAMß1 permitting replication in Bacillus.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, Nucleic Acids Res. 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, Bacillus, Clostridium, Enterococcus, Geobacillus, Lactobacillus, Lactococcus, Oceanobacillus, Staphylococcus, Streptococcus, and Streptomyces. Gram-negative bacteria include, but are not limited to, Campylobacter, E. coli, Flavobacterium, Fusobacterium, Helicobacter, Ilyobacter, Neisseria, Pseudomonas, Salmonella, and Ureaplasma.

The bacterial host cell may be any Bacillus cell including, but not limited to, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, and Bacillus thuringiensis cells.

The bacterial host cell may also be any Streptococcus cell including, but not limited to, Streptococcus equisimilis, Streptococcus pyogenes, Streptococcus uberis, and Streptococcus equi subsp. Zooepidemicus cells.

The bacterial host cell may also be any Streptomyces cell including, but not limited to, Streptomyces achromogenes, Streptomyces avermitilis, Streptomyces coelicolor, Streptomyces griseus, and Streptomyces lividans cells.

The introduction of DNA into a Bacillus cell may be effected by protoplast transformation (see, e.g., Chang and Cohen, 1979, Mol. Gen. Genet. 168: 111-115), competent cell transformation (see, e.g., Young and Spizizen, 1961, J. Bacteriol. 81: 823-829, or Dubnau and Davidoff-Abelson, 1971, J. Mol. Biol. 56: 209-221), electroporation (see, e.g., Shigekawa and Dower, 1988, Biotechniques 6: 742-751), or conjugation (see, e.g., Koehler and Thorne, 1987, J. Bacteriol. 169: 5271-5278). The introduction of DNA into an E. coli cell may be effected by protoplast transformation (see, e.g., Hanahan, 1983, J. Mol. Biol. 166: 557-580) or electroporation (see, e.g., Dower et al., 1988, Nucleic Acids Res. 16: 6127-6145). The introduction of DNA into a Streptomyces cell may be effected by protoplast transformation, electroporation (see, e.g., Gong et al., 2004, Folia Microbiol. (Praha) 49: 399-405), conjugation (see, e.g., Mazodier et al., 1989, J. Bacteriol. 171: 3583-3585), or transduction (see, e.g., Burke et al., 2001, Proc. Natl. Acad. Sci. USA 98: 6289-6294). The introduction of DNA into a Pseudomonas cell may be effected by electroporation (see, e.g., Choi et al., 2006, J. Microbiol. Methods 64: 391-397) or conjugation (see, e.g., Pinedo and Smets, 2005, Appl. Environ. Microbiol. 71: 51-57). The introduction of DNA into a Streptococcus cell may be effected by natural competence (see, e.g., Perry and Kuramitsu, 1981, Infect. Immun. 32: 1295-1297), protoplast transformation (see, e.g., Catt and Jollick, 1991, Microbios 68: 189-207), electroporation (see, e.g., Buckley et al., 1999, Appl. Environ. Microbiol. 65: 3800-3804), or conjugation (see, e.g., Clewell, 1981, Microbiol. Rev. 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

The yeast host cell may be a Candida, Hansenula, Kluyveromyces, Pichia, Saccharomyces, Schizosaccharomyces, or Yarrowia cell, such as a Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, or Yarrowia lipolytica cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

The filamentous fungal host cell may be an Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell.

For example, the filamentous fungal host cell may be an Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi,

*Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is an *Aspergillus* cell. In another aspect, the cell is an *Aspergillus oryzae* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

In one embodiment, the invention further comprises producing the polypeptide by cultivating the recombinant host cell further comprising a polynucleotide encoding a second polypeptide of interest; preferably an enzyme of interest; more preferably a secreted enzyme of interest; even more preferably a hydrolase, isomerase, ligase, lyase, oxidoreductase, or a transferase; and most preferably the secreted enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.

In one embodiment, the second polypeptide of interest is heterologous or homologous to the host cell.

In one embodiment, the recombinant host cell is a fungal host cell; preferably a filamentous fungal host cell; more preferably an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell; most preferably an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia*

*radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

In one embodiment, the recombinant host cell is a bacterial host cell; preferably a prokaryotic host cell; more preferably a Gram-positive host cell; even more preferably a *Bacillus, Clostridium, Enterococcus, Geobacillus, Lactobacillus, Lactococcus, Oceanobacillus, Staphylococcus, Streptococcus,* or *Streptomyces* host cell; and most preferably a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* host cell.

In one embodiment, a method of producing the second polypeptide of interest comprises cultivating the host cell under conditions conducive for production of the second polypeptide of interest.

In one embodiment, the method further comprises recovering the second polypeptide of interest.

Compositions

The present invention further concerns a detergent composition comprising at least one DNase variant according to the invention and preferably a detergent adjunct ingredient. The detergent composition may be used for preventing, reducing or removing biofilm from an item, for preventing, reducing or removing the stickiness of an item, for pretreating stains on the item, for preventing, reducing or removing redeposition of soil during a wash cycle, for reducing or removing adherence of soil to an item, for maintaining or improving the whiteness of an item and for preventing, reducing or removing malodor from an item, such as E-2-nonenal as described in Assay II. The detergent compositions comprising the polypeptides of the present invention overcomes the problems of the prior art. The DNase variants of the invention are useful in powder and liquid detergent.

One embodiment of the invention relates to a detergent composition comprising a DNase variant which compared to SEQ ID NO: 1 comprises an alteration at one or more positions selected from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 185, 186, 187, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 and 221 and a detergent adjunct.

In one embodiment of the invention, the detergent composition comprises a DNase variant which compared to SEQ ID NO: 1 comprises one or more alterations selected from the group consisting of: V1*, V1A, V1D, V1E, V1F, V1G, V1H, V1I, V1K, V1L, V1M, V1N, V1P, V1Q, V1R, V1S, V1T, V1W, V1Y, P2*, P2A, P2D, P2E, P2F, P2G, P2H, P2I, P2K, P2L, P2M, P2N, P2Q, P2R, P2S, P2T, P2V, P2W, P2Y, V3*, V3A, V3C, V3D, V3E, V3F, V3G, V3H, V3I, V3K, V3L, V3M, V3N, V3P, V3R, V3S, V3T, V3W, V3Y, N4*, N4A, N4D, N4E, N4F, N4G, N4H, N4I, N4K, N4L, N4M, N4P, N4Q, N4R, N4S, N4T, N4V, N4W, N4Y, P5*, P5A, P5D, P5E, P5F, P5G, P5H, P5I, P5K, P5L, P5M, P5N, P5Q, P5R, P5S, P5T, P5V, P5W, P5Y, E6*, E6A, E6D, E6F, E6G, E6H, E6I, E6K, E6L, E6M, E6N, E6P, E6Q, E6R, E6S, E6T, E6V, E6W, E6Y, P7*, P7A, P7D, P7E, P7F, P7G, P7H, P7I, P7K, P7L, P7M, P7N, P7Q, P7R, P7S, P7T, P7V, P7W, P7Y, D8*, D8A, D8E, D8F, D8G, D8H, D8I, D8K, D8L, D8M, D8N, D8P, D8Q, D8R, D8S, D8T, D8V, D8W, D8Y, A9*, A9D, A9E, A9F, A9G, A9H, A9I, A9K, A9L, A9M, A9N, A9P, A9Q, A9R, A9S, A9T, A9V, A9W, A9Y, T10*, T10A, T10D, T10E, T10F, T10G, T10H, T10I, T10K, T10L, T10M, T10N, T10P, T10Q, T10R, T10S, T10V, T10W, T10Y, S11*, S11A, S11D, S11E, S11F, S11G, S11H, S11I, S11K, S11L, S11M, S11N, S11P, S11Q, S11R, S11T, S11V, S11W, S11Y, V12*, V12A, V12D, V12E, V12F, V12G, V12H, V12I, V12K, V12L, V12M, V12N, V12P, V12Q, V12R, V12S, V12T, V12W, V12Y, E13*, E13A, E13D, E13F, E13G, E13H, E13I, E13K, E13L, E13M, E13N, E13P, E13Q, E13R, E13S, E13T, E13V, E13W, E13Y, N14*, N14A, N14D, N14E, N14F, N14G, N14H, N14I, N14K, N14L, N14M, N14P, N14Q, N14R, N14S, N14T, N14V, N14W, N14Y, V15*, V15A, V15D, V15E, V15F, V15G, V15H, V15I, V15K, V15L, V15M, V15N, V15P, V15Q, V15R, V15S, V15T, V15W, V15Y, A16*, A16D, A16E, A16F, A16G, A16H, A16I, A16K, A16L, A16M, A16N, A16P, A16Q, A16R, A16S, A16T, A16V, A16W, A16Y, L17*, L17A, L17D, L17E, L17F, L17G, L17H, L17I, L17K, L17M, L17N, L17P, L17Q, L17R, L17S, L17T, L17V, L17W, L17Y, K18*, K18A, K18D, K18E, K18F, K18G, K18H, K18I, K18L, K18M, K18N, K18P, K18Q, K18R, K18S, K18T, K18V, K18W, K18Y, T19*, T19A, T19D, T19E, T19F, T19G, T19H, T19I, T19K, T19L, T19M, T19N, T19P, T19Q, T19R, T19S, T19V, T19W, T19Y, G20*, G20A, G20D, G20E, G20F, G20H, G20I, G20K, G20L, G20M, G20N, G20P, G20Q, G20R, G20S, G20T, G20V, G20W, G20Y, S21*, S21A, S21D, S21E, S21F, S21G, S21H, S21I, S21K, S21L, S21M, S21N, S21P, S21Q, S21R, S21T, S21V, S21W, S21Y, G22*, G22A, G22D, G22E, G22F, G22H, G22I, G22K, G22L, G22M, G22N, G22P, G22Q, G22R, G22S, G22T, G22V, G22W, G22Y, D23*, D23A, D23E, D23F, D23G, D23H, D23I, D23K, D23L, D23M, D23N, D23P, D23Q, D23R, D23S, D23T, D23V, D23W, D23Y, S24*, S24A, S24D, S24E, S24F, S24G, S24H, S24I, S24K, S24L, S24M, S24N, S24P, S24Q, S24R, S24T, S24V, S24W, S24Y, Q25*, Q25A, Q25D, Q25E, Q25F, Q25G, Q25H, Q25I, Q25K, Q25L, Q25M, Q25N, Q25P, Q25R, Q25S, Q25T, Q25V, Q25W, Q25Y, S26*, S26A, S26D, S26E, S26F, S26G, S26H, S26I, S26K, S26L, S26M, S26N, S26P, S26Q, S26R, S26T, S26V, S26W, S26Y, D27*, D27A, D27E, D27F, D27G, D27H, D27I, D27K, D27L, D27M, D27N, D27P, D27Q, D27R, D27S, D27T, D27V, D27W, D27Y, P28*, P28A, P28D, P28E, P28F, P28G, P28H, P28I, P28K, P28L, P28M, P28N, P28Q, P28R, P28S, P28T, P28V, P28W, P28Y, I29*, I29A, I29D, I29E, I29F, I29G, I29H, I29K, I29L, I29M, I29N, I29P, I29Q, I29R, I29S, I29T, I29V, I29W, I29Y, K30*, K30A, K30D, K30E, K30F, K30G, K30H, K30I, K30L, K30M, K30N, K30P, K30Q, K30R, K30S, K30T, K30V, K30W, K30Y, A31*, A31D, A31E, A31F, A31G, A31H, A31I, A31K, A31L, A31M, A31N, A31P, A31Q, A31R, A31S, A31T, A31V, A31W, A31Y, D32*, D32A, D32E, D32F, D32G, D32H, D32I, D32K, D32L, D32M, D32N, D32P, D32Q, D32R, D32S, D32T, D32V, D32W, D32Y, L33*, L33A, L33D, L33E, L33F, L33G, L33H, L33I, L33K, L33M, L33N, L33P, L33Q, L33R, L33S, L33T, L33V, L33W, L33Y, E34*, E34A, E34D, E34F, E34G, E34H, E34I, E34K, E34L, E34M, E34N, E34P, E34Q, E34R, E34S, E34T, E34V, E34W, E34Y, V35*, V35A, V35D, V35E, V35F, V35G, V35H, V35I, V35K, V35L, V35M, V35N, V35P, V35Q, V35R, V35S, V35T, V35W, V35Y, K36*, K36A, K36D, K36E, K36F, K36G, K36H, K36I, K36L, K36M, K36N, K36P, K36Q, K36R, K36S, K36T, K36V, K36W, K36Y, G37*, G37A, G37D, G37E, G37F, G37H, G37I, G37K, G37L, G37M, G37N, G37P, G37Q, G37R, G37S, G37T, G37V, G37W, G37Y, Q38*, Q38A, Q38D, Q38E, Q38F, Q38G, Q38H, Q38I, Q38K, Q38L, Q38M, Q38N, Q38P, Q38R, Q38S, Q38T, Q38V, Q38W, Q38Y, S39*, S39A, S39D, S39E, S39F, S39G, S39H, S39I, S39K, S39L, S39M, S39N, S39P, S39Q, S39R, S39T, S39V, S39W, S39Y, A40*, A40D, A40E, A40F, A40G, A40H, A40I, A40K, A40L, A40M, A40N, A40P, A40Q, A40R, A40S, A40T, A40V, A40W, A40Y, L41*, L41A, L41D, L41E, L41F, L41G, L41H, L41I, L41K, L41M, L41N, L41P, L41Q, L41R, L41S, L41T, L41V, L41W, L41Y, P42*, P42A, P42D, P42E, P42F, P42G, P42H, P42I, P42K, P42L, P42M, P42N, P42Q, P42R, P42S, P42T, P42V, P42W, P42Y, F43*, F43A, F43D, F43E, F43G, F43H, F43I, F43K, F43L, F43M, F43N, F43P, F43Q, F43R, F43S, F43T, F43V, F43W, F43Y, D44*, D44A, D44E, D44F, D44G, D44H, D44I, D44K, D44L, D44M, D44N, D44P, D44Q, D44R, D44S, D44T, D44V, D44W, D44Y, V45*, V45A, V45D, V45E, V45F, V45G, V45H, V45I, V45K, V45L, V45M, V45N, V45P, V45Q, V45R, V45S, V45T, V45W, V45Y, D46*, D46A, D46E, D46F, D46G, D46H, D46I, D46K, D46L, D46M, D46N, D46P, D46Q, D46R, D46S, D46T, D46V, D46W, D46Y, C47A, C47D, C47E, C47F, C47G, C47H, D47I, C47K, C47L, C47M, C47N, C47P, C47Q, C47R, C47S, C47T, 047V, C47W, C47Y, W48*, W48A, W48D, W48E, W48F, W48G, W48H, W48I, W48K, W48L, W48M, W48N, W48P, W48Q, W48R, W48S, W48T, W48V, W48Y, A49*, A49D, A49E, A49F, A49G, A49H, A49I, A49K, A49L, A49M, A49N, A49P, A49Q, A49R, A49S, A49T, A49V, A49W, A49Y, I50*, I50A, I50D, I50E, I50F, I50G, I50H, I50K, I50L, I50M, I50N, I50P, I50Q, I50R, I50S, I50T, I50V, I50W, I50Y, L51*, L51A, L51D, L51E, L51F, L51G, L51H, L51I, L51K, L51M, L51N, L51P, L51Q, L51R, L51S, L51T, L51V, L51W, L51Y, K53*, K53A, K53D, K53E, K53F, K53G, K53H, K53I, K53L, K53M, K53N, K53P, K53Q, K53R, K53S, K53T, K53V, K53W, K53Y, G54*, G54A, G54D, G54E, G54F, G54H, G54I, G54K, G54L, G54M, G54N, G54P, G54Q, G54R, G54S, G54T, G54V, G54W, G54Y, A55*, A55D, A55E, A55F, A55G, A55H, A55I, A55K, A55L, A55M, A55N, A55P, A55Q, A55R, A55S, A55T, A55V, A55W, A55Y, P56*, P56A, P56D, P56E, P56F, P56G, P56H, P56I, P56K, P56L, P56M, P56N, P56Q, P56R, P56S, P56T, P56V, P56W, P56Y, N57*, N57A, N57D, N57E, N57F, N57G, N57H, N57I, N57K, N57L, N57M, N57P, N57Q, N57R, N57S, N57T, N57V, N57W, N57Y, V58*, V58A, V58D, V58E, V58F, V58G, V58H, V58I, V58K, V58L, V58M, V58N, V58P, V58Q, V58R, V58S, V58T, V58W, V58YL59*, L59A, L59D, L59E, L59F, L59G, L59H, L59I, L59K, L59M, L59N, L59P, L59Q, L59R, L59S, L59T, L59V, L59W, L59Y, Q60*, Q60A, Q60D, Q60E, Q60F, Q60G, Q60H, Q60I, Q60K, Q60L, Q60M, Q60N, Q60P, Q60R, Q60S, Q60T, Q60V, Q60W, Q60Y, R61*, R61A, R61D, R61E, R61F, R61G, R61H, R61I, R61K, R61L, R61M, R61N, R61P, R61Q, R61S, R61T, R61V, R61W, R61Y, V62*, V62A, V62D, V62E, V62F, V62G, V62H, V62I, V62K, V62L, V62M, V62N, V62P, V62Q, V62R, V62S, V62T, V62W, V62Y, N63*, N63A, N63D, N63E, N63F, N63G, N63H, N63I, N63K, N63L, N63M, N63P, N63Q, N63R, N63S, N63T, N63V, N63W, N63Y, E64*, E64A, E64D, E64F, E64G, E64H, E64I, E64K, E64L, E64M, E64N, E64P, E64Q, E64R, E64S, E64T, E64V, E64W, E64Y, K65*, K65A, K65D, K65E, K65F, K65G, K65H, K65I, K65L, K65M, K65N, K65P, K65Q, K65R, K65S, K65T, K65V, K65W, K65Y, T66*, T66A, T66D, T66E, T66F, T66G, T66H, T66I, T66K, T66L, T66M, T66N, T66P, T66Q, T66R, T66S, T66V, T66W, T66Y, K67*, K67A, K67D, K67E, K67F, K67G, K67H, K67I, K67L, K67M, K67N, K67P, K67Q, K67R, K67S, K67T, K67V, K67W, K67Y, N68*, N68A, N68D, N68E, N68F, N68G, N68H, N68I, N68K, N68L, N68M, N68P, N68Q, N68R, N68S, N68T, N68V, N68W, N68Y, S69*, S69A, S69D, S69E, S69F, S69G, S69H, S69I, S69K, S69L, S69M, S69N, S69P, S69Q, S69R, S69T, S69V, S69W, S69Y, N70*, N70A, N70D, N70E, N70F, N70G, N70H, N70I, N70K, N70L, N70M, N70P, N70Q, N70R, N70S, N70T, N70V, N70W, N70Y, R71*, R71A, R71D, R71E, R71F, R71G, R71H, R71I, R71K, R71L, R71M, R71N, R71P, R71Q, R71S, R71T, R71V, R71W, R71Y, D72*, D72A, D72E, D72F, D72G, D72H, D72I, D72K, D72L, D72M, D72N, D72P, D72Q, D72R, D72S, D72T, D72V, D72W, D72Y, R73*, R73A, R73D, R73E, R73F, R73G, R73I, R73K, R73L, R73M, R73N, R73P, R73Q, R73S, R73T, R73V, R73W, R73Y, S74*, S74A, S74D, S74E, S74F, S74G, S74H, S74I, S74K, S74L, S74M, S74N, S74P, S74Q, S74R, S74T, S74V, S74W, S74Y, G75*, G75A, G75D, G75E, G75F, G75H, G75I, G75K, G75L, G75M, G75N, G75P, G75Q, G75R, G75S, G75T, G75V, G75W, G75Y, A76*, A76D, A76E, A76F, A76G, A76H, A76I, A76K, A76L, A76M, A76N, A76P, A76Q, A76R, A76S, A76T, A76V, A76W, A76Y, N77*, N77A, N77D, N77E, N77F, N77G, N77H, N77I, N77K, N77L, N77M, N77P, N77Q, N77R, N77S, N77T, N77V, N77W, N77Y, K78*, K78A, K78D, K78E, K78F, K78G, K78H, K78I, K78L, K78M, K78N, K78P, K78Q, K78R, K78S, K78T, K78V, K78W, K78Y, G79*, G79A, G79D, G79E, G79F, G79H, G79I, G79K, G79L, G79M, G79N, G79P, G79Q, G79R, G79S, G79T, G79V, G79W, G79Y, P80*, P80A, P80D, P80E, P80F, P80G, P80H, P80I, P80K, P80L, P80M, P80N, P80Q, P80R, P80S, P80T, P80V, P80W, P80Y, F81*, F81A, F81D, F81E, F81G, F81H, F81I, F81K, F81L, F81M, F81N, F81P, F81Q, F81R, F81S, F81T, F81V, F81W, F81Y, K82*, K82A, K82D, K82E, K82F, K82G, K82H, K82I, K82L, K82M, K82N, K82P, K82Q, K82R, K82S, K82T, K82V, K82W, K82Y, D83*, D83A, D83E, D83F, D83G, D83H, D83I, D83K, D83L, D83M, D83N, D83P, D83Q, D83R, D83S, D83T, D83V, D83W, D83Y, P84*, P84A, P84D, P84E, P84F, P84G, P84H, P84I, P84K, P84L, P84M, P84N, P84Q, P84R, P84S, P84T, P84V, P84W, P84Y, Q85*, Q85A, Q85D, Q85E, Q85F, Q85G, Q85H, Q85I, Q85K, Q85L, Q85M, Q85N, Q85P, Q85R, Q85S, Q85T, Q85V, Q85W, Q85Y, K86*, K86A, K86D, K86E, K86F, K86G, K86H, K86I, K86L, K86M, K86N, K86P, K86Q, K86R, K86S, K86T, K86V, K86W, K86Y, W87*, W87A, W87D, W87E, W87F, W87G, W87H, W87I, W87K, W87L, W87M, W87N, W87P, W87Q, W87R, W87S, W87T, W87V, W87Y, G88*, G88A, G88D, G88E, G88F, G88H, G88I, G88K, G88L, G88M, G88N, G88P, G88Q, G88R, G88S, G88T, G88V, G88W, G88Y, I89*, I89A, I89D, I89E, I89F, I89G, I89H, I89K, I89L, I89M, I89N, I89P, I89Q, I89R, I89S, I89T, I89V, I89W, I89Y, K90*, K90A, K90D, K90E, K90F, K90G, K90H, K90I, K90L, K90M, K90N, K90P, K90Q, K90R, K90S, K90T, K90V, K90W, K90Y, A91*, A91D, A91E, A91F, A91G, A91H, A91I, A91K, A91L, A91M, A91N, A91P, A91Q, A91R, A91S, A91T, A91V, A91W, A91Y, L92*, L92A, L92D, L92E, L92F, L92G, L92H, L92I, L92K, L92M, L92N, L92P, L92Q, L92R, L92S, L92T, L92V, L92W, L92Y, P93*, P93A, P93D, P93E, P93F, P93G, P93H, P93I, P93K, P93L, P93M, P93N, P93Q, P93R, P93S, P93T, P93V, P93W, P93Y, P94*, P94A, P94D, P94E, P94F, P94G, P94H, P94I, P94K, P94L, P94M, P94N, P94Q, P94R, P94S, P94T, P94V, P94W, P94Y, K95*, K95A, K95D, K95E, K95F, K95G, K95H, K95I, K95L, K95M, K95N, K95P, K95Q, K95R, K95S, K95T, K95V, K95W, K95Y, N96*, N96A, N96D, N96E, N96F, N96G, N96H, N96I, N96K, N96L, N96M, N96P, N96Q, N96R, N96S, N96T, N96V, N96W, N96Y, P97*, P97A, P97D, P97E, P97F, P97G, P97H, P97I, P97K, P97L, P97M, P97N, P97Q, P97R, P97S, P97T, P97V, P97W, P97Y, S98*, S98A, S98D, S98E, S98F, S98G, S98H, S98I, S98K, S98L, S98M, S98N, S98P, S98Q, S98R, S98T, S98V, S98W, S98Y, W99*, W99A, W99D, W99E, W99F, W99G, W99H, W99I, W99K, W99L, W99M, W99N, W99P, W99Q, W99R, W99S, W99T, W99V, W99Y, S100*, S100A, S100D, S100E, S100F, S100G, S100H, S100I, S100K, S100L, S100M, S100N, S100P, S100Q, S100R, S100T, S100V, S100W, S100Y, A101*, A101D, A101E, A101F, A101G, A101H, A101I, A101K, A101L, A101M, A101N, A101P, A101Q, A101R, A101S, A101T, A101V, A101W, A101Y, Q102*, Q102A, Q102D, Q102E, Q102F, Q102G, Q102H, Q102I, Q102K, Q102L, Q102M, Q102N, Q102P, Q102R, Q102S, Q102T, Q102V, Q102W, Q102Y, Q103*, D103A, D103E, D103F, D103G, D103H, D103I, D103K, D103L, D103M, D103N, D103P, D103Q, D103R, D103S, D103T, D103V, D103W, D103Y, F104*, F104A, F104D, F104E, F104G, F104H, F104I, F104K, F104L, F104M, F104N, F104P, F104Q, F104R, F104S, F104T, F104V, F104W, F104Y, K105*, K105A, K105D, K105E, K105F, K105G, K105H, K105I, K105L, K105M, K105N, K105P, K105Q, K105R, K105S, K105T, K105V, K105W, K105Y, S106*, S106A, S106D, S106E, S106F, S106G, S106H, S106I, S106K, S106L, S106M, S106N, S106P, S106Q, S106R, S106T, S106V, S106W, S106Y, P107*, P107A, P107D, P107E, P107F, P107G, P107H, P107I, P107K, P107L, P107M, P107N, P107Q, P107R, P107S, P107T, P107V, P107W, P107Y, E108*, E108A, E108D, E108F, E108G, E108H, E108I, E108K, E108L, E108M, E108N, E108P, E108Q, E108R, E108S, E108T, E108V, E108W, E108Y, E109*, E109A, E109D, E109F, E109G, E109H, E109I, E109K, E109L, E109M, E109N, E109P, E109Q, E109R, E109S, E109T, E109V, E109Y, Y110*, Y110A, Y110D, Y110E, Y110F, Y110G, Y110H, Y110I, Y110K, Y110L, Y110M, Y110N, Y110P, Y110Q, Y110R, Y110S, Y110T, Y110V, Y110W, A111*, A111D, A111E, A111F, A111G, A111H, A111I, A111K, A111L, A111M, A111N, A111P, A111Q, A111R, A111S, A111T, A111V, A111W, A111Y, F112*, F112A, F112D, F112E, F112G, F112H, F112I, F112K, F112L, F112M, F112N, F112P, F112Q, F112R, F112S, F112T, F112V, F112W, F112Y, A113*, A113D, A113E, A113F, A113G, A113H, A113I, A113K, A113L, A113M, A113N, A113P, A113Q, A113R, A113S, A113T, A113V, A113W, A113Y, S114*, S114A, S114D, S114E, S114F, S114G, S114H, S114I, S114K, S114L, S114M, S114N, S114P, S114Q, S114R, S114T, S114V, S114W, S114Y, S115*, S115A, S115D, S115E, S115F, S115G, S115H, S115I, S115K, S115L, S115M, S115N, S115P, S115Q, S115R, S115T, S115V, S115W, S115Y, L116*, L116A, L116D, L116E, L116F, L116G, L116H, L116I, L116K, L116M, L116N, L116P, L116Q, L116R, L116S, L116T, L116V, L116W, L116Y, Q117*, Q117A, Q117D, Q117E, Q117F, Q117G, Q117H, Q117I, Q117K, Q117L, Q117M, Q117N, Q117P, Q117R, Q117S, Q117T, Q117V, Q117W, Q117Y, G118*, G118A, G118D, G118E, G118F, G118H, G118I, G118K, G118L, G118M, G118N, G118P, G118Q, G118R, G118S, G118T, G118V, G118W, G118Y, G119*, G119A, G119D, G119E, G119F, G119H, G119I, G119K, G119L, G119M, G119N, G119P, G119Q, G119R, G119S, G119T, G119V, G119W, G119Y, T120*, T120A, T120D, T120E, T120F, T120G, T120H, T120I, T120K, T120L, T120M, T120N, T120P, T120Q, T120R, T120S, T120V, T120W, T120Y, N121*, N121A, N121D, N121E, N121F, N121G, N121H, N121I, N121K, N121L, N121M, N121P, N121Q, N121R, N121S, N121T, N121V, N121W, N121Y, A122*, A122D, A122E, A122F, A122G, A122H, A122I, A122K, A122L, A122M, A122N, A122P, A122Q, A122R, A122S, A122T, A122V, A122W, A122Y, I123*, I123A, I123D, I123E, I123F, I123G, I123H, I123K, I123L, I123M, I123N, I123P, I123Q, I123R, I123S, I123T, I123V, I123W, I123Y, L124*, L124A, L124D, L124E, L124F, L124G, L124H, L124I, L124K, L124M, L124N, L124P, L124Q, L124R, L124S, L124T, L124V, L124W, L124Y, A125*, A125D, A125E, A125F, A125G, A125H, A125I, A125K, A125L, A125M, A125N, A125P, A125Q, A125R, A125S, A125T, A125V, A125W, A125Y, P126*, P126A, P126D, P126E, P126F, P126G, P126H, P126I, P126K, P126L, P126M, P126N, P126Q, P126R, P126S, P126T, P126V, P126W, P126Y, V127*, V127A, V127D, V127E, V127F, V127G, V127H, V127I, V127K, V127L, V127M, V127N, V127P, V127Q, V127R, V127S, V127T, V127W, V127Y, N128*, N128A, N128D, N128E, N128F, N128G, N128H, N128I, N128K, N128L, N128M, N128P, N128Q, N128R, N128S, N128T, N128V, N128W, N128Y, L129*, L129A, L129D, L129E, L129F, L129G, L129H, L129I, L129K, L129M, L129N, L129P, L129Q, L129R, L129S, L129T, L129V, L129W, L129Y, A130*, A130D, A130E, A130F, A130G, A130H, A130I, A130K, A130L, A130M, A130N, A130P, A130Q, A130R, A130S, A130T, A130V, A130W, A130Y, S131*, S131A, S131D, S131E, S131F, S131G, S131H, S131I, S131K, S131L, S131M, S131N, S131P, S131Q, S131R, S131T, S131V, S131W, S131Y, Q132*, Q132A, Q132D, Q132E, Q132F, Q132G, Q132H, Q132I, Q132K, Q132L, Q132M, Q132N, Q132P, Q132R, Q132S, Q132T, Q132V, Q132W, Q132Y, N133*, N133A, N133D, N133E, N133F, N133G, N133H, N133I, N133K, N133L, N133M, N133P, N133Q, N133R, N133S, N133T, N133V, N133W, N133Y, S134*, S134A, S134D, S134E, S134F, S134G, S134H, S134I, S134K, S134L, S134M, S134N, S134P, S134Q, S134R, S134T, S134V, S134W, S134Y, Q135*, Q135A, Q135D, Q135E, Q135F, Q135G, Q135H, Q135I, Q135K, Q135L, Q135M, Q135N, Q135P, Q135R, Q135S, Q135T, Q135V, Q135W, Q135Y, G136*, G136A, G136D, G136E, G136F, G136H, G136I, G136K, G136L, G136M, G136N, G136P, G136Q, G136R, G136S, G136T, G136V, G136W, G136Y, G137*, G137A, G137D, G137E, G137F, G137H, G137I, G137K, G137L, G137M, G137N, G137P, G137Q, G137R, G137S, G137T, G137V, G137W, G137Y, V138*, V138A, V138D, V138E, V138F, V138G, V138H, V138I, V138K, V138L, V138M, V138N, V138P, V138Q, V138R, V138S, V138T, V138W, V138Y, L139*, L139A, L139D, L139E, L139F, L139G, L139H, L139I, L139K, L139M, L139N, L139P, L139Q, L139R, L139S, L139T, L139V, L139W, L139Y, N140*, N140A, N140D, N140E, N140F, N140G, N140H, N140I, N140K, N140L, N140M, N140P, N140Q, N140R, N140S, N140T, N140V, N140W, N140Y, G141*, G141A, G141D, G141E, G141F, G141H, G141I, G141K, G141L, G141M, G141N, G141P, G141Q, G141R, G141S, G141T, G141V, G141W, G141Y, F142*, F142A, F142D, F142E, F142G, F142H, F142I, F142K, F142L, F142M, F142N, F142P, F142Q, F142R, F142S, F142T, F142V, F142W, F142Y, Y143*, Y143A, Y143D, Y143E, Y143F, Y143G, Y143H, Y143I, Y143K, Y143L, Y143M, Y143N, Y143P, Y143Q, Y143R, Y143S, Y143T, Y143V, Y143W, S144*, S144A, S144D, S144E, S144F, S144G, S144H, S144I, S144K, S144L, S144M, S144N, S144P, S144Q, S144R, S144T, S144V, S144W, S144Y, A145*, A145D, A145E, A145F, A145G, A145H, A145I, A145K, A145L, A145M, A145N, A145P, A145Q, A145R, A145S, A145T, A145V, A145W, A145Y, N146*, N146A, N146D, N146E, N146F, N146G, N146H, N146I, N146K, N146L, N146M, N146P, N146Q, N146R, N146S, N146T, N146V, N146W, N146Y, K147*, K147A, K147D, K147E, K147F, K147G, K147H, K147I, K147L, K147M, K147N, K147P, K147Q, K147R, K147S, K147T, K147V, K147W, K147Y, V148*, V148A, V148D, V148E, V148F, V148G, V148H, V148I, V148K, V148L, V148M, V148N, V148P, V148Q, V148R, V148S, V148T, V148W, V148Y, A149*, A149D, A149E, A149F, A149G, A149H, A149I, A149K, A149L, A149M, A149N, A149P, A149Q, A149R, A149S, A149T, A149V, A149W, A149Y, Q150*, Q150A, Q150D, Q150E, Q150F, Q150G, Q150H, Q150I, Q150K, Q150L, Q150M, Q150N, Q150P, Q150R, Q150S, Q150T, Q150V, Q150W, Q150Y, F151*, F151A, F151D, F151E, F151G, F151H, F151I, F151K, F151L, F151M, F151N, F151P, F151Q, F151R, F151S, F151T, F151V, F151W, F151Y, D152*, D152A, D152E, D152F, D152G, D152H, D152I, D152K, D152L, D152M, D152N, D152P, D152Q, D152R, D152S, D152T, D152V, D152W, D152Y, P153*, P153A, P153D, P153E, P153F, P153G, P153H, P153I, P153K, P153L, P153M, P153N, P153Q, P153R, P153S, P153T, P153V, P153W, P153Y, S154*, S154A, S154D, S154E, S154F, S154G, S154H, S154I, S154K, S154L, S154M, S154N, S154P, S154Q, S154R, S154T, S154V, S154W, S154Y, K155*, K155A, K155D, K155E, K155F, K155G, K155H, K155I, K155L, K155M, K155N, K155P, K155Q, K155R, K155S, K155T, K155V, K155W, K155Y, P156*, P156A, P156D, P156E, P156F, P156G, P156H, P156I, P156K, P156L, P156M, P156N, P156Q, P156R, P156S, P156T, P156V, P156W, P156Y, Q157*, Q157A, Q157D, Q157E, Q157F, Q157G, Q157H, Q157I, Q157K, Q157L, Q157M, Q157N, Q157P, Q157R, Q157S, Q157T, Q157V, Q157W, Q157Y, Q158*, Q158A, Q158D, Q158E, Q158F, Q158G, Q158H, Q158I, Q158K, Q158L, Q158M, Q158N, Q158P, Q158R, Q158S, Q158T, Q158V, Q158W, Q158Y, T159*, T159A, T159D, T159E, T159F, T159G, T159H, T159I, T159K, T159L, T159M, T159N, T159P, T159Q, T159R, T159S, T159V, T159W, T159Y, K160*, K160A, K160D, K160E, K160F, K160G, K160H, K160I, K160L, K160M, K160N, K160P, K160Q, K160R, K160S, K160T, K160V, K160W, K160Y, G161*, G161A, G161D, G161E, G161F, G161H, G161I, G161K, G161L, G161M, G161N, G161P, G161Q, G161R, G161S, G161T, G161V, G161W, G161Y, T162A, T162D, T162E, T162F, T162G, T162H, T162I, T162K, T162L, T162M, T162N, T162P, T162Q, T162R, T162S, T162T, T162V, T162W, T162Y, W163*, W163A, W163D, W163E, W163F, W163G, W163H, W163I, W163K, W163L, W163M, W163N, W163P, W163Q, W163R, W163S, W163T, W163V, W163Y, F164*, F164A, F164D, F164E, F164G, F164H, F164I, F164K, F164L, F164M, F164N, F164P, F164Q, F164R, F164S, F164T, F164V, F164W, F164Y, Q165*, Q165A, Q165D, Q165E, Q165F, Q165G, Q165H, Q165I, Q165K, Q165L, Q165M, Q165N, Q165P, Q165R, Q165S, Q165T, Q165V, Q165W, Q165Y, I166*, I166A, I166D, I166E, I166F, I166G, I166H, I166K, I166L, I166M, I166N, I166P, I166Q, I166R, I166S, I166T, I166V, I166W, I166Y, T167*, T167D, T167E, T167F, T167G, T167H, T167I, T167K, T167L, T167M, T167N, T167P, T167Q, T167R, T167S, T167V, T167W, T167Y, K168*, K168A, K168D, K168E, K168F, K168G, K168H, K168I, K168L, K168M, K168N, K168P, K168Q, K168R, K168S, K168T, K168V, K168W, K168Y, F169*, F169A, F169D, F169E, F169G, F169H, F169I, F169K, F169L, F169M, F169N, F169P, F169Q, F169R, F169S, F169T, F169V, F169W, F169Y, T170*, T170A, T170D, T170E, T170F, T170G, T170H, T170I, T170K, T170L, T170M, T170N, T170P, T170Q, T170R, T170S, T170V, T170W, T170Y, G171*, G171A, G171D, G171E, G171F, G171H, G171I, G171K, G171L, G171M, G171N, G171P, G171Q, G171R, G171S, G171T, G171V, G171W, G171Y, A172*, A172D, A172E, A172F, A172G, A172H, A172I, A172K, A172L, A172M, A172N, A172P, A172Q, A172R, A172S, A172T, A172V, A172W, A172Y, A173*, A173D, A173E, A173F, A173G, A173H, A173I, A173K, A173L, A173M, A173N, A173P, A173Q, A173R, A173S, A173T, A173V, A173W, A173Y, G174*, G174A, G174D, G174E, G174F, G174H, G174I, G174K, G174L, G174M, G174N, G174P, G174Q, G174R, G174S, G174T, G174V, G174W, G174Y, P175*, P175A, P175D, P175E, P175F, P175G, P175H, P175I, P175K, P175L, P175M, P175N, P175Q, P175R, P175S, P175T, P175V, P175W, P175Y, Y176*, Y176A, Y176D, Y176E, Y176F, Y176G, Y176H, Y176I, Y176K, Y176L, Y176M, Y176N, Y176P, Y176Q, Y176R, Y176S, Y176T, Y176V, Y176W, K178*, K178A, K178D, K178E, K178F, K178G, K178H, K178I, K178L, K178M, K178N, K178P, K178Q, K178R, K178S, K178T, K178V, K178W, K178Y, A179*, A179D, A179E, A179F, A179G, A179H, A179I, A179K, A179L, A179M, A179N, A179P, A179Q, A179R, A179S, A179T, A179V, A179W, A179Y, L180*, L180A, L180D, L180E, L180F, L180G, L180H, L180I, L180K, L180M, L180N, L180P, L180Q, L180R, L180S, L180T, L180V, L180W, L180Y, G181*, G181A, G181D, G181E, G181F, G181H, G181I, G181K, G181L, G181M, G181N, G181P, G181Q, G181R, G181S, G181T, G181V, G181W, G181Y, S182*, S182A, S182D, S182E, S182F, S182G, S182H, S182I, S182K, S182L, S182M, S182N, S182P, S182Q, S182R, S182T, S182V, S182W, S182Y, N183*, N183A, N183D, N183E, N183F, N183G, N183H, N183I, N183K, N183L, N183M, N183P, N183Q, N183R, N183S, N183T, N183V, N183W, N183Y, D184*, D184A, D184E, D184F, D184G, D184H, D184I, D184K, D184L, D184M, D184N, D184P, D184Q, D184R, D184S, D184T, D184V, D184W, D184Y, K185*, K185A, K185D, K185E, K185F, K185G, K185H, K185I, K185L, K185M, K185N, K185P, K185Q, K185R, K185S, K185T, K185V, K185W, K185Y, S186*, S186A, S186D, S186E, S186F, S186G, S186H, S186I, S186K, S186L, S186M, S186N, S186P, S186Q, S186R, S186T, S186V, S186W, S186Y, V187*, V187A, V187D, V187E, V187F, V187G, V187H, V187I, V187K, V187L, V187M, V187N, V187P, V187Q, V187R, V187S, V187T, V187W, V187Y, D189*, D189A, D189E, D189F, D189G, D189H, D189I, D189K, D189L, D189M, D189N, D189P, D189Q, D189R, D189S, D189T, D189V, D189W, D189Y, K190*, K190A, K190D, K190E, K190F, K190G, K190H, K190I, K190L, K190M, K190N, K190P, K190Q, K190R, K190S, K190T, K190V, K190W, K190Y, N191*, N191A, N191D, N191E, N191F, N191G, N191H, N191I, N191K, N191L, N191M, N191P, N191Q, N191R, N191S, N191T, N191V, N191W, N191Y, K192*, K192A, K192D, K192E, K192F, K192G, K192H, K192I, K192L, K192M, K192N, K192P, K192Q, K192R, K192S, K192T, K192V, K192W, K192Y, N193*, N193A, N193D, N193E, N193F, N193G, N193H, N193I, N193K, N193L, N193M, N193P, N193Q, N193R, N193S, N193T, N193V, N193W, N193Y, I194*, I194A, I194D, I194E, I194F, I194G, I194H, I194K, I194L, I194M, I194N, I194P, I194Q, I194R, I194S, I194T, I194V, I194W, I194Y, A195\*, A195D, A195E, A195F, A195G, A195H, A195I, A195K, A195L, A195M, A195N, A195P, A195Q, A195R, A195S, A195T, A195V, A195W, A195Y, G196\*, G196A, G196D, G196E, G196F, G196H, G196I, G196K, G196L, G196M, G196N, G196P, G196Q, G196R, G196S, G196T, G196V, G196W, G196Y, D197\*, D197A, D197E, D197F, D197G, D197H, D197I, D197K, D197L, D197M, D197N, D197P, D197Q, D197R, D197S, D197T, D197V, D197W, D197Y, W198\*, W198A, W198D, W198E, W198F, W198G, W198H, W198I, W198K, W198L, W198M, W198N, W198P, W198Q, W198R, W198S, W198T, W198V, W198Y, G199\*, G199A, G199D, G199E, G199F, G199H, G199I, G199K, G199L, G199M, G199N, G199P, G199Q, G199R, G199S, G199T, G199V, G199W, G199Y, F200\*, F200A, F200D, F200E, F200G, F200H, F200I, F200K, F200L, F200M, F200N, F200P, F200Q, F200R, F200S, F200T, F200V, F200W, F200Y, D201\*, D201A, D201E, D201F, D201G, D201H, D201I, D201K, D201L, D201M, D201N, D201P, D201Q, D201R, D201S, D201T, D201V, D201W, D201Y, P202\*, P202A, P202D, P202E, P202F, P202G, P202H, P202I, P202K, P202L, P202M, P202N, P202Q, P202R, P202S, P202T, P202V, P202W, P202Y, A203\*, A203D, A203E, A203F, A203G, A203H, A203I, A203K, A203L, A203M, A203N, A203P, A203Q, A203R, A203S, A203T, A203V, A203W, A203Y, K204\*, K204A, K204D, K204E, K204F, K204G, K204H, K204I, K204L, K204M, K204N, K204P, K204Q, K204R, K204S, K204T, K204V, K204W, K204Y, W205\*, W205A, W205D, W205E, W205F, W205G, W205H, W205I, W205K, W205L, W205M, W205N, W205P, W205Q, W205R, W205S, W205T, W205V, W205Y, A206\*, A206D, A206E, A206F, A206G, A206H, A206I, A206K, A206L, A206M, A206N, A206P, A206Q, A206R, A206S, A206T, A206V, A206W, A206Y, Y207\*, Y207A, Y207D, Y207E, Y207F, Y207G, Y207H, Y207I, Y207K, Y207L, Y207M, Y207N, Y207P, Y207Q, Y207R, Y207S, Y207T, Y207V, Y207W, Q208\*, Q208A, Q208D, Q208E, Q208F, Q208G, Q208H, Q208I, Q208K, Q208L, Q208M, Q208N, Q208P, Q208R, Q208S, Q208T, Q208V, Q208W, Q208Y, Y209\*, Y209A, Y209D, Y209E, Y209F, Y209G, Y209H, Y209I, Y209K, Y209L, Y209M, Y209N, Y209P, Y209Q, Y209R, Y209S, Y209T, Y209V, Y209W, D210\*, D210A, D210E, D210F, D210G, D210H, D210I, D210K, D210L, D210M, D210N, D210P, D210Q, D210R, D210S, D210T, D210V, D210W, D210Y, E211\*, E211A, E211D, E211F, E211G, E211H, E211I, E211K, E211L, E211M, E211N, E211P, E211Q, E211R, E211S, E211T, E211V, E211W, E211Y, K212\*, K212A, K212D, K212E, K212F, K212G, K212H, K212I, K212L, K212M, K212N, K212P, K212Q, K212R, K212S, K212T, K212V, K212W, K212Y, N213\*, N213A, N213D, N213E, N213F, N213G, N213H, N213I, N213K, N213L, N213M, N213P, N213Q, N213R, N213S, N213T, N213V, N213W, N213Y, N214\*, N214A, N214D, N214E, N214F, N214G, N214H, N214I, N214K, N214L, N214M, N214P, N214Q, N214R, N214S, N214T, N214V, N214W, N214Y, K215\*, K215A, K215D, K215E, K215F, K215G, K215H, K215I, K215L, K215M, K215N, K215P, K215Q, K215R, K215S, K215T, K215V, K215W, K215Y, F216\*, F216A, F216D, F216E, F216G, F216H, F216I, F216K, F216L, F216M, F216N, F216P, F216Q, F216R, F216S, F216T, F216V, F216W, F216Y, N217\*, N217A, N217D, N217E, N217F, N217G, N217H, N217I, N217K, N217L, N217M, N217P, N217Q, N217R, N217S, N217T, N217V, N217W, Y218\*, Y218A, Y218D, Y218E, Y218F, Y218G, Y218H, Y218I, Y218K, Y218L, Y218M, Y218N, Y218P, Y218Q, Y218R, Y218S, Y218T, Y218V, Y218W, V219\*, V219A, V219D, V219E, V219F, V219G, V219H, V219I, V219K, V219L, V219M, V219N, V219P, V219Q, V219R, V219S, V219T, V219W, V219Y, G220\*, G220A, G220D, G220E, G220F, G220H, G220I, G220K, G220L, G220M, G220N, G220P, G220Q, G220R, G220S, G220T, G220V, G220W, G220Y, K221\*, K221A, K221D, K221E, K221F, K221G, K221H, K221I, K221L, K221M, K221N, K221P, K221Q, K221R, K221S, K221T, K221V, K221W and K221Y and a detergent adjunct.

In one embodiment of the invention, the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments.

The detergent adjunct ingredient may be a surfactant. One advantage of including a surfactant in a detergent composition comprising a DNase variant is that the wash performance is improved. In one embodiment, the detergent adjunct ingredient is a builder or a clay soil removal/anti-redeposition agent.

In one embodiment, detergent adjunct ingredient is an enzyme. The detergent composition may comprise one or more enzymes, as specified below. The one or more enzymes may be selected from the group consisting of proteases, lipases, cutinases, amylases, carbohydrases, cellulases, pectinases, mannanases, arabinases, galactanases, xylanases and oxidases. Specific enzymes suitable for the detergent compositions of the invention are described below.

In one embodiment, the detergent composition comprising a DNase variant is capable of reducing adhesion of bacteria selected from the group consisting of *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. to a surface, or releasing the bacteria from a surface to which they adhere. Biofilm growth in laundry items may originate from many organisms as described previously. One particular abundant bacterium in biofilm originates from *Brevundimonas*. The DNase variants of the invention are particularly effective in reducing the growth of the bacterium and reducing the malodor, stickiness and re-deposition coursed by these bacteria. In one embodiment of the invention, the surface is a textile surface. The textile can be made of cotton, Cotton/Polyester, Polyester, Polyamide, Polyacryl and/or silk.

The detergent composition may be formulated as a bar, a homogenous tablet, and a tablet having two or more layers, a pouch having one or more compartments, a regular or compact powder, a granule, a paste, a gel, or a regular, compact or concentrated liquid. The detergent composition can be a liquid detergent, a powder detergent or a granule detergent.

The DNase variants of the invention are suitable for use in cleaning such as laundry. The invention further relates a method for laundering an item, which method comprises the steps of:
 a. Exposing an item to a wash liquor comprising a DNase variant of the invention;
 b. Completing at least one wash cycle; and
 c. Optionally rinsing the item, wherein the item is a textile.

The pH of the liquid solution is in the range of 1 to 11, such as in the range 5.5 to 11, such as in the range of 7 to 9, in the range of 7 to 8 or in the range of 7 to 8.5.

The wash liquor may have a temperature in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C. In one embodiment the temperature of the wash liquor is 30° C.

In one embodiment of the invention, the method for laundering an item further comprises draining of the wash liquor or part of the wash liquor after completion of a wash cycle. The wash liquor can then be re-used in a subsequent wash cycle or in a subsequent rinse cycle. The item may be exposed to the wash liquor during a first and optionally a second or a third wash cycle. In one embodiment the item is rinsed after being exposed to the wash liquor. The item can be rinsed with water or with water comprising a conditioner. The invention further concerns an item washed according to the method.

The DNases of the invention may be added to a wash liquor.

The concentration of the DNase variants in the wash liquor is typically in the range of 0.00004-100 ppm enzyme protein, such as in the range of 0.00008-100, in the range of 0.0001-100, in the range of 0.0002-100, in the range of 0.0004-100, in the range of 0.0008-100, in the range of 0.001-100 ppm enzyme protein, 0.01-100 ppm enzyme protein, preferably 0.05-50 ppm enzyme protein, more preferably 0.1-50 ppm enzyme protein, more preferably 0.1-30 ppm enzyme protein, more preferably 0.5-20 ppm enzyme protein, and most preferably 0.5-10 ppm enzyme protein.

The DNase variant of the present invention may be added to a detergent composition in an amount corresponding to at least 0.002 mg of DNase protein, such as at least 0.004 mg of DNase protein, at least 0.006 mg of DNase protein, at least 0.008 mg of DNase protein, at least 0.01 mg of DNase protein, at least 0.1 mg of protein, preferably at least 1 mg of protein, more preferably at least 10 mg of protein, even more preferably at least 15 mg of protein, most preferably at least 20 mg of protein, and even most preferably at least 25 mg of protein. Thus, the detergent composition may comprise at least 0.00008% DNase protein, preferably at least 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% of DNase protein.

Liquid Detergent Composition

The DNase variants of the invention may also be formulated in liquid laundry compositions such as a liquid laundry compositions composition comprising:

a) at least 0.005 mg of active DNase variant protein per litre detergent,
b) 2 wt % to 60 wt % of at least one surfactant, and
c) 5 wt % to 50 wt % of at least one builder The surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and in particular alkyl ether sulphates, especially C-9-15 alcohol ethersulfates, C12-15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl)ammonium, bis(2-hydroxyethyl)ammonium and tris(2-hydroxyethyl) ammonium salts. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. Commercially available nonionic surfactants includes Plurafac™, Lutensol™ and Pluronic™ from BASF, Dehypon™ series from Cognis and Genapol™ series from Clariant.

The builder is preferably selected among phosphates, sodium citrate builders, sodium carbonate, sodium silicate, sodium aluminosilicate (zeolite). Suitable builders are alkali metal or ammonium phosphates, polyphosphates, phosphonates, polyphosphates, carbonates, bicarbonates, borates, citrates, and polycarboxylates. Citrate builders, e.g., citric acid and soluble salts thereof (particularly sodium salt), are polycarboxylate builders. Citrates can be used in combination with zeolite, silicates like the BRITESIL types, and/or layered silicate builders. The builder is preferably added in an amount of about 0-65% by weight, such as about 5% to about 50% by weight. In a laundry detergent, the level of builder is typically about 40-65% by weight, particularly about 50-65% by weight, particularly from 20% to 50% by weight. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), and (carboxymethyl) inulin (CMI), and combinations thereof. Further non-limiting examples of builders include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycine-N,N- diacetic acid (MGDA), glutamic acid-N,N-diacetic acid (GLDA), 1-hydroxyethane-1,1-diphosphonic acid, N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(sulfomethyl)aspartic acid (SMAS), N-(2-sulfoethyl)-aspartic acid (SEAS), N-(sulfomethylglutamic acid (SMGL), N-(2-sulfoethyl)-glutamic acid (SEGL), N-methyliminodiacetic acid (MIDA), serine-N,N-diacetic acid (SEDA), isoserine-N,N-diacetic acid (ISDA), phenylalanine-N,N-diacetic acid (PH DA), anthranilic acid-N,N-diacetic acid (ANDA), sulfanilic acid-N,N-diacetic acid (SLDA), taurine-N,N-diacetic acid (TUDA) and N'-(2-hydroxyethyl)ethylenediamine-N,N,N'-triacetic acid (HEDTA), diethanolglycine (DEG), and combinations and salts thereof. Phosphonates suitable for use herein include 1-hydroxyethane-1,1-diphosphonic acid (HEDP), ethylenediaminetetrakis (methylenephosphonicacid) (EDTMPA), diethylenetriaminepentakis(methylenephosphonic acid) (DTMPA or DTPMPA or DTPMP), nitrilotris(methylenephosphonic acid) (ATMP or NTMP), 2-phosphonobutane-1,2,4-tricarboxylic acid (PBTC), hexamethylenediaminetetrakis(methylenephosphonic acid) (HDTMP).

The composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly (acrylic acid) (PAA) or copoly(acrylic acid/maleic acid) (PAA/PMA) or polyaspartic acid. Further exemplary builders and/or co-builders are described in, e.g., WO 09/102854, U.S. Pat. No. 5,977,053

In one preferred embodiment, the builder is a non-phosphorus based builder such as citric acid and/or methylglycine-N,N-diacetic acid (MGDA) and/or glutamic-N,N-diacetic acid (GLDA) and/or salts thereof.

The laundry composition may also be phosphate free in the instance the preferred builders includes citrate and/or methylglycine-N,N-diacetic acid (MGDA) and/or glutamic-N,N-diacetic acid (GLDA) and/or salts thereof.

One embodiment of the invention concerns a liquid laundry compositions composition comprising:
a) at least 0.005 mg of DNase variant per litre of composition,
b) 1% to 15% by weight of at least one surfactant wherein the surfactant is LAS, AEOS and/or SLES, and
c) 5% to 50% by weight of at least one builder selected from HEDP, DTMPA or DTPMPA.

The liquid detergent composition may typically containing at least 20% by weight and up to 95% water, such as up to 70% water, up to 50% water, up to 40% water, up to 30% water, or up to 20% water. Other types of liquids, including without limitation, alkanols, amines, diols, ethers and polyols may be included in an aqueous liquid detergent. An aqueous liquid detergent may contain from 0-30% organic solvent. A liquid detergent may even be non-aqueous, wherein the water content is below 10%, preferably below 5%.

Powder Compositions

The detergent composition may also be formulated into a granular detergent for laundry or dish wash. One embodiment of the invention concerns a granular detergent composition comprising
a) at least 0.005 mg of DNase variant per gram of composition,
b) 5 wt % to 50 wt % anionic surfactant
c) 1 wt % to 8 wt % nonionic surfactant, and
d) 5 wt % to 40 wt % builder such as carbonates, zeolites, phosphate builder, calcium sequestering builders or complexing agents The surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and in particular alkyl ether sulphates, especially C-9-15 alcohol ethersulfates, C12-15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof. The anionic surfactants are preferably added to the detergent in the form of salts. Suitable cations in these salts are alkali metal ions, such as sodium, potassium and lithium and ammonium salts, for example (2-hydroxyethyl) ammonium, bis(2-hydroxyethyl)ammonium and tris(2-hydroxyethyl)ammonium salts.

Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

Commercially available nonionic surfactants includes Plurafac™, Lutensol™ and Pluronic™ range from BASF, Dehypon™ series from Cognis and Genapol™ series from Clariant.

The builder is may be non-phosphate such as citrate preferably as a sodium salt and/or zeolites. Phosphonate builder may be any of those described above.

The builder is preferably selected among phosphates and sodium citrate builders, sodium carbonate, sodium silicate, sodium aluminosilicate (zeolite) as described above. Suitable builders are described above and include alkali metal or ammonium phosphates, polyphosphates, phosphonates, polyphosphonates, carbonates, bicarbonates, borates, polyhydroxysulfonates, polyacetates, carboxylates, citrates, and polycarboxylates. Citrate builders, e.g., citric acid and soluble salts thereof (particularly sodium salt), are polycarboxylate builders. The builder is preferably added in an amount of about 0-65% by weight, such as about 5% to about 50% by weight, such as 5 to 40% by weight, such as 10 to 40% by weight, such as 10 to 30% by weight, such as 15 to 20% by weight or such as 20 to 40% by weight. The builder may be a phosphonate builder including 1-hydroxyethane-1,1-diphosphonic acid (HEDP), ethylenediaminetetra (methylenephosphonic acid) (EDTMPA), diethylenetriaminepentakis (methylenephosphonic acid) (DTMPA or DTPMPA), diethylenetriamine penta (methylenephosphonic acid) (DTPMP), aminotris(methylenephosphonic acid) (ATMP), 2-phosphonobutane-1,2,4-tricarboxylic acid (PBTC) and hexamethylenediaminetetra (methylenephosphonic acid) (HDTMP). Preferred phosphonates includes 1-hydroxyethane-1,1-diphosphonic acid (HEDP) and/or diethylenetriaminepentakis (methylenephosphonic acid) (DTMPA or DTPMPA). The phosphonate is preferably added in an amount of about in a level of from about 0.01 to about 10% by weight, preferably from 0.1% to about 5% by weight, more preferably from 0.5% to 3% by weight of the composition.

The laundry composition may also be phosphate free in the instance the preferred builders includes citrate, carbonates and/or sodium aluminosilicate (zeolite).

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of hydrogen peroxide: Suitable sources of hydrogen peroxide are inorganic persalts, including alkali metal salts such as sodium percarbonate and sodium perborates (usually mono- or tetrahydrate), and hydrogen peroxide-urea (1/1).

Sources of peracids: Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore acetyl triethyl citrate and triacetin have good hydrolytical stability in the product upon storage and are efficient bleach activators. Finally ATC is multifunctional, as the citrate released in the perhydrolysis reaction may function as a builder.

Bleach catalysts and boosters: The bleaching system may also include a bleach catalyst or booster. Some non-limiting examples of bleach catalysts that may be used in the compositions of the present invention include manganese oxalate, manganese acetate, manganese-collagen, cobaltamine catalysts and manganese triazacyclononane (Mn-TACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Mea-TACN)Mn(O) 3Mn(Me3-TACN)](PF6)2, and [2,2',2"-nitrilotris(ethane-1, 2-diylazanylylidene-κN-methanylylidene)triphenolato-κ3O]manganese(III). The bleach catalysts may also be other metal compounds, such as iron or cobalt complexes.

In some embodiments, where a source of a peracid is included, an organic bleach catalyst or bleach booster may be used having one of the following formulae:

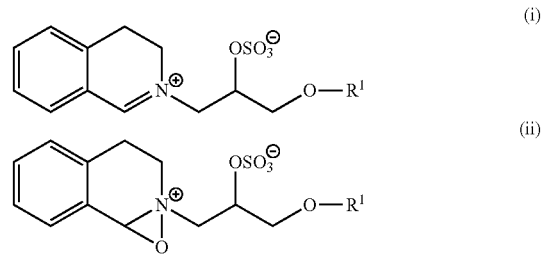

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO 2007/087258, WO 2007/087244, WO 2007/087259, EP 1867708 (Vitamin K) and WO 2007/087242. Suitable photobleaches may for example be sulfonated zinc or aluminium phthalocyanines.

According to one embodiment and any of the previous embodiments the invention also relates to a detergent composition comprising;
 a) at least 0.005 mg of DNase variant per gram of composition,
 b) 10-50 wt % builder and
 c) at least one bleach component, wherein the bleach is a peroxide and the bleach catalyst is a manganese compound.

The oxygen bleach is preferably percarbonate and the manganese catalyst preferably 1,4,7-trimethyl-1,4,7-triazacyclononane or manganese (III) acetate tetrahydrate According to one embodiment and any of the previous embodiments the invention also relates to a cleaning composition comprising;
a) at least 0.005 mg of active DNase variant,
b) 10-50 wt % builder selected from citric acid, methyl glycine-N,N-diacetic acid (MGDA) and/or glutamic-N,N-diacetic acid (GLDA) and mixtures thereof, and
c) at least one bleach component, wherein the bleach is an oxygen bleach and the bleach catalyst is a manganese compound.

The oxygen bleach is preferably percarbonate and the manganese catalyst preferably 1,4,7-trimethyl-1,4,7-triaza-cyclo-nonane or manganese (II) acetate tetrahydrate According to one embodiment and any of the previous embodiments the invention also relates to a detergent composition comprising;
a) at least 0.005 mg of active DNase variant per gram of composition,
b) 10-50 wt % builder selected from citric acid, methyl glycine-N,N-diacetic acid (MGDA) and/or glutamic-N,N-diacetic acid (GLDA) and mixtures thereof, and
c) 0.1-40 wt %, preferably from 0.5-30 wt %, of bleaching components, wherein the bleach components are a peroxide, preferably percarbonate and a metal-containing bleach catalyst preferably 1,4,7-trimethyl-1,4,7-triazacyclononane or manganese (II) acetate tetrahydrate (MnTACN).

The choice of detergent components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan, including the exemplary non-limiting components set forth below.

Hydrotropes

The detergent composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof Polymers The detergent composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fibre protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly (vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent composition of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO 2007/087243.

Enzymes

The detergent composition may comprise one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/001544.

Other cellulases are endo-beta-1,4-glucanase enzyme having a sequence of at least 97% identity to the amino acid sequence of position 1 to position 773 of SEQ ID NO: 2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those obtained from *Bacillus* such as *Bacillus lentus*, *B. alkalophilus*, *B. subtilis*, *B. amyloliquefaciens, Bacillus pumilus* and *Bacillus gibsonii* described in; U.S. Pat. No. 7,262,042 and WO 09/021867, and subtilisin *lentus*, subtilisin Novo, subtilisin Carlsberg, *Bacillus licheniformis*, subtilisin BPN', subtilisin 309, subtilisin 147 and subtilisin 168 described in WO 89/06279 and protease PD138 described in (WO 93/18140). Other useful proteases may be those described in WO 92/175177, WO 01/016285, WO 02/026024 and WO 02/016547. Examples of trypsin-like proteases are trypsin (e.g. of porcine or bovine origin) and the *Fusarium* protease described in WO 89/06270, WO 94/25583 and WO 05/040372, and the chymotrypsin proteases obtained from *Cellulomonas* described in WO 05/052161 and WO 05/052146.

A further preferred protease is the alkaline protease from *Bacillus lentus* DSM 5483, as described for example in WO 95/23221, and variants thereof which are e.g. described in WO 92/21760, WO 95/23221, EP 1921147 and EP 1921148.

Examples of metalloproteases are the neutral metalloprotease as described in WO 07/044993 (Genencor Int.) such as those obtained from *Bacillus amyloliquefaciens*.

Examples of useful proteases are the variants described in: WO 92/19729, WO 96/034946, WO 98/20115, WO 98/20116, WO 99/011768, WO 01/44452, WO 03/006602, WO 04/03186, WO 04/041979, WO 07/006305, WO 11/036263, WO 11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, 5130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Durazalase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP 258068 and EP 305216, cutinase from *Humicola*, e.g. *H. insolens* (WO 96/13580), lipase from strains of *Pseudomonas* (some of these now renamed to *Burkholderia*), e.g. *P. alcaligenes* or *P. pseudoalcaligenes* (EP 218272), *P. cepacia* (EP 331376), *P.* sp. strain SD705 (WO 95/06720 & WO 96/27002), *P. wisconsinensis* (WO 96/12012), GDSL-type *Streptomyces* lipases (WO 10/065455), cutinase from *Magnaporthe grisea* (WO 10/107560), cutinase from *Pseudomonas mendocina* (U.S. Pat. No. 5,389,536), lipase from *Thermobifida fusca* (WO 11/084412), *Geobacillus stearothermophilus* lipase (WO 11/084417), lipase from *Bacillus subtilis* (WO 11/084599), and lipase from *Streptomyces griseus* (WO 11/150157) and *S. pristinaespiralis* (WO 12/137147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO 07/87508 and WO 09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO 10/111143), acyltransferase from *Mycobacterium smegmatis* (WO 05/56782), perhydrolases from the CE 7 family (WO 09/67279), and variants of the *M. smegmatis* perhydrolase in particular the S54V variant used in the commercial product Gentle Power Bleach from Huntsman Textile Effects Pte Ltd (WO 10/100028).

Amylases

Suitable amylases which can be used together with the DNases of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 1 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase obtained from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A18I, N190, M197, I201, A209 and Q264. Most preferred variants of the hybrid alpha-amylase comprising residues 1-33 of the alpha-amylase obtained from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R18I, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID NO. 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T16S, K178, R180, S181, T182, G183, M20I, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO 01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R18I, G182, D183, G184, G186, W189, N195, M202, Y298, N299, K302, S303, N306, R310, N314; R320, H324, E345, Y396, R400, W439, R444, N445, K446, Q449, R458, N47I, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO 2011/098531, WO 2013/001078 and WO 2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment obtained therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as Caldariomyces, e.g., *C. fumago, Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In a preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment obtained therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be obtained from plants, bacteria or fungi (including filamentous fungi and yeasts).

Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase obtained from *Coprinopsis* or *Myceliophthora* is preferred; in particular a laccase obtained from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Other Materials

Any detergent components known in the art for use in the cleaning composition of the invention may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in detergents may be utilized. The choice of such ingredients is well within the skill of the artisan.

Dispersants

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent composition may preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4- anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxyethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Tinopal CBS-X is a 4.4'-bis-(sulfostyryl)-biphenyl disodium salt also known as Disodium Distyrylbiphenyl Disulfonate. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition may be in any convenient form, e.g., a bar, a homogenous tablet, a tablet having two or more layers, a regular or compact powder, a granule, a paste, a gel, or a regular, compact or concentrated liquid.

Detergent formulation forms: Layers (same or different phases), Pouches, versus forms for machine dosing unit.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polylactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US 2009/0011970 A1)

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

Definition/Characteristics of the Forms

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Granular Detergent Formulations

A granular detergent may be formulated as described in WO 09/092699, EP 1705241, EP 1382668, WO 07/001262, U.S. Pat. No. 6,472,364, WO 04/074419 or WO 09/102854. Other useful detergent formulations are described in WO 09/124162, WO 09/124163, WO 09/117340, WO 09/117341, WO 09/117342, WO 09/072069, WO 09/063355, WO 09/132870, WO 09/121757, WO 09/112296, WO 09/112298, WO 09/103822, WO 09/087033, WO 09/050026, WO 09/047125, WO 09/047126, WO 09/047127, WO 09/047128, WO 09/021784, WO 09/010375, WO 09/000605, WO 09/122125, WO 09/095645, WO 09/040544, WO 09/040545, WO 09/024780, WO 09/004295, WO 09/004294, WO 09/121725, WO 09/115391, WO 09/115392, WO 09/074398, WO 09/074403, WO 09/068501, WO 09/065770, WO 09/021813, WO 09/030632, and WO 09/015951.

WO 2011025615, WO 2011016958, WO 2011005803, WO 2011005623, WO 2011005730, WO 2011005844, WO 2011005904, WO 2011005630, WO 2011005830, WO 2011005912, WO 2011005905, WO 2011005910, WO 2011005813, WO 2010135238, WO 2010120863, WO 2010108002, WO 2010111365, WO 2010108000, WO 2010107635, WO 2010090915, WO 2010033976, WO 2010033746, WO 2010033747, WO 2010033897, WO 2010033979, WO 2010030540, WO 2010030541, WO 2010030539, WO 2010024467, WO 2010024469, WO 2010024470, WO 2010025161, WO 2010014395, WO 2010044905,

WO 2010145887, WO 2010142503, WO 2010122051, WO 2010102861, WO 2010099997, WO 2010084039, WO 2010076292, WO 2010069742, WO 2010069718, WO 2010069957, WO 2010057784, WO 2010054986, WO 2010018043, WO 2010003783, WO 2010003792,

WO 2011023716, WO 2010142539, WO 2010118959, WO 2010115813, WO 2010105942, WO 2010105961, WO 2010105962, WO 2010094356, WO 2010084203, WO 2010078979, WO 2010072456, WO 2010069905, WO 2010076165, WO 2010072603, WO 2010066486, WO 2010066631, WO 2010066632, WO 2010063689, WO 2010060821, WO 2010049187, WO 2010031607, WO 2010000636.

Formulation of Enzyme in Co-Granule

The DNase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

The invention is further described in the following non-limiting embodiments;

1. One embodiment relates to a DNase variant, comprising an alteration compared to SEQ ID NO: 1 at one or more positions corresponding to positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 185, 186, 187, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 or 221 of SEQ ID NO: 1, wherein the variant has a sequence identity to SEQ ID NO: 1 of at least 60% and the variant has DNase activity.

2. A variant of embodiment 1, which comprises one or more alterations compared to SEQ ID NO: 1, wherein the one or more alteration(s) is selected from the group consisting of V1*, V1A, V1D, V1E, V1F, V1G, V1H, V1I, V1K, V1L, V1M, V1N, V1P, V1Q, V1R, V1S, V1T, V1W, V1Y, P2*, P2A, P2D, P2E, P2F, P2G, P2H, P2I, P2K, P2L, P2M, P2N, P2Q, P2R, P2S, P2T, P2V, P2W, P2Y, V3*, V3A, V3C, V3D, V3E, V3F, V3G, V3H, V3I, V3K, V3L, V3M, V3N, V3P, V3R, V3S, V3T, V3W, V3Y, N4*, N4A, N4D, N4E, N4F, N4G, N4H, N4I, N4K, N4L, N4M, N4P, N4Q, N4R, N4S, N4T, N4V, N4W, N4Y, P5*, P5A, P5D, P5E, P5F, P5G, P5H, P5I, P5K, P5L, P5M, P5N, P5Q, P5R, P5S, P5T, P5V, P5W, P5Y, E6*, E6A, E6D, E6F, E6G, E6H, E6I, E6K, E6L, E6M, E6N, E6P, E6Q, E6R, E6S, E6T, E6V, E6W, E6Y, P7*, P7A, P7D, P7E, P7F, P7G, P7H, P7I, P7K, P7L, P7M, P7N, P7Q, P7R, P7S, P7T, P7V, P7W, P7Y, D8*, D8A, D8E, D8F, D8G, D8H, D8I, D8K, D8L, D8M, D8N, D8P, D8Q, D8R, D8S, D8T, D8V, D8W, D8Y, A9*, A9D, A9E, A9F, A9G, A9H, A9I, A9K, A9L, A9M, A9N, A9P, A9Q, A9R, A9S, A9T, A9V, A9W, A9Y, T10*, T10A, T10D, T10E, T10F, T10G, T10H, T10I, T10K, T10L, T10M, T10N, T10P, T10Q, T10R, T10S, T10V, T10W, T10Y, S11*, S11A, S11D, S11E, S11F, S11G, S11H, S11I, S11K, S11L, S11M, S11N, S11P, S11Q, S11R, S11T, S11V, S11W, S11Y, V12*, V12A, V12D, V12E, V12F, V12G, V12H, V12I, V12K, V12L, V12M, V12N, V12P, V12Q, V12R, V12S, V12T, V12W, V12Y, E13*, E13A, E13D, E13F, E13G, E13H, E13I, E13K, E13L, E13M, E13N, E13P, E13Q, E13R, E13S, E13T, E13V, E13W, E13Y, N14*, N14A, N14D, N14E, N14F, N14G, N14H, N14I, N14K, N14L, N14M, N14P, N14Q, N14R, N14S, N14T, N14V, N14W, N14Y, V15*, V15A, V15D, V15E, V15F, V15G, V15H, V15I, V15K, V15L, V15M, V15N, V15P, V15Q, V15R, V15S, V15T, V15W, V15Y, A16*, A16D, A16E, A16F, A16G, A16H, A16I, A16K, A16L, A16M, A16N, A16P, A16Q, A16R, A16S, A16T, A16V, A16W, A16Y, L17*, L17A, L17D, L17E, L17F, L17G, L17H, L17I, L17K, L17M, L17N, L17P, L17Q, L17R, L17S, L17T, L17V, L17W, L17Y, K18*, K18A, K18D, K18E, K18F, K18G, K18H, K18I, K18L, K18M, K18N, K18P, K18Q, K18R, K18S, K18T, K18V, K18W, K18Y, T19*, T19A, T19D, T19E, T19F, T19G, T19H, T19I, T19K, T19L, T19M, T19N, T19P, T19Q, T19R, T19S, T19V, T19W, T19Y, G20*, G20A, G20D, G20E, G20F, G20H, G20I, G20K, G20L, G20M, G20N, G20P, G20Q, G20R, G20S, G20T, G20V, G20W, G20Y, S21*, S21A, S21D, S21E, S21F, S21G, S21H, S21I, S21K, S21L, S21M, S21N, S21P, S21Q, S21R, S21T, S21V, S21W, S21Y, G22*, G22A, G22D, G22E, G22F, G22H, G22I, G22K, G22L, G22M, G22N, G22P, G22Q, G22R, G22S, G22T, G22V, G22W, G22Y, D23*, D23A, D23E, D23F, D23G, D23H, D23I, D23K, D23L, D23M, D23N, D23P, D23Q, D23R, D23S, D23T, D23V, D23W, D23Y, S24*, S24A, S24D, S24E, S24F, S24G, S24H, S24I, S24K, S24L, S24M, S24N, S24P, S24Q, S24R, S24T, S24V, S24W, S24Y, Q25*, Q25A, Q25D, Q25E, Q25F, Q25G, Q25H, Q25I, Q25K, Q25L, Q25M, Q25N, Q25P, Q25R, Q25S, Q25T, Q25V, Q25W, Q25Y, S26*, S26A, S26D, S26E, S26F, S26G, S26H, S26I, S26K, S26L, S26M, S26N, S26P, S26Q, S26R, S26T, S26V, S26W, S26Y, D27*, D27A, D27E, D27F, D27G, D27H, D27I, D27K, D27L, D27M, D27N, D27P, D27Q, D27R, D27S, D27T, D27V, D27W, D27Y, P28*, P28A, P28D, P28E, P28F, P28G, P28H, P28I, P28K, P28L, P28M, P28N, P28Q, P28R, P28S, P28T, P28V, P28W, P28Y, I29*, I29A, I29D, I29E, I29F, I29G, I29H, I29K, I29L, I29M, I29N, I29P, I29Q, I29R, I29S, I29T, I29V, I29W, I29Y, K30*, K30A, K30D, K30E, K30F, K30G, K30H, K30I, K30L, K30M, K30N, K30P, K30Q, K30R, K30S, K30T, K30V, K30W, K30Y, A31*, A31D, A31E, A31F, A31G, A31H, A31I, A31K, A31L, A31M, A31N, A31P, A31Q, A31R, A31S, A31T, A31V, A31W, A31Y, D32*, D32A, D32E, D32F, D32G, D32H, D32I, D32K, D32L, D32M, D32N, D32P, D32Q, D32R, D32S, D32T, D32V, D32W, D32Y, L33*, L33A, L33D, L33E, L33F, L33G, L33H, L33I, L33K, L33M, L33N, L33P, L33Q, L33R, L33S, L33T, L33V, L33W, L33Y, E34*, E34A, E34D, E34F, E34G, E34H, E34I, E34K, E34L, E34M, E34N, E34P, E34Q, E34R, E34S, E34T, E34V, E34W, E34Y, V35*, V35A, V35D, V35E, V35F, V35G, V35H, V35I, V35K, V35L, V35M, V35N, V35P, V35Q, V35R, V35S, V35T, V35W, V35Y, K36*, K36A, K36D, K36E, K36F, K36G, K36H, K36I, K36L, K36M, K36N, K36P, K36Q, K36R, K36S, K36T, K36V, K36W, K36Y, G37*, G37A, G37D, G37E, G37F, G37H, G37I, G37K, G37L, G37M, G37N, G37P, G37Q, G37R, G37S, G37T, G37V, G37W, G37Y, Q38*, Q38A, Q38D, Q38E, Q38F, Q38G, Q38H, Q38I, Q38K, Q38L, Q38M, Q38N, Q38P, Q38R, Q38S, Q38T, Q38V, Q38W, Q38Y, S39*, S39A, S39D, S39E, S39F, S39G, S39H, S39I, S39K, S39L, S39M, S39N, S39P, S39Q, S39R, S39T, S39V, S39W, S39Y, A40*, A40D, A40E, A40F, A40G, A40H, A40I, A40K, A40L, A40M, A40N, A40P, A40Q, A40R, A40S, A40T, A40V, A40W, A40Y, L41*, L41A, L41D, L41E, L41F, L41G, L41H, L41I, L41K, L41M, L41N, L41P, L41Q, L41R, L41S, L41T, L41V, L41W, L41Y, P42*, P42A, P42D, P42E, P42F, P42G, P42H, P42I, P42K, P42L, P42M, P42N, P42Q, P42R, P42S, P42T, P42V, P42W, P42Y, F43*, F43A, F43D, F43E, F43G, F43H, F43I, F43K, F43L, F43M, F43N, F43P, F43Q, F43R, F43S, F43T, F43V, F43W, F43Y, D44*, D44A, D44E, D44F, D44G, D44H, D44I, D44K, D44L, D44M, D44N, D44P, D44Q, D44R, D44S, D44T, D44V, D44W, D44Y, V45*, V45A, V45D, V45E, V45F, V45G, V45H, V45I, V45K, V45L, V45M, V45N, V45P, V45Q, V45S, V45T, V45W, V45Y, D46*, D46A, D46E, D46F, D46G, D46H, D46I, D46K, D46L, D46M, D46N, D46P, D46Q, D46R, D46S, D46T, D46V, D46W, D46Y, 047A, C47D, C47E, C47F, C47G, C47H, C47I, C47K, C47L, C47M, C47N, C47P, C47Q, C47R, C47S, C47T, 047V, C47W, C47Y, W48*, W48A, W48D, W48E, W48F, W48G, W48H, W48I, W48K, W48L, W48M, W48N, W48P, W48Q, W48R, W48S, W48T, W48V, W48Y, A49*, A49D, A49E, A49F, A49G, A49H, A49I, A49K, A49L, A49M, A49N, A49P, A49Q, A49R, A49S, A49T, A49V, A49W, A49Y, I50*, I50A, I50D, I50E, I50F, I50G, I50H, I50K, I50L, I50M, I50N, I50P, I50Q, I50R, I50S, I50T, I50V, I50W, I50Y, L51*, L51A, L51D, L51E, L51F, L51G, L51H, L51I, L51K, L51M, L51N, L51P, L51Q, L51R, L51S, L51T, L51V, L51W, L51Y, K53*, K53A, K53D, K53E, K53F, K53G, K53H, K53I, K53L, K53M, K53N, K53P, K53Q, K53R, K53S, K53T, K53V, K53W, K53Y, G54*, G54A, G54D, G54E, G54F, G54H, G54I, G54K, G54L, G54M, G54N, G54P, G54Q, G54R, G54S, G54T, G54V, G54W, G54Y, A55*, A55D, A55E, A55F, A55G, A55H, A55I, A55K, A55L, A55M, A55N, A55P, A55Q, A55R, A55S, A55T, A55V, A55W, A55Y, P56*, P56A, P56D, P56E, P56F, P56G, P56H, P56I, P56K, P56L, P56M, P56N, P56Q, P56R, P56S, P56T, P56V, P56W, P56Y, N57*, N57A, N57D, N57E, N57F, N57G, N57H, N57I, N57K, N57L, N57M, N57P, N57Q, N57R, N57S, N57T, N57V, N57W, N57Y, V58*, V58A, V58D, V58E, V58F, V58G, V58H, V58I, V58K, V58L, V58M, V58N, V58P, V58Q, V58R, V58S, V58T, V58W, V58YL59*, L59A, L59A, L59D, L59D, L59A, L59D, L59E, L59E, L59F, L59F, L59E, L59F, L59G, L59G, L59H, L59H, L59G, L59H, L59I, L59I, L59K, L59K, L59I, L59K, L59M, L59ML59M, L59N, L59N, L59N, L59P, L59P, L59Q, L59Q, L59P, L59Q, L59R, L59R, L59S, L59S, L59R, L59S, L59T, L59T, L59V, L59V, L59T, L59V, L59W, L59W, L59Y, L59YL59W, L59Y, Q60*, Q60A, Q60D, Q60E, Q60F, Q60G, Q60H, Q60I, Q60K, Q60L, Q60M, Q60N, Q60P, Q60R, Q60S, Q60T, Q60V, Q60W, Q60Y, R61*, R61A, R61D, R61E, R61F, R61G, R61H, R61I, R61K, R61L, R61M, R61N, R61P, R61Q, R61S, R61T, R61V, R61W, R61Y, V62*, V62A, V62D, V62E, V62F, V62G, V62H, V62I, V62K, V62L, V62M, V62N, V62P, V62Q, V62R, V62S, V62T, V62W, V62Y, N63*, N63A, N63D, N63E, N63F, N63G, N63H, N63I, N63K, N63L, N63M, N63P, N63Q, N63R, N63S, N63T, N63V, N63W, N63Y, E64*, E64A, E64D, E64F, E64G, E64H, E64I, E64K, E64L, E64M, E64N, E64P, E64Q, E64R, E64S, E64T, E64V, E64W, E64Y, K65*, K65A, K65D, K65E, K65F, K65G, K65H, K65I, K65L, K65M, K65N, K65P, K65Q, K65R, K65S, K65T, K65V, K65W, K65Y, T66*, T66A, T66D, T66E, T66F, T66G, T66H, T66I, T66K, T66L, T66M, T66N, T66P, T66Q, T66R, T66S, T66V, T66W, T66Y, K67*, K67A, K67D, K67E, K67F, K67G, K67H, K67I, K67L, K67M, K67N, K67P, K67Q, K67R, K67S, K67T, K67V, K67W, K67Y, N68*, N68A, N68D, N68E, N68F, N68G, N68H, N68I, N68K, N68L, N68M, N68P, N68Q, N68R, N68S, N68T, N68V, N68W, N68Y, S69*, S69A, S69D, S69E, S69F, S69G, S69H, S69I, S69K, S69L, S69M, S69N, S69P, S69Q, S69R, S69T, S69V, S69W, S69Y, N70*, N70A, N70D, N70E, N70F, N70G, N70H, N70I, N70K, N70L, N70M, N70P, N70Q, N70R, N70S, N70T, N70V, N70W, N70Y, R71*, R71A, R71D, R71E, R71F, R71G, R71H, R71I, R71K, R71L, R71M, R71N, R71P, R71Q, R71S, R71T, R71V, R71W, R71Y, D72*, D72A, D72E, D72F, D72G, D72H, D72I, D72K, D72L, D72M, D72N, D72P, D72Q, D72R, D72S, D72T, D72V, D72W, D72Y, R73*, R73A, R73D, R73E, R73F, R73G, R73H, R73I, R73K, R73L, R73M, R73N, R73P, R73Q, R73S, R73T, R73V, R73W, R73Y, S74*, S74A, S74D, S74E, S74F, S74G, S74H, S74I, S74K, S74L, S74M, S74N, S74P, S74Q, S74R, S74T, S74V, S74W, S74Y, G75*, G75A, G75D, G75E, G75F, G75H, G75I, G75K, G75L, G75M, G75N, G75P, G75Q, G75R, G75S, G75T, G75V, G75W, G75Y, A76*, A76D, A76E, A76F, A76G, A76H, A76I, A76K, A76L, A76M, A76N, A76P, A76Q, A76R, A76S, A76T, A76V, A76W, A76Y, N77*, N77A, N77D, N77E, N77F, N77G, N77H, N77I, N77K, N77L, N77M, N77P, N77Q, N77R, N77S, N77T, N77V, N77W, N77Y, K78*, K78A, K78D, K78E, K78F, K78G, K78H, K78I, K78L, K78M, K78N, K78P, K78Q, K78R, K78S, K78T, K78V, K78W, K78Y, G79*, G79A, G79D, G79E, G79F, G79H, G79I, G79K, G79L, G79M, G79N, G79P, G79Q, G79R, G79S, G79T, G79V, G79W, G79Y, P80*, P80A, P80D, P80E, P80F, P80G, P80H, P80I, P80K, P80L, P80M, P80N, P80Q, P80R, P80S, P80T, P80V, P80W, P80Y, F81*, F81A, F81D, F81E, F81G, F81H, F81I, F81K, F81L, F81M, F81N, F81P, F81Q, F81R, F81S, F81T, F81V, F81W, F81Y, K82*, K82A, K82D, K82E, K82F, K82G, K82H, K82I, K82L, K82M, K82N, K82P, K82Q, K82R, K82S, K82T, K82V, K82W, K82Y, D83*, D83A, D83E, D83F, D83G, D83H, D83I, D83K, D83L, D83M, D83N, D83P, D83Q, D83R, D83S, D83T, D83V, D83W, D83Y, P84*, P84A, P84D, P84E, P84F, P84G, P84H, P84I, P84K, P84L, P84M, P84N, P84Q, P84R, P84S, P84T, P84V, P84W, P84Y, Q85*, Q85A, Q85D, Q85E, Q85F, Q85G, Q85H, Q85I, Q85K, Q85L, Q85M, Q85N, Q85P, Q85R, Q85S, Q85T, Q85V, Q85W, Q85Y, K86*, K86A, K86D, K86E, K86F, K86G, K86H, K86I, K86L, K86M, K86N, K86P, K86Q, K86R, K86S, K86T, K86V, K86W, K86Y, W87*, W87A, W87D, W87E, W87F, W87G, W87H, W87I, W87K, W87L, W87M, W87N, W87P, W87Q, W87R, W87S, W87T, W87V, W87Y, G88*, G88A, G88D, G88E, G88F, G88H, G88I, G88K, G88L, G88M, G88N, G88P, G88Q, G88R, G88S, G88T, G88V, G88W, G88Y, I89*, I89A, I89D, I89E, I89F, I89G, I89H, I89K, I89L, I89M, I89N, I89P, I89Q, I89R, I89S, I89T, I89V, I89W, I89Y, K90*, K90A, K90D, K90E, K90F, K90G, K90H, K90I, K90L, K90M, K90N, K90P, K90Q, K90R, K90S, K90T, K90V, K90W, K90Y, A91*, A91D, A91E, A91F, A91G, A91H, A91I, A91K, A91L, A91M, A91N, A91P, A91Q, A91R, A91S, A91T, A91V, A91W, A91Y, L92*, L92A, L92D, L92E, L92F, L92G, L92H, L92I, L92K, L92M, L92N, L92P, L92Q, L92R, L92S, L92T, L92V, L92W, L92Y, P93*, P93A, P93D, P93E, P93F, P93G, P93H, P93I, P93K, P93L, P93M, P93N, P93Q, P93R, P93S, P93T, P93V, P93W, P93Y, P94*, P94A, P94D, P94E, P94F, P94G, P94H, P94I, P94K, P94L, P94M, P94N, P94Q, P94R, P94S, P94T, P94V, P94W, P94Y, K95*, K95A, K95D, K95E, K95F, K95G, K95H, K95I, K95L, K95M, K95N, K95P, K95Q, K95R, K95S, K95T, K95V, K95W, K95Y, N96*, N96A, N96D, N96E, N96F, N96G, N96H, N96I, N96K, N96L, N96M, N96P, N96Q, N96R, N96S, N96T, N96V, N96W, N96Y, P97*, P97A, P97D, P97E, P97F, P97G, P97H, P97I, P97K, P97L, P97M, P97N, P97Q, P97R, P97S, P97T, P97V, P97W, P97Y, S98*, S98A, S98D, S98E, S98F, S98G, S98H, S98I, S98K, S98L, S98M, S98N, S98P, S98Q, S98R, S98T, S98V, S98W, S98Y, W99*, W99A, W99D, W99E, W99F, W99G, W99H, W99I, W99K, W99L, W99M, W99N, W99P, W99Q, W99R, W99S, W99T, W99V, W99Y, S100*, S100A, S100D, S100E, S100F, S100G, S100H, S100I, S100K, S100L, S100M, S100N, S100P, S100Q, S100R, S100T, S100V, S100W, S100Y, A101*, A101D, A101E, A101F, A101G, A101H, A101I, A101K, A101L, A101M, A101N, A101P, A101Q, A101R, A101S, A101T, A101V, A101W, A101Y, Q102*, Q102A, Q102D, Q102E, Q102F, Q102G, Q102H, Q102I, Q102K, Q102L, Q102M, Q102N, Q102P, Q102R, Q102S, Q102T, Q102V, Q102W, Q102Y, D103*, D103A, D103E, D103F, D103G, D103H, D103I, D103K, D103L, D103M, D103N, D103P, D103Q, D103R, D103S, D103T, D103V, D103W, D103Y, F104*, F104A, F104D, F104E, F104G, F104H, F104I, F104K, F104L, F104M, F104N, F104P, F104Q, F104R, F104S, F104T, F104V, F104W, F104Y, K105*, K105A, K105D, K105E, K105F, K105G, K105H, K105I, K105L, K105M, K105N, K105P, K105Q, K105R, K105S, K105T, K105V, K105W, K105Y, S106*, S106A, S106D, S106E, S106F, S106G, S106H, S106I, S106K, S106L, S106M, S106N, S106P, S106Q, S106R, S106T, S106V, S106W, S106Y, P107*, P107A, P107D, P107E, P107F, P107G, P107H, P107I, P107K, P107L, P107M, P107N, P107Q, P107R, P107S, P107T, P107V, P107W, P107Y, E108*, E108A, E108D, E108F, E108G, E108H, E108I, E108K, E108L, E108M, E108N, E108P, E108Q, E108R, E108S, E108T, E108V, E108W, E108Y, E109*, E109A, E109D, E109F, E109G, E109H, E109I, E109K, E109L, E109M, E109N, E109P, E109Q, E109R, E109S, E109T, E109V, E109W, E109Y, Y110*, Y110A, Y110D, Y110E, Y110F, Y110G, Y110H, Y110I, Y110K, Y110L, Y110M, Y110N, Y110P, Y110Q, Y110R, Y110S, Y110T, Y110V, Y110W, A111*, A111D, A111E, A111F, A111G, A111H, A111I, A111K, A111L, A111M, A111N, A111P, A111Q, A111R, A111S, A111T, A111V, A111W, A111Y, F112*, F112A, F112D, F112E, F112G, F112H, F112I, F112K, F112L, F112M, F112N, F112P, F112Q, F112R, F112S, F112T, F112V, F112W, F112Y, A113*, A113D, A113E, A113F, A113G, A113H, A113I, A113K, A113L, A113M, A113N, A113P, A113Q, A113R, A113S, A113T, A113V, A113W, A113Y, S114*, S114A, S114D, S114E, S114F, S114G, S114H, S114I, S114K, S114L, S114M, S114N, S114P, S114Q, S114R, S114T, S114V, S114W, S114Y, S115*, S115A, S115D, S115E, S115F, S115G, S115H, S115I, S115K, S115L, S115M, S115N, S115P, S115Q, S115R, S115T, S115V, S115W, S115Y, L116*, L116A, L116D, L116E, L116F, L116G, L116H, L116I, L116K, L116M, L116N, L116P, L116Q, L116R, L116S, L116T, L116V, L116W, L116Y, Q117*, Q117A, Q117D, Q117E, Q117F, Q117G, Q117H, Q117I, Q117K, Q117L, Q117M, Q117N, Q117P, Q117R, Q117S, Q117T, Q117V, Q117W, Q117Y, G118*, G118A, G118D, G118E, G118F, G118H, G118I, G118K, G118L, G118M, G118N, G118P, G118Q, G118R, G118S, G118T, G118V, G118W, G118Y, G119*, G119A, G119D, G119E, G119F, G119H, G119I, G119K, G119L, G119M, G119N, G119P, G119Q, G119R, G119S, G119T, G119V, G119W, G119Y, T120*, T120A, T120D, T120E, T120F, T120G, T120H, T120I, T120K, T120L, T120M, T120N, T120P, T120Q, T120R, T120S, T120V, T120W, T120Y, N121*, N121*N121*, N121A, N121A, N121D, N121D, N121A, N121D, N121E, N121EN121E, N121F, N121F, N121F, N121G, N121G, N121G, N121H, N121H, N121I, N121IN121H, N121I, N121K, N121K, N121L, N121LN121K, N121L, N121M, N121M, N121P, N121PN121M, N121P, N121Q, N121Q, N121R, N121R, N121Q, N121R, N121S, N121S, N121S, N121T, N121T, N121T, N121V, N121VN121V, N121W, N121WN121W, N121Y, N121Y, N121Y, A122*, A122D, A122E, A122F, A122G, A122H, A122I, A122K, A122L, A122M, A122N, A122P, A122Q, A122R, A122S, A122T, A122V, A122W, A122Y, I123*, I123A, I123D, I123E, I123F, I123G, I123H, I123K, I123L, I123M, I123N, I123P, I123Q, I123R, I123S, I123T, I123V, I123W, I123Y, L124*, L124A, L124D, L124E, L124F, L124G, L124H, L124I, L124K, L124M, L124N, L124P, L124Q, L124R, L124S, L124T, L124V, L124W, L124Y, A125*, A125D, A125E, A125F, A125G, A125H, A125I, A125K, A125L, A125M, A125N, A125P, A125Q, A125R, A125S, A125T, A125V, A125W, A125Y, P126*, P126A, P126D, P126E, P126F, P126G, P126H, P126I, P126K, P126L, P126M, P126N, P126Q, P126R, P126S, P126T, P126V, P126W, P126Y, V127*, V127A, V127D, V127E, V127F, V127G, V127H, V127I, V127K, V127L, V127M, V127N, V127P, V127Q, V127R, V127S, V127T, V127W, V127Y, N128*, N128A, N128D, N128E, N128F, N128G, N128H, N128I, N128K, N128L, N128M, N128P, N128Q, N128R, N128S, N128T, N128V, N128W, N128Y, L129*, L129A, L129D, L129E, L129F, L129G, L129H, L129I, L129K, L129M, L129N, L129P, L129Q, L129R, L129S, L129T, L129V, L129W, L129Y, A130*, A130D, A130E, A130F, A130G, A130H, A130I, A130K, A130L, A130M, A130N, A130P, A130Q, A130R, A130S, A130T, A130V, A130W, A130Y, S131*, S131A, S131D, S131E, S131F, S131G, S131H, S131I, S131K, S131L, S131M, S131N, S131P, S131Q, S131R, S131T, S131V, S131W, S131Y, Q132*, Q132A, Q132D, Q132E, Q132F, Q132G, Q132H, Q132I, Q132K, Q132L, Q132M, Q132N, Q132P, Q132R, Q132S, Q132T, Q132V, Q132W, Q132Y, N133*, N133A, N133D, N133E, N133F, N133G, N133H, N133I, N133K, N133L, N133M, N133P, N133Q, N133R, N133S, N133T, N133V, N133W, N133Y, S134*, S134A, S134D, S134E, S134F, S134G, S134H, S134I, S134K, S134L, S134M, S134N, S134P, S134Q, S134R, S134T, S134V, S134W, S134Y, Q135*, Q135A, Q135D, Q135E, Q135F, Q135G, Q135H, Q135I, Q135K, Q135L, Q135M, Q135N, Q135P, Q135R, Q135S, Q135T, Q135V, Q135W, Q135Y, G136*, G136A, G136D, G136E, G136F, G136H, G136I, G136K, G136L, G136M, G136N, G136P, G136Q, G136R, G136S, G136T, G136V, G136W, G136Y, G137*, G137A, G137D, G137E, G137F, G137H, G137I, G137K, G137L, G137M, G137N, G137P, G137Q, G137R, G137S, G137T, G137V, G137W, G137Y, V138*, V138A, V138D, V138E, V138F, V138G, V138H, V138I, V138K, V138L, V138M, V138N, V138P, V138Q, V138R, V138S, V138T, V138W, V138Y, L139*, L139A, L139D, L139E, L139F, L139G, L139H, L139I, L139K, L139M, L139N, L139P, L139Q, L139R, L139S, L139T, L139V, L139W, L139Y, N140*, N140A, N140D, N140E, N140F, N140G, N140H, N140I, N140K, N140L, N140M, N140P, N140Q, N140R, N140S, N140T, N140V, N140W, N140Y, G141*, G141A, G141D, G141E, G141F, G141H, G141I, G141K, G141L, G141M, G141N, G141P, G141Q, G141R, G141S, G141T, G141V, G141W, G141Y, F142*, F142A, F142D, F142E, F142G, F142H, F142I, F142K, F142L, F142M, F142N, F142P, F142Q, F142R, F142S, F142T, F142V, F142W, F142Y, Y143*, Y143A, Y143D, Y143E, Y143F, Y143G, Y143H, Y143I, Y143K, Y143L, Y143M, Y143N, Y143P, Y143Q, Y143R, Y143S, Y143T, Y143V, Y143W, S144*, S144A, S144D, S144E, S144F, S144G, S144H, S144I, S144K, S144L, S144M, S144N, S144P, S144Q, S144R, S144T, S144V, S144W, S144Y, A145*, A145D, A145E, A145F, A145G, A145H, A145I, A145K, A145L, A145M, A145N, A145P, A145Q, A145R, A145S, A145T, A145V, A145W, A145Y, N146*, N146A, N146D, N146E, N146F, N146G, N146H, N146I, N146K, N146L, N146M, N146P, N146Q, N146R, N146S, N146T, N146V, N146W, N146Y, K147*, K147A, K147D, K147E, K147F, K147G, K147H, K147I, K147L, K147M, K147N, K147P, K147Q, K147R, K147S, K147T, K147V, K147W, K147Y, V148*, V148A, V148D, V148E, V148F, V148G, V148H, V148I, V148K, V148L, V148M, V148N, V148P, V148Q, V148R, V148S, V148T, V148W, V148Y, A149*, A149D, A149E, A149F, A149G, A149H, A149I, A149K, A149L, A149M, A149N, A149P, A149Q, A149R, A149S, A149T, A149V, A149W, A149Y, Q150*, Q150A, Q150D, Q150E, Q150F, Q150G, Q150H, Q150I, Q150L, Q150M, Q150N, Q150P, Q150R, Q150S, Q150T, Q150V, Q150W, Q150Y, F151*, F151A, F151D, F151E, F151G, F151H, F151I, F151K, F151L, F151M, F151N, F151P, F151Q, F151R, F151S, F151T, F151V, F151W, F151Y, D152*, D152A, D152E, D152F, D152G, D152H, D152I, D152K, D152L, D152M, D152N, D152P, D152Q, D152R, D152S, D152T, D152V, D152W, D152Y, P153*, P153A, P153E, P153F, P153G, P153H, P153I, P153K, P153L, P153M, P153N, P153Q, P153R, P153S, P153T, P153V, P153W, P153Y, S154*, S154A, S154D, S154E, S154F, S154G, S154H, S154I, S154K, S154L, S154M, S154N, S154P, S154Q, S154R, S154T, S154V, S154W, S154Y, K155*, K155A, K155D, K155E, K155F, K155G, K155H, K155I, K155L, K155M, K155N, K155P, K155Q, K155R, K155S, K155T, K155V, K155W, K155Y, P156*, P156A, P156D, P156E, P156F, P156G, P156H, P156I, P156K, P156L, P156M, P156N, P156Q, P156R, P156S, P156T, P156V, P156W, P156Y, Q157*, Q157A, Q157D, Q157E, Q157F, Q157G, Q157H, Q157I, Q157K, Q157L, Q157M, Q157N, Q157P, Q157R, Q157S, Q157T, Q157V, Q157W, Q157Y, Q158*, Q158A, Q158D, Q158E, Q158F, Q158G, Q158H, Q158I, Q158K, Q158L, Q158M, Q158N, Q158P, Q158R, Q158S, Q158T, Q158V, Q158W, Q158Y, T159*, T159A, T159D, T159E, T159F, T159G, T159H, T159I, T159K, T159L, T159M, T159N, T159P, T159Q, T159R, T159S, T159V, T159W, T159Y, K160*, K160A, K160D, K160E, K160F, K160G, K160H, K160I, K160L, K160M, K160N, K160P, K160Q, K160R, K160S, K160T, K160V, K160W, K160Y, G161*, G161A, G161D, G161E, G161F, G161H, G161I, G161K, G161L, G161M, G161N, G161P, G161Q, G161R, G161S, G161T, G161V, G161W, G161Y, T162A, T162D, T162E, T162F, T162G, T162H, T162I, T162K, T162L, T162M, T162N, T162P, T162Q, T162R, T162S, T162T, T162V, T162W, T162Y, W163*, W163A, W163D, W163E, W163F, W163G, W163H, W163I, W163K, W163L, W163M, W163N, W163P, W163Q, W163R, W163S, W163T, W163V, W163Y, F164*, F164A, F164D, F164E, F164G, F164H, F164I, F164K, F164L, F164M, F164N, F164P, F164Q, F164R, F164S, F164T, F164V, F164W, F164Y, Q165*, Q165A, Q165D, Q165E, Q165F, Q165G, Q165H, Q165I, Q165K, Q165L, Q165M, Q165N, Q165P, Q165R, Q165S, Q165T, Q165V, Q165W, Q165Y, I166*, I166A, I166D, I166E, I166F, I166G, I166H, I166K, I166L, I166M, I166N, I166P, I166Q, I166R, I166S, I166T, I166V, I166W, I166Y, T167*, T167A, T167D, T167E, T167F, T167G, T167H, T167I, T167K, T167L, T167M, T167N, T167P, T167Q, T167R, T167S, T167V, T167W, T167Y, K168*, K168A, K168D, K168E, K168F, K168G, K168H, K168I, K168L, K168M, K168N, K168P, K168Q, K168R, K168S, K168T, K168V, K168W, K168Y, F169*, F169A, F169D, F169E, F169G, F169H, F169I, F169K, F169L, F169M, F169N, F169P, F169Q, F169R, F169S, F169T, F169V, F169W, F169Y, T170*, T170A, T170D, T170E, T170F, T170G, T170H, T170I, T170K, T170L, T170M, T170N, T170P, T170Q, T170R, T170S, T170V, T170W, T170Y, G171*, G171A, G171D, G171E, G171F, G171H, G171I, G171K, G171L, G171M, G171N, G171P, G171Q, G171R, G171S, G171T, G171V, G171W, G171Y, A172*, A172D, A172E, A172F, A172G, A172H, A172I, A172K, A172L, A172M, A172N, A172P, A172Q, A172R, A172S, A172T, A172V, A172W, A172Y, A173*, A173D, A173E, A173F, A173G, A173H, A173I, A173K, A173L, A173M, A173N, A173P, A173Q, A173R, A173S, A173T, A173V, A173W, A173Y, G174*, G174A, G174A, G174D, G174DG174A, G174D, G174E, G174E, G174F, G174FG174E, G174F, G174H, G174I, G174I G174H, G174I, G174K, G174K, G174L, G174LG174K, G174L, G174M, G174M, G174N, G174N, G174M, G174N, G174P, G174P, G174Q, G174QG174P, G174Q, G174R, G174R, G174S, G174SG174R, G174S, G174T, G174T, G174V, G174VG174T, G174V, G174W, G174W, G174Y, G174YG174W, G174Y, P175*, P175A, P175D, P175E, P175F, P175G, P175H, P175I, P175K, P175L, P175M, P175N, P175Q, P175R, P175S, P175T, P175V, P175W, P175Y, Y176*, Y176A, Y176D, Y176E, Y176F, Y176G, Y176H, Y176I, Y176K, Y176L, Y176M, Y176N, Y176P, Y176Q, Y176R, Y176S, Y176T, Y176V, Y176W, K178*, K178A, K178D, K178E, K178F, K178G, K178H, K178I, K178L, K178M, K178N, K178P, K178Q, K178R, K178S, K178T, K178V, K178W, K178Y, A179*, A179D, A179E, A179F, A179G, A179H, A179I, A179K, A179L, A179M, A179N, A179P, A179Q, A179R, A179S, A179T, A179V, A179W, A179Y, L180*, L180A, L180D, L180E, L180F, L180G, L180H, L180I, L180K, L180M, L180N, L180P, L180Q, L180R, L180S, L180T, L180V, L180W, L180Y, G181*, G181A, G181D, G181E, G181F, G181H, G181I, G181K, G181L, G181M, G181N, G181P, G181Q, G181R, G181S, G181T, G181V, G181W, G181Y, S182*, S182A, S182D, S182E, S182F, S182G, S182H, S182I, S182K, S182L, S182M, S182N, S182P, S182Q, S182R, S182T, S182V, S182W, S182Y, N183*, N183A, N183D, N183E, N183F, N183G, N183H, N183I, N183K, N183L, N183M, N183P, N183Q, N183R, N183S, N183T, N183V, N183W, N183Y, D184*, D184A, D184E, D184F, D184G, D184H, D184I, D184K, D184L, D184M, D184N, D184P, D184Q, D184R, D184S, D184T, D184V, D184W, D184Y, K185*, K185A, K185D, K185E, K185F, K185G, K185H, K185I, K185L, K185M, K185N, K185P, K185Q, K185R, K185S, K185T, K185V, K185W, K185Y, S186*, S186A, S186D, S186E, S186F, S186G, S186H, S186I, S186K, S186L, S186M, S186N, S186P, S186Q, S186R, S186T, S186V, S186W, S186Y, V187*, V187A, V187D, V187E, V187F, V187G, V187H, V187I, V187K, V187L, V187M, V187N, V187P, V187Q, V187R, V187S, V187T, V187W, V187Y, D189*, D189A, D189E, D189F, D189G, D189H, D189I, D189K, D189L, D189M, D189N, D189P, D189Q, D189R, D189S, D189T, D189V, D189W, D189Y, K190*, K190A, K190D, K190E, K190F, K190G, K190H, K190I, K190L, K190M, K190N, K190P, K190Q, K190R, K190S, K190T, K190V, K190W, K190Y, N191*, N191A, N191D, N191E, N191F, N191G, N191H, N191I, N191K, N191L, N191M, N191P, N191Q, N191R, N191S, N191T, N191V, N191W, N191Y, K192*, K192A, K192D, K192E, K192F, K192G, K192H, K192I, K192L, K192M, K192N, K192P, K192Q, K192R, K192S, K192T, K192V, K192W, K192Y, N193*, N193A, N193D, N193E, N193F, N193G, N193H, N193I, N193K, N193L, N193M, N193P, N193Q, N193R, N193S, N193T, N193V, N193W, N193Y, I194*, I194A, I194D, I194E, I194F, I194G, I194H, I194K, I194L, I194M, I194N, I194P, I194Q, I194R, I194S, I194T, I194V, I194W, I194Y, A195*, A195D, A195E, A195F, A195G, A195H, A195I, A195K, A195L, A195M, A195N, A195P, A195Q, A195R, A195S, A195T, A195V, A195W, A195Y, G196*, G196A, G196D, G196E, G196F, G196H, G196I, G196K, G196L, G196M, G196N, G196P, G196Q, G196R, G196S, G196T, G196V, G196W, G196Y, D197*, D197A, D197E, D197F, D197G, D197H, D197I, D197K, D197L, D197M, D197N, D197P, D197Q, D197R, D197S, D197T, D197V, D197W, D197Y, W198*, W198A, W198D, W198E, W198F, W198G, W198H, W198I, W198K, W198L, W198M, W198N, W198P, W198Q, W198R, W198S, W198T, W198V, W198Y, G199*, G199A, G199D, G199E, G199F, G199H, G199I, G199K, G199L, G199M, G199N, G199P, G199Q, G199R, G199S, G199T, G199V, G199W, G199Y, F200*, F200A, F200D, F200E, F200G, F200H, F200I, F200K, F200L, F200M, F200N, F200P, F200Q, F200R, F200S, F200T, F200V, F200W, F200Y, D201*, D201A, D201E, D201F, D201G, D201H, D201I, D201K, D201L, D201M, D201N, D201P, D201Q, D201R, D201S, D201T, D201V, D201W, D201Y, P202*, P202A, P202D, P202E, P202F, P202G, P202H, P202I, P202K, P202L, P202M, P202N, P202Q, P202R, P202S, P202T, P202V, P202W, P202Y, A203*, A203D, A203E, A203F, A203G, A203H, A203I, A203K, A203L, A203M, A203N, A203P, A203Q, A203R, A203S, A203T, A203V, A203W, A203Y, K204*, K204A, K204D, K204E, K204F, K204G, K204H, K204I, K204L, K204M, K204N, K204P, K204Q, K204R, K204S, K204T, K204V, K204W, K204Y, W205*, W205A, W205D, W205E, W205F, W205G, W205H, W205I, W205K, W205L, W205M, W205N, W205P, W205Q, W205R, W205S, W205T, W205V, W205Y, A206*, A206D, A206E, A206F, A206G, A206H, A206I, A206K, A206L, A206M, A206N, A206P, A206Q, A206R, A206S, A206T, A206V, A206W, A206Y, Y207*, Y207A, Y207D, Y207E, Y207F, Y207G, Y207H, Y207I, Y207K, Y207L, Y207M, Y207N, Y207P, Y207Q, Y207R, Y207S, Y207T, Y207V, Y207W, Q208*, Q208A, Q208D, Q208E, Q208F, Q208G, Q208H, Q208I, Q208K, Q208L, Q208M, Q208N, Q208P, Q208R, Q208S, Q208T, Q208V, Q208W, Q208Y, Y209*, Y209A, Y209D, Y209E, Y209F, Y209G, Y209H, Y209I, Y209K, Y209L, Y209M, Y209N, Y209P, Y209Q, Y209R, Y209S, Y209T, Y209V, Y209W, D210*, D210A, D210E, D210F, D210G, D210H, D210I, D210K, D210L, D210M, D210N, D210P, D210Q, D210R, D210S, D210T, D210V, D210W, D210Y, E211*, E211A, E211D, E211F, E211G, E211H, E211I, E211K, E211L, E211M, E211N, E211P, E211Q, E211R, E211S, E211T, E211V, E211W, E211Y, K212*, K212A, K212D, K212E, K212F, K212G, K212H, K212I, K212L, K212M, K212N, K212P, K212Q, K212R, K212S, K212T, K212V, K212W, K212Y, N213*, N213A, N213D, N213E, N213F, N213G, N213H, N213I, N213K, N213L, N213M, N213P, N213Q, N213R, N213S, N213T, N213V, N213W, N213Y, N214*, N214A, N214D, N214E, N214F, N214G, N214H, N214I, N214K, N214L, N214M, N214P, N214Q, N214R, N214S, N214T, N214V, N214W, N214Y, K215*, K215A, K215D, K215E, K215F, K215G, K215H, K215I, K215L, K215M, K215N, K215P, K215Q, K215R, K215S, K215T, K215V, K215W, K215Y, F216*, F216A, F216D, F216E, F216G, F216H, F216I, F216K, F216L, F216M, F216N, F216P, F216Q, F216R, F216S, F216T, F216V, F216W, F216Y, N217*, N217A, N217D, N217E, N217F, N217G, N217H, N217I, N217K, N217L, N217M, N217P, N217Q, N217R, N217S, N217T, N217V, N217W, N217Y, Y218*, Y218A, Y218D, Y218E, Y218F, Y218G, Y218H, Y218I, Y218K, Y218L, Y218M, Y218N, Y218P, Y218Q, Y218R, Y218S, Y218T, Y218V, Y218W, V219*, V219A, V219D, V219E, V219F, V219G, V219H, V219I, V219K, V219L, V219M, V219N, V219P, V219Q, V219R, V219S, V219T, V219W, V219Y, G220*, G220A, G220D, G220E, G220F, G220H, G220I, G220K, G220L, G220M, G220N, G220P, G220Q, G220R, G220S, G220T, G220V, G220W, G220Y, K221*, K221A, K221D, K221E, K221F, K221G, K221H, K221I, K221L, K221M, K221N, K221P, K221Q, K221R, K221S, K221T, K221V, K221W and K221Y, wherein the variant has a sequence identity to SEQ ID NO: 1 of at least 60% and the variant has DNase activity.

3. The variant of any of embodiments 1-2, which has an improved detergent stability compared to the parent or compared to the DNase with SEQ ID NO: 1.

4. The variant of any of embodiments 1-3, wherein the variant has at least 80%, at least 85%, at least 90%, at least 95%, at least 96%, at least 97%, at least 98%, at least 99 sequence identity to the mature polypeptide of SEQ ID NO: 1.

5. The variant of any of embodiments 1-4, wherein the total number of alterations compared to SEQ ID NO: 1 is 1-20, e.g. 1-10 and 1-5, such as 1, 2, 3, 4, 5, 6, 7, 8, 9 or 10 alterations.

6. A detergent composition comprising a variant according to any of embodiments 1 to 5.

7. The detergent composition of embodiment 6, further comprising one or more detergent components.

8. The detergent composition according to any of embodiments 6-7, further comprising one or more additional enzymes selected from the group comprising of proteases, amylases, lipases, cutinases, cellulases, endoglucanases, xyloglucanases, pectinases, pectin lyases, xanthanases, peroxidaes, haloperoxygenases, catalases and mannanases, or any mixture thereof.

9 The detergent composition according to any of embodiments 6-8 in form of a bar, a homogenous tablet, a tablet having two or more layers, a pouch having one or more compartments, a regular or compact powder, a granule, a paste, a gel, or a regular, compact or concentrated liquid.

10. Use of a detergent composition according to any of embodiments 6-9 in a cleaning process, such as laundry or hard surface cleaning such as dish wash.

11. A method for obtaining a DNase variant, comprising introducing into a parent DNase an alteration at one or more positions corresponding to positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 185, 186, 187, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 or 221 of SEQ ID NO 1, wherein the variant has an amino acid sequence which is at least 60% identical to SEQ ID NO 1, and recovering the variant.

12. The method of embodiment 11, wherein the variant comprises two, three, four or five alterations compared to SEQ ID NO: 1.

13. The method according to any of embodiments 11 or 12, wherein the variant comprises one or more alterations selected from the group consisting of V1*, V1A, V1D, V1E, V1F, V1G, V1H, V1I, V1K, V1L, VIM, V1N, VIP, V1Q, V1R, V1S, V1T, V1W, V1Y, P2*, P2A, P2D, P2E, P2F, P2G, P2H, P2I, P2K, P2L, P2M, P2N, P2Q, P2R, P2S, P2T, P2V, P2W, P2Y, V3*, V3A, V3C, V3D, V3E, V3F, V3G, V3H, V3I, V3K, V3L, V3M, V3N, V3P, V3R, V3S, V3T, V3W, V3Y, N4*, N4A, N4D, N4E, N4F, N4G, N4H, N4I, N4K, N4L, N4M, N4P, N4Q, N4R, N4S, N4T, N4V, N4W, N4Y, P5*, P5A, P5D, P5E, P5F, P5G, P5H, P5I, P5K, P5L, P5M, P5N, P5Q, P5R, P5S, P5T, P5V, P5W, P5Y, E6*, E6A, E6D, E6F, E6G, E6H, E6I, E6K, E6L, E6M, E6N, E6P, E6Q, E6R, E6S, E6T, E6V, E6W, E6Y, P7*, P7A, P7D, P7E, P7F, P7G, P7H, P7I, P7K, P7L, P7M, P7N, P7Q, P7R, P7S, P7T, P7V, P7W, P7Y, D8*, D8A, D8E, D8F, D8G, D8H, D8I, D8K, D8L, D8M, D8N, D8P, D8Q, D8R, D8S, D8T, D8V, D8W, D8Y, A9*, A9D, A9E, A9F, A9G, A9H, A9I, A9K, A9L, A9M, A9N, A9P, A9Q, A9R, A9S, A9T, A9V, A9W, A9Y, T10*, T10A, T10D, T10E, T10F, T10G, T10H, T10I, T10K, T10L, T10M, T10N, T10P, T10Q, T10R, T10S, T10V, T10W, T10Y, S11*, S11A, S11D, S11E, S11F, S11G, S11H, S11I, S11K, S11L, S11M, S11N, S11P, S11Q, S11R, S11T, S11V, S11W, S11Y, V12*, V12A, V12D, V12E, V12F, V12G, V12H, V12I, V12K, V12L, V12M, V12N, V12P, V12Q, V12R, V12S, V12T, V12W, V12Y, E13*, E13A, E13D, E13F, E13G, E13H, E13I, E13K, E13L, E13M, E13N, E13P, E13Q, E13R, E13S, E13T, E13V, E13W, E13Y, N14*, N14A, N14D, N14E, N14F, N14G, N14H, N14I, N14K, N14L, N14M, N14P, N14Q, N14R, N14S, N14T, N14V, N14W, N14Y, V15*, V15A, V15D, V15E, V15F, V15G, V15H, V15I, V15K, V15L, V15M, V15N, V15P, V15Q, V15R, V15S, V15T, V15W, V15Y, A16*, A16D, A16E, A16F, A16G, A16H, A16I, A16K, A16L, A16M, A16N, A16P, A16Q, A16R, A16S, A16T, A16V, A16W, A16Y, L17*, L17A, L17D, L17E, L17F, L17G, L17H, L17I, L17K, L17M, L17N, L17P, L17Q, L17R, L17S, L17T, L17V, L17W, L17Y, K18*, K18A, K18D, K18E, K18F, K18G, K18H, K18I, K18L, K18M, K18N, K18P, K18Q, K18R, K18S, K18T, K18V, K18W, K18Y, T19*, T19A, T19D, T19E, T19F, T19G, T19H, T19I, T19K, T19L, T19M, T19N, T19P, T19Q, T19R, T19S, T19V, T19W, T19Y, G20*, G20A, G20D, G20E, G20F, G20H, G20I, G20K, G20L, G20M, G20N, G20P, G20Q, G20R, G20S, G20T, G20V, G20W, G20Y, S21*, S21A, S21D, S21E, S21F, S21G, S21H, S21I, S21K, S21L, S21M, S21N, S21P, S21Q, S21R, S21T, S21V, S21W, S21Y, G22*, G22A, G22D, G22E, G22F, G22H, G22I, G22K, G22L, G22M, G22N, G22P, G22Q, G22R, G22S, G22T, G22V, G22W, G22Y, D23*, D23A, D23E, D23F, D23G, D23H, D23I, D23K, D23L, D23M, D23N, D23P, D23Q, D23R, D23S, D23T, D23V, D23W, D23Y, S24*, S24A, S24D, S24E, S24F, S24G, S24H, S24I, S24K, S24L, S24M, S24N, S24P, S24Q, S24R, S24T, S24V, S24W, S24Y, Q25*, Q25A, Q25D, Q25E, Q25F, Q25G, Q25H, Q25I, Q25K, Q25L, Q25M, Q25N, Q25P, Q25R, Q25S, Q25T, Q25V, Q25W, Q25Y, S26*, S26A, S26D, S26E, S26F, S26G, S26H, S26I, S26K, S26L, S26M, S26N, S26P, S26Q, S26R, S26T, S26V, S26W, S26Y, D27*, D27A, D27E, D27F, D27G, D27H, D27I, D27K, D27L, D27M, D27N, D27P, D27Q, D27R, D27S, D27T, D27V, D27W, D27Y, P28*, P28A, P28D, P28E, P28F, P28G, P28H, P28I, P28K, P28L, P28M, P28N, P28Q, P28R, P28S, P28T, P28V, P28W, P28Y, I29*, I29A, I29D, I29E, I29F, I29G, I29H, I29K, I29L, I29M, I29N, I29P, I29Q, I29R, I29S, I29T, I29V, I29W, I29Y, K30*, K30A, K30D, K30E, K30F, K30G, K30H, K30I, K30L, K30M, K30N, K30P, K30Q, K30R, K30S, K30T, K30V, K30W, K30Y, A31*, A31D, A31E, A31F, A31G, A31H, A31I, A31K, A31L, A31M, A31N, A31P, A31Q, A31R, A31S, A31T, A31V, A31W, A31Y, D32*, D32A, D32E, D32F, D32G, D32H, D32I, D32K, D32L, D32M, D32N, D32P, D32Q, D32R, D32S, D32T, D32V, D32W, D32Y, L33*, L33A, L33D, L33E, L33F, L33G, L33H, L33I, L33K, L33M, L33N, L33P, L33Q, L33R, L33S, L33T, L33V, L33W, L33Y, E34*, E34A, E34D, E34F, E34G, E34H, E34I, E34K, E34L, E34M, E34N, E34P, E34Q, E34R, E34S, E34T, E34V, E34W, E34Y, V35*, V35A, V35D, V35E, V35F, V35G, V35H, V35I, V35K, V35L, V35M, V35N, V35P, V35Q, V35R, V35S, V35T, V35W, V35Y, K36*, K36A, K36D, K36E, K36F, K36G, K36H, K36I, K36L, K36M, K36N, K36P, K36Q, K36R, K36S, K36T, K36V, K36W, K36Y, G37*, G37A, G37D, G37E, G37F, G37H, G37I, G37K, G37L, G37M, G37N, G37P, G37Q, G37R, G37S, G37T, G37V, G37W, G37Y, Q38*, Q38A, Q38D, Q38E, Q38F, Q38G, Q38H, Q38I, Q38K, Q38L, Q38M, Q38N, Q38P, Q38R, Q38S, Q38T, Q38V, Q38W, Q38Y, S39*, S39A, S39D, S39E, S39F, S39G, S39H, S39I, S39L, S39M, S39N, S39P, S39Q, S39R, S39T, S39V, S39W, S39Y, A40*, A40D, A40E, A40F, A40G, A40H, A40I, A40K, A40L, A40M, A40N, A40P, A40Q, A40R, A40S, A40T, A40V, A40W, A40Y, L41*, L41A, L41D, L41E, L41F, L41G, L41H, L41I, L41K, L41M, L41N, L41P, L41Q, L41R, L41S, L41T, L41V, L41W, L41Y, P42*, P42A, P42D, P42E, P42F, P42G, P42H, P42I, P42K, P42L, P42M, P42N, P42Q, P42R, P42S, P42T, P42V, P42W, P42Y, F43*, F43A, F43D, F43E, F43G, F43H, F43I, F43K, F43L, F43M, F43N, F43P, F43Q, F43R, F43S, F43T, F43V, F43W, F43Y, D44*, D44A, D44E, D44F, D44G, D44H, D44I, D44K, D44L, D44M, D44N, D44P, D44Q, D44R, D44S, D44T, D44V, D44W, D44Y, V45*, V45A, V45D, V45E, V45F, V45G, V45H, V45I, V45K, V45L, V45M, V45N, V45P, V45Q, V45R, V45S, V45T, V45W, V45Y, D46*, D46A, D46E, D46F, D46G, D46H, D46I, D46K, D46L, D46M, D46N, D46P, D46Q, D46R, D46S, D46T, D46V, D46W, D46Y, 047A, C47D, C47E, C47F, C47G, C47H, D47I, C47K, C47L, C47M, C47N, C47P, C47Q, C47R, C47S, C47T, 047V, C47W, C47Y, W48*, W48A, W48D, W48E, W48F, W48G, W48H, W48I, W48K, W48L, W48M, W48N, W48P, W48Q, W48R, W48S, W48T, W48V, W48Y, A49*, A49D, A49E, A49F, A49G, A49H, A49I, A49K, A49L, A49M, A49N, A49P, A49Q, A49R, A49S, A49T, A49V, A49W, A49Y, I50*, I50A, I50D, I50E, I50F, I50G, I50H, I50K, I50L, I50M, I50N, I50P, I50Q, I50R, I50S, I50T, I50V, I50W, I50Y, L51*, L51A, L51D, L51E, L51F, L51G, L51H, L51I, L51K, L51M, L51N, L51P, L51Q, L51R, L51S, L51T, L51V, L51W, L51Y, K53*, K53A, K53D, K53E, K53F, K53G, K53H, K53I, K53L, K53M, K53N, K53P, K53Q, K53R, K53S, K53T, K53V, K53W, K53Y, G54*, G54A, G54D, G54E, G54F, G54H, G54I, G54K, G54L, G54M, G54N, G54P, G54Q, G54R, G54S, G54T, G54V, G54W, G54Y, A55*, A55D, A55E, A55F, A55G, A55H, A55I, A55K, A55L, A55M, A55N, A55P, A55Q, A55R, A55S, A55T, A55V, A55W, A55Y, P56*, P56A, P56D, P56E, P56F, P56G, P56H, P56I, P56K, P56L, P56M, P56N, P56Q, P56R, P56S, P56T, P56V, P56W, P56Y, N57*, N57A, N57D, N57E, N57F, N57G, N57H, N57I, N57K, N57L, N57M, N57P, N57Q, N57R, N57S, N57T, N57V, N57Y, V58*, V58A, V58D, V58E, V58F, V58G, V58H, V58I, V58K, V58L, V58M, V58N, V58P, V58Q, V58R, V58S, V58T, V58W, V58YL59*, L59A, L59A, L59D, L59D, L59A, L59D, L59E, L59E, L59F, L59F, L59E, L59F, L59G, L59G, L59H, L59H, L59G, L59H, L59I, L59I, L59K, L59K, L59I, L59K, L59M, L59ML59M, L59N, L59N, L59N, L59P, L59P, L59Q, L59Q, L59P, L59Q, L59R, L59R, L59S, L59S, L59R, L59S, L59T, L59T, L59V, L59V, L59T, L59V, L59W, L59W, L59Y, L59YL59W, L59Y, Q60*, Q60A, Q60D, Q60E, Q60F, Q60G, Q60H, Q60I, Q60K, Q60L, Q60M, Q60N, Q60P, Q60R, Q60S, Q60T, Q60V, Q60W, Q60Y, R61*, R61A, R61D, R61E, R61F, R61G, R61H, R61I, R61K, R61L, R61M, R61N, R61P, R61Q, R61S, R61T, R61V, R61W, R61Y, V62*, V62A, V62D, V62E, V62F, V62G, V62H, V62I, V62K, V62L, V62M, V62N, V62P, V62Q, V62R, V62S, V62T, V62W, V62Y, N63*, N63A, N63D, N63E, N63F, N63G, N63H, N63I, N63K, N63L, N63M, N63Q, N63R, N63S, N63T, N63V, N63W, N63Y, E64*, E64A, E64D, E64F, E64G, E64H, E64I, E64K, E64L, E64M, E64N, E64P, E64Q, E64R, E64S, E64T, E64V, E64W, E64Y, K65*, K65A, K65D, K65E, K65F, K65G, K65H, K65I, K65L, K65M, K65N, K65P, K65Q, K65R, K65S, K65T, K65V, K65W, K65Y, T66*, T66A, T66D, T66E, T66F, T66G, T66H, T66I, T66K, T66L, T66M, T66N, T66P, T66Q, T66R, T66S, T66V, T66W, T66Y, K67*, K67A, K67D, K67E, K67F, K67G, K67H, K67I, K67L, K67M, K67N, K67P, K67Q, K67R, K67S, K67T, K67V, K67W, K67Y, N68*, N68A, N68D, N68E, N68F, N68G, N68H, N68I, N68K, N68L, N68M, N68P, N68Q, N68R, N68S, N68T, N68V, N68W, N68Y, S69*, S69A, S69D, S69E, S69F, S69G, S69H, S69I, S69K, S69L, S69M, S69N, S69P, S69Q, S69R, S69T, S69V, S69W, S69Y, N70*, N70A, N70D, N70E, N70F, N70G, N70H, N70I, N70K, N70L, N70M, N70P, N70Q, N70R, N70S, N70T, N70V, N70W, N70Y, R71*, R71A, R71D, R71E, R71F, R71G, R71H, R71I, R71K, R71L, R71M, R71N, R71P, R71Q, R71S, R71T, R71V, R71W, R71Y, D72*, D72A, D72E, D72F, D72G, D72H, D72I, D72K, D72L, D72M, D72N, D72P, D72Q, D72R, D72S, D72T, D72V, D72W, D72Y, R73*, R73A, R73D, R73E, R73F, R73G, R73H, R73I, R73K, R73L, R73M, R73N, R73P, R73Q, R73S, R73T, R73V, R73W, R73Y, S74*, S74A, S74D, S74E, S74F, S74G, S74H, S74I, S74K, S74L, S74M, S74N, S74P, S74Q, S74R, S74T, S74V, S74W, S74Y, G75*, G75A, G75D, G75E, G75F, G75H, G75I, G75K, G75L, G75M, G75N, G75P, G75Q, G75R, G75S, G75T, G75V, G75W, G75Y, A76*, A76D, A76E, A76F, A76G, A76H, A76I, A76K, A76L, A76M, A76N, A76P, A76Q, A76R, A76S, A76T, A76V, A76W, A76Y, N77*, N77A, N77D, N77E, N77F, N77G, N77H, N77I, N77K, N77L, N77M, N77P, N77Q, N77R, N77S, N77T, N77V, N77W, N77Y, K78*, K78A, K78D, K78E, K78F, K78G, K78H, K78I, K78L, K78M, K78N, K78P, K78Q, K78R, K78S, K78T, K78V, K78W, K78Y, G79*, G79A, G79D, G79E, G79F, G79H, G79I, G79K, G79L, G79M, G79N, G79P, G79Q, G79R, G79S, G79T, G79V, G79W, G79Y, P80*, P80A, P80D, P80E, P80F, P80G, P80H, P80I, P80K, P80L, P80M, P80N, P80Q, P80R, P80S, P80T, P80V, P80W, P80Y, F81*, F81A, F81D, F81E, F81G, F81H, F81I, F81K, F81L, F81M, F81N, F81P, F81Q, F81R, F81S, F81T, F81V, F81W, F81Y, K82*, K82A, K82D, K82E, K82F, K82G, K82H, K82I, K82L, K82M, K82N, K82P, K82Q, K82R, K82S, K82T, K82V, K82W, K82Y, D83*, D83A, D83E, D83F, D83G, D83H, D83I, D83K, D83L, D83M, D83N, D83P, D83Q, D83R, D83S, D83T, D83V, D83W, D83Y, P84*, P84A, P84D, P84E, P84F, P84G, P84H, P84I, P84K, P84L, P84M, P84N, P84Q, P84R, P84S, P84T, P84V, P84W, P84Y, Q85*, Q85A, Q85D, Q85E, Q85F, Q85G, Q85H, Q85I, Q85K, Q85L, Q85M, Q85N, Q85P, Q85R, Q85S, Q85T, Q85V, Q85W, Q85Y, K86*, K86A, K86D, K86E, K86F, K86G, K86H, K86I, K86L, K86M, K86N, K86P, K86Q, K86R, K86S, K86T, K86V, K86W, K86Y, W87*, W87A, W87D, W87E, W87F, W87G, W87H, W87I, W87K, W87L, W87M, W87N, W87P, W87Q, W87R, W87S, W87T, W87V, W87Y, G88*, G88A, G88D, G88E, G88F, G88H, G88I, G88K, G88L, G88M, G88N, G88P, G88Q, G88R, G88S, G88T, G88V, G88W, G88Y, I89*, I89A, I89D, I89E, I89F, I89G, I89H, I89K, I89L, I89M, I89N, I89P, I89Q, I89R, I89S, I89T, I89V, I89W, I89Y, K90*, K90A, K90D, K90E, K90F, K90G, K90H, K90I, K90L, K90M, K90N, K90P, K90Q, K90R, K90S, K90T, K90V, K90W, K90Y, A91*, A91D, A91E, A91F, A91G, A91H, A91I, A91K, A91L, A91M, A91N, A91P, A91Q, A91R, A91S, A91T, A91V, A91W, A91Y, L92*, L92A, L92D, L92E, L92F, L92G, L92H, L92I, L92K, L92M, L92N, L92P, L92Q, L92R, L92S, L92T, L92V, L92W, L92Y, P93*, P93A, P93D, P93E, P93F, P93G, P93H, P93I, P93K, P93L, P93M, P93N, P93Q, P93R, P93S, P93T, P93V, P93W, P93Y, P94*, P94A, P94D, P94E, P94F, P94G, P94H, P94I, P94K, P94L, P94M, P94N, P94Q, P94R, P94S, P94T, P94V, P94W, P94Y, K95*, K95A, K95D, K95E, K95F, K95G, K95H, K95I, K95L, K95M, K95N, K95P, K95Q, K95R, K95S, K95T, K95V, K95W, K95Y, N96*, N96A, N96D, N96E, N96F, N96G, N96H, N96I, N96K, N96L, N96M, N96P, N96Q, N96R, N96S, N96T, N96V, N96W, N96Y, P97*, P97A, P97D, P97E, P97F, P97G, P97H, P97I, P97K, P97L, P97M, P97N, P97Q, P97R, P97S, P97T, P97V, P97W, P97Y, S98*, S98A, S98D, S98E, S98F, S98G, S98H, S98I, S98K, S98L, S98M, S98N, S98P, S98Q, S98R, S98T, S98V, S98W, S98Y, W99*, W99A, W99D, W99E, W99F, W99G, W99H, W99I, W99K, W99L, W99M, W99N, W99P, W99Q, W99R, W99S, W99T, W99V, W99Y, S100*, S100A, S100D, S100E, S100F, S100G, S100H, S100I, S100K, S100L, S100M, S100N, S100P, S100Q, S100R, S100T, S100V, S100W, S100Y, A101*, A101D, A101E, A101F, A101G, A101H, A101I, A101K, A101L, A101M, A101N, A101P, A101Q, A101R, A101S, A101T, A101V, A101W, A101Y, Q102*, Q102A, Q102D, Q102E, Q102F, Q102G, Q102H, Q102I, Q102K, Q102L, Q102M, Q102N, Q102P, Q102R, Q102S, Q102T, Q102V, Q102W, Q102Y, D103*, D103A, D103E, D103F, D103G, D103H, D103I, D103K, D103L, D103M, D103N, D103P, D103Q, D103R, D103S, D103T, D103V, D103W, D103Y, F104*, F104A, F104D, F104E, F104G, F104H, F104I, F104K, F104L, F104M, F104N, F104P, F104Q, F104R, F104S, F104T, F104V, F104W, F104Y, K105*, K105A, K105D, K105E, K105F, K105G, K105H, K105I, K105L, K105M, K105N, K105P, K105Q, K105R, K105S, K105T, K105V, K105W, K105Y, S106*, S106A, S106D, S106E, S106F, S106G, S106H, S106I, S106K, S106L, S106M, S106N, S106P, S106Q, S106R, S106T, S106V, S106W, S106Y, P107*, P107A, P107D, P107E, P107F, P107G, P107H, P107I, P107K, P107L, P107M, P107N, P107Q, P107R, P107S, P107T, P107V, P107W, P107Y, E108*, E108A, E108D, E108F, E108G, E108H, E108I, E108K, E108L, E108M, E108N, E108P, E108Q, E108R, E108S, E108T, E108V, E108W, E108Y, E109*, E109A, E109D, E109F, E109G, E109H, E109I, E109K, E109L, E109M, E109N, E109P, E109Q, E109R, E109S, E109T, E109V, E109W, E109Y, Y110*, Y110A, Y110D, Y110E, Y110F, Y110G, Y110H, Y110I, Y110K, Y110L, Y110M, Y110N, Y110P, Y110Q, Y110R, Y110S, Y110T, Y110V, Y110W, A111*, A111D, A111E, A111F, A111G, A111H, A111I, A111K, A111L, A111M, A111N, A111P, A111Q, A111R, A111S, A111T, A111V, A111W, A111Y, F112*, F112A, F112D, F112E, F112G, F112H, F112I, F112K, F112L, F112M, F112N, F112P, F112Q, F112R, F112S, F112T, F112V, F112W, F112Y, A113*, A113D, A113E, A113F, A113G, A113H, A113I, A113K, A113L, A113M, A113N, A113P, A113Q, A113R, A113S, A113T, A113V, A113W, A113Y, S114*, S114A, S114D, S114E, S114F, S114G, S114H, S114I, S114K, S114L, S114M, S114N, S114P, S114Q, S114R, S114T, S114V, S114W, S114Y, S115*, S115A, S115D, S115E, S115F, S115G, S115H, S115I, S115K, S115L, S115M, S115N, S115P, S115Q, S115R, S115T, S115V, S115W, S115Y, L116*, L116A, L116D, L116E, L116F, L116G, L116H, L116I, L116K, L116M, L116N, L116P, L116Q, L116R, L116S, L116T, L116V, L116W, L116Y, Q117*, Q117A, Q117D, Q117E, Q117F, Q117G, Q117H, Q117I, Q117K, Q117L, Q117M, Q117N, Q117P, Q117R, Q117S, Q117T, Q117V, Q117W, Q117Y, G118*, G118A, G118D, G118E, G118F, G118H, G118I, G118K, G118L, G118M, G118N, G118P, G118Q, G118R, G118S, G118T, G118V, G118W, G118Y, G119*, G119A, G119D, G119E, G119F, G119H, G119I, G119K, G119L, G119M, G119N, G119P, G119Q, G119R, G119S, G119T, G119V, G119W, G119Y, T120*, T120A, T120D, T120E, T120F, T120G, T120H, T120I, T120K, T120L, T120M, T120N, T120P, T120Q, T120R, T120S, T120V, T120W, T120Y, N121*, N121*N121*, N121A, N121A, N121D, N121D, N121A, N121D, N121E, N121EN121E, N121F, N121F, N121F, N121G, N121G, N121G, N121H, N121H, N121I, N121IN121H, N121I, N121K, N121K, N121L, N121LN121K, N121L, N121M, N121M, N121P, N121PN121M, N121P, N121Q, N121Q, N121R, N121R, N121Q, N121R, N121S, N121S, N121S, N121T, N121T, N121T, N121V, N121VN121V, N121W, N121WN121W, N121Y, N121Y, N121Y, A122*, A122D, A122E, A122F, A122G, A122H, A122I, A122K, A122L, A122M, A122N, A122P, A122Q, A122R, A122S, A122T, A122V, A122W, A122Y, I123*, I123A, I123D, I123E, I123F, I123G, I123H, I123K, I123L, I123M, I123N, I123P, I123Q, I123R, I123S, I123T, I123V, I123W, I123Y, L124*, L124A, L124D, L124E, L124F, L124G, L124H, L124I, L124K, L124M, L124N, L124P, L124Q, L124R, L124S, L124T, L124V, L124W, L124Y, A125*, A125D, A125E, A125F, A125G, A125H, A125I, A125K, A125L, A125M, A125N, A125P, A125Q, A125R, A125S, A125T, A125V, A125W, A125Y, P126*, P126A, P126D, P126E, P126F, P126G, P126H, P126I, P126K, P126L, P126M, P126N, P126Q, P126R, P126S, P126T, P126V, P126Y, V127*, V127A, V127D, V127E, V127F, V127G, V127H, V127I, V127K, V127L, V127M, V127N, V127P, V127Q, V127R, V127S, V127T, V127W, V127Y, N128*, N128A, N128D, N128E, N128F, N128G, N128H, N128I, N128K, N128L, N128M, N128P, N128Q, N128R, N128S, N128T, N128V, N128W, N128Y, L129*, L129A, L129D, L129E, L129F, L129G, L129H, L129I, L129K, L129M, L129N, L129P, L129Q, L129R, L129S, L129T, L129V, L129W, L129Y, A130*, A130D, A130E, A130F, A130G, A130H, A130I, A130K, A130L, A130M, A130N, A130P, A130Q, A130R, A130S, A130T, A130V, A130W, A130Y, S131*, S131A, S131D, S131E, S131F, S131G, S131H, S131I, S131K, S131L, S131M, S131N, S131P, S131Q, S131R, S131T, S131V, S131W, S131Y, Q132*, Q132A, Q132D, Q132E, Q132F, Q132G, Q132H, Q132I, Q132K, Q132L, Q132M, Q132N, Q132P, Q132R, Q132S, Q132T, Q132V, Q132W, Q132Y, N133*, N133A, N133D, N133E, N133F, N133G, N133H, N133I, N133K, N133L, N133M, N133P, N133Q, N133R, N133S, N133T, N133V, N133W, N133Y, S134*, S134A, S134D, S134E, S134F, S134G, S134H, S134I, S134K, S134L, S134M, S134N, S134P, S134Q, S134R, S134T, S134V, S134W, S134Y, Q135*, Q135A, Q135D, Q135E, Q135F, Q135G, Q135H, Q135I, Q135K, Q135L, Q135M, Q135N, Q135P, Q135R, Q135S, Q135T, Q135V, Q135W, Q135Y, G136*, G136A, G136D, G136E, G136F, G136H, G136I, G136K, G136L, G136M, G136N, G136P, G136Q, G136R, G136S, G136T, G136V, G136W, G136Y, G137*, G137A, G137D, G137E, G137F, G137H, G137I, G137K, G137L, G137M, G137N, G137P, G137Q, G137R, G137S, G137T, G137V, G137W, G137Y, V138*, V138A, V138D, V138E, V138F, V138G, V138H, V138I, V138K, V138L, V138M, V138N, V138P, V138Q, V138R, V138S, V138T, V138W, V138Y, L139*, L139A, L139D, L139E, L139F, L139G, L139H, L139I, L139K, L139M, L139N, L139P, L139Q, L139R, L139S, L139T, L139V, L139W, L139Y, N140*, N140A, N140D, N140E, N140F, N140G, N140H, N140I, N140K, N140L, N140M, N140P, N140Q, N140R, N140S, N140T, N140V, N140W, N140Y, G141*, G141A, G141D, G141E, G141F, G141H, G141I, G141K, G141L, G141M, G141N, G141P, G141Q, G141R, G141S, G141T, G141V, G141W, G141Y, F142*, F142A, F142D, F142E, F142G, F142H, F142I, F142K, F142L, F142M, F142N, F142P, F142Q, F142R, F142S, F142T, F142V, F142W, F142Y, Y143*, Y143A, Y143D, Y143E, Y143F, Y143G, Y143H, Y143I, Y143K, Y143L, Y143M, Y143N, Y143P, Y143Q, Y143R, Y143S, Y143T, Y143V, Y143W, S144*, S144A, S144D, S144E, S144F, S144G, S144H, S144I, S144K, S144L, S144M, S144N, S144P, S144Q, S144R, S144T, S144V, S144W, S144Y, A145*, A145D, A145E, A145F, A145G, A145H, A145I, A145K, A145L, A145M, A145N, A145P, A145Q, A145R, A145S, A145T, A145V, A145W, A145Y, N146*, N146A, N146D, N146E, N146F, N146G, N146H, N146I, N146K, N146L, N146M, N146P, N146Q, N146R, N146S, N146T, N146V, N146W, N146Y, K147*, K147A, K147D, K147E, K147F, K147G, K147H, K147I, K147L, K147M, K147N, K147P, K147Q, K147R, K147S, K147T, K147V, K147W, K147Y, V148*, V148A, V148D, V148E, V148F, V148G, V148H, V148I, V148K, V148L, V148M, V148N, V148P, V148Q, V148R, V148S, V148T, V148W, V148Y, A149*, A149D, A149E, A149F, A149G, A149H, A149I, A149K, A149L, A149M, A149N, A149P, A149Q, A149R, A149S, A149T, A149V, A149W, A149Y, Q150*, Q150A, Q150D, Q150E, Q150F, Q150G, Q150H, Q150I, Q150K, Q150L, Q150M, Q150N, Q150P, Q150R, Q150S, Q150T, Q150V, Q150W, Q150Y, F151*, F151A, F151D, F151E, F151G, F151H, F151I, F151K, F151L, F151M, F151N, F151P, F151Q, F151R, F151S, F151T, F151V, F151W, F151Y, D152*, D152A, D152E, D152F, D152G, D152H, D152I, D152K, D152L, D152M, D152N, D152P, D152Q, D152R, D152S, D152T, D152V, D152W, D152Y, P153*, P153A, P153D, P153E, P153F, P153G, P153H, P153I, P153K, P153L, P153M, P153N, P153Q, P153R, P153S, P153T, P153V, P153W, P153Y, S154*, S154A, S154D, S154E, S154F, S154G, S154H, S154I, S154K, S154L, S154M, S154N, S154P, S154Q, S154R, S154T, S154V, S154W, S154Y, K155*, K155A, K155D, K155E, K155F, K155G, K155H, K155I, K155L, K155M, K155N, K155P, K155Q, K155R, K155S, K155T, K155V, K155W, K155Y, P156*, P156A, P156D, P156E, P156F, P156G, P156H, P156I, P156K, P156L, P156M, P156N, P156Q, P156R, P156S, P156T, P156V, P156W, P156Y, Q157*, Q157A, Q157D, Q157E, Q157F, Q157G, Q157H, Q157I, Q157K, Q157L, Q157M, Q157N, Q157P, Q157R, Q157S, Q157T, Q157V, Q157W, Q157Y, Q158*, Q158A, Q158D, Q158E, Q158F, Q158G, Q158H, Q158I, Q158K, Q158L, Q158M, Q158N, Q158P, Q158R, Q158S, Q158T, Q158V, Q158W, Q158Y, T159*, T159A, T159D, T159E, T159F, T159G, T159H, T159I, T159K, T159L, T159M, T159N, T159P, T159Q, T159R, T159S, T159V, T159W, T159Y, K160*, K160A, K160D, K160E, K160F, K160G, K160H, K160I, K160L, K160M, K160N, K160P, K160Q, K160R, K160S, K160T, K160V, K160W, K160Y, G161*, G161A, G161D, G161E, G161F, G161H, G161I, G161K, G161L, G161M, G161N, G161P, G161Q, G161R, G161S, G161T, G161V, G161W, G161Y, T162A, T162D, T162E, T162F, T162G, T162H, T162I, T162K, T162L, T162M, T162N, T162P, T162Q, T162R, T162S, T162T, T162V, T162W, T162Y, W163*, W163A, W163D, W163E, W163F, W163G, W163H, W163I, W163K, W163L, W163M, W163N, W163P, W163Q, W163R, W163S, W163T, W163V, W163Y, F164*, F164A, F164D, F164E, F164G, F164H, F164I, F164K, F164L, F164M, F164N, F164P, F164Q, F164R, F164S, F164T, F164V, F164W, F164Y, Q165*, Q165A, Q165D, Q165E, Q165F, Q165G, Q165H, Q165I, Q165K, Q165L, Q165M, Q165N, Q165P, Q165R, Q165S, Q165T, Q165V, Q165W, Q165Y, I166*, I166A, I166D, I166E, I166F, I166G, I166H, I166K, I166L, I166M, I166N, I166P, I166Q, I166R, I166S, I166T, I166V, I166W, I166Y, T167*, T167A, T167D, T167E, T167F, T167G, T167H, T167I, T167K, T167L, T167M, T167N, T167P, T167Q, T167R, T167S, T167V, T167W, T167Y, K168*, K168A, K168D, K168E, K168F, K168G, K168H, K168I, K168L, K168M, K168N, K168P, K168Q, K168R, K168S, K168T, K168V, K168W, K168Y, F169*, F169A, F169D, F169E, F169G, F169H, F169I, F169K, F169L, F169M, F169N, F169P, F169Q, F169R, F169S, F169T, F169V, F169W, F169Y, T170*, T170A, T170D, T170E, T170F, T170G, T170H, T170I, T170K, T170L, T170M, T170N, T170P, T170Q, T170R, T170S, T170V, T170W, T170Y, G171*, G171A, G171D, G171E, G171F, G171H, G171I, G171K, G171L, G171M, G171N, G171P, G171Q, G171R, G171S, G171T, G171V, G171W, G171Y, A172*, A172D, A172E, A172F, A172G, A172H, A172I, A172K, A172L, A172M, A172N, A172P, A172Q, A172R, A172S, A172T, A172V, A172W, A172Y, A173*, A173D, A173E, A173F, A173G, A173H, A173I, A173K, A173L, A173M, A173N, A173P, A173Q, A173R, A173S, A173T, A173V, A173W, A173Y, G174*, G174A, G174A, G174D, G174DG174A, G174D, G174E, G174E, G174F, G174FG174E, G174F, G174H, G174H, G174I, G174IG174H, G174I, G174K, G174K, G174L, G174LG174K, G174L, G174M, G174M, G174N, G174N, G174M, G174N, G174P, G174P, G174Q, G174QG174P, G174Q, G174R, G174R, G174S, G174SG174R, G174S, G174T, G174T, G174V, G174VG174T, G174V, G174W, G174W, G174Y, G174YG174W, G174Y, P175*, P175A, P175D, P175E, P175F, P175G, P175H, P175I, P175K, P175L, P175M, P175N, P175Q, P175R, P175S, P175T, P175V, P175W, P175Y, Y176*, Y176A, Y176D, Y176E, Y176F, Y176G, Y176H, Y176I, Y176K, Y176L, Y176M, Y176N, Y176P, Y176Q, Y176R, Y176S, Y176T, Y176V, Y176W, K178*, K178A, K178D, K178E, K178F, K178G, K178H, K178I, K178L, K178M, K178N, K178P, K178Q, K178R, K178S, K178T, K178V, K178W, K178Y, A179*, A179D, A179E, A179F, A179G, A179H, A179I, A179K, A179L, A179M, A179N, A179P, A179Q, A179R, A179S, A179T, A179V, A179W, A179Y, L180*, L180A, L180D, L180E, L180F, L180G, L180H, L180I, L180K, L180M, L180N, L180P, L180Q, L180R, L180S, L180T, L180V, L180W, L180Y, G181*, G181A, G181D, G181E, G181F, G181H, G181I, G181K, G181L, G181M, G181N, G181P, G181Q, G181R, G181S, G181T, G181V, G181W, G181Y, S182*, S182A, S182D, S182E, S182F, S182G, S182H, S182I, S182K, S182L, S182M, S182N, S182P, S182Q, S182R, S182T, S182V, S182W, S182Y, N183*, N183A, N183D, N183E, N183F, N183G, N183H, N183I, N183K, N183L, N183M, N183P, N183Q, N183R, N183S, N183T, N183V, N183W, N183Y, D184*, D184A, D184E, D184F, D184G, D184H, D184I, D184K, D184L, D184M, D184N, D184P, D184Q, D184R, D184S, D184T, D184V, D184W, D184Y, K185*, K185A, K185D, K185E, K185F, K185G, K185H, K185I, K185L, K185M, K185N, K185P, K185Q, K185R, K185S, K185T, K185V, K185W, K185Y, S186*, S186A, S186D, S186E, S186F, S186G, S186H, S186I, S186K, S186L, S186M, S186N, S186P, S186Q, S186R, S186T, S186V, S186W, S186Y, V187*, V187A, V187D, V187E, V187F, V187G, V187H, V187I, V187K, V187L, V187M, V187N, V187P, V187Q, V187R, V187S, V187T, V187W, V187Y, D189*, D189A, D189E, D189F, D189G, D189H, D189I, D189K, D189L, D189M, D189N, D189P, D189Q, D189R, D189S, D189T, D189V, D189W, D189Y, K190*, K190A, K190D, K190E, K190F, K190G, K190H, K190I, K190L, K190M, K190N, K190P, K190Q, K190R, K190S, K190T, K190V, K190W, K190Y, N191*, N191A, N191D, N191E, N191F, N191G, N191H, N191I, N191K, N191L, N191M, N191P, N191Q, N191R, N191S, N191T, N191V, N191W, N191Y, K192*, K192A, K192D, K192E, K192F, K192G, K192H, K192I, K192L, K192M, K192N, K192P, K192Q, K192R, K192S, K192T, K192V, K192W, K192Y, N193*, N193A, N193D, N193E, N193F, N193G, N193H, N193I, N193K, N193L, N193M, N193P, N193Q, N193R, N193S, N193T, N193V, N193W, N193Y, I194*, I194A, I194D, I194E, I194F, I194G, I194H, I194K, I194L, I194M, I194N, I194P, I194Q, I194R, I194S, I194T, I194V, I194W, I194Y, A195*, A195D, A195E, A195F, A195G, A195H, A195I, A195K, A195L, A195M, A195N, A195P, A195Q, A195R, A195S, A195T, A195V, A195W, A195Y, G196*, G196A, G196D, G196E, G196F, G196H, G196I, G196K, G196L, G196M, G196N, G196P, G196Q, G196R, G196S, G196T, G196V, G196W, G196Y, D197*, D197A, D197E, D197F, D197G, D197H, D197I, D197K, D197L, D197M, D197N, D197P, D197Q, D197R, D197S, D197T, D197V, D197W, D197Y, W198*, W198A, W198D, W198E, W198F, W198G, W198H, W198I, W198K, W198L, W198M, W198N, W198P, W198Q, W198R, W198S, W198T, W198V, W198Y, G199*, G199A, G199D, G199E, G199F, G199H, G199I, G199K, G199L, G199M, G199N, G199P, G199Q, G199R, G199S, G199T, G199V, G199W, G199Y, F200*, F200A, F200D, F200E, F200G, F200H, F200I, F200K, F200L, F200M, F200N, F200P, F200Q, F200R, F200S, F200T, F200V, F200W, F200Y, D201*, D201A, D201E, D201F, D201G, D201H, D201I, D201K, D201L, D201M, D201N, D201P, D201Q, D201R, D201S, D201T, D201V, D201W, D201Y, P202*, P202A, P202D, P202E, P202F, P202G, P202H, P202I, P202K, P202L, P202M, P202N, P202Q, P202R, P202S, P202T, P202V, P202W, P202Y, A203*, A203D, A203E, A203F, A203G, A203H, A203I, A203K, A203L, A203M, A203N, A203P, A203Q, A203R, A203S, A203T, A203V, A203W, A203Y, K204*, K204A, K204D, K204E, K204F, K204G, K204H, K204I, K204L, K204M, K204N, K204P, K204Q, K204R, K204S, K204T, K204V, K204W, K204Y, W205*, W205A, W205D, W205E, W205F, W205G, W205H, W205I, W205K, W205L, W205M, W205N, W205P, W205Q, W205R, W205S, W205T, W205V, W205Y, A206*, A206D, A206E, A206F, A206G, A206H, A206I, A206K, A206L, A206M, A206N, A206P, A206Q, A206R, A206S, A206T, A206V, A206W, A206Y, Y207*, Y207A, Y207D, Y207E, Y207F, Y207G, Y207H, Y207I, Y207K, Y207L, Y207M, Y207N, Y207P, Y207Q, Y207R, Y207S, Y207T, Y207V, Y207W, Q208*, Q208A, Q208D, Q208E, Q208F, Q208G, Q208H, Q208I, Q208K, Q208L, Q208M, Q208N, Q208P, Q208R, Q208S, Q208T, Q208V, Q208W, Q208Y, Y209*, Y209A, Y209D, Y209E, Y209F, Y209G, Y209H, Y209I, Y209K, Y209L, Y209M, Y209N, Y209P, Y209Q, Y209R, Y209S, Y209T, Y209V, Y209W, D210*, D210A, D210E, D210F, D210G, D210H, D210I, D210K, D210L, D210M, D210N, D210P, D210Q, D210R, D210S, D210T, D210V, D210W, D210Y, E211*, E211A, E211D, E211F, E211G, E211H, E211I, E211K, E211L, E211M, E211N, E211P, E211Q, E211R, E211S, E211T, E211V, E211W, E211Y, K212*, K212A, K212D, K212E, K212F, K212G, K212H, K212I, K212L, K212M, K212N, K212P, K212Q, K212R, K212S, K212T, K212V, K212W, K212Y, N213*, N213A, N213D, N213E, N213F, N213G, N213H, N213I, N213K, N213L, N213M, N213P, N213Q, N213R, N213S, N213T, N213V, N213W, N213Y, N214*, N214A, N214D, N214E, N214F, N214G, N214H, N214I, N214K, N214L, N214M, N214P, N214Q, N214R, N214S, N214T, N214V, N214W, N214Y, K215*, K215A, K215D, K215E, K215F, K215G, K215H, K215I, K215L, K215M, K215N, K215P, K215Q, K215R, K215S, K215T, K215V, K215W, K215Y, F216*, F216A, F216D, F216E, F216G, F216H, F216I, F216K, F216L, F216M, F216N, F216P, F216Q, F216R, F216S, F216T, F216V, F216W, F216Y, N217*, N217A, N217D, N217E, N217F, N217G, N217H, N217I, N217K, N217L, N217M, N217P, N217Q, N217R, N217S, N217T, N217V, N217W, N217Y, Y218*, Y218A, Y218D, Y218E, Y218F, Y218G, Y218H, Y218I, Y218K, Y218L, Y218M, Y218N, Y218P, Y218Q, Y218R, Y218S, Y218T, Y218V, Y218W, V219*, V219A, V219D, V219E, V219F, V219G, V219H, V219I, V219K, V219L, V219M, V219N, V219P, V219Q, V219R, V219S, V219T, V219W, V219Y, G220*, G220A, G220D, G220E, G220F, G220H, G220I, G220K, G220L, G220M, G220N, G220P, G220Q, G220R, G220S, G220T, G220V, G220W, G220Y, K221*, K221A, K221D, K221E, K221F, K221G, K221H, K221I, K221L, K221M, K221N, K221P, K221Q, K221R, K221S, K221T, K221V, K221W and K221Y compared to SEQ ID NO: 1.

14. The method according to any of embodiments 11-13, wherein the DNase variant has at least 60%, such as at least 70%, at least 80%, at least 90%, at least 95%, at least 96%, at least 97%, at least 98%, or at least 99%, sequence identity to the mature polypeptide of SEQ ID NO: 1.

Assays and Detergent Compositions

Composition of Model Detergent A (Liquid)

Ingredients: 12% LAS, 11% AEO Biosoft N25-7 (NI), 7% AEOS (SLES), 6% MPG (monopropylene glycol), 3% ethanol, 3% TEA, 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w)

Composition of Model Detergent T (Powder)

Ingredients: 11% LAS, 2% AS/AEOS, 2% soap, 3% AEO, 15.15% sodium carbonate, 3% sodium slilcate, 18.75% zeolite, 0.15% chelant, 2% sodium citrate, 1.65% AA/MA copolymer, 2.5% CMC and 0.5% SRP (all percentages are w/w).

Composition of Model Detergent X (Powder)

Ingredients: 16.5% LAS, 15% zeolite, 12% sodium disilicate, 20% sodium carbonate, 1% sokalan, 35.5% sodium sulfate (all percentages are w/w).

Assay I: Testing of DNase Activity

DNase activity was determined on DNase Test Agar with Methyl Green (BD, Franklin Lakes, N.J., USA), which was prepared according to the manual from supplier. Briefly, 21 g of agar was dissolved in 500 ml water and then autoclaved for 15 min at 121° C. Autoclaved agar was temperated to 48° C. in water bath, and 20 ml of agar was poured into petridishes with and allowed to solidify by incubation o/n at room temperature. On solidified agar plates, 5 µl of enzyme solutions are added and DNase activity is observed as colorless zones around the spotted enzyme solutions.

Assay II: Analysis of E-2-Nonenal on Textile Using an Electronic Nose.

One way of testing for the presence of malodor on textiles is by using E-2-Nonenal as a marker for the malodor, as this compound contributes to the malodor on laundry.

Add a solution of E-2-nonenal to a 5 cm×5 cm textile swatch and place the swatch in a 20 mL glass vial for GC analysis and cap the vial. Analyze 5 mL headspace from the capped vials in a Heracles II Electronic nose from Alpha M.O.S., France (double column gas chromatograph with 2 FIDs, column 1: MXT5 and column 2: MXT1701) after 20 minutes incubation at 40° C.

Methods

General methods of PCR, cloning, ligation nucleotides etc. are well-known to a person skilled in the art and may for example be found in in "Molecular cloning: A laboratory manual", Sambrook et al. (1989), Cold Spring Harbor lab., Cold Spring Harbor, N.Y.; Ausubel, F. M. et al. (eds.);

"Current protocols in Molecular Biology", John Wiley and Sons, (1995); Harwood, C. R., and Cutting, S. M. (eds.); "DNA Cloning: A Practical Approach, Volumes I and II", D. N. Glover ed. (1985); "Oligonucleotide Synthesis", M. J. Gait ed. (1984); "Nucleic Acid Hybridization", B. D. Hames & S. J. Higgins eds (1985); "A Practical Guide To Molecular Cloning", B. Perbal, (1984).

EXAMPLES

Example 1: Preparation of DNase Variants

Site-directed variants (SD) were generated using specific primers that contained the desired new mutation. The new codon selected was the codon with the highest natural abundance for the specific amino acid in *Aspergillus oryzae*. The transformation substrate was made in two rounds of PCR:
1) Separate amplification of N-terminal and C-terminal fragment, relative to the mutation site. The N-terminal fragment was amplified using a universal forward primer and a position specific reverse primer. The C-terminal fragment was amplified using a mutation specific forward primer and universal reverse primer. Both universal primers are complementary to sequences necessary for homologous integration in *Aspergillus* genome.
2) Assembly of the N-terminal and C-terminal fragments by fusion (SOE) PCR.

The resulting transformation substrate was transformed into *Aspergillus oryzae* and transformants selected for by growth on nitrate as sole nitrogen source. Three single colonies of each type were picked into MTP and grown for 4 days at 30° C. in broth specific for *Aspergillus*. The supernatants were used for screening.

Example 2: Testing DNase Variants for Stability

The stability of DNase variants compared to DNase with SEQ ID NO: 1 was determined by incubating the DNase samples under defined conditions ("stress conditions") in a model detergent solution (Model detergent A). The variants were tested using two different set of conditions stress conditions given by temperature and duration.
  A) Set A was chosen such that the remaining activity of the DNase with SEQ ID NO: 1 after the incubation is equal to approximately 50% of the activity of a similar sample incubated under defined conditions ("reference conditions") that do not lead to loss of activity when incubated for the same duration. The samples were normalized by activity as described below and the normalized samples stressed in PCR machines at 50° C. for 20 hrs. The activity after incubation under stress conditions or reference conditions was determined using viscosity assay described below.
  B) Set B was chosen such that the remaining activity of the DNase with SEQ ID NO: 1 after the incubation is equal to approximately 20% of the activity of a similar sample incubated under defined conditions ("reference conditions") that do not lead to loss of activity when incubated for the same duration. The samples were normalized by ELISA as described below and the normalized samples stressed in heating cabinet at 50° C. for 72 hrs. The activity after incubation under stress conditions or reference conditions was determined using viscosity assay described below.

Normalization of Samples by Activity

A 96 well plate with supernatants of *Aspergillus* cultures expressing DNase variants was shaken for 2 minutes at 600 rpm on an BioSan Thermo-Shaker (PST-100HL) before loaded on the Hamilton STAR robot equipped with a 96 channel TADM head which allows the simultaneous measuring of pressure in the head space of each single pipette channel. 10 µl of the supernatant from each of the 96 wells is transferred to 96 wells on an empty plate with each well containing 90 µl 50 mM Tris-HCl, pH 7. From each of the 96 wells 5 µl of this 10× dilution is transferred to a new plate with each well containing 195 µl of DNA substrate (3.3 mg DNA/ml, 50 mM Tris-HCl, 5 mM MgCl2 at pH7; DNA: Deoxyribonucleic acid sodium salt from salmon testes, Sigma D1626).

The Hamilton STAR measures the viscosity using ViPr assay technology as described in (WO2011/107472 A1) of the solution in all 96 wells for 30 min at a 1 min interval by aspirating 100 µl with a standard clear CORE 300 µl tip at a speed of 50 µl/s with the addition of the diluted DNase sample after the second measurement. The solution is dispensed back to the original well at 10 µl/s.

The pressure data during the aspiration step from all of the 96 wells are collected and the pressure value at 1000 ms after start of the aspiration is taken for calculation of the DNase activity in Relative units (RU) from a standard that is loaded on each plate. The standard on each plate is 1, 5 and 10 ppm wt DNase and is in replica. Relative units are calculated by division of the buffer value (blank; 1000 ms) by the pressure value (1000 ms) of a given sample subtracted by 1. Relative units for the standard curve are plotted against the concentration and a linear curve fitting is applied. From the RU values of the samples the concentration in ppm can be obtained using the standard curve. Based on the concentration determination the original samples are normalized to 10 ppm in 50 mM Tris HCL pH7 or the maximum obtainable concentration in case of low expressing variants for the subsequent stability screening.

Normalization of Samples by ELISA Assay for Protein Content Determination

The DNase variants and the concentration of the reference DNase (SEQ ID NO: 1) was alternative determined by ELISA after a 9750-fold dilution of supernatants in TBS-T buffer (20 mM Tris, 150 mM NaCl, 0.1 v/v Tween 20, pH 7.5)). For protein quantification the sandwich ELISA technique was used. Microplate wells coated with rabbit polyclonal anti-protein antibodies constitute the solid phase. Test samples, standards, and controls are added to the coated wells and incubated with incubation buffer. If the protein of interest is present in the test sample, it will be captured and immobilised by the protein-specific antibody coated on the wells. After incubation and washing, another polyclonal anti-protein antibody is added to the wells. This antibody is labeled with horseradish peroxidase (HRP). The HRP-labeled antibody binds to the immobilised protein of interest, thus forming a sandwich. After incubation and washing, an enzyme substrate is added to the wells and incubated. The degree of enzymatic activity of the immobilised HRP is determined by measuring the optical density of the oxidized enzymatic product in the wells at 620 nm. The absorbance at 620 nm is proportional to the amount of protein in the test sample. A set of standards is used to generate a standard curve of absorbance versus protein concentration. This curve is used for calculating the concentrations of test samples and controls. Based on the concentration determination the original samples are normalized to 10 ppm in 50 mM Tris HCL pH7.

Stability Assay

A DNase standard (0, 5 and 10 ppm) is added to the Normalization plate containing the samples normalized to 10+ ppm or the maximum obtainable concentration when below 10 ppm. 12 µl sample from the normalized plate is added to 228 µl Model detergent A in a well of a standard 96 well microtiter plate. Detergent and samples are mixed by shaking for 90 seconds at 2000 rpm using a Hamilton Heater Shaker (HHS) that is mounted on the Hamilton STAR. After the mixing 200 µl of the sample is aspirated and 80 µl of the sample is added to all wells of two 96 well PCR plates The plates are sealed and one plate is stored at 4° C. (unstressed) while the replica plate is incubated at 50° C. (stressed) in a PCR machine for 20 hours or in a heating cabinet for 72 hrs respectively.

Residual Activity Determination

10 µl of sample from column 1-6 or 7-12 from the stress and unstressed plate respectively are transferred to a standard 96 well plate with each well filled with 190 µl of DNase substrate (3.3 mg DNA/ml, 50 mM Tris-HCl, 5 mM MgCl2 at pH7; DNA: Deoxyribonucleic acid sodium salt from salmon testes, Sigma D1626). The stressed and unstressed samples are subsequently mixed by 5 consecutive aspirations and dispense steps with a volume of 100 µl. After mixing the plates are incubated for 1.5 h at 37° C. followed by 30 min incubation at room temperature.

Subsequently the viscosity of the samples was measured by 5 consecutive aspirations and dispenses steps with a volume of 100 µl and an aspirate speed of 50 µl/s a Hamilton STAR equipped with a 96 channel TADM head using VIPR (WO2011/107472 A1). The pressure data during the aspiration step from all of the 96 wells are collected and the average pressure value at 1000 ms after start of the aspiration is calculated for the for the 4 last aspiration steps; both for the stressed and unstressed samples including the buffer blanks and the reference samples (SEQ ID NO: 1) located on each plate. Relative units are calculated by division of the buffer value (blank; 1000 ms) by the pressure value (1000 ms) of a given sample subtracted by 1. This is calculated for both the stressed and unstressed sample. The ratio between RU for the stressed and unstressed sample is calculated in percent which is equivalent to the residual activity (RA %).

Half-Life Improvement Factor

The half-life improvement factor (IF) correlates the residual activity percentage (RA %) of a DNase variant with that of the reference DNase (SEQ ID NO: 1). Calculation of the improvement factor based on residual activity percentage was done according to the following equation:

$$IF=(\ln(0.5)/\ln(RA \% \text{ of variant}))/(\ln(0.5)/\ln(RA \% \text{ of SEQ ID NO: 1}))$$

The value for RA % of reference DNase (SEQ ID NO: 1) employed was always calculated from samples residing on the same screening plate as the DNase variant. The following criteria was used for qualification of data for a given sample: The pressure value (1000 ms) for the unstressed sample must be lower than −400 Pa, the calculated relative unit for the unstressed sample must be between 0.2 and 2, the calculated residual activity percentage (RA %) should be between 0 and 100% and RA % of reference DNase must be between 10 and 60%.

An improvement factor that is greater than 1 (IF>1) indicates an improved stability of a variant as compared to the reference, while an IF of 1 (1F=1) identifies a variant which is on par with the reference, and an IF of less than 1 (IF<1) identifies a variant that is less stable the reference.

The improvement factor was ranked on a scale from 1-3 using a scale that considered the variation in the calculated improvement factor between three biological replicates. Also, two different scales were employed to account for IF variations between set A and set B when changing screening conditions. The intervals used for ranking IF from set A were:

1: IF<1.25
2: 1.25<=IF<2
3: 2<=IF

The intervals used for ranking IF from set B were:
1: IF<1.5
2: 1.5<=IF<3
3: 3<=IF For each variant, the raking from three biological replicates was combined to an overall score. The median of the ranking was used when the value could be calculated for all three biological replicates. The lowest ranking was used when two biological replicates were represented, while the ranking was disregarded when only a singular value was obtainable.

The assay rankings and scores for a selection of DNase variants are listed in the table 1 below:

TABLE 1

| Position | Variant | Rank (set A) | Rank (set B) |
|---|---|---|---|
| 4 | N4E | 2 | |
| 17 | L17E | 2 | |
| 19 | T19A | 2 | |
| 19 | T19G | 2 | |
| 19 | T19I | 2 | |
| 36 | K36P | | 2 |
| 38 | Q38P | | 2 |
| 39 | S39V | 2 | |
| 39 | S39R | 3 | |
| 40 | A40P | | 2 |
| 40 | A40H | | 2 |
| 41 | L41T | | 3 |
| 41 | L41H | | 2 |
| 45 | V45H | 2 | |
| 51 | L51G | | 2 |
| 53 | K53T | | 2 |
| 53 | K53P | | 2 |
| 54 | G54P | | 2 |
| 55 | A55P | | 2 |
| 56 | P56* | | 2 |
| 57 | N57H | | 2 |
| 64 | E64A | 2 | |
| 64 | E64Q | 2 | |
| 64 | E64R | 2 | |
| 64 | E64T | 2 | |
| 64 | E64I | 3 | |
| 64 | E64S | 3 | |
| 66 | T66H | 2 | |
| 67 | K67A | 2 | |
| 67 | K67T | 2 | |
| 68 | N68V | | 2 |
| 68 | N68P | | 3 |
| 68 | N68I | | 2 |
| 68 | N68H | | 2 |
| 69 | S69A | 2 | |
| 69 | S69D | 2 | |
| 69 | S69E | 2 | |
| 69 | S69K | 2 | |
| 69 | S69L | 2 | |
| 69 | S69W | 2 | |
| 69 | S69Y | 2 | |
| 69 | S69Q | 3 | |
| 70 | N70T | | 3 |
| 70 | N70H | | 2 |
| 70 | N70G | | 2 |
| 71 | R71T | | 3 |
| 72 | D72E | 2 | |

TABLE 1-continued

| Position | Variant | Rank (set A) | Rank (set B) |
|---|---|---|---|
| 74 | S74H | | 2 |
| 74 | S74G | | 2 |
| 75 | G75I | | 2 |
| 77 | N77T | | 2 |
| 82 | K82P | | 2 |
| 82 | K82I | | 2 |
| 83 | D83T | | 2 |
| 83 | D83P | | 3 |
| 83 | D83I | | 2 |
| 83 | D83H | | 2 |
| 83 | D83G | | 2 |
| 84 | P84H | | 2 |
| 84 | P84* | | 2 |
| 85 | Q85T | | 2 |
| 85 | Q85P | | 2 |
| 85 | Q85H | | 2 |
| 86 | K86T | | 2 |
| 86 | K86P | | 2 |
| 86 | K86H | | 2 |
| 88 | G88P | | 2 |
| 88 | G88H | | 2 |
| 88 | G88* | | 2 |
| 91 | A91P | | 2 |
| 99 | W99T | | 3 |
| 101 | A101W | 2 | |
| 105 | K105E | 2 | |
| 105 | K105N | 2 | |
| 105 | K105T | 2 | |
| 105 | K105D | 3 | |
| 106 | S106T | | 2 |
| 115 | S115T | | 2 |
| 116 | L116I | 2 | |
| 135 | Q135L | | 3 |
| 136 | G136L | | 3 |
| 138 | V138I | 2 | |
| 138 | V138L | 2 | |
| 138 | V138P | 2 | |
| 138 | V138Q | 2 | |
| 139 | L139A | | 2 |
| 139 | L139* | | 3 |
| 140 | N140R | | 2 |
| 140 | N140L | | 3 |
| 140 | N140A | | 2 |
| 141 | G141L | | 2 |
| 151 | F151R | | 2 |
| 152 | D152Y | | 2 |
| 152 | D152L | | 2 |
| 152 | D152I | | 2 |
| 152 | D152A | | 2 |
| 153 | P153E | | 2 |
| 154 | S154R | | 2 |
| 162 | T162R | | 2 |
| 163 | W163E | | 2 |
| 164 | F164R | | 2 |
| 166 | I166Y | | 2 |
| 166 | I166R | | 2 |
| 168 | K168N | 2 | |
| 169 | F169R | | 2 |
| 169 | F169E | | 2 |
| 173 | A173I | 2 | |
| 173 | A173R | 2 | |
| 173 | A173T | 2 | |
| 179 | A179* | | 2 |
| 180 | L180* | | 2 |
| 182 | S182R | | 2 |
| 183 | N183E | | 2 |
| 184 | D184I | | 2 |
| 185 | K185Y | | 2 |
| 186 | S186I | | 2 |
| 189 | D189G | 2 | |
| 189 | D189H | 2 | |
| 212 | K212G | 2 | |
| 212 | K212P | 2 | |
| 215 | K215I | | 2 |

The invention claimed is:

1. A DNase variant, comprising:
a polypeptide having at least 90% sequence identity to SEQ ID NO: 1;
wherein the polypeptide includes an amino acid substitution at position 39 of SEQ ID NO: 1 that is S39V or S39R;
wherein the polypeptide has DNase activity; and
wherein the polypeptide has improved stability as compared to the polypeptide of SEQ ID NO: 1.

2. The DNase variant of claim 1, including an additional amino acid substitution at one or more positions of the polypeptide corresponding to positions 4, 17, 19, 36, 38, 40, 41, 45, 51, 53, 54, 55, 57, 64, 66, 67, 68, 69, 70, 71, 72, 74, 75, 77, 82, 83, 84, 85, 86, 88, 91, 99, 101, 105, 106, 115, 116, 135, 136, 138, 139, 140, 141, 151, 152, 153, 154, 162, 163, 164, 166, 168, 169, 173, 182, 183, 184, 185, 186, 189, 212 and 215 of SEQ ID NO: 1.

3. The DNase variant of claim 1, including one or more additional amino acid substitutions in the polypeptide that include N4E, L17E, T19A, T19G, T19I, K36P, Q38P, A40P, A40H, L41T, L41H, V45H, L51G, K53T, K53P, G54P, A55P, N57H, E64A, E64Q, E64R, E64T, E64I, E64S, T66H, K67A, K67T, N68V, N68P, N68I, N68H, S69A, S69D, S69E, S69K, S69L, S69W, S69Y, S69Q, N70T, N70H, N70G, R71T, D72E, S74H, S74G, G75I, N77T, K82P, K82I, D83T, D83P, D83I, D83H, D83G, P84H, Q85T, Q85P, Q85H, K86T, K86P, K86H, G88P, G88H, A91P, W99T, A101W, K105E, K105N, K105T, K105D, S106T, S115T, L116I, Q135L, G136L, V138I, V138L, V138P, V138Q, L139A, N140R, N140L, N140A, G141L, F151R, D152Y, D152L, D152I, D152A, P153E, S154R, T162R, W163E, F164R, I166Y, I166R, K168N, F169R, F169E, A173I, A173R, A173T, S182R, N183E, D184I, K185Y, S186I, D189G, D189H, K212G, K212P and K215I.

4. A composition comprising the DNase variant of claim 1, wherein the composition additionally includes a surfactant and a builder.

5. The composition of claim 4, including one or more additional enzymes selected from the group consisting of proteases, amylases, lipases, cutinases, cellulases, endoglucanases, xyloglucanases, pectinases, pectin lyases, xanthanases, peroxidaes, haloperoxygenases, catalases, mannanases, and mixtures thereof.

6. The DNase variant of claim 1, wherein the DNase variant has an Improvement Factor (IF) of at least 1.1 as compared to the polypeptide shown in SEQ ID NO: 1.

7. The DNase variant of claim 1, wherein the variant has at least 95% sequence identity to the polypeptide of SEQ ID NO: 1.

8. The DNase variant of claim 1, wherein the total number of amino acid substitutions compared to SEQ ID NO: 1 is between 1-20.

9. A composition comprising the DNase variant of claim 1, wherein the composition comprises:
(a) at least 0.002 ppm of the DNase variant,
(b) 2 wt % to 60 wt % of at least one surfactant,
(c) 5 wt % to 50 wt % of at least one builder, and
(d) optionally at least one additional enzyme.

10. The composition of claim 9, wherein the composition is a detergent composition.

11. The composition of claim 9, wherein the composition further comprises one or more additional enzymes selected from the group consisting of proteases, amylases, lipases, cutinases, cellulases, endoglucanases, xyloglucanases, pectinases, pectin lyases, xanthanases, peroxidaes, haloperoxygenases, catalases and mannanases, or any mixture thereof.

12. The composition of claim 9 in form of a bar, a homogenous tablet, a tablet having two or more layers, a pouch having one or more compartments, a regular or compact powder, a granule, a paste, a gel, or a regular, compact or concentrated liquid.

13. A method of cleaning laundry or a hard surface, comprising washing the laundry or the hard surface with the composition of claim 4.

* * * * *